(12) United States Patent
Dyring et al.

(10) Patent No.: US 9,371,533 B2
(45) Date of Patent: Jun. 21, 2016

(54) PROTEIN EXPRESSION SYSTEM

(75) Inventors: Charlotte Dyring, Rungsted Kyst (DK);
Willem Adriaan De Jongh, Valby (DK);
Peter Birk Rasmussen, Holte (DK);
Helene Lykkegaard, Hillerod (DK)

(73) Assignee: Expres2ion Biotechnologies ApS, Hørsholm (DK)

( * ) Notice: Subject to any disclaimer, the term of this patent is extended or adjusted under 35 U.S.C. 154(b) by 1161 days.

(21) Appl. No.: 12/997,072

(22) PCT Filed: Jun. 12, 2009

(86) PCT No.: PCT/EP2009/057278
§ 371 (c)(1),
(2), (4) Date: Feb. 22, 2011

(87) PCT Pub. No.: WO2009/150222
PCT Pub. Date: Dec. 17, 2009

(65) Prior Publication Data
US 2011/0136171 A1    Jun. 9, 2011

Related U.S. Application Data

(60) Provisional application No. 61/061,959, filed on Jun. 16, 2008.

(30) Foreign Application Priority Data

Jun. 12, 2008   (EP) ..................... 08158168

(51) Int. Cl.
| *C07G 3/00* | (2006.01) |
| *C07H 21/02* | (2006.01) |
| *C12Q 1/68* | (2006.01) |
| *C12P 21/06* | (2006.01) |
| *C12N 5/07* | (2010.01) |
| *C12N 15/79* | (2006.01) |
| *C07K 14/435* | (2006.01) |

(52) U.S. Cl.
CPC .......... *C12N 15/79* (2013.01); *C07K 14/43581* (2013.01)

(58) Field of Classification Search
None
See application file for complete search history.

(56) References Cited

U.S. PATENT DOCUMENTS 7,135,558 B1 * 11/2006 Yandell ................. 536/23.1

FOREIGN PATENT DOCUMENTS

WO    WO 94/28114 A1    12/1994
WO    2005/012534       2/2005

OTHER PUBLICATIONS

Roman et al. A new series of *Drosophila* Expression Vectors for Behavioral Rescue. Jul. 1999. Biotechniques. vol. 27, No. 1, pp. 54-56.*
Alignment of SEQ ID No. 68 with SEQ ID No. 421 of U.S. Pat. No. 7,135,558. Dec. 4, 2013, 2 pages.*
Alignment of SEQ ID No. 6 with SEQ ID No. 421 of U.S. Pat. No. 7,135,558. Search conducted on Jul. 2, 2014, 2 pages.*
Japanese Patent Office "Decision of Refusal" in parallel Japanese Patent Application No. 2011-512990, mailed Jan. 15, 2013; (Including English Translation), 7 pages.
Santel et al., "The initiator element of *Drosophila* β2 tubulin gene promoter contributes to gene expression in vivo but not required for male germ-cell specific expression", Nucleic Acids Research, 2000, vol. 28, No. 6, pp. 1439-1446.
Chang et al., "Regulation of the feedback antagonist naked cuticle by Wingless signaling", Developmental Biology, vol. 321, 2008, pp. 446-454.
Schwyter, et al., "The decapentaplegic core promoter region plays an integral role in the spatial control of transcription", Molecular and Cellular Biology, vol. 15, No. 7, 1995, pp. 3960-3968.
Fang, et al., "C-terminal-binding protein directly activates and represses Wnt transcriptional targets in *Drosophila*", The EMBO Journal, vol. 25, 2006, pp. 2735-2745.
Japanese Patent Office, "Notice of Reason for Refusal" in parallel Japanese Patent Application No. 2011-512990, mailed Jul. 24, 2012; (Including English Translation), 11 pages.
Corces et al., "Identification of Sequences Involved in the Transcriptional Control of a *Drosophila* Heat-Shock Gene", The Journal of Biological Chemistry, vol. 259, No. 23; Dec. 1984; pp. 14812-14817.
Lee et al., "A Baculovirus Superinfection System: Efficient Vehicle for Gene Transfer into *Drosophila* S2 Cells", Journal of Virology, vol. 74, No. 24; Dec. 2000; pp. 11873-11880.
Huynh et al., "Construction of Modular and Versatile Plasmid Vectors for the High-Level Expression of Single or Multiple Genes in insects and insect Cell Lines", J. Mol. Biol. (1999) 288, pp. 13-20.
Slater et al., "Transcriptional Regulation of an hsp70 Heat Shock Gene in the Yeast *Saccharomyces cerevisiae*", Molecular and Cellular Biology, vol. 7, No. 5; May 1987; pp. 1906-1916.

(Continued)

*Primary Examiner* — Catherine S Hibbert
*Assistant Examiner* — Channing S Mahatan
(74) *Attorney, Agent, or Firm* — McHale & Slavin, P.A.

(57) ABSTRACT

Disclosed is a DNA polynucleotide comprising a nucleic acid sequence having promoter activity in a *Drosophila* S2 cell, where said nucleic acid sequence is selected from (i) a nucleotide sequence of SEQ ID NO: 1, SEQ ID NO:2, SEQ ID NO:3, SEQ ID NO:4, SEQ ID NO: 5, SEQ ID NO:6, SEQ ID NO:33, SEQ ID NO:36, SEQ ID NO: 37, or SEQ ID NO: 68 with or without flanking restriction site sequences at either terminus; (ii) a functional nucleotide sequence with a sequence identity of at least 80% to any one sequence of (i); (iii) a nucleotide which is a functional fragment of at least 6 contiguous nucleotides of any one sequence of (i) or (ii); (iv) a functional nucleotide sequence with a sequence identity of at least 80% to said functional fragment of (iii); (v) a first chimeric nucleotide sequence comprising two or more sequences of any one sequence of (i), (ii), (iii) and (iv), and (vi) a second chimeric nucleotide sequence, comprising at least 6 nucleotides and including consecutive nucleotide stretches from at least 2 nucleotide sequences of (iii) and/or (iv), where each of said consecutive stretches alone does not have promoter activity in a *Drosophila* S2 cell. Also disclosed are vectors and cells comprising the polynucleotide and a method for producing a polypeptide of interest by use of the polynucleotide.

39 Claims, 15 Drawing Sheets

(56) References Cited

OTHER PUBLICATIONS

Hugh R..B. Pelham et al; A Synthetic Heat-Shock Promoter Element Foncers Heat-Inducibility on the Herpes Simplex Virus Thymidine Kinase Gene; The EMBO Journal vol. 1 No. 11(pp. 1473-1477) (1982).

Monical L. Angelichio et al; Comparison of Several Promoters and Polyadenylation Signals for Use in Heterologous Gene Expression in Cultured *Drosophila* Cells; Nucleic Acids Research, vol. 19, No. 18 (pp. 5037-5043) 1991.

Lucy Lu and John Tower; A Transcriptional Insulator Element, the su(Hw) Binding Site, Protects a Chromosomal DNA Replication Origin from Position Effects; Molecular and Cellular Biology, Apr. 1997 (pp. 2202-2206).

Yang-Tsung Chung et al; Positive and Negative Regulatory Elements Mediating Transcription from the *Drosophila melanogaster* Actin 5C Distal Promoter; Molecular and Cellular Biology, Dec. 1990 (pp. 6172-6180).

Robert B. Kirkpatrick et al; Heavy Chain Dimers as well as Complete Antibodies are Efficiently Formed and Secreted from *Drosophila* via a BiP-mediated Pathway; the Journal of Biological Chemistry; vol. 270., No. 34, Aug. 1995 (pp. 19800-19805).

Hongjun Zhang and John Tower; Sequence requirements for function of the *Drosophila chorion* gene locus ACE3 replicator and ori-β origin elements; Develoopment 131, 2089-2099; Pub. by The Company of Biologists 2004.

Janet L. Carminati et al; The *Drosophila* ACE3 Chorion Element Autonomously Induces Amplification; Molecular and Cellular Biology, May 1992 (pp. 2444-2453).

David A. Dean et al; Sequence Requirements for Plasmid Nuclear Import; Experimental Cell Research 253 (pp. 713-722) 1999.

S. Li et al; Muscle-Specific Enhancement of Gene Expression by Incorporation of SV40 Enhancer in the Expression Plasmid; Gene Therapy (2001) 8 (pp. 494-497).

Jong Hwa Park et al; Optimization of Transecton Conditons for Expession of Green Fluorescent Protein in *Drosophila melanogaster* S2 Cells; Enzyme and Microbial Technology 25 (1999) (pp. 558-563).

Nick S. Berrow et al; A Versatile Ligation-Independent Cloning Method Suitable for High-Throughput Expression Screening Applications; Nucleic Acids Research, 2007 vol. 35. No. 6, pp. 1-12.

Koei Okazaki et al; High-Frequency Transformation Method and Library Transducing Vectors for Cloning Mammalian cDNAs by Trans-Complementation of Schizosaccharomyces Pombe; Nucleic Acids Research, vol. 18, No. 22, Nov. 25, 1990, pp. 6485-6489.

H. Zieler and C.Q. Huynh; Intron-Dependent Stimulation of marker Gene Expression in Cultured Insect Cells; Insect Molecular Biology (2002) 11(1), (pp. 87-95).

Roman et al; A new series of *Drosophila* Expression Vectors for Behavioral Rescue; Database embl. Jul. 20, 1999, 1 page.

J. Feder et al, "The consequences of expressing hsp70 in *Drosophila* cells at normal temperature", Genes & Development, 6:1402-1413 (1992).

Novy, R. et al, "Ligation Independent Cloning: Efficient Directional Cloning of PCR Products", Novagen, Inc. Innovations 5, pp. 1-3, (1996).

Thompson, J. et al, "Clustal W: improving the sensitivity of progressive multiple sequence alignment through sequence weighting, position-specific gap penalties and weight matrix choice", Nucleic Acids Research, 22:22:4673-4680, Oxford University Press, (1994).

Smith, T. et al, "Comparison of Biosequences", Advances in Applied Mathematics, vol. 2, pp. 482-489, Academic Press, Inc., (1981).

Pearson, W. et al, "Improved tools for biological sequence comparison", Proc. Natl. Acad. Sci. USA, vol. 85, pp. 2444-2448, (Apr. 1988).

Altschul, S. et al, "Basic local alignment search tool", J. Mol. Biol., vol. 215, pp. 403-410, (1990).

\* cited by examiner

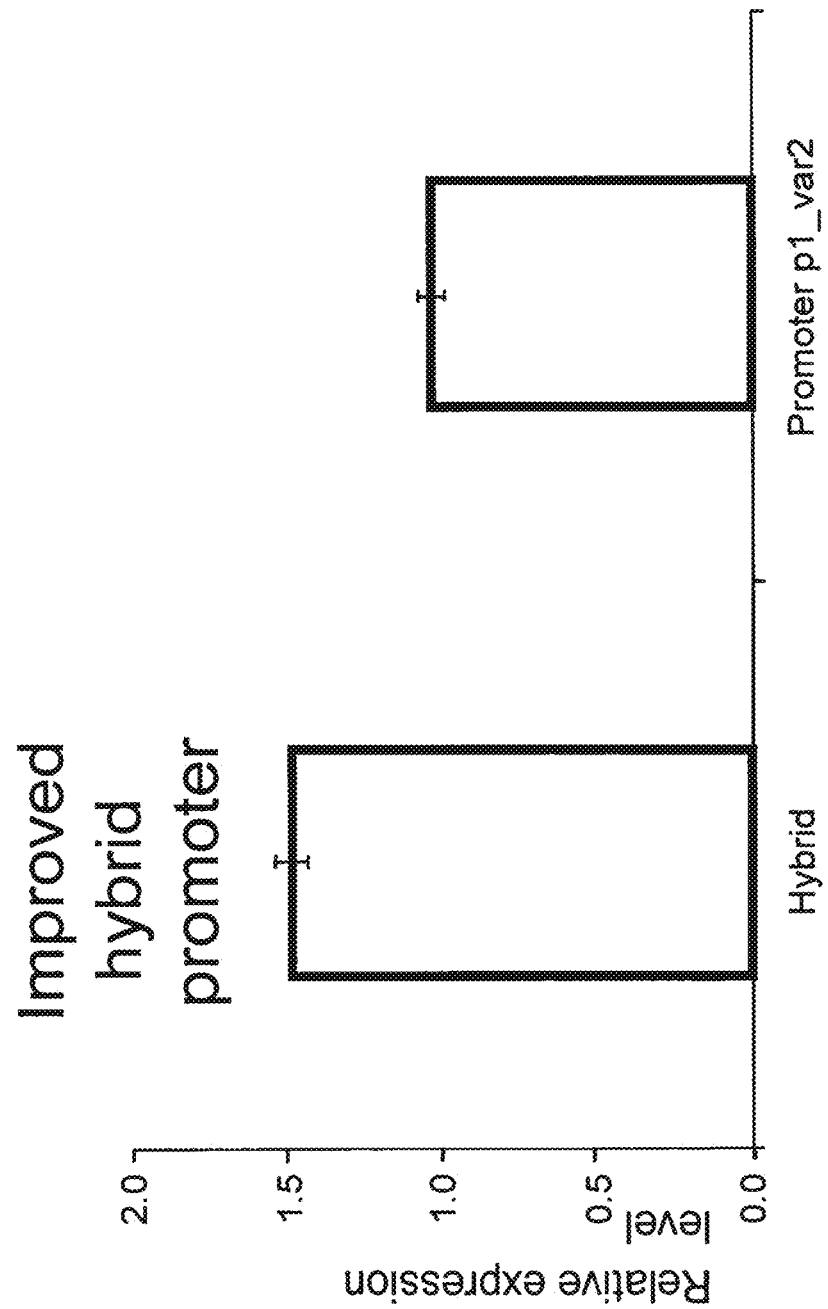

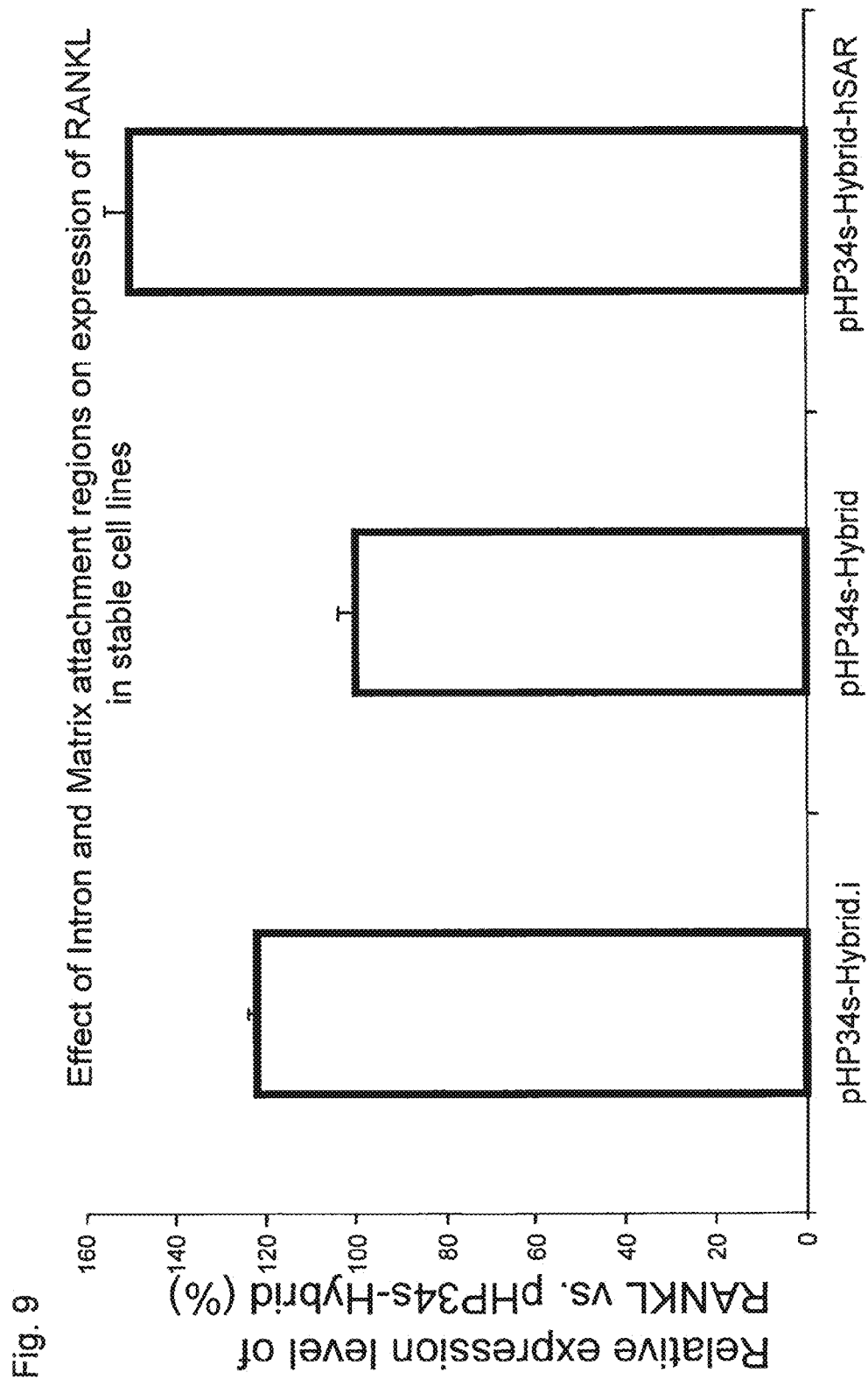

PROTEIN EXPRESSION SYSTEM

CROSS REFERENCE TO RELATED APPLICATIONS

This application is a §371 national phase entry of International Application No. PCT/EP2009/057278, filed Jun. 12, 2009, which claims priority to European Patent Application No. 08158168.8, filed Jun. 12, 2008, and U.S. Provisional Patent Application No. 61/061,959, filed Jun. 16, 2008, the entire contents of which are incorporated herein by reference.

FIELD OF THE INVENTION

The present invention relates to the field of genetic engineering and molecular biology. In particular, the present invention relates to novel promoter DNA polynucleotides and its use as a tool for improved protein expression in host cells, notably in *Drosophila melanogaster*. Furthermore, the present invention relates to vectors containing the polynucleotide and also the use of these in recombinant expression of polypeptides, in particular heterologous expression of proteins, such as industrial enzymes or proteins for pharmaceutical use including eukaryotic (e.g. mammalian, such as human, but also protozoan or helminthic) and viral proteins. The invention is particularly relevant in the field of protein expression where the expression product is secreted from recombinant host cells, especially if these host cells are insect cells.

BACKGROUND OF THE INVENTION

Protein production systems, in which polypeptides or proteins of interest are produced in recombinant organisms or cells, are the backbone of commercial biotechnology. The earliest systems, based on bacterial expression in hosts such as *E. coli*, have been joined by systems based on eukaryotic hosts, in particular mammalian cells in culture, insect cells both in culture and in the form of whole insects, and transgenic mammals such as sheep and goats.

Prokaryotic cell culture systems are easy to maintain and cheap to operate. However, prokaryotic cells are not capable of post-translational modification of eukaryotic proteins. Moreover, many proteins are incorrectly folded, requiring specific procedures to refold them, which adds to the cost of production.

Eukaryotic cell culture systems have been described for a number of applications. For example, mammalian cells are capable of post-translational modification, and generally produce proteins which are correctly folded and soluble. The chief disadvantages of mammalian cell systems include the requirement for specialised and expensive culture facilities, the risk of infection, which can lead to loss of the whole culture, and the risk of contaminating the end product with potentially hazardous mammalian proteins.

Insect cells are also used for polypeptide expression. The most widespread expression system used in insect cells is based on baculovirus vectors. A baculovirus expression vector is constructed by replacing the polyhedrin gene of baculovirus, which encodes a major structural protein of the baculovirus, with a heterologous gene, under the control of the strong native polyhedrin promoter. Cultured insect host cells are infected with the recombinant virus, and the protein produced thereby can be recovered from the cells themselves or from the culture medium if suitable secretion signals are employed. These systems also, however, suffer from problems associated with reproducibility of expression level and quality, infection of the culture, and may require specialised culture facilities. Furthermore, baculovirus stocks, which for the production of certain proteins may have to be made under GMP conditions, is not always stable over time.

Suitable promoters used in *Drosophila melanogaster* S2 cells for protein expression also include the pMT promoter and the P2ZOp2F (OPIE2 promoter)

Chung et al. Molecular and Cellular Biology, Vol. 10, No. 12, 1992 relates to characterization of positive and negative regulatory elements in the Actin5C distal promoter.

Angelichio et al. Nucleic Acids Research, Vol. 19, No. 18 5037-5043, 1991 relates to a comparison of several promoters and polyadenylation signals for use in heterologous gene expression in cultured *Drosophila* cells.

It is an object of the present invention to provide more efficient expression and/or secretion in host cells, notably in *Drosophila melanogaster*. It is a further object to provide polynucleotides and vectors that facilitate this efficient expression and secretion.

SUMMARY OF THE INVENTION

In a broad aspect the present invention relates to promoter DNA polynucleotides, suitable for use in the heterologous expression of a polypeptide of interest. In another broad aspect the present invention relates to an isolated DNA polynucleotide, a so-called expression vector, comprising such promoter DNA polynucleotides suitable for expression and production in relatively high amounts of a protein of interest, such as therapeutically effective proteins or industrial enzymes.

Thus, in a first aspect the present invention relates to a promoter DNA polynucleotide comprising at least one sequence selected from the group consisting of:
  (i) a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37 or SEQ ID NO: 68 with or without flanking restriction site sequences at either terminus;
  (ii) a functional nucleotide sequence with a sequence identity of at least 80% to any one sequence of (i) and having promoter activity in a *Drosophila* S2 cell;
  (iii) a nucleotide which is a functional fragment of at least 6 contiguous nucleotides of any one sequence of (i) or (ii), said functional fragment having promoter activity in a *Drosophila* S2 cell;
  (iv) a functional nucleotide sequence with a sequence identity of at least 80% to said functional fragment of (iii) and having promoter activity in a *Drosophila* S2 cell;
  (v) a first chimeric nucleotide sequence comprising two or more sequences of any one sequence of (i), (ii), (iii) and (iv), and
  (vi) a second chimeric nucleotide sequence having promoter activity in a *Drosophila* S2 cell, comprising at least 6 nucleotides and including consecutive nucleotide stretches from at least 2 nucleotide sequences of (iii) and/or (iv), where each of said consecutive stretches alone does not have promoter activity in a *Drosophila* S2 cell.

In a second aspect the present invention relates to an isolated DNA polynucleotide suitable for heterologous expression of a polypeptide of interest in an insect cell the DNA polynucleotide comprising
a promoter DNA polynucleotide comprising at least one sequence selected from the group consisting of:
  (i) a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37, or SEQ ID NO: 68 with or without flanking restriction site sequences at either terminus;
(ii) a functional nucleotide sequence with a sequence identity of at least 80% to any one sequence of (i) and having promoter activity in a *Drosophila* S2 cell;
(iii) a nucleotide which is a functional fragment of at least 6 contiguous nucleotides of any one sequence of (i) or (ii), said functional fragment having promoter activity in a *Drosophila* S2 cell;
(iv) a functional nucleotide sequence with a sequence identity of at least 80% to said functional fragment of (iii) and having promoter activity in a *Drosophila* S2 cell;
(v) a first chimeric nucleotide sequence comprising two or more sequences of any one sequence of (i), (ii), (iii) and (iv), and
(vi) a second chimeric nucleotide sequence having promoter activity in a *Drosophila* S2 cell, comprising at least 6 nucleotides and including consecutive nucleotide stretches from at least 2 nucleotide sequences of (iii) and/or (iv), where each of said consecutive stretches alone does not have promoter activity in a *Drosophila* S2 cell.

In a third aspect the present invention relates to a cell comprising a DNA polynucleotide suitable for heterologous expression of a polypeptide of interest in an insect cell the DNA, the polynucleotide comprising a promoter DNA polynucleotide comprising at least one sequence selected from the group consisting of:
(i) a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37, or SEQ ID NO: 68 with or without flanking restriction site sequences at either terminus;
(ii) a functional nucleotide sequence with a sequence identity of at least 80% to any one sequence of (i) and having promoter activity in a *Drosophila* S2 cell;
(iii) a nucleotide which is a functional fragment of at least 6 contiguous nucleotides of any one sequence of (i) or (ii), said functional fragment having promoter activity in a *Drosophila* S2 cell;
(iv) a functional nucleotide sequence with a sequence identity of at least 80% to said functional fragment of (iii) and having promoter activity in a *Drosophila* S2 cell;
(v) a first chimeric nucleotide sequence comprising two or more sequences of any one sequence of (i), (ii), (iii) and (iv), and
(vi) a second chimeric nucleotide sequence having promoter activity in a *Drosophila* S2 cell, comprising at least 6 nucleotides and including consecutive nucleotide stretches from at least 2 nucleotide sequences of (iii) and/or (iv), where each of said consecutive stretches alone does not have promoter activity in a *Drosophila* S2 cell.

In a further aspect the present invention relates to a method for the production of a polypeptide of interest encoded by a polynucleotide the method comprising the steps of
(a) obtaining a polynucleotide sequence encoding the polypeptide of interest;
(b) inserting the polynucleotide sequence encoding the polypeptide of interest into a DNA polynucleotide suitable for heterologous expression of a polypeptide of interest in an insect cell, the polynucleotide comprising a promoter DNA polynucleotide comprising at least one sequence selected from the group consisting of:
(i) a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37, or SEQ ID NO: 68 with or without flanking restriction site sequences at either terminus;
(ii) a functional nucleotide sequence with a sequence identity of at least 80% to any one sequence of (i) and having promoter activity in a *Drosophila* S2 cell;
(iii) a nucleotide which is a functional fragment of at least 6 contiguous nucleotides of any one sequence of (i) or (ii), said functional fragment having promoter activity in a *Drosophila* S2 cell;
(iv) a functional nucleotide sequence with a sequence identity of at least 80% to said functional fragment of (iii) and having promoter activity in a *Drosophila* S2 cell;
(v) a first chimeric nucleotide sequence comprising two or more sequences of any one sequence of (i), (ii), (iii) and (iv), and
(vi) a second chimeric nucleotide sequence having promoter activity in a *Drosophila* S2 cell, comprising at least 6 nucleotides and including consecutive nucleotide stretches from at least 2 nucleotide sequences of (iii) and/or (iv), where each of said consecutive stretches alone does not have promoter activity in a *Drosophila* S2 cell;
(c) transforming a host cell with the polynucleotide obtained under step (b);
(d) allowing for the expression of the polynucleotide obtained under step (b) to produce the polypeptide; and
(e) obtaining the polypeptide there from.

In a further aspect the present invention relates to a polypeptide produced by a method comprising the steps of
(a) obtaining a polynucleotide sequence encoding the polypeptide of interest;
(b) inserting the polynucleotide sequence encoding the polypeptide of interest into a DNA polynucleotide suitable for heterologous expression of a polypeptide of interest in an insect cell, the polynucleotide comprising a promoter DNA polynucleotide comprising at least one sequence selected from the group consisting of:
(i) a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37, or SEQ ID NO: 68 with or without flanking restriction site sequences at either terminus;
(ii) a functional nucleotide sequence with a sequence identity of at least 80% to any one sequence of (i) and having promoter activity in a *Drosophila* S2 cell;
(iii) a nucleotide which is a functional fragment of at least 6 contiguous nucleotides of any one sequence of (i) or (ii), said functional fragment having promoter activity in a *Drosophila* S2 cell;
(iv) a functional nucleotide sequence with a sequence identity of at least 80% to said functional fragment of (iii) and having promoter activity in a *Drosophila* S2 cell;
(v) a first chimeric nucleotide sequence comprising two or more sequences of any one sequence of (i), (ii), (iii) and (iv), and
(vi) a second chimeric nucleotide sequence having promoter activity in a *Drosophila* S2 cell, comprising at least 6 nucleotides and including consecutive nucleotide stretches from at least 2 nucleotide sequences of (iii) and/or (iv), where each of said consecutive stretches alone does not have promoter activity in a *Drosophila* S2 cell;
(c) transforming a host cell with the polynucleotide obtained under step (b);
(d) allowing for the expression of the polynucleotide obtained under step (b) to produce the polypeptide; and
(e) obtaining the polypeptide there from.

BRIEF DESCRIPTION OF FIGURES

FIG. 8: Comparison of the expression levels of the Actin-HSP70 core hybrid promoter and the truncated Actin 5c promoter (named Promoter p1_var 2 in graph). Duplicate transient expression experiments. (See table A3 for raw data).

FIG. 9: Effect of adding either the intron or two flanking matrix attachment regions to the pHP34s-hybrid vector. The experiments were conducted as triplicate shake flask experiments using stable polyclonal cell lines made from independent triplicate transfections. (See table A2 for raw data).

DETAILED DESCRIPTION OF THE INVENTION

Figure 1:
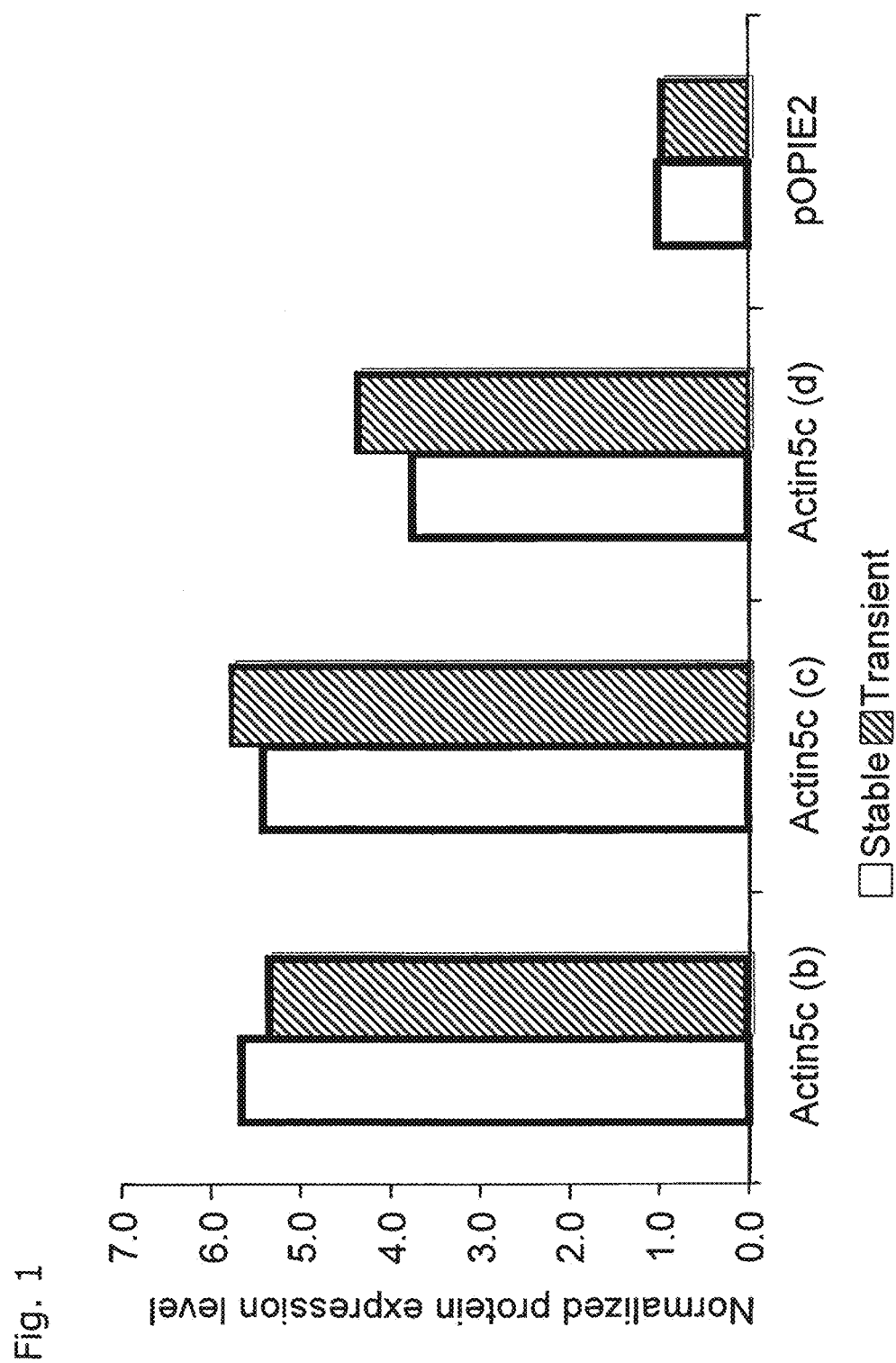
FIG. 1: Normalized protein expression level compared to the pOPIE2 promoter in the p2ZOP2F vector for different transfections of a mutant Actin5C promoter for stable and transient transformations. (b) . . . (d) refers to separate transfections using the mutant Actin5C promoter containing plasmid pHP11.

As discussed above the inventors of the present invention have found particular highly efficient promoters as well as regulatory elements and their combination suitable for the high level expression of heterologous proteins in insect cells.

A "heterologous expression" as used herein refers to the expression of a polypeptide not normally expressed and secreted by the host cell used to express that particular polypeptide. The term "Promoter DNA polynucleotide" as used herein means a nucleotide sequence that provides a cell with the regulatory sequences for expression of a coding sequence operably linked thereto. In general, a coding sequence is located 3' to a promoter sequence. The promoter DNA polynucleotide may consists of proximal and more distal upstream elements as well as other functional fragments or elements, the latter elements often referred to as enhancers.

As used herein the terms "functional fragment", "elements" and "enhancers" refers to DNA sequences and parts of the promoter, which can stimulate promoter activity and may be an innate element of the promoter or a heterologous element inserted to enhance the level or tissue-specificity of a promoter. It is understood by those skilled in the art that different promoters may direct the expression of a gene in different tissues or cell types, or at different stages of development, or in response to different environmental conditions. An unregulated promoter that allows for continual transcription of its associated gene is often referred to as "constitutive promoter".

Unless otherwise stated the term "Sequence identity" for nucleic acids as used herein refers to the sequence identity calculated as $(n_{ref}-n_{dif}) \cdot 100/n_{ref}$, wherein $n_{dif}$ is the total number of non-identical residues in the two sequences when aligned and wherein $n_{ref}$ is the number of residues in one of the sequences. Hence, the DNA sequence agtcagtc will have a sequence identity of 75% with the sequence aatcaatc ($n_{dif}=2$ and $n_{ref}=8$).

In some embodiments the sequence identity is determined by conventional methods, e.g., Smith and Waterman, 1981, Adv. Appl. Math. 2:482, by the search for similarity method of Pearson & Lipman, 1988, Proc. Natl. Acad. Sci. USA 85:2444, using the CLUSTAL W algorithm of Thompson et al., 1994, Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., 1990, Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, etc., are used.

A "chimeric nucleotide sequence" as used herein refers to a nucleotide sequence consisting of a first nucleotide sequence derived from a first original nucleotide sequence fused to a second nucleotide sequence derived from a second original nucleotide sequence, which first and second original sequence are not normally fused to each other in the same sequence.

When indicating that a first polynucleotide exhibits an improved/higher "protein expression level" compared to a second polynucleotide is herein meant that the first polynucleotide provides for a larger amount of recoverable protein expression product than does the second polynucleotide when transforming and culturing a reference cell (typically an insect cell, such as a *Drosophila* S2 cell) with the polynucleotides so as to obtain expression of the polynucleotides under identical conditions.

An "S2 cell" refers to a cell from the Schneider-2 embryonic *Drosophila melanogaster* cell line, which is i.a. available from DSMZ—Deutsche Sammlung von Mikroorganismen und Zellkulturen GmbH, Inhoffenstraβe 7 B, 38124 Braunschweig, Germany under the deposit number DSMZ ACC 130 and from American Type Culture Collection (ATCC), P.O. Box 1549, Manassas, Va. 20108, USA, under the deposit number CRL-1963.

In some embodiments the promoter DNA polynucleotide according to the invention comprises a sequence selected from the group consisting of:
a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37, or SEQ ID NO: 68 with or without flanking restriction site sequences at either terminus.

In some embodiments the promoter DNA polynucleotide comprises a nucleotide sequence of SEQ ID NO:1. In some embodiments the promoter DNA polynucleotide comprises a nucleotide sequence of SEQ ID NO:2. In some embodiments the promoter DNA polynucleotide comprises a nucleotide sequence of SEQ ID NO:3. In some embodiments the promoter DNA polynucleotide comprises a nucleotide sequence of SEQ ID NO:4. In some embodiments the promoter DNA polynucleotide comprises a nucleotide sequence of SEQ ID NO:5. In some embodiments the promoter DNA polynucleotide comprises a nucleotide sequence of SEQ ID NO:6. In some embodiments the promoter DNA polynucleotide comprises a nucleotide sequence of SEQ ID NO:33. In some embodiments the promoter DNA polynucleotide comprises a nucleotide sequence of SEQ ID NO:36. In some embodiments the promoter DNA polynucleotide comprises a nucleotide sequence of SEQ ID NO:37. In some embodiments the promoter DNA polynucleotide comprises a nucleotide sequence of SEQ ID NO: 68, optionally lacking residues 1 or 1-2 or 1-3 or 1-4 or 1-5 or 1-6 and/or optionally lacking residues 587-592 or 588-592 or 589-592 or 590-592 or 591-592 or 592.

In some embodiments the promoter DNA polynucleotide according to the invention comprises a sequence with a sequence identity of at least 80% to any one sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37, or SEQ ID NO: 68.

In some embodiments the promoter DNA polynucleotide according to the invention comprises a functional nucleotide sequence with a sequence identity of at least 80% to any one sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37 or SEQ ID NO: 68 said functional nucleotide sequence having promoter activity in a *Drosophila* S2 cell.

In some embodiments the promoter DNA polynucleotide according to the invention comprises a sequence with a sequence identity of at least 80% to the sequence of SEQ ID NO:1. In some embodiments the promoter DNA polynucleotide according to the invention comprises a sequence with a sequence identity of at least 80% to the sequence of SEQ ID NO:2. In some embodiments the promoter DNA polynucleotide according to the invention comprises a sequence with a sequence identity of at least 80% to the sequence of SEQ ID NO:3. In some embodiments the promoter DNA polynucleotide according to the invention comprises a sequence with a sequence identity of at least 80% to the sequence of SEQ ID NO:4. In some embodiments the promoter DNA polynucleotide according to the invention comprises a sequence with a sequence identity of at least 80% to the sequence of SEQ ID NO:5. In some embodiments the promoter DNA polynucleotide according to the invention comprises a sequence with a sequence identity of at least 80% to the sequence of SEQ ID NO:6. In some embodiments the promoter DNA polynucleotide according to the invention comprises a sequence with a sequence identity of at least 80% to the sequence of SEQ ID NO:33. In some embodiments the promoter DNA polynucleotide according to the invention comprises a sequence with a sequence identity of at least 80% to the sequence of SEQ ID NO:36. In some embodiments the promoter DNA polynucleotide according to the invention comprises a sequence with a sequence identity of at least 80% to the sequence of SEQ ID NO:37. In some embodiments the promoter DNA polynucleotide according to the invention comprises a sequence with a sequence identity of at least 80% to the sequence of SEQ ID NO:68. In specific embodiments the sequence identity in each of these cases is at least 85%, such as at least 90%, such as at least 95%, such as at least 98%.

In some embodiments the promoter DNA polynucleotide according to the invention comprises a functional fragment of at least 6 contiguous nucleotides of any one sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37, or SEQ ID NO: 68.

In some embodiments the promoter DNA polynucleotide according to the invention comprises a functional fragment of at least 6 contiguous nucleotides of any one sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, or SEQ ID NO:37, or SEQ ID NO: 68 said functional fragment having promoter activity in a *Drosophila* S2 cell.

In some embodiments the promoter DNA polynucleotide according to the invention comprises a functional fragment of at least 6 contiguous nucleotides of the sequence of SEQ ID NO:1. In some embodiments the promoter DNA polynucleotide according to the invention comprises a functional fragment of at least 6 contiguous nucleotides of the sequence of SEQ ID NO:2. In some embodiments the promoter DNA polynucleotide according to the invention comprises a functional fragment of at least 6 contiguous nucleotides of the sequence of SEQ ID NO:3. In some embodiments the promoter DNA polynucleotide according to the invention comprises a functional fragment of at least 6 contiguous nucleotides of the sequence of SEQ ID NO:4. In some embodiments the promoter DNA polynucleotide according to the invention comprises a functional fragment of at least 6 contiguous nucleotides of the sequence of SEQ ID NO:5. In some embodiments the promoter DNA polynucleotide according to the invention comprises a functional fragment of at least 6 contiguous nucleotides of the sequence of SEQ ID NO:6. In some embodiments the promoter DNA polynucleotide according to the invention comprises a functional fragment of at least 6 contiguous nucleotides of the sequence of SEQ ID NO:33. In some embodiments the promoter DNA polynucleotide according to the invention comprises a functional fragment of at least 6 contiguous nucleotides of the sequence of SEQ ID NO:36. In some embodiments the promoter DNA polynucleotide according to the invention comprises a functional fragment of at least 6 contiguous nucleotides of the sequence of SEQ ID NO:39. In some embodiments the promoter DNA polynucleotide according to the invention comprises a functional fragment of at least 6 contiguous nucleotides of the sequence of SEQ ID NO:68.

In some embodiments the promoter DNA polynucleotide according to the invention comprises a sequence with a sequence identity of at least 80% to the functional fragment of at least 6 contiguous nucleotides of any one sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37 or SEQ ID NO: 68.

In some embodiments the promoter DNA polynucleotide according to the invention comprises a functional nucleotide sequence with a sequence identity of at least 80% to said functional fragment of at least 6 contiguous nucleotides of any one sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37 or SEQ ID NO: 68, said functional nucleotide sequence having promoter activity in a *Drosophila* S2 cell.

In some embodiments the promoter DNA polynucleotide according to the invention comprises a sequence with a sequence identity of at least 80% to the functional fragment of at least 6 contiguous nucleotides of the sequence of SEQ ID NO:1. In some embodiments the promoter DNA polynucleotide according to the invention comprises a sequence with a sequence identity of at least 80% to the functional fragment of at least 6 contiguous nucleotides of the sequence of SEQ ID NO:2. In some embodiments the promoter DNA polynucleotide according to the invention comprises a sequence with a sequence identity of at least 80% to the functional fragment of at least 6 contiguous nucleotides of the sequence of SEQ ID NO:3. In some embodiments the promoter DNA polynucleotide according to the invention comprises a sequence with a sequence identity of at least 80% to the functional fragment of at least 6 contiguous nucleotides of the sequence of SEQ ID NO:4. In some embodiments the promoter DNA polynucleotide according to the invention comprises a sequence with a sequence identity of at least 80% to the functional fragment of at least 6 contiguous nucleotides of the sequence of SEQ ID NO:5. In some embodiments the promoter DNA polynucleotide according to the invention comprises a sequence with a sequence identity of at least 80% to the functional fragment of at least 6 contiguous nucleotides of the sequence of SEQ ID NO:6. In some embodiments the promoter DNA polynucleotide according to the invention comprises a sequence with a sequence identity of at least 80% to the functional fragment of at least 6 contiguous nucleotides of the sequence of SEQ ID NO:33. In some embodiments the promoter DNA polynucleotide according to the invention comprises a sequence with a sequence identity of at least 80% to the functional fragment of at least 6 contiguous nucleotides of the sequence of SEQ ID NO:36. In some embodiments the promoter DNA polynucleotide according to the invention comprises a sequence with a sequence identity of at least 80% to the functional fragment of at least 6 contiguous nucleotides of the sequence of SEQ ID NO:37. In some embodiments the promoter DNA polynucleotide according to the invention comprises a sequence with a sequence identity of at least 80% to the functional fragment of at least 6 contiguous nucleotides of the sequence of SEQ ID NO:68.

In some embodiments the promoter DNA polynucleotide according to the invention comprises a chimeric sequence comprising two or more sequences selected from the following group
a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, or SEQ ID NO:37;
a sequence with a sequence identity of at least 80% to any one sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, or SEQ ID NO:37;
a functional fragment of at least 6 contiguous nucleotides of any one sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, or SEQ ID NO:37;
a sequence with a sequence identity of at least 80% to a functional fragment of at least 6 contiguous nucleotides of any one sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, or SEQ ID NO:37.

An example of such a chimeric sequence is the hybrid promoter sequence set forth in SEQ ID NO: 68.

In some embodiments the promoter DNA polynucleotide according to the invention comprises a chimeric nucleotide sequence comprising two or more sequences selected from
(i) a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, or SEQ ID NO:37;
(ii) a functional nucleotide sequence with a sequence identity of at least 80% to any one sequence of (i) and having promoter activity in a *Drosophila* S2 cell;
(iii) a nucleotide which is a functional fragment of at least 6 contiguous nucleotides of any one sequence of (i) or (ii), said functional fragment having promoter activity in a *Drosophila* S2 cell; and
(iv) a functional nucleotide sequence with a sequence identity of at least 80% to said functional fragment of (iii) and having promoter activity in a *Drosophila* S2 cell.

In some embodiments the promoter DNA polynucleotide according to the invention comprises a chimeric nucleotide sequence as defined in (vi) above.

In some embodiments the functional fragment of at least 6 contiguous nucleotides according to the invention is at least 7, such as at least 8, such as at least 9, such as at least 10, such as at least 11, such as at least 12, such as at least 13, such as at least 14, such as at least 15, such as at least 16, such as at least 17, such as at least 18, such as at least 19, such as at least 20, such as at least 21, such as at least 22, such as at least 23, such as at least 24, such as at least 25, such as at least 26, such as at least 27, such as at least 28, such as at least 29, such as at least 30, such as at least 31, such as at least 32, such as at least 33, such as at least 34, such as at least 35, such as at least 36, such as at least 37, such as at least 38, such as at least 39, such as at least 40, such as at least 41, such as at least 42, such as at least 43, such as at least 44, such as at least 45, such as at least 46, such as at least 47, such as at least 48, such as at least 49, such as at least 50, such as at least 51, such as at least 52, such as at least 53, such as at least 54, such as at least 55, such as at least 56, such as at least 57, such as at least 58, such as at least 59, such as at least 60, such as at least 61, such as at least 62, such as at least 63, such as at least 64, such as at least 65, such as at least 66, such as at least 67, such as at least 68, such as at least 69, such as at least 70, such as at least 71, such as at least 72, such as at least 73, such as at least 74, such as at least 75, such as at least 76, such as at least 77, such as at least 78, such as at least 79, such as at least 80, such as at least 81, such as at least 82, such as at least 83, such as at least 84, such as at least 85, such as at least 86, such as at least 87, such as at least 88, such as at least 89, such as at least 90, such as at least 91, such as at least 92, such as at least 93, such as at least 94, such as at least 95, such as at least 96, such as at least 97, such as at least 98, such as at least 99, such as at least 100, such as at least 101, such as at least 102, such as at least 103, such as at least 104, such as at least 105, such as at least 106, such as at least 107, such as at least 108, such as at least 109, such as at least 110, such as at least 111, such as at least 112, such as at least 113, such as at least 114, such as at least 115, such as at least 116, such as at least 117, such as at least 118, such as at least 119, such as at least 120, such as at least 121, such as at least 122, such as at least 123, such as at least 124, such as at least 125, such as at least 126, such as at least 127, such as at least 128, such as at least 129, such as at least 130, such as at least 131, such as at least 132, such as at least 133, such as at least 134, such as at least 135, such as at least 136, such as at least 137, such as at least 138, such as at least 139, such as at least 140, such as at least 141, such as at least 142, such as at least 143, such as at least 144, such as at least 145, such as at least 146, such as at least 147, such as at least 148, such as at least 149, such as at least 150, such as at least 151, such as at least 152, such as at least 153, such as at least 154, such as at least 155, such as at least 156, such as at least 157, such as at least 158, such as at least 159, such as at least 160, such as at least 161, such as at least 162, such as at least 163, such as at least 164, such as at least 165, such as at least 166, such as at least 167, such as at least 168, such as at least 169, such as at least 170, such as at least 171, such as at least 172, such as at least 173, such as at least 174, such as at least 175, such as at least 176, such as at least 177, such as at least 178, such as at least 179, such as at least 180, such as at least 181, such as at least 182, such as at least 183, such as at least 184, such as at least 185, such as at least 186, such as at least 187, such as at least 188, such as at least 189, such as at least 190, such as at least 191, such as at least 192, such as at least 193, such as at least 194, such as at least 195, such as at least 196, such as at least 197, such as at least 198, such as at least 199, such as at least 200, such as at least 201, such as at least 202, such as at least 203, such as at least 204, such as at least 205, such as at least 206, such as at least 207, such as at least 208, such as at least 209, such as at least 210, such as at least 211, such as at least 212, such as at least 213, such as at least 214, such as at least 215, such as at least 216, such as at least 217, such as at least 218, such as at least 219, such as at least 220, such as at least 221, such as at least 222, such as at least 223, such as at least 224, such as at least 225, such as at least 226, such as at least 227, such as at least 228, such as at least 229, such as at least 230, such as at least 231, such as at least 232, such as at least 233, such as at least 234, such as at least 235, such as at least 236, such as at least 237, such as at least 238, such as at least 239, such as at least 240, such as at least 241, such as at least 242, such as at least 243, such as at least 244, such as at least 245, such as at least 246, such as at least 247, such as at least 248, such as at least 249, such as at least 250, such as at least 251, such as at least 252, such as at least 253, such as at least 254, such as at least 255, such as at least 256, such as at least 257, such as at least 258, such as at least 259, such as at least 260, such as at least 261, such as at least 262, such as at least 263, such as at least 264, such as at least 265, such as at least 266, such as at least 267, such as at least 268, such as at least 269, such as at least 270, such as at least 271, such as at least 272, such as at least 273, such as at least 274, such as at least 275, such as at least 276, such as at least 277, such as at least 278, such as at least 279, such as at least 280, such as at least 281, such as at least 282, such as at least 283, such as at least 284, such as at least 285, such as at least 286, such as at least 287, such as at least 288, such as at least 289, such as at least 290, such as at least 291, such as at least 292, such as at least 293, such as at least 294, such as at least 295, such as at least 296, such as at least 297, such as at least 298, such as at least 299, such as at least 300, such as at least 301, such as at least 302, such as at least 303, such as at least 304, such as at least 305, such as at least 306, such as at least 307, such as at least 308, such as at least 309, such as at least 310, such as at least 311, such as at least 312, such as at least 313, such as at least 314, such as at least 315, such as at least 316, such as at least 317, such as at least 318, such as at least 319, such as at least 320, such as at least 321, such as at least 322, such as at least 323, such as at least 324, such as at least 325, such as at least 326, such as at least 327, such as at least 328, such as at least 329, such as at least 330, such as at least 331, such as at least 332, such as at least 333, such as at least 334, such as at least 335, such as at least 336, such as at least 337, such as at least 338, such as at least 339, such as at least 340, such as at least 341, such as at least 342, such as at least 343, such as at least 344, such as at least 345, such as at least 346, such as at least 347, such as at least 348, such as at least 349, such as at least 350, such as at least 351, such as at least 352, such as at least 353, such as at least 354, such as at least 355, such as at least 356, such as at least 357, such as at least 358, such as at least 359, such as at least 360, such as at least 361, such as at least 362, such as at least 363, such as at least 364, such as at least 365, such as at least 366, such as at least 367, such as at least 368, such as at least 369, such as at least 370, such as at least 371, such as at least 372, such as at least 373, such as at least 374, such as at least 375, such as at least 376, such as at least 377, such as at least 378, such as at least 379, such as at least 380, such as at least 381, such as at least 382, such as at least 383, such as at least 384, such as at least 385, such as at least 386, such as at least 387, such as at least 388, such as at least 389, such as at least 390, such as at least 391, such as at least 392, such as at least 393, such as at least 394, such as at least 395, such as at least 396, such as at least 397, such as at least 398, such as at least 399, such as at least 400, such as at least 401, such as at least 402, such as at least 403, such as at least 404, such as at least 405, such as at least 406, such as at least 407, such as at least 408, such as at least 409, such as at least 410, such as at least 411, such as at least 412, such as at least 413, such as at least 414, such as at least 415, such as at least 416, such as at least 417, such as at least 418, such as at least 419, such as at least 420, such as at least 421, such as at least 422, such as at least 423, such as at least 424, such as at least 425, such as at least 426, such as at least 427, such as at least 428, such as at least 429, such as at least 430, such as at least 431, such as at least 432, such as at least 433, such as at least 434, such as at least 435, such as at least 436, such as at least 437, such as at least 438, such as at least 439, such as at least 440, such as at least 441, such as at least 442, such as at least 443, such as at least 444, such as at least 445, such as at least 446, such as at least 447, such as at least 448, such as at least 449, such as at least 450, such as at least 451, such as at least 452, such as at least 453, such as at least 454, such as at least 455, such as at least 456, such as at least 457, such as at least 458, such as at least 459, such as at least 460, such as at least 461, such as at least 462, such as at least 463, such as at least 464, such as at least 465, such as at least 466, such as at least 467, such as at least 468, such as at least 469, such as at least 470, such as at least 471, such as at least 472, such as at least 473, such as at least 474, such as at least 475, such as at least 476, such as at least 477, such as at least 478, such as at least 479, such as at least 480, such as at least 481, such as at least 482, such as at least 483, such as at least 484, such as at least 485, such as at least 486, such as at least 487, such as at least 488, such as at least 489, such as at least 490, such as at least 491, such as at least 492, such as at least 493, such as at least 494, such as at least 495, such as at least 496, such as at least 497, such as at least 498, such as at least 499, such as at least 500, such as at least 501, such as at least 502, such as at least 503, such as at least 504, such as at least 505, such as at least 506, such as at least 507, such as at least 508, such as at least 509, such as at least 510, such as at least 511, such as at least 512, such as at least 513, such as at least 514, such as at least 515, such as at least 516, such as at least 517, such as at least 518, such as at least 519, such as at least 520, such as at least 521, such as at least 522, such as at least 523, such as at least 524, such as at least 525, such as at least 526, such as at least 527, such as at least 528, such as at least 529, such as at least 530, such as at least 531, such as at least 532, such as at least 533, such as at least 534, such as at least 535, such as at least 536, such as at least 537, such as at least 538, such as at least 539, such as at least 540, such as at least 541, such as at least 542, such as at least 543, such as at least 544, such as at least 545, such as at least 546, such as at least 547, such as at least 548, such as at least 549, such as at least 550, such as at least 551, such as at least 552, such as at least 553, such as at least 554, such as at least 555, such as at least 556, such as at least 557, such as at least 558, such as at least 559, such as at least 560, such as at least 561, such as at least 562, such as at least 563, such as at least 564, such as at least 565, such as at least 566, such as at least 567, such as at least 568, such as at least 569, such as at least 570, such as at least 571, such as at least 572, such as at least 573, such as at least 574, such as at least 575, such as at least 576, such as at least 577, such as at least 578, such as at least 579, such as at least 580, such as at least 581, such as at least 582, such as at least 583, such as at least 584, such as at least 585, such as at least 586, such as at least 587, such as at least 588, such as at least 589, such as at least 590, such as at least 591 contiguous nucleotides.

In some embodiments the functional fragment of at least 20 contiguous nucleotides according to the invention is not more than 999 contiguous nucleotides, such as not more than 998, such as not more than 997, such as not more than 996, such as not more than 995, such as not more than 994, such as not more than 993, such as not more than 992, such as not more than 991, such as not more than 990, such as not more than 989, such as not more than 988, such as not more than 987, such as not more than 986, such as not more than 985, such as not more than 984, such as not more than 983, such as not more than 982, such as not more than 981, such as not more than 980, such as not more than 979, such as not more than 978, such as not more than 977, such as not more than 976, such as not more than 975, such as not more than 974, such as not more than 973, such as not more than 972, such as not more than 971, such as not more than 970, such as not more than 969, such as not more than 968, such as not more than 967, such as not more than 966, such as not more than 965, such as not more than 964, such as not more than 963, such as not more than 962, such as not more than 961, such as not more than 960, such as not more than 959, such as not more than 958, such as not more than 957, such as not more than 956, such as not more than 955, such as not more than 954, such as not more than 953, such as not more than 952, such as not more than 951, such as not more than 950, such as not more than 949, such as not more than 948, such as not more than 947, such as not more than 946, such as not more than 945, such as not more than 944, such as not more than 943, such as not more than 942, such as not more than 941, such as not more than 940, such as not more than 939, such as not more than 938, such as not more than 937, such as not more than 936, such as not more than 935, such as not more than 934, such as not more than 933, such as not more than 932, such as not more than 931, such as not more than 930, such as not more than 929, such as not more than 928, such as not more than 927, such as not more than 926, such as not more than 925, such as not more than 924, such as not more than 923, such as not more than 922, such as not more than 921, such as not more than 920, such as not more than 919, such as not more than 918, such as not more than 917, such as not more than 916, such as not more than 915, such as not more than 914, such as not more than 913, such as not more than 912, such as not more than 911, such as not more than 910, such as not more than 909, such as not more than 908, such as not more than 907, such as not more than 906, such as not more than 905, such as not more than 904, such as not more than 903, such as not more than 902, such as not more than 901, such as not more than 900, such as not more than 899, such as not more than 898, such as not more than 897, such as not more than 896, such as not more than 895, such as not more than 894, such as not more than 893, such as not more than 892, such as not more than 891, such as not more than 890, such as not more than 889, such as not more than 888, such as not more than 887, such as not more than 886, such as not more than 885, such as not more than 884, such as not more than 883, such as not more than 882, such as not more than 881, such as not more than 880, such as not more than 879, such as not more than 878, such as not more than 877, such as not more than 876, such as not more than 875, such as not more than 874, such as not more than 873, such as not more than 872, such as not more than 871, such as not more than 870, such as not more than 869, such as not more than 868, such as not more than 867, such as not more than 866, such as not more than 865, such as not more than 864, such as not more than 863, such as not more than 862, such as not more than 861, such as not more than 860, such as not more than 859, such as not more than 858, such as not more than 857, such as not more than 856, such as not more than 855, such as not more than 854, such as not more than 853, such as not more than 852, such as not more than 851, such as not more than 850, such as not more than 849, such as not more than 848, such as not more than 847, such as not more than 846, such as not more than 845, such as not more than 844, such as not more than 843, such as not more than 842, such as not more than 841, such as not more than 840, such as not more than 839, such as not more than 838, such as not more than 837, such as not more than 836, such as not more than 835, such as not more than 834, such as not more than 833, such as not more than 832, such as not more than 831, such as not more than 830, such as not more than 829, such as not more than 828, such as not more than 827, such as not more than 826, such as not more than 825, such as not more than 824, such as not more than 823, such as not more than 822, such as not more than 821, such as not more than 820, such as not more than 819, such as not more than 818, such as not more than 817, such as not more than 816, such as not more than 815, such as not more than 814, such as not more than 813, such as not more than 812, such as not more than 811, such as not more than 810, such as not more than 809, such as not more than 808, such as not more than 807, such as not more than 806, such as not more than 805, such as not more than 804, such as not more than 803, such as not more than 802, such as not more than 801, such as not more than 800, such as not more than 799, such as not more than 798, such as not more than 797, such as not more than 796, such as not more than 795, such as not more than 794, such as not more than 793, such as not more than 792, such as not more than 791, such as not more than 790, such as not more than 789, such as not more than 788, such as not more than 787, such as not more than 786, such as not more than 785, such as not more than 784, such as not more than 783, such as not more than 782, such as not more than 781, such as not more than 780, such as not more than 779, such as not more than 778, such as not more than 777, such as not more than 776, such as not more than 775, such as not more than 774, such as not more than 773, such as not more than 772, such as not more than 771, such as not more than 770, such as not more than 769, such as not more than 768, such as not more than 767, such as not more than 766, such as not more than 765, such as not more than 764, such as not more than 763, such as not more than 762, such as not more than 761, such as not more than 760, such as not more than 759, such as not more than 758, such as not more than 757, such as not more than 756, such as not more than 755, such as not more than 754, such as not more than 753, such as not more than 752, such as not more than 751, such as not more than 750, such as not more than 749, such as not more than 748, such as not more than 747, such as not more than 746, such as not more than 745, such as not more than 744, such as not more than 743, such as not more than 742, such as not more than 741, such as not more than 740, such as not more than 739, such as not more than 738, such as not more than 737, such as not more than 736, such as not more than 735, such as not more than 734, such as not more than 733, such as not more than 732, such as not more than 731, such as not more than 730, such as not more than 729, such as not more than 728, such as not more than 727, such as not more than 726, such as not more than 725, such as not more than 724, such as not more than 723, such as not more than 722, such as not more than 721, such as not more than 720, such as not more than 719, such as not more than 718, such as not more than 717, such as not more than 716, such as not more than 715, such as not more than 714, such as not more than 713, such as not more than 712, such as not more than 711, such as not more than 710, such as not more than 709, such as not more than 708, such as not more than 707, such as not more than 706, such as not more than 705, such as not more than 704, such as not more than 703, such as not more than 702, such as not more than 701, such as not more than 700, such as not more than 699, such as not more than 698, such as not more than 697, such as not more than 696, such as not more than 695, such as not more than 694, such as not more than 693, such as not more than 692, such as not more than 691, such as not more than 690, such as not more than 689, such as not more than 688, such as not more than 687, such as not more than 686, such as not more than 685, such as not more than 684, such as not more than 683, such as not more than 682, such as not more than 681, such as not more than 680, such as not more than 679, such as not more than 678, such as not more than 677, such as not more than 676, such as not more than 675, such as not more than 674, such as not more than 673, such as not more than 672, such as not more than 671, such as not more than 670, such as not more than 669, such as not more than 668, such as not more than 667, such as not more than 666, such as not more than 665, such as not more than 664, such as not more than 663, such as not more than 662, such as not more than 661, such as not more than 660, such as not more than 659, such as not more than 658, such as not more than 657, such as not more than 656, such as not more than 655, such as not more than 654, such as not more than 653, such as not more than 652, such as not more than 651, such as not more than 650, such as not more than 649, such as not more than 648, such as not more than 647, such as not more than 646, such as not more than 645, such as not more than 644, such as not more than 643, such as not more than 642, such as not more than 641, such as not more than 640, such as not more than 639, such as not more than 638, such as not more than 637, such as not more than 636, such as not more than 635, such as not more than 634, such as not more than 633, such as not more than 632, such as not more than 631, such as not more than 630, such as not more than 629, such as not more than 628, such as not more than 627, such as not more than 626, such as not more than 625, such as not more than 624, such as not more than 623, such as not more than 622, such as not more than 621, such as not more than 620, such as not more than 619, such as not more than 618, such as not more than 617, such as not more than 616, such as not more than 615, such as not more than 614, such as not more than 613, such as not more than 612, such as not more than 611, such as not more than 610, such as not more than 609, such as not more than 608, such as not more than 607, such as not more than 606, such as not more than 605, such as not more than 604, such as not more than 603, such as not more than 602, such as not more than 601, such as not more than 600, such as not more than 599, such as not more than 598, such as not more than 597, such as not more than 596, such as not more than 595, such as not more than 594, such as not more than 593, such as not more than 592, such as not more than 591, such as not more than 590, such as not more than 589, such as not more than 588, such as not more than 587, such as not more than 586, such as not more than 585, such as not more than 584, such as not more than 583, such as not more than 582, such as not more than 581, such as not more than 580, such as not more than 579, such as not more than 578, such as not more than 577, such as not more than 576, such as not more than 575, such as not more than 574, such as not more than 573, such as not more than 572, such as not more than 571, such as not more than 570, such as not more than 569, such as not more than 568, such as not more than 567, such as not more than 566, such as not more than 565, such as not more than 564, such as not more than 563, such as not more than 562, such as not more than 561, such as not more than 560, such as not more than 559, such as not more than 558, such as not more than 557, such as not more than 556, such as not more than 555, such as not more than 554, such as not more than 553, such as not more than 552, such as not more than 551, such as not more than 550, such as not more than 549, such as not more than 548, such as not more than 547, such as not more than 546, such as not more than 545, such as not more than 544, such as not more than 543, such as not more than 542, such as not more than 541, such as not more than 540, such as not more than 539, such as not more than 538, such as not more than 537, such as not more than 536, such as not more than 535, such as not more than 534, such as not more than 533, such as not more than 532, such as not more than 531, such as not more than 530, such as not more than 529, such as not more than 528, such as not more than 527, such as not more than 526, such as not more than 525, such as not more than 524, such as not more than 523, such as not more than 522, such as not more than 521, such as not more than 520, such as not more than 519, such as not more than 518, such as not more than 517, such as not more than 516, such as not more than 515, such as not more than 514, such as not more than 513, such as not more than 512, such as not more than 511, such as not more than 510, such as not more than 509, such as not more than 508, such as not more than 507, such as not more than 506, such as not more than 505, such as not more than 504, such as not more than 503, such as not more than 502, such as not more than 501, such as not more than 500, such as not more than 499, such as not more than 498, such as not more than 497, such as not more than 496, such as not more than 495, such as not more than 494, such as not more than 493, such as not more than 492, such as not more than 491, such as not more than 490, such as not more than 489, such as not more than 488, such as not more than 487, such as not more than 486, such as not more than 485, such as not more than 484, such as not more than 483, such as not more than 482, such as not more than 481, such as not more than 480, such as not more than 479, such as not more than 478, such as not more than 477, such as not more than 476, such as not more than 475, such as not more than 474, such as not more than 473, such as not more than 472, such as not more than 471, such as not more than 470, such as not more than 469, such as not more than 468, such as not more than 467, such as not more than 466, such as not more than 465, such as not more than 464, such as not more than 463, such as not more than 462, such as not more than 461, such as not more than 460, such as not more than 459, such as not more than 458, such as not more than 457, such as not more than 456, such as not more than 455, such as not more than 454, such as not more than 453, such as not more than 452, such as not more than 451, such as not more than 450, such as not more than 449, such as not more than 448, such as not more than 447, such as not more than 446, such as not more than 445, such as not more than 444, such as not more than 443, such as not more than 442, such as not more than 441, such as not more than 440, such as not more than 439, such as not more than 438, such as not more than 437, such as not more than 436, such as not more than 435, such as not more than 434, such as not more than 433, such as not more than 432, such as not more than 431, such as not more than 430, such as not more than 429, such as not more than 428, such as not more than 427, such as not more than 426, such as not more than 425, such as not more than 424, such as not more than 423, such as not more than 422, such as not more than 421, such as not more than 420, such as not more than 419, such as not more than 418, such as not more than 417, such as not more than 416, such as not more than 415, such as not more than 414, such as not more than 413, such as not more than 412, such as not more than 411, such as not more than 410, such as not more than 409, such as not more than 408, such as not more than 407, such as not more than 406, such as not more than 405, such as not more than 404, such as not more than 403, such as not more than 402, such as not more than 401, such as not more than 400, such as not more than 399, such as not more than 398, such as not more than 397, such as not more than 396, such as not more than 395, such as not more than 394, such as not more than 393, such as not more than 392, such as not more than 391, such as not more than 390, such as not more than 389, such as not more than 388, such as not more than 387, such as not more than 386, such as not more than 385, such as not more than 384, such as not more than 383, such as not more than 382, such as not more than 381, such as not more than 380, such as not more than 379, such as not more than 378, such as not more than 377, such as not more than 376, such as not more than 375, such as not more than 374, such as not more than 373, such as not more than 372, such as not more than 371, such as not more than 370, such as not more than 369, such as not more than 368, such as not more than 367, such as not more than 366, such as not more than 365, such as not more than 364, such as not more than 363, such as not more than 362, such as not more than 361, such as not more than 360, such as not more than 359, such as not more than 358, such as not more than 357, such as not more than 356, such as not more than 355, such as not more than 354, such as not more than 353, such as not more than 352, such as not more than 351, such as not more than 350, such as not more than 349, such as not more than 348, such as not more than 347, such as not more than 346, such as not more than 345, such as not more than 344, such as not more than 343, such as not more than 342, such as not more than 341, such as not more than 340, such as not more than 339, such as not more than 338, such as not more than 337, such as not more than 336, such as not more than 335, such as not more than 334, such as not more than 333, such as not more than 332, such as not more than 331, such as not more than 330, such as not more than 329, such as not more than 328, such as not more than 327, such as not more than 326, such as not more than 325, such as not more than 324, such as not more than 323, such as not more than 322, such as not more than 321, such as not more than 320, such as not more than 319, such as not more than 318, such as not more than 317, such as not more than 316, such as not more than 315, such as not more than 314, such as not more than 313, such as not more than 312, such as not more than 311, such as not more than 310, such as not more than 309, such as not more than 308, such as not more than 307, such as not more than 306, such as not more than 305, such as not more than 304, such as not more than 303, such as not more than 302, such as not more than 301, such as not more than 300, such as not more than 299, such as not more than 298, such as not more than 297, such as not more than 296, such as not more than 295, such as not more than 294, such as not more than 293, such as not more than 292, such as not more than 291, such as not more than 290, such as not more than 289, such as not more than 288, such as not more than 287, such as not more than 286, such as not more than 285, such as not more than 284, such as not more than 283, such as not more than 282, such as not more than 281, such as not more than 280, such as not more than 279, such as not more than 278, such as not more than 277, such as not more than 276, such as not more than 275, such as not more than 274, such as not more than 273, such as not more than 272, such as not more than 271, such as not more than 270, such as not more than 269, such as not more than 268, such as not more than 267, such as not more than 266, such as not more than 265, such as not more than 264, such as not more than 263, such as not more than 262, such as not more than 261, such as not more than 260, such as not more than 259, such as not more than 258, such as not more than 257, such as not more than 256, such as not more than 255, such as not more than 254, such as not more than 253, such as not more than 252, such as not more than 251, such as not more than 250, such as not more than 249, such as not more than 248, such as not more than 247, such as not more than 246, such as not more than 245, such as not more than 244, such as not more than 243, such as not more than 242, such as not more than 241, such as not more than 240, such as not more than 239, such as not more than 238, such as not more than 237, such as not more than 236, such as not more than 235, such as not more than 234, such as not more than 233, such as not more than 232, such as not more than 231, such as not more than 230, such as not more than 229, such as not more than 228, such as not more than 227, such as not more than 226, such as not more than 225, such as not more than 224, such as not more than 223, such as not more than 222, such as not more than 221, such as not more than 220, such as not more than 219, such as not more than 218, such as not more than 217, such as not more than 216, such as not more than 215, such as not more than 214, such as not more than 213, such as not more than 212, such as not more than 211, such as not more than 210, such as not more than 209, such as not more than 208, such as not more than 207, such as not more than 206, such as not more than 205, such as not more than 204, such as not more than 203, such as not more than 202, such as not more than 201, such as not more than 200, such as not more than 199, such as not more than 198, such as not more than 197, such as not more than 196, such as not more than 195, such as not more than 194, such as not more than 193, such as not more than 192, such as not more than 191, such as not more than 190, such as not more than 189, such as not more than 188, such as not more than 187, such as not more than 186, such as not more than 185, such as not more than 184, such as not more than 183, such as not more than 182, such as not more than 181, such as not more than 180, such as not more than 179, such as not more than 178, such as not more than 177, such as not more than 176, such as not more than 175, such as not more than 174, such as not more than 173, such as not more than 172, such as not more than 171, such as not more than 170, such as not more than 169, such as not more than 168, such as not more than 167, such as not more than 166, such as not more than 165, such as not more than 164, such as not more than 163, such as not more than 162, such as not more than 161, such as not more than 160, such as not more than 159, such as not more than 158, such as not more than 157, such as not more than 156, such as not more than 155, such as not more than 154, such as not more than 153, such as not more than 152, such as not more than 151, such as not more than 150, such as not more than 149, such as not more than 148, such as not more than 147, such as not more than 146, such as not more than 145, such as not more than 144, such as not more than 143, such as not more than 142, such as not more than 141, such as not more than 140, such as not more than 139, such as not more than 138, such as not more than 137, such as not more than 136, such as not more than 135, such as not more than 134, such as not more than 133, such as not more than 132, such as not more than 131, such as not more than 130, such as not more than 129, such as not more than 128, such as not more than 127, such as not more than 126, such as not more than 125, such as not more than 124, such as not more than 123, such as not more than 122, such as not more than 121, such as not more than 120, such as not more than 119, such as not more than 118, such as not more than 117, such as not more than 116, such as not more than 115, such as not more than 114, such as not more than 113, such as not more than 112, such as not more than 111, such as not more than 110, such as not more than 109, such as not more than 108, such as not more than 107, such as not more than 106, such as not more than 105, such as not more than 104, such as not more than 103, such as not more than 102, such as not more than 101, such as not more than 100, such as not more than 99, such as not more than 98, such as not more than 97, such as not more than 96, such as not more than 95, such as not more than 94, such as not more than 93, such as not more than 92, such as not more than 91, such as not more than 90, such as not more than 89, such as not more than 88, such as not more than 87, such as not more than 86, such as not more than 85, such as not more than 84, such as not more than 83, such as not more than 82, such as not more than 81, such as not more than 80, such as not more than 79, such as not more than 78, such as not more than 77, such as not more than 76, such as not more than 75, such as not more than 74, such as not more than 73, such as not more than 72, such as not more than 71, such as not more than 70, such as not more than 69, such as not more than 68, such as not more than 67, such as not more than 66, such as not more than 65, such as not more than 64, such as not more than 63, such as not more than 62, such as not more than 61, such as not more than 60, such as not more than 59, such as not more than 58, such as not more than 57, such as not more than 56, such as not more than 55, such as not more than 54, such as not more than 53, such as not more than 52, such as not more than 51, such as not more than 50, such as not more than 49, such as not more than 48, such as not more than 47, such as not more than 46, such as not more than 45, such as not more than 44, such as not more than 43, such as not more than 42, such as not more than 41, such as not more than 40, such as not more than 39, such as not more than 38, such as not more than 37, such as not more than 36, such as not more than 35, such as not more than 34, such as not more than 33, such as not more than 32, such as not more than 31, such as not more than 30, such as not more than 29, such as not more than 28, such as not more than 27, such as not more than 26, such as not more than 25 contiguous nucleotides.

In some embodiments the promoter DNA polynucleotide according to the invention exhibits an increased protein expression level as compared to the protein expression level of any one of the promoter DNA polynucleotides having the sequence of SEQ ID NO:1 or SEQ ID NO:4.

In some embodiments the increase in protein expression level is from about 50 percent to about 300 percent relative to the protein expression level of any one of the promoter DNA polynucleotides having the sequence of SEQ ID NO:1 or SEQ ID NO:4, or to the pOPIE2 promoter. In some embodiments the increase in protein expression level is more than 300 percent relative to the protein expression level of any one of the promoter DNA polynucleotides having the sequence of SEQ ID NO:1 or SEQ ID NO:4, or to the pOPIE2 promoter.

In some embodiments the increase in protein expression level is 2 fold to 10 fold relative to the protein expression level of any one of the promoter DNA polynucleotides having the sequence of SEQ ID NO:1 or SEQ ID NO:4, or to the pOPIE2 promoter.

In some embodiments the increase in protein expression level is 10 fold to 100, such as 20 to 80, such as 20 to 40 fold, relative to the protein expression level of any one of the promoter DNA polynucleotides having the sequence of SEQ ID NO:1 or SEQ ID NO:4, or to the pOPIE2 promoter.

It is to be understood that the increase in activity is measured and compared to the reference under same and standard conditions.

In some embodiments the isolated DNA polynucleotide according to the invention further comprises a selection marker, such as a selection marker selected from the group consisting of a Zeocin selection marker, a Neomycin selection marker, a Hygromycin selection marker, a Puromycin selection marker, and a Blasticidin selection marker.

In some embodiments the isolated DNA polynucleotide according to the invention further comprises a bacterial promoter, such as the pKANR bacterial promoter, such as a functional fragment of Kanamycin promoter.

In some embodiments the isolated DNA polynucleotide according to the invention further comprises a second promoter DNA polynucleotide suitable to drive the expression of the selection marker in an insect cell. In some embodiments this second promoter is selected from the group consisting of
 (i) a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, or SEQ ID NO:37;
 (ii) a nucleotide sequence with a sequence identity of at least 80% to any one sequence of (i) and having promoter activity in a *Drosophila* S2 cell;
 (iii) a nucleotide which is a functional fragment of at least 6 contiguous nucleotides of any one sequence of (i) or (ii), said functional fragment having promoter activity in a *Drosophila* S2 cell;
 (iv) a nucleotide sequence with a sequence identity of at least 80% to said functional fragment of (iii) and having promoter activity in a *Drosophila* S2 cell;

(v) a first chimeric nucleotide sequence comprising two or more sequences of any one sequence of (i), (ii), (iii) and (iv), and (vi) a second chimeric nucleotide sequence having promoter activity in a *Drosophila* S2 cell, comprising at least 6 nucleotides and including consecutive nucleotide stretches from at least 2 nucleotide sequences of (iii) and/or (iv), where each of said consecutive stretches alone does not have promoter activity in a *Drosophila* S2 cell.

In some embodiments the isolated DNA polynucleotide according to the invention further comprises one or more ubiquitous chromatin opening element upstream and/or downstream relative to the a multiple cloning site.

In some embodiments the isolated DNA polynucleotide according to the invention further comprises at least one Transcriptional insulator element, such as Su(Hw) or Gypsy (GSu(Hw)) insulator sequence. (Mol Cell Biol. 1997 April; 17(4): 2202-2206.)

In some embodiments the isolated DNA polynucleotide according to the invention further comprises a dihydrofolate reductase (dhfr) coding sequence suitable for selection in insect cells.

In some embodiments the isolated DNA polynucleotide according to the invention further comprises at least one polyadenylation signal sequence such as SV40 polyA signal and/or an OPIE2 polyA signal.

In some embodiments the isolated DNA polynucleotide according to the invention further comprises an *E. coli* origin.

In some embodiments the isolated DNA polynucleotide according to the invention further comprises at least one protein export signal polynucleotide sequence, such as one selected from the list consisting of BIP and CPY.

In some embodiments the isolated DNA polynucleotide according to the invention is essentially free of viral DNA.

In some embodiments the isolated DNA polynucleotide according to the invention further comprises at least one HIS-tag sequence. In some embodiments the HIS-tag is an N-terminal HIS-tag. In some embodiments the HIS-tag sequence is according to the following sequence: atgaaacaccaacaccaacatcaacatcaacatcaacatcaa (SEQ ID NO: 38)

In some embodiments the isolated DNA polynucleotide according to the invention further comprises a multiple cloning site downstream of the promoter DNA polynucleotide for insertion of the gene encoding a polypeptide of interest into the isolated DNA polynucleotide.

In some embodiments the isolated DNA polynucleotide according to the invention further comprises at least one 72 bp elements from SV40. In some embodiments the isolated DNA polynucleotide according to the invention further comprises two 72 bp elements from SV40. In some embodiments the isolated DNA polynucleotide according to the invention further comprises at least one 72 bp elements from SV40 upstream of the promoter and at least one 72 bp elements from SV40 downstream of the promoter.

In some embodiments the isolated DNA polynucleotide according to the invention further comprises at least one PRE element from Hepatitis B virus. In some embodiments the PRE element from Hepatitis B virus is according to SEQ ID NO:40, such as nucleotides 10 to 574 of SEQ ID NO:40.

In some embodiments the isolated DNA polynucleotide according to the invention further comprises at least one amplification control element.

In some embodiments the isolated DNA polynucleotide according to the invention further comprises at least one Ori-beta element.

In some embodiments the isolated DNA polynucleotide according to the invention further comprises at least one matrix attachment region (MAR) element.

In some embodiments the promoter DNA polynucleotide sequence according to the invention controls the expression of a gene or other DNA sequence to which it is linked.

In some embodiments the isolated DNA polynucleotide according to the invention further comprises at least one polynucleotide sequence encoding a polypeptide heterologous to the promoter DNA polynucleotide sequence.

In some embodiments the isolated DNA polynucleotide according to the invention further comprises at least one nucleotide sequence which is a functional fragment of at least three contiguous nucleotides of any one sequence of a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37, or SEQ ID NO: 68; and a functional nucleotide sequence with a sequence identity of at least 80% thereof, said functional fragment having promoter enhancer activity in a *Drosophila* S2 cell.

In some embodiments the isolated DNA polynucleotide according to the invention is a cloning vector.

In some embodiments the isolated DNA polynucleotide according to the invention is an expression vector.

One aspect relates to a cell comprising the isolated DNA polynucleotide according to the invention. In some embodiments the cell is an insect cell. In some embodiments the cell is a *Drosophila melanogaster* cell. In some embodiments the cell is a *Drosophila melanogaster* S2 cell.

In some embodiments the cell comprising the isolated DNA polynucleotide according to the invention is stably transfected with said isolated DNA polynucleotide.

As used herein "stably transfected" refers to a cell that has been transfected with a DNA polynucleotide according to the invention to produce permanent lines of cultured cells with a new gene inserted into their genome. Usually this is done by linking the desired gene with a "selectable" gene, i.e. a gene which confers resistance to a antibiotic (like Zeocin). Upon putting the antibiotic into the culture medium, only those cells which incorporate the resistance gene will survive, and essentially all of those will also have incorporated the DNA polynucleotide according to the invention.

A "cloning vector" means a plasmid DNA which can be used to insert a DNA fragment of interest into a host cell, normally in order to produce multiple copies of the fragment and hence the vector.

"Expression vector" means a plasmid or viral DNA containing necessary regulatory signals for the synthesis of mRNA derived from gene sequences, which can be inserted into the vector. The gene sequences being e.g. a chimeric polynucleotide as defined above.

A "polyadenylation sequence" as used herein refers to a DNA sequence which when transcribed is recognized by the expression host to add polyadenosine residues to transcribed mRNA. It is operably linked to the 3'-end of the DNA encoding the polypeptide to be expressed. Suitable polyadenylation sequences includes the OPIE2 polyA tail and the late SV40 polyA tail as described in Angelichio et al. 1991, *Comparison of several promoters and polyadenylation signals for use in heterologous gene expression in cultured Drosophila cells*, Nucleic Acids Research, Vol. 19, No. 18 5037-5043.

A "selectable marker" as used herein refers to a genetic element present in an expression vector, which, when expressed, provides an indication of successful transformation of the host cell. For instance, the selectable marker may provide the transformed host cell with resistance to an antibiotic (a dominant type marker) one or with the ability to metabolise a particular nutrient (an auxotrophic type of selectable marker, i.e. a marker that "cures" a deficiency in the host). Typically, the selectable marker is under the control of a promoter that is separate from the promoter that controls expression of the gene to be expressed by the vector.

The term "operably linked" refers to the association of nucleic acid sequences on a single nucleic acid fragment so that the function of one is affected by the other. For example, a promoter is operably linked to a coding sequence when it is capable of affecting the expression of that coding sequence (i.e., that the coding sequence is under the transcriptional control of the promoter).

The term "expression", as used herein, refers to complete biological process in a host cell that sets out from the transcription and stable accumulation of mRNA derived from the isolated DNA polynucleotide of the invention (where this further comprises a polynucleotide sequence encoding a polypeptide) through subsequent translation of mRNA into a polypeptide product and finally to post-translational modifications of the polypeptide product effected by the host cell. "Overexpression" refers to the production of a gene product in transformed cells that exceeds levels of production in normal, non-transformed cells.

As used herein a "protein export signal polynucleotide sequence" refers to a sequence that directs or facilitates the translocation of an expressed protein across the membrane of the host expression cell. A "protein export signal polynucleotide sequence" may be present in the N-terminus of a precursor polypeptide (a pre-peptide or pre-pro-peptide) to directs its translocation across a membrane. Typically, a precursor polypeptide is processed by cleavage of the signal sequence to generate a mature peptide or a pro-peptide. If the product of off-cleavage of the signal peptide is a pro-peptide, the mature peptide is the product of subsequent post-translational modifications that involve further removal of amino acids.

Other suitable "protein export signal polynucleotide sequence" within this definition includes the *Drosophila* BiP signal sequence for secretion and CPY.

The *Drosophila* BiP protein encodes an immunoglobulin-binding chaperone protein. This secretion signal efficiently targets high levels of BiP into the secretory pathway of S2 cells (see Kirkpatrick, R. B. et al. (1995) *J. Biol. Chem.* 270: 19800-19805).

The terms "ubiquitous chromatin opening element" or "UCOE" as used herein refers to a DNA sequence which opens chromatin or maintains chromatin in an open state and facilitates reproducible expression of an operably-linked gene in cells.

The terms "matrix attachment region" or "MAR" or "Scaffold/matrix attachment region" as used herein refers to a nucleotide sequence in the DNA of eukaryotic chromosomes where the nuclear matrix attaches. MARs mediate structural organization of the chromatin within the nucleus. These elements constitute anchor points of the DNA for the chromatin scaffold and serve to organize the chromatin into structural domains. Studies on individual genes led to the conclusion that the dynamic and complex organization of the chromatin mediated by S/MAR elements plays an important role in the regulation of gene expression.

The terms "amplification control element" or "Ace" as used herein refers to an element, which is involved in initiating amplification of DNA from the replication origin. Deletion analyses of transgenic constructs derived from the third chromosome cluster have identified a 320-bp amplification control element (ACE3) required for amplification. Thus within this definition is included the *D. melanogaster* ACE3 element. Included within this definition is also amplification enhancing regions (AERs).

The terms "Ori-beta element" or "oriB" as used herein refers to an origin of replication. The origin of replication (also called the replication origin) is a particular sequence in a genome or plasmid at which replication is initiated. This can either be DNA replication in living organisms such as prokaryotes and eukaryotes, or RNA replication in RNA viruses, such as double-stranded RNA viruses. DNA replication may proceed from this point bidirectionally or unidirectionally. The origin of replication binds the pre-replication complex, a protein complex that recognizes, unwinds, and begins to copy DNA. One specific "Ori-beta element" within this definition is the *D. melanogaster* Ori-beta element.

For sequence requirements for functional ACE3 and ori-B elements see Hongjun Zhang and John Tower, 2004, *Sequence requirements for function of the Drosophila chorion gene locus ACE3 replicator and ori-b origin elements*, Development 131, 2089-2099, 2004 and Carminati et al. 1992, *The Drosophila ACE3 Chorion Element Autonomously Induces Amplification*, MOLECULAR AND CELLULAR BIOLOGY, May 1992, p. 2444-2453.

Effect of SV40 72 bp Element on DNA Vaccines

Nuclear import in non-dividing cells such as muscle cells is one of the problems for non-viral gene delivery systems. This can result in lowered synthesis of the antigen that will subsequently result in poor antigen presentation. A 72 bp repeat of the SV40 enhancer region that enhances nuclear transport of nonviral DNA in non dividing cells has been identified. The enhancer region has several transcription factor binding sites. As soon as the plasmid enters the cytoplasm, it is bound by several transcription factors thus allowing the nonviral DNA to be rapidly transferred to the nucleus by providing the nuclear localization signal (Exp Cell Res. 1999, 253, 713). Enhancement in gene expression was also observed using the SV40 enhancer element containing vector injected in murine muscle by electroporation (Gene Ther., 2001, 8, 494).

The term "72 bp elements from SV40" as used herein refers to the 72 bp repeat of the SV40 enhancer region that enhances nuclear transport of nonviral DNA in non dividing cells. In particular embodiments the "72 bp elements from SV40" refers to an element with the following sequence ATGCTTTGCATACTTCTGCCTGCTGGG-GAGCCTGGGGACTTTCCACACCCTAACT-GACACACATTCCA CAGCTGGTT corresponding to nucleotide no. 10 to nucleotide no. 86 of SEQ ID NO:39 In particular embodiments the "72 bp elements from SV40" refers to an element with the sequence of SEQ ID NO:39.

PRE Element from Hepatitis B Virus (SEQ ID NO:40)

Some eukaryotic or viral mRNA contains inhibitory sequences preventing them from being transported out of nucleus to the cytoplasm where they can be translated. Hepatitis B virus S transcripts contain a region, known as the posttranscriptional regulatory element (PRE) that functions in cis to activate their transportation. This element can partially substitute for the human immunodeficiency virus Rev-response element (RRE). It has been shown that adding this element or elements with similar function in the 3' untranslated region of the gene encoding the antigen (such as HIV-1 Gag) can increase the expression level of the antigen and improve immune responses.

The term "insulator sequence", as used herein refers to DNA sequences that affect interactions between promoters and enhancers/silencers and function as barriers for spreading of repressive chromatin. Included within this definition is the (su(Hw)) insulator sequence as described in Lu L, Tower 3, 1997, A transcriptional insulator element, the su(Hw) binding site, protects a chromosomal DNA replication origin from position effects, Mol Cell Biol. April; 17(4): 2202-2206. Among the variety of sequences with an insulator function present in the *Drosophila melanogaster* genome, the well-studied and perhaps the strongest insulator consisting of reiterated binding sites for the Su(Hw) protein, first found in the gypsy retrotransposon may be used. The Su(Hw) insulator is a versatile modulator of regulatory interactions, blocking more than a score of different enhancers. Recently, an endogenous Su(Hw)-dependent but structurally distinct insulator has been found between the yellow and achaete genes.

The term "ligation independent cloning" or "LIC" is used herein according to the definition by Robert E. Navy, Keith W. Yaeger and Kristin M. Kolb in the article *"Efficient Directional Cloning of PCR Products"*, ligation independent cloning (LIC) can be described as follows: "Ligation independent cloning (LIC) was developed for the directional cloning of PCR products without restriction enzyme digestion or ligation reactions. LIC vectors are created by treating a linearized backbone with T4 DNA polymerase in the presence of only one dNTP. The 3' to 5' exonuclease activity of T4 DNA polymerase removes nucleotides until it encounters a residue corresponding to the single dNTP present in the reaction mix. At this point, the 5' to 3' polymerase activity of the enzyme counteracts the exonuclease activity to effectively prevent further excision. Plasmid sequences adjacent to the site of linearization are designed to produce specific noncomplementary 13- or 14-base single stranded overhangs in the LIC vector. PCR products with complementary overhangs are created by building appropriate 5' extensions into the primers. The PCR product is purified to remove dNTPs (and original plasmid if it was used as template) and then treated with T4 DNA polymerase in the presence of the appropriate dNTP to generate the specific vector-compatible overhangs. The annealed LIC vector and insert are transformed into competent *E. coli* cells. Covalent bond formation at the vector insert junctions occurs within the cell to yield circular plasmid."

A detailed description of LIC methodology can be found in Nick S. Berrow et al. 2007 *"A versatile ligation-independent cloning method suitable for high-throughput expression screening applications"*, Nucleic Acids Research.

A number of specific embodiments of LIC enabled vectors of the present invention are provided in SEQ ID NOs. 69-73.

In one specific embodiment the isolated DNA polynucleotide according to the invention consists of the following elements:
1. Insect selection marker, with an insect promoter driving expression, such as Truncated *D. melanogaster* Actin5C promoter or HSP70 promoter with a nucleotide sequence according to SEQ ID NO:5, SEQ ID NO:6, or SEQ ID NO:2;
2. bacterial promoter, such as the pKANR bacterial promoter;
3. Zeocin selection marker with SV40 polyA tail;
4. *E. coli* origin;
5. Hybrid *Drosophila melongaster* 612 bp Actin5C promoter with a nucleotide sequence according to SEQ ID NO:6, wherein parts or the whole of the actin core sequence (such as nucleotides 478 to 572 of SEQ ID NO:6) have been replaced with the HSP70 core promoter with a nucleotide sequence according to SEQ ID NO:1, SEQ ID NO:2, SEQ ID NO:37, or a fragment thereof to drive protein expression;
6. BIP protein export signal sequence;
7. Multiple cloning site; and
8. OPIE2 polyA tail.

In one specific embodiment the isolated DNA polynucleotide according to the invention consists of the following elements:
1. Insect selection marker, with an insect promoter driving expression, such as Truncated *D. melanogaster* Actin5C promoter or HSP70 promoter with a nucleotide sequence according to SEQ ID NO:5, SEQ ID NO:6, or SEQ ID NO:2;
2. bacterial promoter, such as the pKANR bacterial promoter;
3. Zeocin selection marker with SV40 polyA tail;
4. *E. coli* origin;
5. *Drosophila* melongaster 457 bp Actin5C promoter with a nucleotide sequence according to nucleotides 2076-2532 of SEQ ID NO:3;
6. BIP protein export signal sequence;
7. Multiple cloning site; and
8. OPIE2 polyA tail.

In one specific embodiment the isolated DNA polynucleotide according to the invention consists of the following elements:
1. Insect selection marker, with an insect promoter driving expression, such as Truncated *D. melanogaster* Actin5C promoter or HSP70 promoter with a nucleotide sequence according to SEQ ID NO:5, SEQ ID NO:6, or SEQ ID NO:2;
2. bacterial promoter, such as the pKANR bacterial promoter;
3. Zeocin selection marker with SV40 polyA tail;
4. *E. coli* origin;
5. Hybrid of *Drosophila melongaster* 457 bp Actin5C promoter with a nucleotide sequence according to nucleotides 2076-2532 of SEQ ID NO:3, wherein parts or the whole of the actin core sequence (such as nucleotides 2392 to 2487 of SEQ ID NO:3) have been replaced with the HSP70 core promoter with a nucleotide sequence according to SEQ ID NO:1, SEQ ID NO:2, SEQ ID NO:37, or a fragment thereof to drive protein expression;
6. BIP protein export signal sequence;
7. Multiple cloning site; and
8. OPIE2 polyA tail.

In one specific embodiment the isolated DNA polynucleotide according to the invention consists of the following elements:
1. Insect selection marker, with an insect promoter driving expression, such as Truncated *D. melanogaster* Actin5C promoter or HSP70 promoter with a nucleotide sequence according to SEQ ID NO:5, SEQ ID NO:6, or SEQ ID NO:2;
2. bacterial promoter, such as the pKANR bacterial promoter;
3. Zeocin selection marker with SV40 polyA tail;
4. *E. coli* origin;
5. HSP70 core promoter with a nucleotide sequence according to SEQ ID NO:1, SEQ ID NO:2, SEQ ID NO:37, or a fragment thereof to drive protein expression and one or more functional fragments of the Actin5C promoter (Actin5c regulatory elements) in cis relative to the HSP70 core promoter;
6. BIP protein export signal sequence;
7. Multiple cloning site; and
8. OPIE2 polyA tail.

In some specific embodiments the following elements will be exchanged in the isolated DNA polynucleotide according to the invention:

1. Su(Hw) elements may be placed in front and after the expression cassette (expression promoter, gene-of-interest and polyA tail); and/or
2. The Zeocin selection marker may be replaced in the expressing vectors by:
   a. Neomycin selection marker, or
   b. Blasticidin selection marker, or
   c. hygromycin selection marker, or,
   d. or puromycin selection marker; and
3. The expression construct will be made with and without the HIS-tag.

One suitable vector according to the invention may consist of:
1. Bacterial selection marker, with a bacterial promoter
   a. pKANR bacterial promoter
   b. Zeocin selection marker (ZeoR and/or KanR)
2. Insect selection marker, with an insect promoter driving expression
   a. Truncated *Drosophila melanogaster* Actin5C promoter or HSP70 promoter
   b. Zeocin selection marker with SV40 polyA tail
3. *E. coli* origin
4. Truncated *Drosophila melanogaster* Actin5C or HSP70 promoters to drive protein expression
5. BIP protein export signal sequence
6. HIS-tag
7. Multiple cloning site
8. OPIE2 polyA tail It is to be understood from the above that the individual elements may be placed in any given order. Accordingly the insect promoter and the bacterial promoter may be placed directly following each other. Also the same selection marker sequence may be used by both the bacterial promoter and by the insect cell promoter.

General Vector Improvements

The following elements may be added to the expression vector to increase expression level.
1. Ubiquitously chromatin opening elements up and downstream of the gene-of-interest expression cassette; and/or
2. Pre-element, and 72 bp element of SV40; and/or
3. MARs (matrix attachment regions); and/or
4. ACE3 and ori-Beta from *D. melanogaste*; and/or
5. Transcriptional insulator element, the su(Hw) binding site (Mol Cell Biol. 1997 April; 17(4): 2202-2206.); and/or
6. CPY element to replace BIP (if CPY found functional in S2); and/or
7. dhfr can be inserted for selection in insect cells; and/or
8. Separate kanamycin or ampicilin resistance cassette may be inserted for bacterial selection; and/or
9. Replace OPIE2 polyA tail with late SV40 polyA tail and/or
10. Introduce an intron downstream of the promotor for driving protein expression and/or
11. a ligation independent cloning cassette can be included.

In some embodiments a polynucleotide sequence according to the invention hybridizes under conditions of moderate stringency to a sequence selected from the group consisting of:
(i) a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, or SEQ ID NO:37, or SEQ ID NO: 58;
(ii) a nucleotide sequence with a sequence identity of at least 80% to any one sequence of (i);
(iii) a functional fragment of at least 6 contiguous nucleotides of any one sequence of (i) or (ii);
(iv) a nucleotide sequence with a sequence identity of at least 80% to the at least 6 nucleotide functional fragment of (iii);
(v) a chimeric nucleotide sequence comprising two or more sequences of any one sequence of (i), (ii), (iii) and (iv).

The term "moderate stringency" as used herein refers to conditions of polynucleotide hybridization in about 50% formamide, 6×SSC at about 42° C. and washing conditions of about 60° C., 0.5×SSC, 0.1% SDS.

Methods of the Invention for Protein Expression

Another aspect of the present invention relates to expression and recovery of polypeptides from host cells.

As detailed above, this aspect of the invention generally utilises the finding that promoter DNA polynucleotide comprising at least one sequence selected from the group consisting of:
(i) a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, or SEQ ID NO:37, or SEQ ID NO: 58;
(ii) a nucleotide sequence with a sequence identity of at least 80% to any one sequence of (i) and having promoter activity in a *Drosophila* S2 cell;
(iii) a nucleotide which is a functional fragment of at least 6 contiguous nucleotides of any one sequence of (i) or (ii), said functional fragment having promoter activity in a *Drosophila* S2 cell;
(iv) a nucleotide sequence with a sequence identity of at least 80% to said functional fragment of (iii) and having promoter activity in a *Drosophila* S2 cell;
(v) a first chimeric nucleotide sequence comprising two or more sequences of any one sequence of (i), (ii), (iii) and (iv), and
(vi) a second chimeric nucleotide sequence having promoter activity in a *Drosophila* S2 cell, comprising at least 6 nucleotides and including consecutive nucleotide stretches from at least 2 nucleotide sequences of (iii) and/or (iv), where each of said consecutive stretches alone does not have promoter activity in a *Drosophila* S2 cell; provides for improved yields when expressing secreted polypeptides.

The present inventor has recently demonstrated that this improved yield (over e.g. construct utilising the pOPIE2 promoter) is a consequence of improved expression levels as well as secretion. As mentioned above the method according to the invention comprises the steps of
(a) obtaining a polynucleotide sequence encoding the polypeptide of interest;
(b) inserting said polynucleotide sequence encoding the polypeptide of interest into the isolated DNA polynucleotide according to any one of claims 1-27;
(c) transforming a host cell with the polynucleotide obtained under step (b);
(d) allowing for the expression of said polynucleotide obtained under step (b) to produce the polypeptide; and
(e) obtaining the polypeptide there from.

Methods for transformation will vary according to the choice of host cell, but typically transfection by means of lithium acetate (Okazaki et al. Nucleic acid Res. 18: 6485-6489, 1990, incorporate by reference herein) or electroporation is used in yeast, whereas both transfection and transduction (i.e. transfer of genetic material by means of a viral vector) may be used in cells from multicellular organisms. Suitable methods for transfection in *Drosophila melano-* gaster S2 cells is described in Park J. H.; Kim H. Y.; Han K. H.; Chung I. S, *Optimization of transfection conditions for expression of green fluorescent protein in Drosophila melanogaster S2 cells—a highly efficient, lipid-mediated DNA-transfection procedure*. Enzyme and Microbial Technology, Volume 25, Number 7, October 1999, pp. 558-563(6)

More general teachings on transformation and culture of transformed cells (yeast or higher) can be found in Sambrook 3 et al., "Molecular Cloning: A laboratory Manual", 3rd edition.

The teachings provided above concerning choice of promoter, functional secretion signal peptides, choice of format of vectors, choice of host cells, use of selectable markers, and use of stabilizing elements, apply mutatis mutandis to the method of the invention. The only difference in these teachings and the teachings pertaining to the method of the invention is the precise composition of the coding sequence in the vector, since the method of the invention does not rely on the presence of a chimeric polynucleotide as defined herein. It is however, preferred that the expression vector used in the method of the invention is an expression vector of the invention.

It some embodiments, the method of the invention comprises the further step of subjecting the polypeptide obtained in step (c) to post-translational modification—this entails both post-translational modifications that are effected by the host cell (and subsequently made before recovery of the polypeptide) and modifications made in vitro after recovery of the polypeptide.

Step (a) of the method of the invention normally comprises the steps of introducing the vector into the host cell and subsequently selecting transformants that express a selectable marker gene present in the vector. Useful selectable marker genes have been detailed above.

The invention will be illustrated by means of the following non-limiting examples.

Example 1

Abbreviations

TABLE 1

| ATCC | The American Type Culture Collection |
| CEP | Cells, Experimental Protocol |
| DMSO | Dimethyl Sulfoxide |
| ELISA | Enzyme Linked Immuno Sorbent Assay |
| FBS | Foetal Bovine Serum |
| LAF | Laminar Air-Flow |
| PCR | Polymerase Chain Reaction |
| T25 | Tissue culture flask, 25 cm$^2$ |
| T75 | Tissue culture flask, 75 cm$^2$ |
| V | Volume |
| Wt | Wild type |
| Bp | Base pair |
| SOE-PCR | Spliced by Overlap Extension |
| ON | Over night |
| LB | Lauria Broth |
| DNA | Deoxyribonucleic |
| *E. coli* | *Escherichia coli* |

Materials and Methods
Cell Line

*Drosophila* S2 cells was derived from ATCC (CRL-1963, lot. no. 3225543)

A vial of *Drosophila* S2 cells from ATCC was resuscitated and expanded in tissue culture flasks. When the cell number exceeded 10$^8$ cells, a cell bank consisting of twenty vials containing 2×10$^7$ *Drosophila* S2 cells in 1 mL freeze medium (Excell420+50% FBS+10% DMSO) was established and stored at −80° C.

Plasmid Construction

TABLE 2

Raw Materials:

| Name | Purpose | Commercial source |
|---|---|---|
| NcoI | Restriction enzyme | New England Biolab |
| HindIII | Restriction enzyme | New England Biolab |
| XbaI | Restriction enzyme | New England Biolab |
| NotI | Restriction enzyme | New England Biolab |
| EcoRI | Restriction enzyme | New England Biolab |
| XmnI | Restriction enzyme | New England Biolab |
| SphI | Restriction enzyme | New England Biolab |
| NheI | Restriction enzyme | New England Biolab |
| SpeI | Restriction enzyme | New England Biolab |
| SAP | Shrimp Alkaline phosphatase | New England Biolab |
| T4 DNA Ligase | Ligase | New England Biolab |
| PfuUltra II polymerase | For PCR of construction fragments | Stratagene |
| Oligoes | For PCR amplification | DNA Technology |
| dNTP | For PCR | New England Biolab |
| BigDye Version 1 | Sequence kit | Applied Biosystem |
| SeaKem GTG argarose | Argarose gels for electrophoresis | New England Biolab |
| SyberSafe | Staining argarose gels | Invitrogen |
| Qiaquick gel extraction | Retrieving DNA fragments form gels | Qiagen |
| TE buffer | Storage buffer for DNA | Qiagen |
| TBE buffer | Electrophoresis buffer | Life Technologies |
| Charge Switch Plasmid Er Mini Kit | Plasmid purification | Invitrogen |
| Thermo cycler | PCR, ligation, sequencing | Biometra |
| ABI PRISM 310 | Sequence analyser | Applied Biosystem |
| Zeocin | Antibiotic | InVitrogen |
| DH10B | Host strain for plasmid amplification | LifeTechnologies |

TABLE 3

Commercially obtained vectors:

| Vector | Promoter | Antibiotic Resistance | Commercial source |
|---|---|---|---|
| p2Zop2F | pOPIE2 | Zeocin | RCT |
| pAc5.1/V5-HisA | pAc5.1 (Actin5C) | Ampicilin for *E. coli*, no marker for S2 | Invitrogen |
| pCoHygro | | Hygromycin | Invitrogen |
| pMT/V5.His | pMT | Ampicilin for *E. coli*, no marker for S2 | Invitrogen |

TABLE 4

Vectors created in this study

| Name | Strain no - host | Plasmid number | Length | Main feature |
|---|---|---|---|---|
| p2ZOp2F-NheI | MR#3070 | P2260 | 2779 | Commercial vector with pOPIE2 promoter and a NheI cut-site inserted |
| pHP10 | MR#3071 | P2261 | 2310 | Actin5C core promoter |
| pHP11 | MR#3072 | P2262 | 4742 | Full-length mutant Actin5C promoter |
| pHP12 | MR#3073 | P2263 | 2503 | Truncated Hsp70 promoter |
| pHP12-AflII | MR#3097 | P2287 | 2506 | Added cut-site to pHp12 |
| pHP13 | MR#3074 | P2264 | 2676 | Full-length genomic HSP70 promoter |

TABLE 4-continued

Vectors created in this study

| Name | Strain no - host | Plasmid number | Length | Main feature |
|---|---|---|---|---|
| pHP14 | MR#3075 | P2265 | 4509 | NA |
| pHP15a | MR#3080 | P2270 | 2040 | Exchange pOPIE2 and EM7 promoters infront of ZeoR for HSP70 and pTRC bacterial promoter |
| pHP15b | MR#3081 | P2271 | 2233 | Exchange pOPIE2 and EM7 promoters infront of ZeoR for Actin5C core and TRC bacterial promoter |
| pHP15c | MR#3082 | P2272 | 2073 | Exchange pOPIE2 and EM7 promoters infront of ZeoR for Actin5C core and KanR bacterial promoter |
| pHP16 | MR#3084 | P2274 | 2309 | HSP70 core promoter |
| pHP17 | MR#3086 | P2276 | 3687 | Truncated actin5c_2 promoter |
| pHP18 | MR#3087 | P2277 | 2830 | Truncated actin5c_3 promoter, 612 bp |
| pHP18-AflII | MR#3098 | P2288 | 2833 | Added cut-site to pHp18 |

(All vectors confer resistance to Zeocin)

For this study the model protein, RANK ligand (RANK-L, or RANKL) was used. This protein was inserted after the BIP-signal sequence, in the multiple cloning site, in each of the tested vectors.

pKanR sequence used according to the present examples:
AAGGGATTTTGGTCATGAA-
CAATAAAACTGTCTGCTTACATAAACAG-
TAATACAAGGGGTGTT CATAGTATAATACGACTCAC-
TATAGGAGGGCC (SEQ ID NO: 63, sequence in bold KanaR promoter, remaining sequence EM7 promoter).

Construction of the S2 vectors pZOp2F-NheI (p2260, strain MR#3070). The vector was created with NheI-site downstream SV40 by using QuikChange Site-Direct Mutagenesis Kit from Stratagene, for cloning vectors with different promoters The QuickChange was made with primers 975 and 976 using p1205 as template. The PCR product was treated with DpnI for one hour at 37° C. and transformed into DH10B cells, plated out on LB Agar plates containing 0.75 ug/ml Zeocin and incubatet ON.

The plasmid has been fully sequenced using primers 590 pHP11 (p2263, strain MR#3073) was constructed by one step PCR amplification. The PCR was made with primers 980 and 979 using p805 (pAc5.1/V5-HisA) as template. The resulting fragment was 2540 bp, containing Actin 5C promoter. The PCR fragment digested with restrictions endonucleases NheI and HindIII and clone into NheI and HindIII digested and SAP treated p2260. Ligated over night in a termo cycler. The ligation product was transformed into DH10B cells, plated out on LB Agar plates containing 0.75 ug/ml Zeocin and incubatet ON.

In the resulting plasmid the insert has been fully sequenced using primers 590, 981, 986 and 917.

pHP12-vector (p2263, strain MR#3073) was constructed by one step PCR amplification. The PCR was made with primers 981 and 982 using p2546 as template. The resulting fragment was 299 bp, containing Hsp70 promoter from Hsp70-pFast-Bac which was taken from genomic DNA from S2-cells.

The PCR fragment digested with restrictions endonucleases NheI and HindIII and clone into NheI and HindIII digested and SAP treated p2260. Ligated over night in a termo cycler. The ligation product was transformed into DH10B cells, plated out on LB Agar plates containing 0.75 ug/ml Zeocin and incubatet ON.

In the resulting plasmid the insert has been fully sequenced using primers 590, 981, 986 and 917.

pHP13 (p2264, strain MR#3074) was constructed by one step PCR amplification. The PCR was made with primers 983 and 984 using p2546 as template. The resulting fragment was 473 bp, containing full-length Hsp70 promoter from Hsp70-pFast-Bac which was taken from genomic DNA from S2-cells.

The PCR fragment digested with restrictions endonucleases NheI and HindIII and clone into NheI and HindIII digested and SAP treated p2260. Ligated over night in a termo cycler. The ligation product was transformed into DH10B cells, plated out on LB Agar plates containing 0.75 ug/ml Zeocin and incubatet ON.

In the resulting plasmid the insert has been fully sequenced using primers 590, 984 and 917.

Change of OpIE2 and EM7 Promoter Upstream of ZeoR Gene in Vectors pHP15a (p2270, strain MR#3080)

The vector containing ptrc promoter instead EM7 promoter and Actin 5C promoter instead of OpIE2 all upstream the ZeoR gene.

The construct was constructed by SOE-PCR. First PCR1 fragment was made with primers 4007 and 4009 using p2263 as template. The resulting PCR-product have the size of 234 bp. The second PCR2 fragment was made with primers 4008 and 4000 using p2263 as template. The fragment have the size of 1134 bp.

The SOE-PCR was made by mixing PCR1 and PCR2 products. Finally the fragment is amplified using primers 4000 and 4009.

The resulting fragment was 1433 bp and digested with restrictions endonucleases EcoRI and NcoI and clone it into EcoRI and NcoI digested and SAP treated p2263. Ligated over night in a termo cycler. The ligation product was transformed into DH10B cells, plated out on LB Agar plates containing 0.75 ug/ml Zeocin and incubatet ON.

In the resulting plasmid the insert has been fully sequenced using primers 1892, 2232, 2233, 2234, 2235, 2236, 2007, 4000, 4002, 4007 and 4009.

pHP15b (p2271, strain MR#3081)

The vector is almost like pHP15a but containing Hsp70 promoter instead of Actin 5C promoter upstream the ZeoR gene. Constructed by one step PCR amplification. The PCR was made with primers 4001 and 4002 using p2270 as template. The resulting fragment was 290 bp, containing actin 5c promoter.

The PCR fragment digested with restrictions endonucleases XmnI and SphI and clone into XmnI and SphI digested and SAP treated p2270. Ligated over night in a termo cycler. The ligation product was transformed into DH10B cells, plated out on LB Agar plates containing 0.75 ug/ml Zeocin and incubatet ON.

In the resulting plasmid the insert has been fully sequenced using primers 2007, 4000 and 4001.

pHP15c (p2272, strain MR#3082) containing promoter sequence upstream for KanaR instead of EM7 promoter upstream the ZeoR gene.

The construct was constructed by SOE-PCR. First PCR1 fragment was made with primers 4003 and 4009 using p2270 as template. The resulting PCR-product have the size of 296 bp.

The second PCR2 fragment was made with primers 4004 and 2007 using p2270 as template. The fragment have the size of 189 bp.

The SOE-PCR was made by mixing PCR1 and PCR2 products. Finally the fragment is amplified using primers 4009 and 2007.

The resulting fragment of 450 bp was digested with restrictions endonuclease(s) SphI and NcoI and cloned into SphI and NcoI digested and SAP treated p2270. Ligated over night in a termo cycler. The ligation product was transformed into DH10B cells, plated out on LB Agar plates containing 0.75 ug/ml Zeocin and incubatet ON.

In the resulting plasmid the insert has been fully sequenced using primers 2007 and 4003

Construction of Truncated Actin 5c Promoter from pHP11 pHP17 (p2276, strain MR#3086) containing truncated sequence from Actin 5c promoter 1486 bp.

Vector p2262 was digested with restrictions endonucleases SphI and NheI and the vector was ligated again with use of Klenow. The ligation product was transformed into DH10B cells, plated out on LB Agar plates containing 0.75 ug/ml Zeocin and incubatet ON.

Colonies were screen by colony PCR using primers 590 and 980. Correct inserts display DNA fragment have size of 1510 bp.

In the resulting plasmid the insert has been fully sequenced using primers 590, 917, 990, 992, 993, 994, 995 and 2509 pHP18 (p2277, MR#3087) containing truncated sequence from Actin 5c promoter 612 bp.

Vector p2262 was digested with restrictions endonucleases SpeI and NheI and the vector was ligated again with use of Klenow. The ligation product was transformed into DH10B cells, plated out on LB Agar plates containing 0.75 ug/ml Zeocin and incubatet ON.

Colonies were screen by colony PCR using primers 590 and 980. Correct inserts display DNA fragment have size of 660 bp.

In the resulting plasmid the insert has been fully sequenced using primers 590, 917, 993, 995 and 2509 pHP12-Afl II (p2287, strain MR#3097) The vector was constructed by SOE-PCR. First PCR1 fragment was made with primers 987 and 4036 using p2263 as template. The resulting PCR-product have the size of 217 bp.

The second PCR2 fragment was made with primers 4035 and 986 using p22630 as template. The fragment have the size of 190 bp.

The SOE-PCR was made by mixing PCR1 and PCR2 products. Finally the fragment is amplified using primers 986 and 987.

The resulting fragment of 362 bp was digested with restrictions endonucleases NheI and HindIII and cloned into NheI and HindIII digested and SAP treated p2263. Ligated over night in a termo cycler. The ligation product was transformed into DH10B cells, plated out on LB Agar plates containing 0.75 ug/ml Zeocin and incubatet ON.

In the resulting plasmid the insert has been fully sequenced using primer 982.

Cloning of Hybrid Vectors with Actin5c Core and Hsp70 Core Promoter.

pHP18-Afl II (p2288, strain MR#3098) The vector was constructed by SOE-PCR. First PCR1 fragment was made with primers 987 and 4038 using p2277 as template. The second PCR2 fragment was made with primers 4037 and 986 using p2277 as template. The fragment have the size of 224 bp.

The SOE-PCR was made by mixing PCR1 and PCR2 products. Finally the fragment is amplified using primers 986 and 987.

The resulting fragment of 689 bp was digested with restrictions endonucleases NheI and HindIII and cloned into NheI and HindIII digested and SAP treated p2277. Ligated over night in a termo cycler. The ligation product was transformed into DH10B cells, plated out on LB Agar plates containing 0.75 ug/ml Zeocin and incubatet ON.

In the resulting plasmid the insert has been fully sequenced using primer 980.

pHP19 hybrid actin5c core vector, containing Actin5C core promoter and Hsp70 promoter sequence upstream the Hsp70 core promoter.

Vector p2288 was digested with restrictions endonucleases AflII and HindIII, the resulting product have the size of 178 bp and the fragment clones into AflII and HindIII digested p2287. Ligated over night in a termo cycler. The ligation product was transformed into DH10B cells, plated out on LB Agar plates containing 0.75 ug/ml Zeocin and incubatet ON.

Colonies were screen by colony PCR using primers 4000 and 917. Correct inserts display DNA fragment of expected size. In the resulting plasmid the insert has been fully sequenced using primers 980 and 917.

pHP20 hybrid-Hsp70-core, containing Hsp70 core promoter and Actin5C promoter sequence upstream the Actin5c core promoter.

Vector p2287 was digested with restrictions endonucleases AflII and HindIII, the resulting product have the size of 144 bp and clone it into AflII and HindIII digested p2288. Ligated over night in a termo cycler. The ligation product was transformed into DH10B cells, plated out on LB Agar plates containing 0.75 ug/ml Zeocin and incubatet ON.

Colonies were screen by colony PCR using primers 993 and 901. Correct inserts display DNA fragment have size 478 bp. In the resulting plasmid the insert has been fully sequenced using primers 986 and 917

Cell Line Growth and Maintenance

Materials

Cryovials, 1.8 ml: Nunc cat. no. 377267

Excell420: SAFC cat. no. 14420

Fetal Bovine Serum, FBS, 500 ml: Life Technologies cat. no. 10099-141

Shake flasks, 250 ml with 0.2 µm vented cap: Corning cat. no. 431144 (Working volume: 25-70 ml)

Shake flasks, 1000 ml with 0.2 µm vented cap: Corning cat. no. 431147 (Working volume: 100-225 ml)

Tissue Culture Flasks, 25 cm$^2$: Greiner cat. no. 690160 (Working volume: 4-8 ml)

Tissue Culture Flasks, 75 cm$^2$: Greiner cat. no. 658170

Initiating of Cell Culture from Frozen Stock

1. Remove one (or more) vial(s) from liquid nitrogen and place in a 23° C. water bath. Thaw rapidly with gentle agitation until cells are almost thawed. Remove the vial(s) from the water bath. Each vial contains 4E7 cells in 1 ml freeze medium (40% Excell420+50% FBS+10% DMSO)
2. Quickly decontaminate the outside of the vial by treating with 70% ethanol and gently transfer the cell suspension to a centrifuge tube containing 7 ml 23° C. medium (Excell420+10% FBS) and centrifuge at 330×g for 2 minutes
3. Discard the medium to remove DMSO, resuspend the cells in 5 ml 23° C. medium (Excell420+10% FBS) and transfer the suspension to a T25
4. Incubate at 23° C. until cells reach a density of 6E6-9E6 cells/ml. This may take 2-4 days. Inspect and count the cells daily by the use of a cell counter and note cell concentration and viability. Viability will typically increase to 80-90% within 3-4 days.

Expansion of the Cells in T-Flasks

1. Transfer the cell culture from the T25 to a T75 and add 10 ml 23° C. medium (Excell420+10% FBS). Incubate at 23° C. until cells reach a density of 6E6-9E6 cells/ml. This may take 2-4 days. Inspect and count the cells daily by the use of a cell counter and note cell concentration and viability. Viability will typically be >90%.
2. Transfer the cell culture in the T75 to two T75s and add 10 ml 23° C. medium (Excell420+10% FBS) to each of them. Incubate at 23° C. until the cells reach a cell density of 6E6-9E6 cells/ml. This may take 2-4 days. Inspect and count the cells daily by the use of a cell counter and note cell concentration and viability. Viability will typically be >90%.
3. Transfer the cell culture from the two T75s to a 250 ml disposable shake flask and add 25 ml 23° C. medium (Excell420). Incubate the cells at 110 rpm and 23° C. until cells reach a density of 1.5E7-2E7 cells/ml. This may take 3-4 days. Inspect and count the cells from day 2 post-transfer by the use of a cell counter and note cell concentration and viability. Viability will typically be >90%.

Expansion of the Cells in Shake Flasks

1. Transfer the cell culture from the R250 to a centrifuge tube and centrifuge the cells at 330×g for 5 minutes. Resuspend the cells in fresh medium (Excell420) to a cell density of 8E6 cells/ml in an appropriate shake flask. Incubate at 110 rpm and 23° C. until cells reach a density of 2.5E7-3.5E7 cells/ml. This may take 3-4 days. Inspect and count the cells from day 2 post-transfer by the use of a cell counter and note cell concentration and viability. Viability will typically be >90%.
2. Expand the cell culture in 1000 ml shake flasks until a total cell number of 8.5E9 cells is obtained: Every 3-4 days, cells are split by centrifugation and resuspension to a cell density of 8E6 cells/ml in fresh medium (Excell420) into new shake flasks. The cells should be used for preparation of the Master Cell Bank two days after the last sub cultivation.

Preparation of a Cell Bank

1. Inspect and count the cells by the use of a cell counter and note cell concentration and viability. Viability will typically be >90%. Transfer cell suspension corresponding to 8E9 cells to a centrifuge tube and centrifuge at 330×g for 5 minutes. Resuspend the cells in 200 ml 4° C. freeze medium (40% Excell420, 50% FBS and 10% DMSO) and quickly aliquot 1 ml cell suspension into each cryovial.
2. Transfer the cryovials to 4° C. Mr. Frosty cryoboxes and place the boxes in a −80° C. freezer.
3. Transfer the cryovials after 6 to 48 hours to liquid Nitrogen for storage.
(Working volume: 12-25 ml).

Transfection of Cells

Use cells from a growing culture maintained as stipulated above, that have been diluted or resuspended after centrifugation one to two days prior to the transfection. Viability should be >90%.

1. Transfer cell suspension corresponding to ca. 3.2E7 cells per transfection to a centrifuge tube and centrifuge at ca. 125×g for ca. three minutes.
2. Resuspend in ca. 4 ml ca. 23° C. medium per transfection and transfer 4 ml cell suspension to each T25s.
3. Transfer ca. 6.3 ug of each DNA to individual eppendorf tubes.
4. Add Buffer EC to the each eppendorf tube containing DNA to give a final volume of 150 ul.
5. Mix DNA and Buffer EC by pipetting up and down a couple of times.
6. Add 50 ul Enhancer to the eppendorf tubes containing DNA and Buffer EC.
7. Vortex the DNA mixture 1 sec.
8. Incubate at 20-25° C. for two-five minutes.
9. Add 140 ul Effectene to the eppendorf tubes containing the DNA mixture.
10. Mix by pipetting up and down five times.
11. Incubate at 20-25° C. for five-ten minutes.
12. Add 1.5 ml medium to the tubes and mix by pipetting up and down a couple of times.
13. Carefully let the DNA-mixture drop to the cell suspension in the T25 and carefully tip the flasks back and forth.
14. Incubate at ca. 23° C.

Other suitable methods for transfection in *Drosophila melanogaster* S2 cells is described in Park J. H.; Kim H. Y.; Han K. H.; Chung I. S, *Optimization of transfection conditions for expression of green fluorescent protein in Drosophila melanogaster S2 cells—a highly efficient, lipid-mediated DNA-transfection procedure.* Enzyme and Microbial Technology, Volume 25, Number 7, October 1999, pp. 558-563(6).

Effectene Transfection Reagent is a non-liposomal lipid formulation that has minimal cytotoxicity by transfecting in the presence of serum and has high transfection efficiency. Effectene Reagent is used in conjunction with the Enhancer and the DNA-condensation buffer (Buffer EC) to achieve high transfection efficiencies.

Transient Transfections

After transfection cells are allowed to grow and produce at 23° C. for 2 to 4 days before a sample is taken for cell number, protein-of-interest and total protein determination. No selection agent should be added during transient transfections.

Preparing Stable Cell Lines

After transfection the cells are allowed to grow for 1 to 2 days before 1.5 mg/mL Zeocin (or other appropriate selection agent at appropriate concentration) is added. The cells are then expanded in T-flasks and shake flasks as described above (Expansion of the cells in T-flasks; Expansion of the cells in shake flasks). After 2 to 4 weeks only cells resistant to the selection marker, because of integration of the resistance marker into the genome, will be present and the cell line can be considered stable. The selection agent can at this point be left out from further cultivation or propagation steps, and the cells can be frozen down as described above.

Analysis

ELISA was used to analyze the model protein (RANK-ligand) used in this study. Bradford total protein analysis was used to determine total protein concentration.

Results

A range of vectors with enhanced protein expression levels have been created. There are 3 main classes of NN2 expression vector: The first class comprises vectors with different variants of the actin5C promoter driving protein expression; the second class refers to vectors employing the HSP70 promoter, while the third involves hybrid actin5C/HSP70 promoters.

A mutant Actin5c promoter (see mutations under sequence alignment section) was investigated to determine its protein expression level (vector pHP11). It was found that the mutant Actin5C promoter resulted in a consistently higher expression level compared to pOPIE2 (See FIG. 1).

Two versions of the *Drosophila melanogaster* S2 HSP70 promoter were also tested. The first promoter was the full-length HSP70 promoter (457 bp, vector pHP 13), while the second was a truncated version of HSP70 (59 bp to 342 bp, see sequences section, vector pHP12). The truncated version was found to have up to five-fold higher protein expression levels compared to the full-length promoter (see FIG. 2). It was also observed that the tuncated HSP70 promoter was expressed at high level in stable as well as transient cell lines (see FIGS. 3 and 4).

The Actin5C promoter mutant and the truncated HSP70 promoter were further studied through truncation. The protein expression results for both transient and stable cell lines can be seen in FIGS. 3 and 4.

Figure 3:
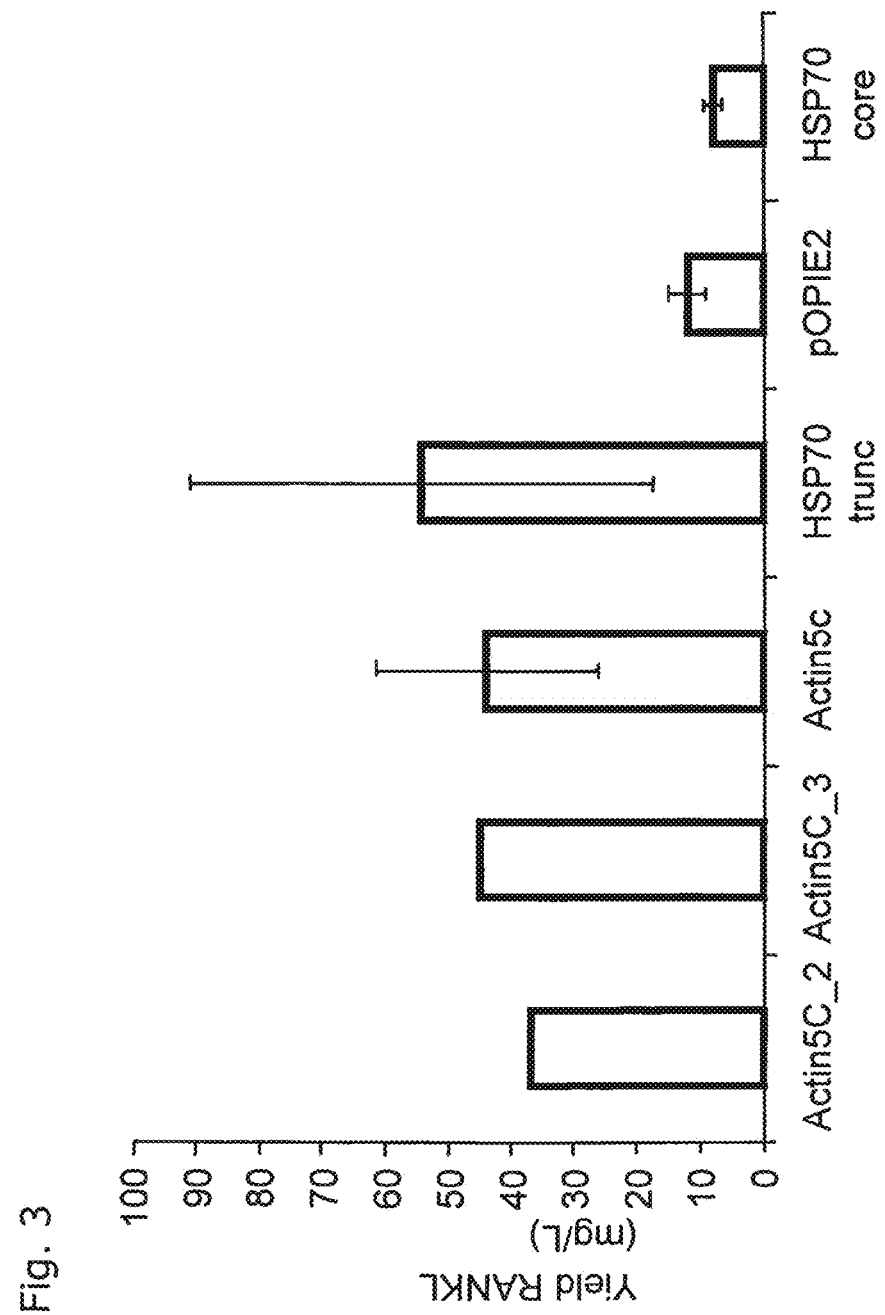
FIG. 3: RANKL production level for stable cell lines using six different promoters to drive protein expression. These include three versions of the mutated Actin5C promoter (the full-length promoter, (2) a truncated version (vector pHP17) and (3) the 612 bp shortest truncation version), two versions of the HSP70 promoter (the truncated HSP70 promoter and the HSP70 core promoter) and the pOPIE2 promoter as control.

A 3 to 9 fold increase in protein expression was achieved over the pOPIE2 promoter for the Actin5C and HSP70 promoter variants in stable cell lines (FIG. 3). Furthermore, an increase in average expression level over the full length Actin5c promoter was achieved by using the shortest truncated Actin5C promoter (Actin5C_3, vector pHP18), although more experiments will be needed to confirm if it has significantly higher expression. However, this trend can also be seen for transient transfections (see FIG. 4). The highest expression level was seen for the HSP70 promoter, while the HSP70 core promoter sequence led to a significantly reduced expression level compared to pOPIE2 as well as the truncated HSP70 promoter. The expression level of the HSP70 truncated promoter, although always higher than pOPIE2, was highly variable from transfection to transfection. It is expected that optimizing the transfection for this construct will reduce the variation in the different stable polyclonal cell lines. However, the stable polyclonal lines, once established, did not show significant variation in expression over time. The resulting stable polyclonal cell lines after transfection should therefore be screened before use to find the best expressing polyclonal pools.

Protein expression levels were increased 4 to 12 fold in transient transformations compared to the pOPIE2 promoter. The shortest truncated Actin5C promoter (vector pHP18) had the highest consistent expression level in transient transfections.

Figure 5:
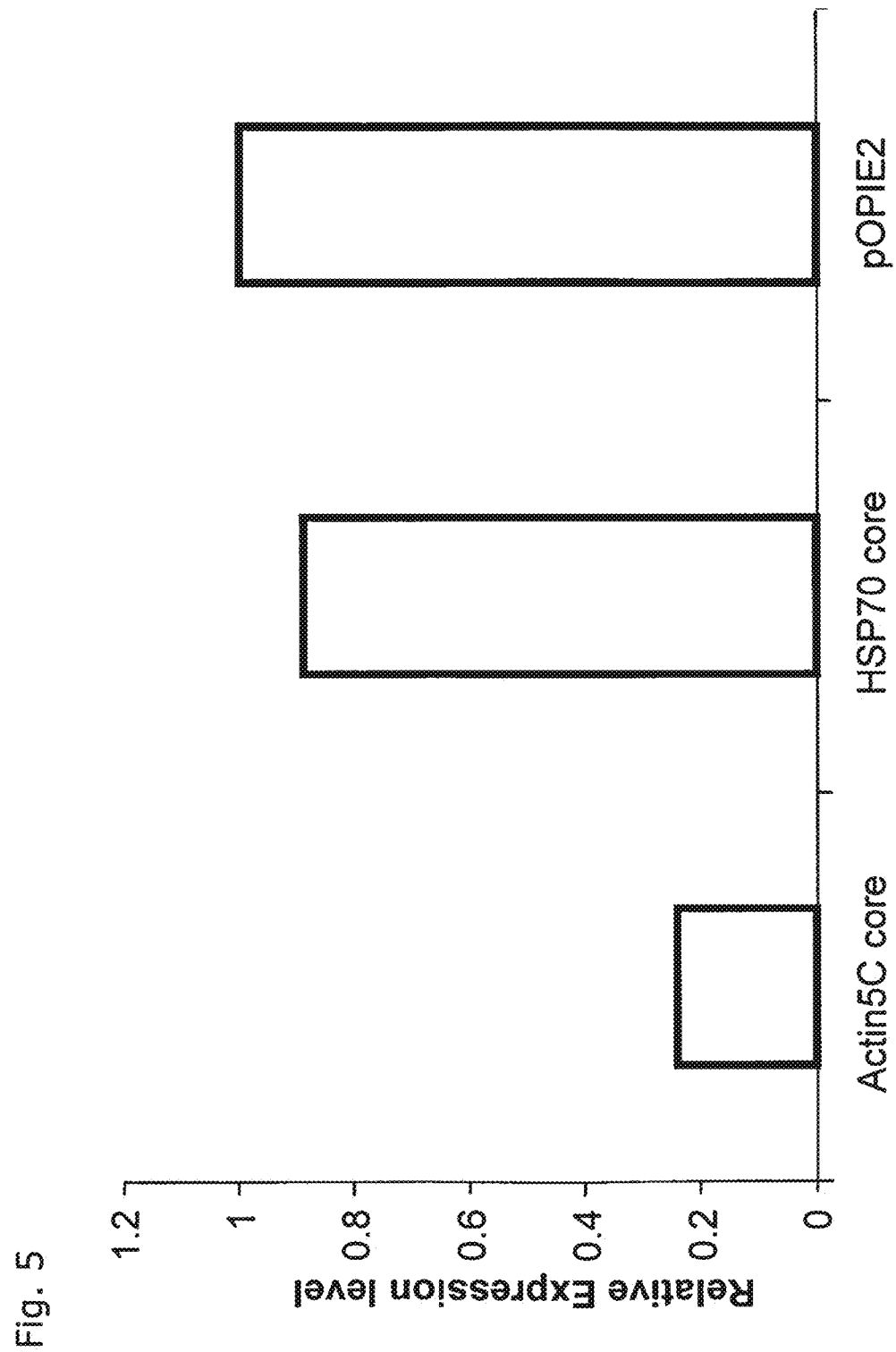
FIG. 5: Expression levels in transient transfection of pOPIE2 and the Actin5C core and HSP70 core promoters.
Figure 6:
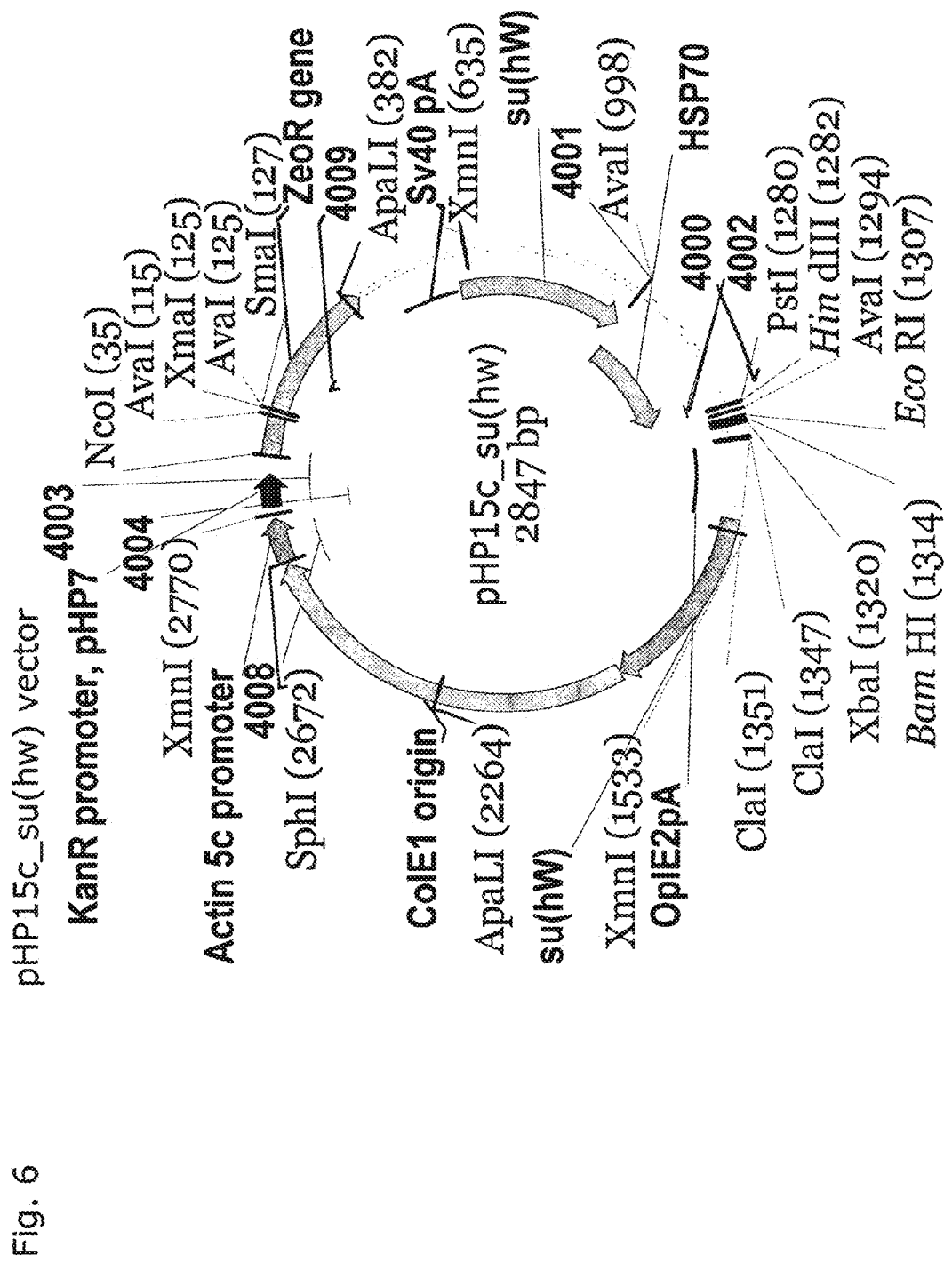
FIG. 6 illustrates one suitable vector, pHP15c_su(hw) vector, according to the invention
Figure 7:
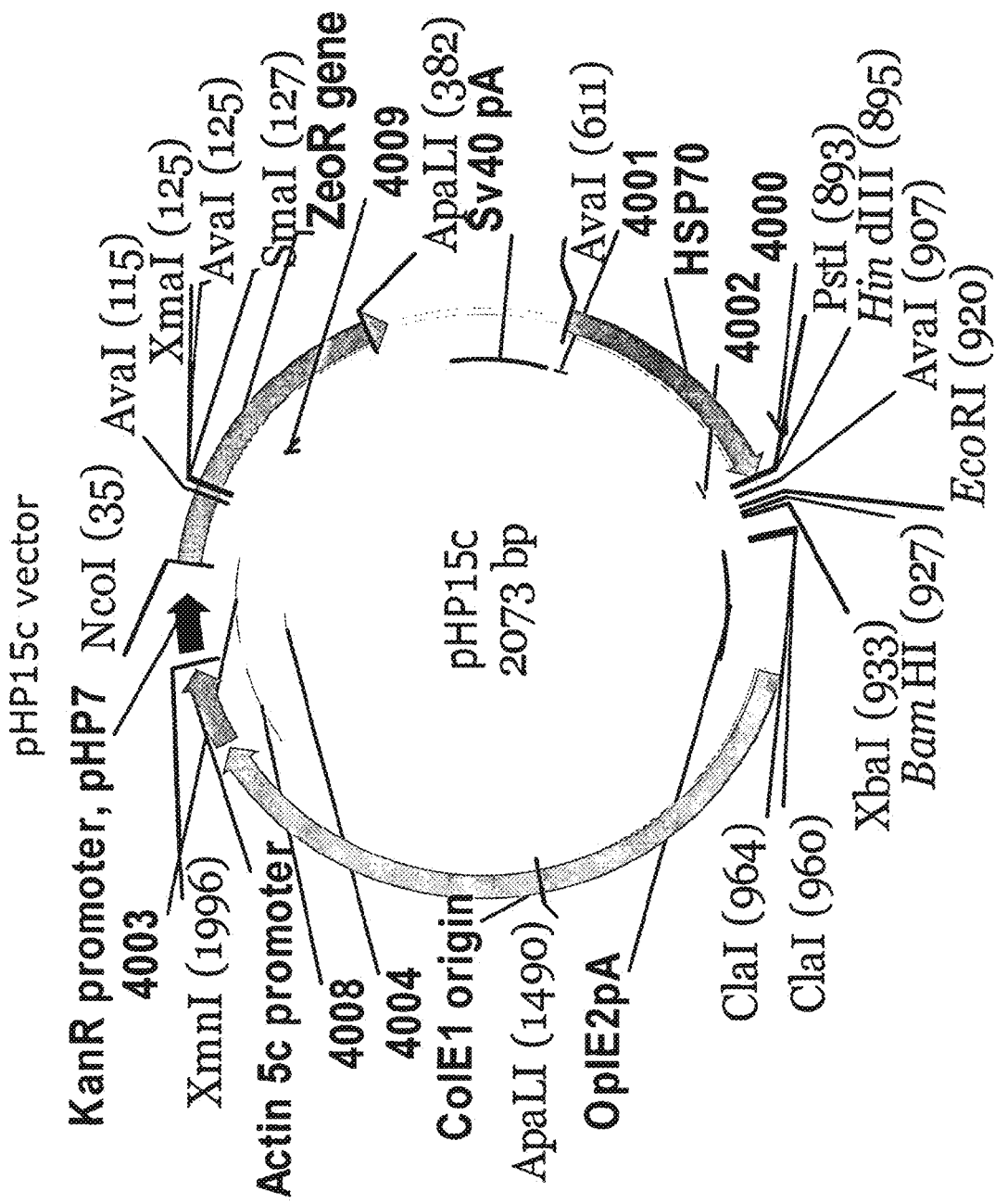
FIG. 7 illustrates one suitable vector, pHP15c vector, according to the invention.
Figure 10A:
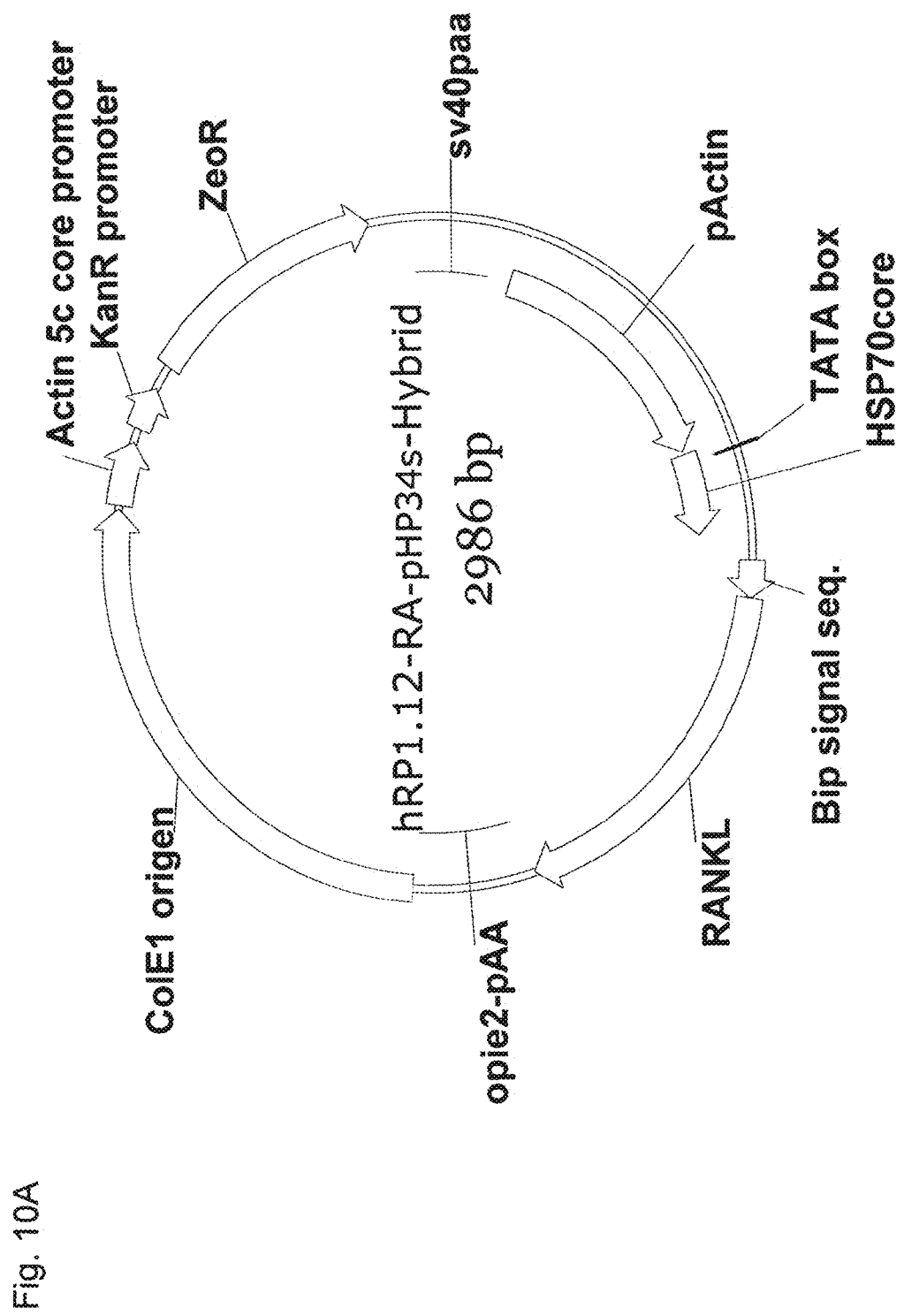
FIG. 10: Vector maps.
(A) Vector map for pHP34s-hybrid vector containing a RANKL encoding region.
(B) The original pHP34s vector containing the truncated actin 5c promoter. The hybrid promoter consists of the upstream part of the truncated actin 5c promoter (minus the Actin 5c core promoter), and the HSP70 core promoter.
Figure 10B:
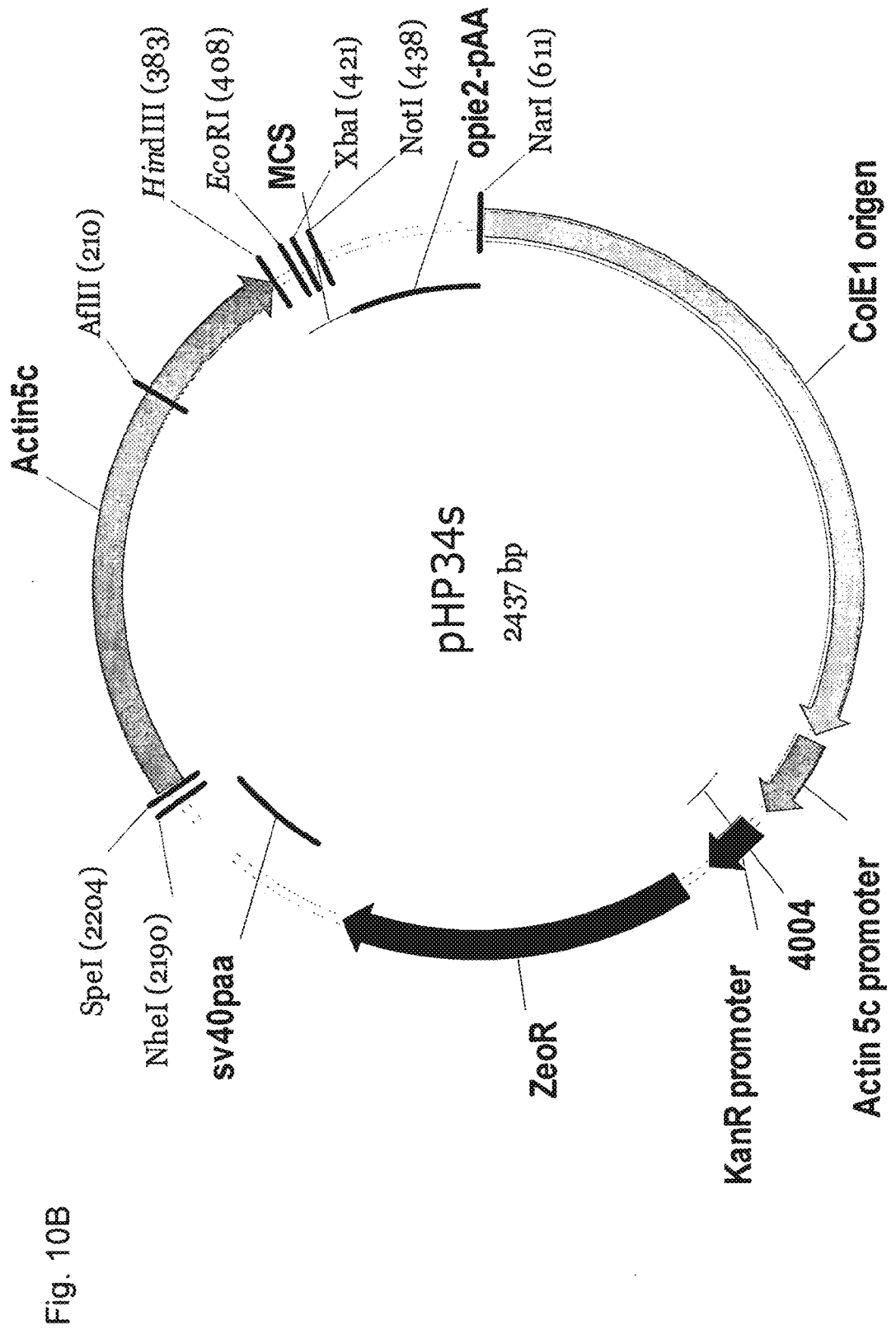
Figure 11:
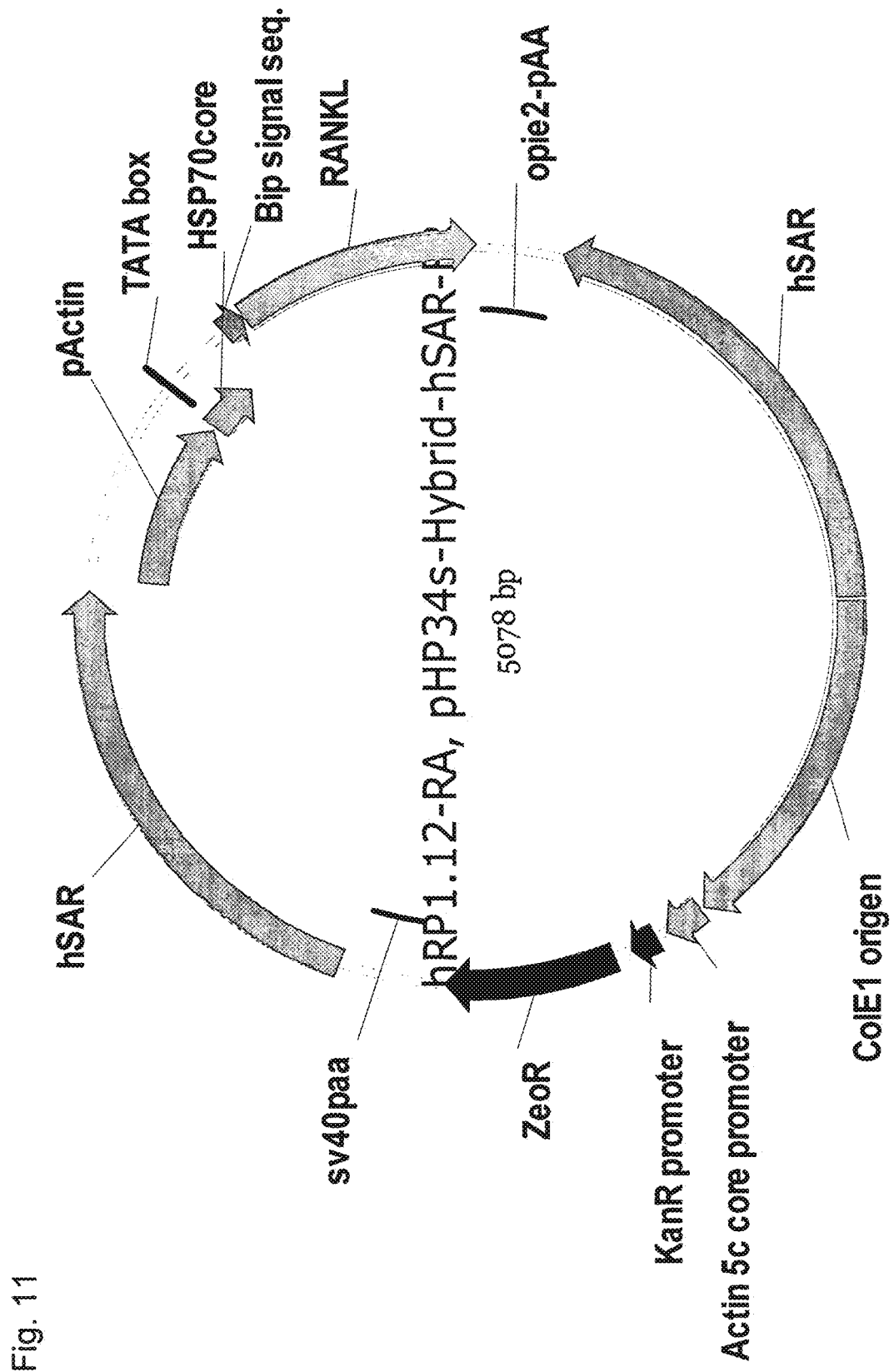
FIG. 11: Vector map for RANKL containing pHP34s-hybrid-hSAR-FR. The hSAR or HSP70 Matrix attachment regions were inserted in the forward and reverse orientation, flanking the expression cassette. The hSAR elements where also inserted in the same positions in the three other possible orientations (reverse-reverse; reverse-forward, forward-forward).
Figure 12:
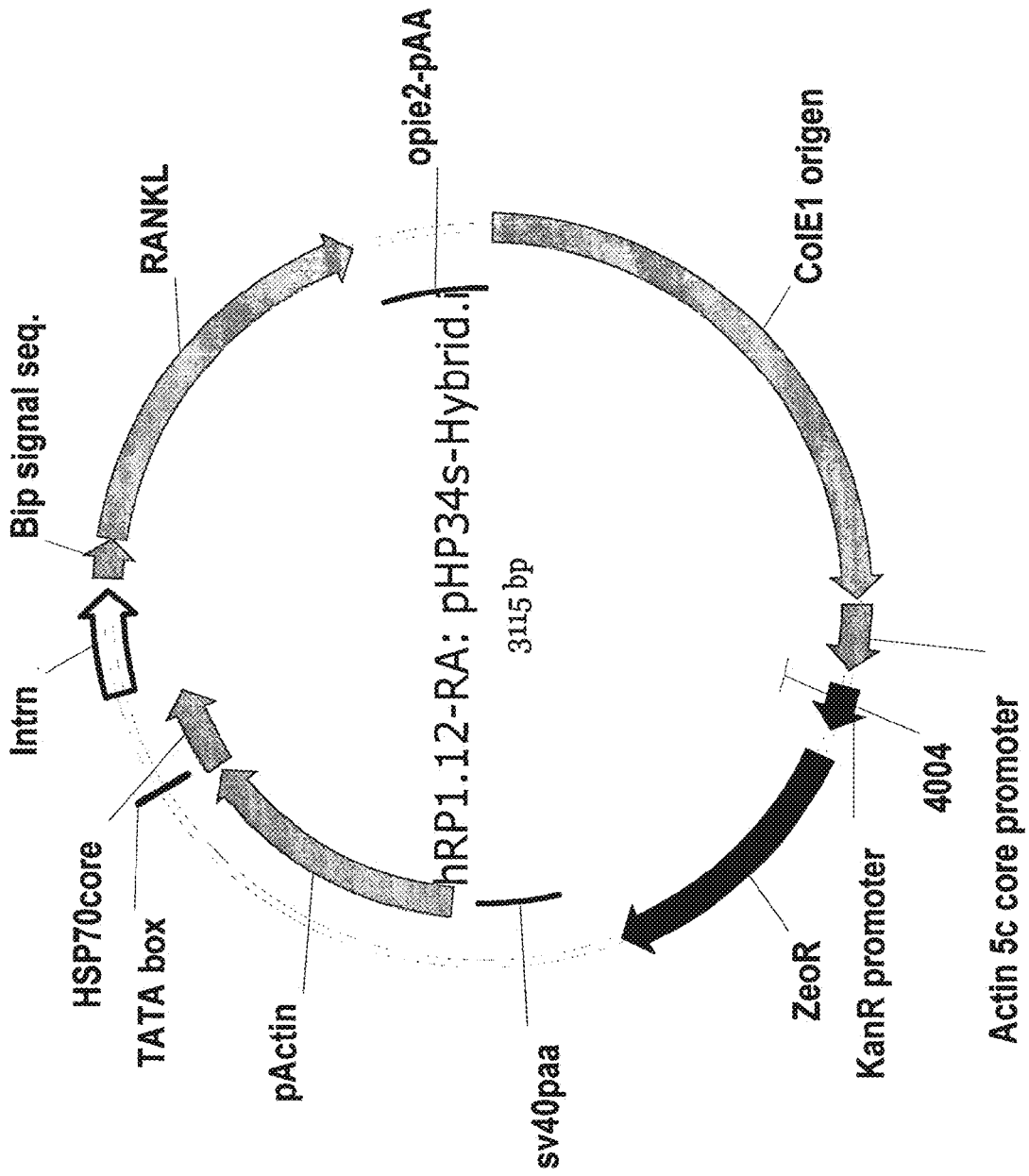
FIG. 12: Vector map for pHP34s-hybrid.i containing a coding sequence for the RANKL protein. The "i" indicates the insertion of an intron upstream of the ATG start codon. The intron is indicated as "intrn" in the vector map.
Figure 13:
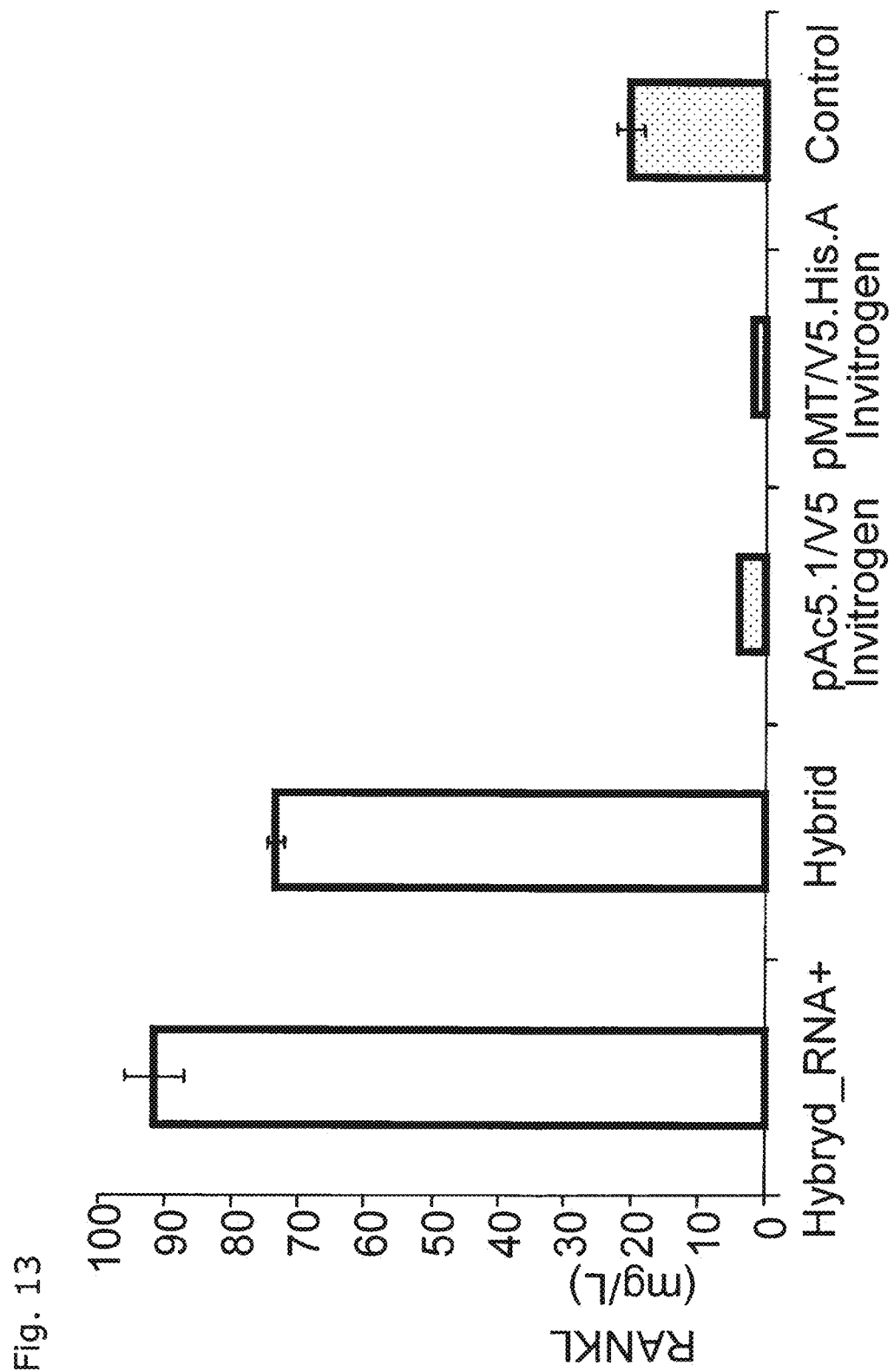
FIG. 13: RANKL expression level of pHP34s-Hybrid (named: Hybrid) and pHP34s-Hybrid.i (containing the intron, named: Hybrid_RNA+), compared to two commercially available vectors. (See table A1 for RAW data).
Figure 14:
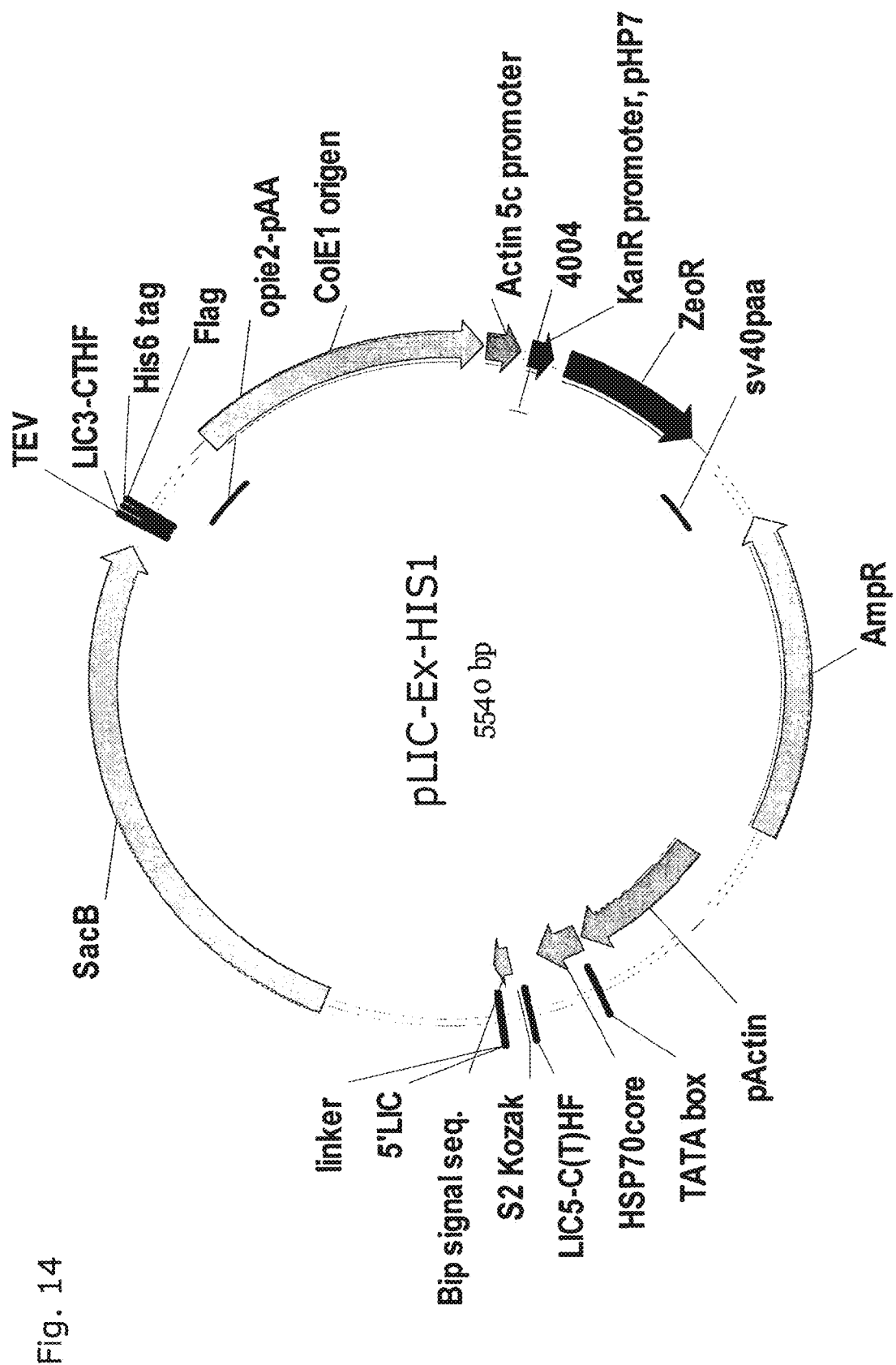
FIG. 14: LIC enabled pHP34s-Hybrid for C-terminally His tagged extracellular expression using the BIP signal sequence. The SacB gene confers sucrose sensitivity to *E. coli* cells. The SacB gene should be removed during LIC cloning by restriction digest and replaced with the gene-of-interest. If the SacB gene is not replaced it acts as a counter selection marker to remove background (incorrect) colonies. The LIC sites are indicated as 5' LIC and LIC3-CTHF. This particular vector has the sequence set forth in SEQ ID NO: 69. SEQ ID NOs. 69-73 show similar vectors where N- or C-terminal His tagging with or without a TEV protease site is enabled, so as to allow intra- or extracellular expression.

The core promoters of Actin5C (vector pHP10) and HSP70 (vector pHP16) were compared to pOPIE2 to gain further insight into their relative properties. The expression level of the HSP70 core promoter is significantly higher than the Actin5C core promoter, although both promoters are significantly weaker than the pOPIE2 promoter that was used as internal control. (FIG. 5)

The Actin5C core promoter was used to express the ZeoR zeocin resistance gene in conjunction with the KanR bacterial promoter (vector pHP15c). This allows Zeocin to be used as selection marker in both *E. coli* and S2 insect cells. In addition, the Actin5C core promoter is significantly weaker than the pOPIE2 promoter used to express the zeocin resistance marker in p2ZOp2F. This leads to a 2-fold decrease in antibiotic resistance after transfection compared to cells transfected with the p2ZOp2F plasmid, leading to 2-fold less Zeocin (0.75 mg/ml vs. 1.5 mg/ml) to be used when selecting for stable cells.

Furthermore, different selection markers were included to allow for greater flexibility in the application of the vectors. The following markers are included: Zeocin, neomycin and blasticidin.

High Expression Level Achieved by a Mutant or Truncated Actin5C Promoter

The expression level of a mutant Actin5C promoter was compared to the commercially available pOPIE2 promoter and found to be significantly higher (see FIG. 1). Further increases in protein production level were achieved by truncating the Actin5C promoter to 612 bp from the full-length 2532 bp (SEQ ID NO:3). The truncated promoter led had a 5 fold increased protein production for stable cell lines when compared to the commercially available p2ZOp2F vector containing the pOPIE2 promoter. Also, transient expression levels where increased up to 12 fold compared to the expression level obtained with the p2ZOp2F vector. (see FIGS. 3 and 4)

Effect of Truncating the Genomic HSP70 Promoter

Figure 2:
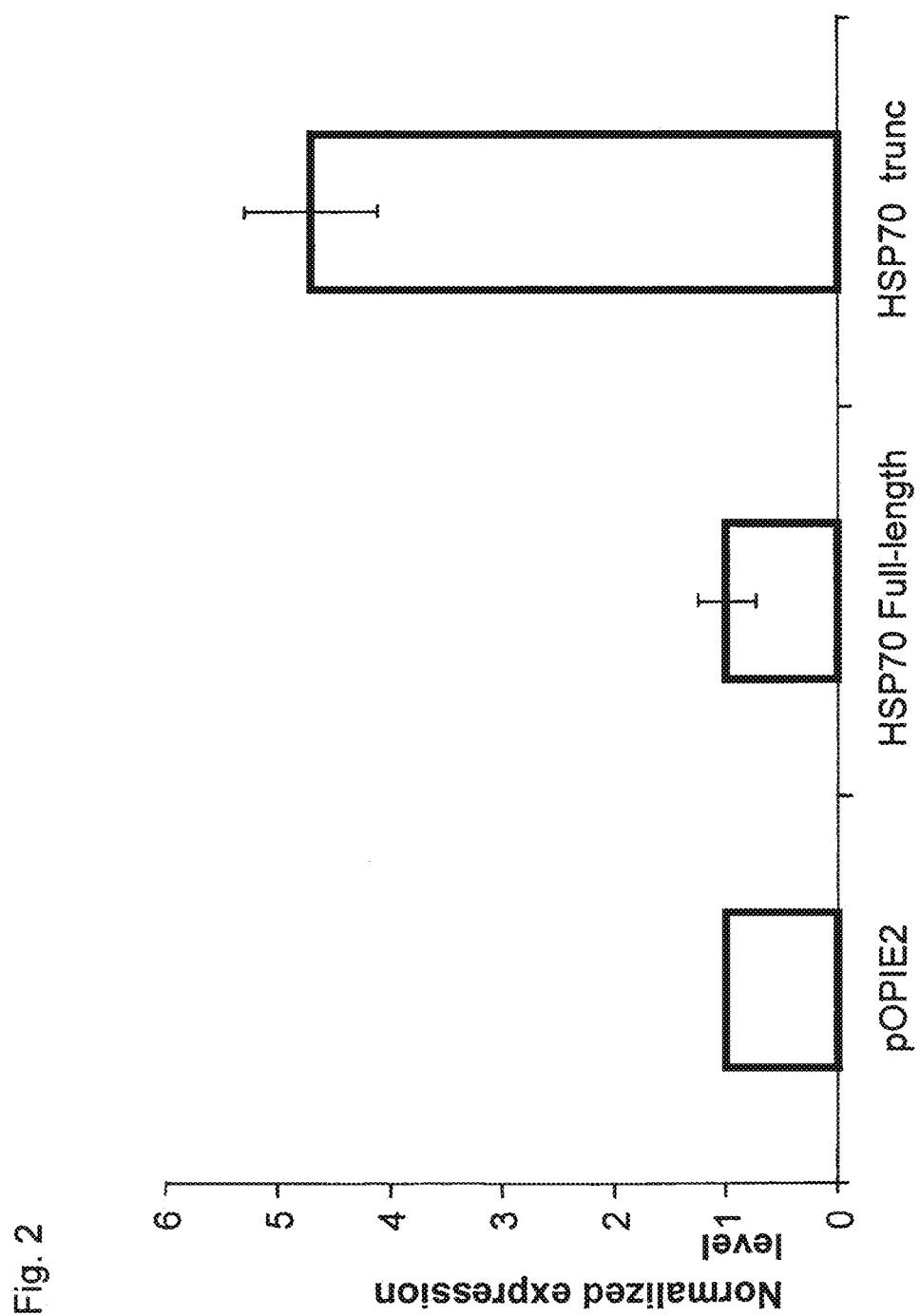
FIG. 2: Expression level of the full-length and truncated HSP70 promoter during transient expression. pOPIE2 was used as control in the experiment.

In *Drosophila melanogaster* S2 cells, regulatory mechanisms not only lead to induction of HSP70 from heat shock, but also prevent expression at normal temperatures (Feder et al. 1992, Genes Dev. August; 6(8):1402-13). Surprisingly, the truncated HSP70 promoter showed the highest expression level in stably transfected cell lines compared to the Actin5C and pOPIE2 promoters (see FIG. 3). However, 58 bp from the upstream end of the genomic full-length promoter and 114 bp from the downstream end of the promoter was removed during cloning to create the truncated promoter. It appears likely that this truncation directly resulted in the deregulated (constitutive) high expression level observed. In FIG. 2 the constitutive high expression level of the truncated HSP70 promoter is contrasted with the low level expression of the full length promoter in transient transfections. This indicates a relief of repression of the promoter.

Reducing Required Zeocin Concentration During Stable Cell Line Selection

Using the significantly weakened expression level (compared to the full-length and pOPIE2 promoters) of Actin5C core promoter along with the KanR bacterial promoter results in hightened Zeocin sensitivity of transfected cell lines (2-fold). Lower resistance could help in selecting higher multicopy integration events to make up for the poor expression level of the ZeoR resistance marker, leading to higher gene-of-interest protein expression level. The ability to select for high copy-number gene-integration events using less Zeocin when making stable cell lines would be an advantage in itself, as Zeocin is a mutagen and could have adverse and unexpected effects on the cells.

Increased Expression Through Hybrid Actin5C/HSP70 Promoters

Figure 4:
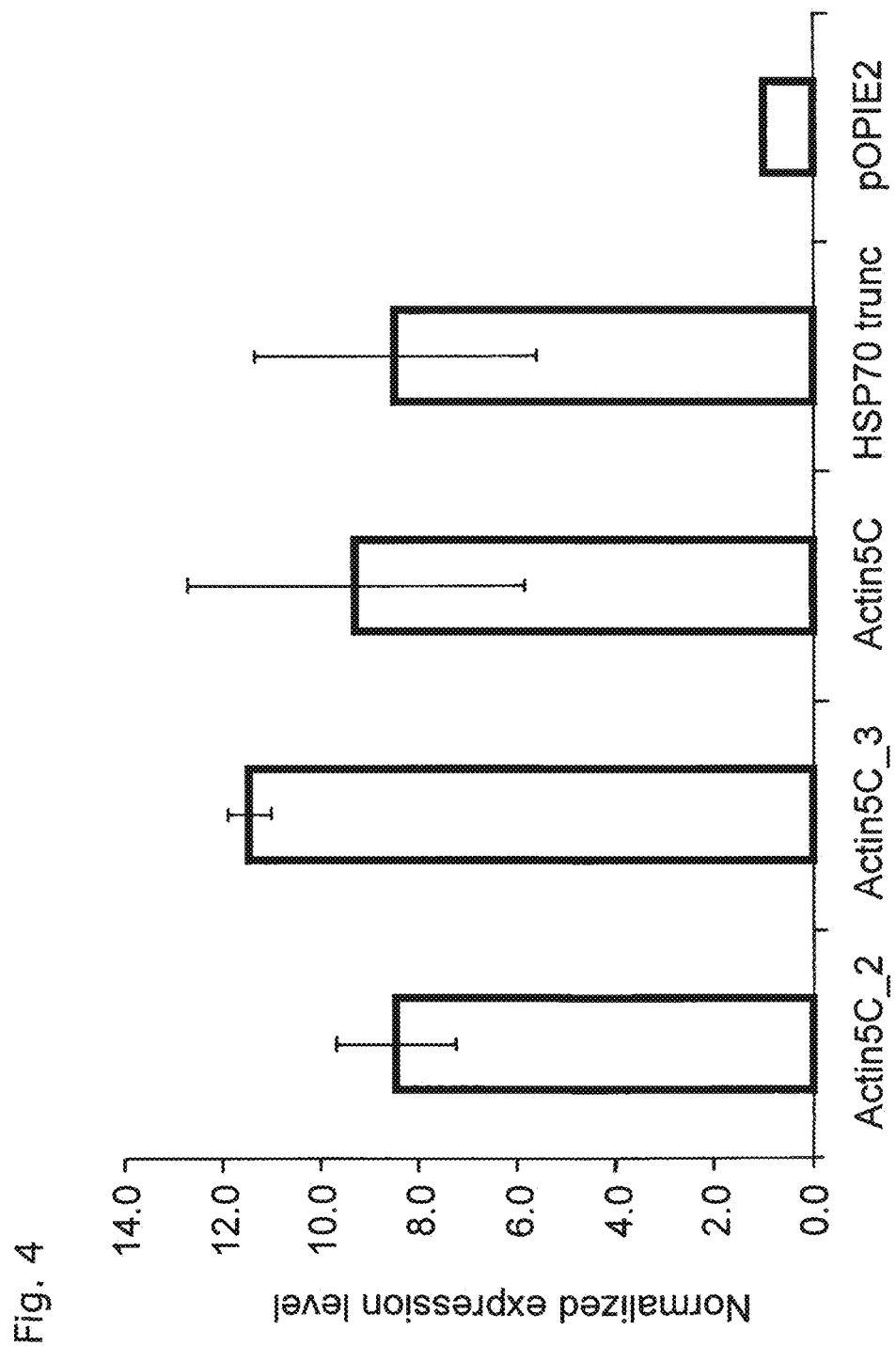
FIG. 4: Normalized expression levels achieved during transient transfection. These include three versions of the mutated Actin5C promoter (the full-length promoter, (2) a truncated version (vector pHP17) and (3) the 612 bp shortest truncation version), the truncated HSP70 promoter and the pOPIE2 promoter as control.

In the above-discussed experiments it was found that the truncated HSP70 promoter led to the highest expression level in stable cell lines (FIG. 3). However, the highest expression level during transient transfections was achieved using the shortest truncated Actin5C promoter (Actin5C_3) (FIG. 4). Furthermore, it was found that the HSP70 core promoter had a 4 fold higher expression level compared to the Actin5C core promoter during transient transfection (FIG. 5).

It was therefore decided to make hybrid promoters, where the core promoter from Actin5C and HSP70 were exchanged in the truncated Actin5C and truncated HSP70 promoters, respectively. This was believed to lead to a significant increase in expression level in the Actin5C-HSP70 core hybrid-promoter compared to the original Actin5C promoter.

Vector Construction

The DNA for the pHP34s vector was ordered synthetically from GeneART, Germany (SEQ ID NO: 58). All vectors created from pHP34s were made using synthetic DNA ordered from GeneART, Germany and primers ordered from DNA-technology, Denmark.

The hybrid promoter coding sequence was created in plasmid pHP34s-Hybrid, by PCR of the HSP70 core promoter encoding sequence from synthetic HSP70 promoter DNA (SEQ ID NO: 37) ordered from GeneART (PCR primers:

GCGAACTTAAGAGCGCCGGAGTATAAATAG (SEQ ID NO: 64) and CCAAGCTTCTGCAGATTGTTTAGCTTG (SEQ ID NO: 65). A second PCR was then done to obtain the Actin 5c promoter upstream part of the promoter (primers: GGTTTGTCCAAACTCATCAATGTAT (SEQ ID NO: 66) and TATACTCCGGCGCTCTTAAGT-TCGCTCGCGTTCAAAACTTTTACC (SEQ ID NO: 67)) from pHP34s, and the two PCR fragments were fused using PCR.

The resulting fused PCR product was then digested with SpeI and HindIII, and ligated into the pHP34s vector digested with SpeI and HindIII according to standard molecular biology procedures. The DNA can also be ordered synthetically for the hybrid promoter and cloned using the SpeI and HindIII into pHP34s-Hybrid.

The intron (synthetic, SEQ ID NO: 60)) was ordered from GeneART and inserted by GeneART into the pHP34s-Hybrid vector between the SacI and EcoRI restriction sites to create the pHP34s-Hybrid.i vector.

The HSP70 matrix attachment region or hSAR element (SEQ ID NO: 59), was inserted into pHP34s-Hybrid in two positions flanking the expression cassette. The hSAR element was ordered as a synthetic sequence from GeneART with flanking SpeI and NarI sites on each side. The pHP34s-hybrid vector and hSAR containing GeneART vector were digested with NarI, the desired fragments gel purified and ligated to produce two vectors, pHP34s-Hybrid-hSAR-F or -R (-F or -R indicated forward or reverse orientation), with the hSAR element inserted in both orientations. Each of these two vectors and the GeneART hSAR containing vector were then digested with SpeI, the desired fragments gel purified and ligated to create four vectors. The four vectors contain two hSAR elements in all four possible orientations.

The above mentioned vectors and synthetically ordered RANKL (variant hRP1.12-RA) and HA model protein DNA encoding sequences were digested with EcoRI and NotI, the desired fragments gel purified and ligated (for instance RANKL with one of the vectors or HA with one of the vectors) to produce the above mentioned vectors with RANKL or HA encoding DNA inserted. The resulting vectors were named with the hRP1.12-RA-vector name or HA-vector name, for instance: hRP1.12-RA, pHP34s-Hybrid.

Creation of RANKL and HA (from H5N1 avian flu) containing pMT/V5.HIS.A and pAC5.1 vectors. The vectors were obtained from Invitrogen, digested with EcoRI and NotI, the desired fragments gel purified and ligated with EcoRI and NotI digested and gel purified synthetic RANKL or HA as described above, to produce pMT/V5 and pAC5.1 vectors with RANKL encoding DNA inserted.

A kanamycin/Geneticin (G418) resistance marker vector was created and named pHP34s-Hybrid-KanR. The vector was created by inserting geneART ordered synthetic DNA coding for the KanR/NeoR gene (optimized for *E. coli* and S2 cell expression) and *E. coli* promoter into the pHP34s-Hybrid vector. The vector and insert were digested with XmnI and SalI, the linear vector and kanR containing fragments were gel purified and ligated according to standard procedures.

The vector map for hRP1.12-RA-pHP34s-Hybrid, pHP34s, pHP34s-hybrid-hSAR-FR, and pHP34s-hybrid.i are shown in FIGS. 10-12.

Transfection

For the comparison experiments the two Invitrogen vectors (pMT/V5.HIS.A and pAC5.1) were used. These two vectors do not contain a selection marker, and therefore were co-transfected with a hygromycin resistance conferring vector also obtained from Invitrogen (pCoHygro). The transfection was conducted according to the same protocol as for the pHP34s derived vectors, but the hygromycin resistance vector was added for the pMT/V5.HIS.A and pAC5.1 vectors at a ratio of 10:1 (10 fold more expression vector than hygromycin resistance vector).

The remaining vectors were transfected according to the standard procedure detailed above.

Preparation of Stable Cell Lines

The hygromycin resistant cells were made stable according to the same method described for the Zeocin resistant cells above, except that 600 ug/mL of Hygromycin was added to the media instead of 1500 ug/mL Zeocin.

The vector conferring kanamycin/Geneticin (G418) resistance was transfected according to the method described above, but selection was done using between 1200 and 1500 ug/mL of G418 in S2 cells or with standard Kanamycin concentration for *E. coli* cells.

Expression Testing $CdCl_2$ Induction.

The pMT/V5.HIS.A vector has a cadmium inducible promoter so for the expression comparison test the cells were induced with $CdCL_2$. The cells were grown in shakeflasks for 2-3 days and then induced using 1 ul of stock per 1 ml media (Stock: 1 mM $CdCl_2$ Sigma C-2544 lot13H0424: 183 mg in 1000 ml $H_20$). The cells were allowed to produce protein for a further three to four days before taking samples for analysis.

The remaining vectors have constitutive promoters and did hence not need to be induced. Samples were taken after 3-4 days of growth and production.

The experiments were conducted as duplicates or triplicates (see raw data below) in shake flasks.

Results

Exchanging the weak core-promoter of the actin 5c promoter with the stronger HSP70 core promoter led to a 50% increase in expression over the truncated Actin 5c promoter (see FIG. 8).

We also tested the effect of a new element, an intron, specifically the intron described in the paper Zieler H., Huynh C Q. "Intron-dependent stimulation of marker gene expression in cultured insect cells", Insect Mol Biol. 2002 1, 87-95. The DNA sequence of this intron is set forth in SEQ ID NO: 60, where it is flanked by two restriction sites. So, according to the invention, the inclusion of a promoter such as SEQ ID NO: 60 between the promoter nucleic acid sequence and the coding sequence for a protein of interest can add significantly to the increased expression levels obtained by the present invention:

FIG. 9 demonstrates the effect of adding either the intron or two flanking matrix attachment regions to the hybrid promoter vector.

FIG. 9 demonstrates that the addition of an intron increased the expression of the model protein by 22% and the addition of two flanking matrix attachment regions enhanced expression by 46% compared to the original hybrid promoter vector. It would be expected that the combination of the intron and matrix attachment regions in one vector would further enhance expression.

Finally, FIG. 13 demonstrates that the vectors of the invention provide significantly higher expression yields than 2 commercially available vectors.

To conclude, a significant increased expression level was obtained using the vectors developed in this work compared to the commercially available vectors.

The vector functionality was also improved by adding a second selection marker, kanamycin/geneticin (G418). This allows co-transfection of two vectors expressing different proteins into one cell. It also allows for consecutive transformation with the Zeocin resistance and then kanamycin resistance markers (in any order).

TABLE A1

Comparison experiment between pHP34s-Hybrid and commmercial vectors for RANKL and HA

| Description | Protein | Antibiotic selection | Induce* | Cell count | Transient (mg/L) | Cell count | Stable (mg/L) | Protien | Cell count | Transient (mg/L) | Cell count | Stable (mg/L) |
|---|---|---|---|---|---|---|---|---|---|---|---|---|
| pHP34s-Hybrid.i | RANKL | Zeocin (1500 ug/mL) | — | 2.9/90" | 5.7 | 45/95 | 87 | HA' | 2.8/96 | 0.4 | 48/90 | 57 |
| pHP34s-Hybrid.i | RANKL | Zeocin (1500 ug/mL) | — | 3.1/91 | 6.7 | 49/96 | 92 | HA | 2.5/92 | 0.5 | 44/90 | 54 |
| pHP34s-Hybrid.i | RANKL | Zeocin (1500 ug/mL) | — | 3.2/92 | 7.1 | 43/95 | 96 | HA | 2.9/96 | 0.6 | 46/90 | 55 |
| pHP34s-Hybrid | RANKL | Zeocin (1500 ug/mL) | — | 3.4/93 | 3.6 | 48/95 | 74 | HA | 2.4/95 | 1.5 | 45/90 | 50 |
| pHP34s-Hybrid | RANKL | Zeocin (1500 ug/mL) | — | 3.2/93 | 3.3 | 53/96 | 73 | HA | 2.9/96 | 1.4 | 45/90 | 53 |
| pHP34s-Hybrid | RANKL | Zeocin (1500 ug/mL) | — | 3.1/92 | 5.1 | 54/96 | 73 | HA | 2.7/96 | 0.7 | 49/90 | 51 |
| pAc5.1/V5 | RANKL | Hygromycin (600 ug/mL) | — | 3.3/90 | 0.9 | 49/96 | 3.8 | HA | 30./96 | 0.2 | 43/93 | 5 |
| pAc5.1/V5 | RANKL | Hygromycin (600 ug/mL) | — | 3.4/91 | 0.9 | 45/96 | 3.8 | HA | 2.7/96 | 0.2 | 43/93 | 5 |
| pAc5.1/V5 | RANKL | Hygromycin (600 ug/mL) | — | 3.2/91 | 1 | 49/96 | 3.8 | HA | 2.7/95 | 0.2 | 41/95 | 5 |
| pMT/V5.His.A | RANKL | Hygromycin (600 ug/mL) | YES | 3.4/91 | 0.3 | 49/92 | 1.6 | HA | 2.6/96 | 0.4 | 45/92 | 26 |
| pMT/V5.His.A | RANKL | Hygromycin (600 ug/mL) | YES | 3.4/90 | 0.3 | 49/93 | 1.7 | HA | 2.5/95 | 0.4 | 43/93 | 30 |
| pMT/V5.His.A | RANKL | Hygromycin (600 ug/mL) | YES | 3.2/91 | 0.4 | 49/92 | 1.7 | HA | 2.9/95 | 0.3 | 42/92 | 31 |

*Induce using CdCl2
'HA of H5N1 avian flu
"The cell count in is shown as (E6 cells/ml)/viability of cells (%)

TABLE A2

Testing of RANKL expression in hSAR containing pHP34s-Hybrid

| Description | Protein | Antibiotic selection | Cell count | Transient (mg/L) | Cell count | Relative exp. Level |
|---|---|---|---|---|---|---|
| pHP34s-Hybrid.i | RANKL | Zeocin (1500 ug/mL) | 2.1E6 | 4.9 | 41/93 | 1.2 |
| pHP34s-Hybrid.i | RANKL | Zeocin (1500 ug/mL) | '2.1E6 | 5.4 | 40/92 | 1.2 |
| pHP34s-Hybrid | RANKL | Zeocin (1500 ug/mL) | 2.1E6 | 1.2 | 45/93 | 1.0 |
| pHP34s-Hybrid | RANKL | Zeocin (1500 ug/mL) | '2.1E6 | 1.6 | 48/93 | 1.0 |
| pHP34s-Hybrid-hSAR-FF | RANKL | Zeocin (1500 ug/mL) | 2.1E6 | 1.4 | 45/92 | 1.4 |
| pHP34s-Hybrid-hSAR-FR | RANKL | Zeocin (1500 ug/mL) | '2.1E6 | 1.2 | 49/92 | 1.5 |
| pHP34s-Hybrid-hSAR-RF | RANKL | Zeocin (1500 ug/mL) | 2.1E6 | 1.4 | 51/91 | 1.3 |
| pHP34s-Hybrid-hSAR-RR | RANKL | Zeocin (1500 ug/mL) | '2.1E6 | 1.1 | 49/92 | 1.4 |

TABLE A3

| Promoter | Protein | Transient (Relative exp level) |
|---|---|---|
| Hybrid -HSP70core | RANKL | 1.53 |
| Hybrid -HSP70core | RANKL | 1.44 |
| Truncated Actin 5C | RANKL | 1.07 |
| Truncated Actin 5C | RANKL | 1.00 |

List of Sequences:

SEQ ID NO: 1:
pHP 16. Full-length HSP70 promoter (bold sequence corresponds to SEQ ID NO: 2)
CTAGAATCCCAAAACAAACTGGTTATTGTGGTAGGTCATTTGTTTGGCAG

AAAGAAAACTCGAGAAATTTCTCTGGCCGTTATTCGTTATTCTCTCTTTT

CTTTTTGGGTCTCTCCCTCTCTGCACTAATGCTCTCTCACTCTGTCACAC

AGTAAACGGCATACTGCTCTCGTTGGTTCGAGAGAGCGCGCCTCGAATGT

TCGCGAAAAGAGCGCCGGAGTATAAATAGAGGCGCTTCGTCTACGGAGCG

ACAATTCAATTCAAACAAGCAAAGTGAACACGTCGCTAAGCGAAAGCTAA

GCAAATAAACAAGCGCAGCTGAACAAGCTAAACAATCTGCAGTAAAGTGC

AAGTTAAAGTGAATCAATTAAAAGTAACCAGCAACCAAGTAAATCAACTG

CAACTACTGAAATCTGCCAAGAAGTAATTATTGAATACAAGAAGAGAACT

CTGAATA

SEQ ID NO: 2:
pHP12 Truncated HSP70 promoter (bold sequence corresponds to HSP70 CORE PROMOTER (SEQ ID NO: 37)
CTCGAGAAATTTCTCTGGCCGTTATTCGTTATTCTCTCTTTTCTTTTTGG

GTCTCTCCCTCTCTGCACTAATGCTCTCTCACTCTGTCACACAGTAAACG

GCATACTGCTCTCGTTGGTTCGAGAGAGCGCGCCTCGAATGTTCGCGAAA

AGAGCGCCGGAGTATAAATAGAGGCGCTTCGTCTACGGAGCGACAATTCA

ATTCAAACAAGCAAAGTGAACACGTCGCTAAGCGAAAGCTAAGCAAATAA

ACAAGCGCAGCTGAACAAGCTAAACAATCTGCAG

SEQ ID NO: 3:
pHP11b Actin5C mutant promoter from NheI-HindIII
GCTAGCTAAAAAAAATCATGAATGGCATCAACTCTGAATCAAATCTTTGC

AGATGCACCTACTTCTCATTTCCACTGTCACATCATTTTTCCAGATCTCG

CTGCCTGTTATGTGGCCCACAAACCAAGACACGTTTTATGGCCATTAAAG

CTGGCTGATCGTCGCCAAACACCAAATACATAATGAATATGTACACATTC

GAGAAAGAAGCGATCAAAGAAGCGTCTTCGGGCGGAGTAGGAGAATGCGG

AGGAGAAGGAGAACGAGCTGATCTAGTATCTCTCCACAATCCAATGCCAA

CTGACCAACTGGCCATATTCGGAGCAATTTGAAGCCAATTTCCATCGCCT

GGCGATCGCTCCATTCTTGGCTATATGTTTTCACCGTTACCCGGGGCCA

TTTTCAAAGACTCGTCGGCAAGATAAGATTGTGTCACTCGCTGTCTCTCT

TCATTTGTCGAAGAATGCTGAGGAATTTCGCGATGACGTCGGCGAGTATT

TTGAAGAATGAGAATAATTTGTATTTATACGAAAATCAGTTAGTGGAATT

TTCTACAAAAACATGTTATCTATAGATAATTTTGTTGCAAAATATGTTGA

CTATGACAAAGATTGTATGTATATACCTTTAATGTATTCTCATTTTCTTA

TGTATTTATAATGGCAATGATGATACTGATGATATTTTAAGATGATGCCA

GACCAAAAGGCTTGAATTTCTGCGTCTTTTGCCGAACGCAGTGCATGTGC

AATTGTTGTTTTTGGAATATTCAATTTTCGGACTGTCCGCTTTGATTTC

AGTTTCTTGGCTTATTCAAAAAGCAAAGTAAAGCCAAAAAAGCGAGATGG

CAATACCAAATGCGGCAAAACGGTAGTGGAAGGAAAGGGGTGCGGGCAG

CGGAAGGAAGGGTGGGGCGGGGCGTGGCGGGGTCTGTGGCTGGGCGCGAC

GTCACCGACGTTGGAGCCACTCCTTTGACCATGTGTGCGTGTGTGTATTA

TTCGTGTCTCGCCACTCGCCGGTTGTTTTTTCTTTTTATGCTGCGCTCT

CTCTAGCGCCATCTCGCTTACGCATGCTCAACGCACCGCATGTTGCCGTT

TCCTTTTATGCGTCATTTTGGCTCGAAATAGGCAATTATTTAAACAAAGA

TTAGTCAACGAAAACGCTAAAATAAATAAGTCTACAATATGGTTACTTAT

TGCCATGTGTGTGCAGCCAACGATAGCAACAAAAGCAACAACACAGGTGG

CTTTCCCTCTTTCACTTTTTGTTTGCAAGCCGCGTGCGAGCAAGACGGCA

CGACCGGCAAACGCAATTACGCTGACAAAGAGCAGACGAAGTTTTGGCGA

AAAACATCAAGGCGCCTGATACGAATGCATTTGCAATAACAATTGCGATA

TTTAATATTGTTTATGAAGCTGTTTGACTTCAAAACACACAAAAAAAAAA

ATAAAACAAATTATTTGAAAGAGAATTAGGAATCGGACGCTTATCGTTAG

GGTAACAACAAGAAATGCTTACTGAGTCACAGCCTCTGGAAAACTGCCGC

AAGCCAGAGAGAGAGAAAAAGAGGGAGAGCAGCTTAGACCGCATGTGC

TTGTGTGTGAGGCGTCTCTCTCTTCGTCTCTGTTGCGCAAACGCATAGAC

TGCACTGAAAAAATCGATTACCTATTTTTATGAATGAATATTTGCACTA

TTACTATTCAAAACTATTAAGATAGCAATCACATTCAATAGCCAAATACT

ATACCACCTGAGCGATGCAACGAAATGATCAATTTGAGCAAAAATGCTGC

ATATTTAGGACGGCATCATTATAGAAATGCTTCTTGCTGTGTACTTTTCT

CTCGTCTGGCAGCTGTTTCGCCGTTATTGTTAAAACCGGCTTAAGTTAGG

TGTGTTTTCTACGACTAGTGAATGCCCTACTAGAAGATGTGTGTTGCACA

AAATGTCCCTGGAATAACCAATTTGAAGTGCAGATAGCAGTAAACGTAAG

CTAATATGAATATTATTTAACTGTAATGTTTTAATATCGCTGGACATTAC

TAATAAACCCACTATAAACACATGTACATATGTATGTTTTGGCATACAAT

GAGTAGTTGGGGAAAAAATGTGTAAAAGCACCGTGACCATCACAGCATAA

AGATAACCAGCTGAAGTATCGAATATGAGTAACCCCCAAATTGAATCACA

TGCCGCAACTGATAGGACCCATGGAAGTACACTCTTCATGGCGATATACA

AGACACACACAAGCACGAACACCCAGTTGCGGAGGAAATTCTCCGTAAAT

GAAAACCCAATCGGCGAACAATTCATACCCATATATGGTAAAAGTTTTGA

ACGCGACTTGAGAGCGGAGAGCATTGCGGCTGATAAGGTTTTAGCGCTAA

GCGGGCTTTATAAAACGGGCTGCGGGACCAGTTTTCATATCACTACCGTT

TGAGTTCTTGTGCTGTGTGGATACTCCTCCCGACACAAAGCCGCTCCATC

AGCCAGCAGTCGTCTAATCCAGAGACAAGCTT

SEQ ID NO: 4:
p805 Actin5C promoter (Sequence from pAc5.1
invitrogen)
GATACTTCTAAAAAAAATCATGAATGGCATCAACTCTGAATCAAATCTTT

GCAGATGCACCTACTTCTCATTTCCACTGTCACATCATTTTTCCAGATCT

CGCTGCCTGTTATGTGGCCCACAAACCAAGACACGTTTTATGGCCATTAA

AGCTGGCTGATCGTCGCCAAACACCAAATACATATCAATATGTACATTCG

AGAAAGAAGCGATCAAAGAAGCGTCTTCGGGCGAGTAGGAGAATGCGGAG

GAGAAGGAGAACGAGCTGATCTAGTATCTCTCCACAATCCAATGCCAACT

GACCAACTGGCCATATTCGGAGCAATTTGAAGCCAATTTCCATCGCCTGG

CGATCGCTCCATTCTTGGCTATATGTTTTCACCGTTCCCGGGGCCATTT

TCAAAGACTCGTCGGTAAGATAAGATTGTGTCACTCGCTGTCTCTCTTCA

TTTGTCGAAGAATGCTGAGGAATTTCGCGATGACGTCGGCGAGTATTTTG

AAGAATGAGAATAATTTGTATTTATACGAAAATCAGTTAGTGGAATTTC

TACAAAAACATGTTATCTATAGATAATTTTGTTGCAAAATATGTTGACTA

TGACAAAGATTGTATGTATATACCTTTAATGTATTCTCATTTTCTTATGT

ATTTATAATGGCAATGATGATACTGATGATATTTTAAGATGATGCCAGAC

CACAGGCTGATTTCTGCGTCTTTTGCCGAACGCAGTGCATGTGCGGTTGT

TGTTTTTTGGAATAGTTTCAATTTTCGGACTGTCCGCTTTGATTTCAGTT

TCTTGGCTTATTCAAAAAGCAAAGTAAAGCCAAAAAAGCGAGATGGCAAT

ACCAAATGCGGCAAAACGGTAGTGGAAGGAAAGGGGTGCGGGCAGCGGA

AGGAAGGGTGGGCGGGGCGTGGCGGGGTCTGTGGCTGGGCGCGACGTCA

CCGACGTTGGAGCCACTCCTTTGACCATGTGTGCGTGTGTATTATTCG

TGTCTCGCCACTCGCCGGTTGTTTTTTCTTTTTATCTCGCTCTCTAG

CGCCATCTCGTACGCATGCTCAACGCACCGCATGTTGCCGTGTCCTTTAT

GCGTCATTTTGGCTCGAAATAGGCAATTATTTAAACAAAGATTAGTCAAC

GAAAACGCTAAAATAAATAAGTCTACAATATGGTTACTTATTGCCATGTG

TGTGCAGCCAACGATAGCAACAAAAGCAACAACACAGTGGCTTTCCCTCT

TTCACTTTTTGTTTGCAAGCCGCGTGCGAGCAAGACGGCACGACCGGCAAA

CGCAATTACGCTGACAAAGAGCAGACGAAGTTTTGGCCGAAAAACATCAA

```
-continued
GGCGCCTGATACGAATGCATTTGCAATAACAATTGCGATATTTAATATTG
TTTATGAAGCTGTTTGACTTCAAAACACACAAAAAAAAAAATAAAACAAA
TTATTTGAAAGAGAATTAGGAATCGGACAGCTTATCGTTACGGGCTAACA
GCACACCGAGACGAAATAGCTTACCTGACGTCACAGCCTCTGGAAGAACT
GCCGCCAAGCAGAGAGAGAGAGAAAAAGAGGGAGAGCAGCTTAGACCGCA
TGTGCTTGTGTGTGAGGCGTCTCTCTCTTCGTCTCCTGTTTGCGCAAACG
CATAGACTGCACTGAGAAAATCGATTACCTATTTTTTATGAATGAATATT
TGCACTATTACTATTCAAAACTATTAAGATAGCAATCACATTCAATAGCC
AAATACTATACCACCTGAGCGATGCAACGAAATGATCAATTTGAGCAAAA
ATGCTGCATATTTAGGACGGCATCATTATAGAAATGCTTCTTGCTGTGTA
CTTTTCTCTCGTCTGGCAGCTGTTTCGCCGTTATTGTTAAAACCGGCTTA
AGTTAGGTGTGTTTTCTACGACTAGTGATGCCCCTACTAGAAGATGTGTG
TTGCACAAATGTCCCTGAATAACCAATTTGAAGTGCAGATAGCAGTAAAC
GTAAGCTAATATGAATATTATTTAACTGTAATGTTTTAATATCGCTGGAC
ATTACTAATAAACCCACTATAAACACATGTACATATGTATGTTTTGGCAT
ACAATGAGTAGTTGGGGAAAAAATGTGTAAAAGCACCGTGACCATCACAG
CATAAAGATAACCAGCTGAAGTATCGAATATGAGTAACCCCCAAATTGAA
TCACATGCCGCAACTGATAGGACCCATGGAAGTACACTCTTCATGGCGAT
ATACAAGACACACACAAGCACGAACACCCAGTTGCGGAGGAAATTCTCCG
TAAATGAAAACCCAATCGGCGAACAATTCATACCCATATATGGTAAAAGT
TTTGAACGCGACTTGAGAGCGGAGAGCATTGCGGCTGATAAGGTTTTAGC
GCTAAGCGGGCTTTATAAAACGGGCTGCGGGACCAGTTTTCATATCACTA
CCGTTTGAGTTCTTGTGCTGTGTGGATACTCCTCCCGACACAAAGCCGCT
CCATCAGCCAGCAGTCGTCTAATCCAGAGACCCCGGAT SEQ ID NO: 5:
pHP17 Truncated Actin5C_2, 1469 nt
GCATGCTCAACGCACCGCATGTTGCCGTGTCCTTTATGCGTCATTTTGGC
TCGAAATAGGCAATTATTTAAACAAAGATTAGTCAACGAAAACGCTAAAA
TAAATAAGTCTACAATATGGTTACTTATTGCCATGTGTGTGCAGCCAACG
ATAGCAACAAAAGCAACAACACAGTGGCTTTCCCTCTTTCACTTTTTGTT
TGCAAGCGCGTGCGAGCAAGACGGCACGACCGGCAAACGCAATTACGCTG
ACAAAGAGCAGACGAAGTTTTGGCCGAAAAACATCAAGGCGCCTGATACG
AATGCATTTGCAATAACAATTGCGATATTTAATATTGTTTATGAAGCTGT
TTGACTTCAAAACACACAAAAAAAAAAATAAAACAAATTATTTGAAAGAG
AATTAGGAATCGGACAGCTTATCGTTACGGGCTAACAGCACACCGAGACG
AAATAGCTTACCTGACGTCACAGCCTCTGGAAGAACTGCCGCCAAGCAGA
GAGAGAGAAAAAGAGGGAGAGCAGCTTAGACCGCATGTGCTTGTGTGT
GAGGCGTCTCTCTCTTCGTCTCCTGTTTGCGCAAACGCATAGACTGCACT
GAGAAAATCGATTACCTATTTTTTATGAATGAATATTTGCACTATTACTA
TTCAAAACTATTAAGATAGCAATCACATTCAATAGCCAAATACTATACCA
CCTGAGCGATGCAACGAAATGATCAATTTGAGCAAAAATGCTGCATATTT
AGGACGGCATCATTATAGAAATGCTTCTTGCTGTGTACTTTTCTCTCGTC
TGGCAGCTGTTTCGCCGTTATTGTTAAAACCGGCTTAAGTTAGGTGTGTT
TTCTACGACTAGTGATGCCCCTACTAGAAGATGTGTGTTGCACAAATGTC
CCTGAATAACCAATTTGAAGTGCAGATAGCAGTAAACGTAAGCTAATATG
AATATTATTTAACTGTAATGTTTTAATATCGCTGGACATTACTAATAAAC
CCACTATAAACACATGTACATATGTATGTTTTGGCATACAATGAGTAGTT
GGGGAAAAAATGTGTAAAAGCACCGTGACCATCACAGCATAAAGATAACC
AGCTGAAGTATCGAATATGAGTAACCCCCAAATTGAATCACATGCCGCAA
CTGATAGGACCCATGGAAGTACACTCTTCATGGCGATATACAAGACACAC
ACAAGCACGAACACCCAGTTGCGGAGGAAATTCTCCGTAAATGAAAACCC
AATCGGCGAACAATTCATACCCATATATGGTAAAAGTTTTGAACGCGACT
TGAGAGCGGAGAGCATTGCGGCTGATAAGGTTTTAGCGCTAAGCGGGCTT
TATAAAACGGGCTGCGGGACCAGTTTTCATATCACTACCGTTTGAGTTCT
TGTGCTGTGTGGATACTCCTCCCGACACAAAGCCGCTCCATCAGCCAGCA
GTCGTCTAATCCAGAGAC SEQ ID NO: 6:
pHP18 Truncated Actin5C_3, 612 nt
CTAGTGAATGCCCTACTAGAAGATGTGTGTTGCACAAAATGTCCCTGGAA
TAACCAATTTGAAGTGCAGATAGCAGTAAACGTAAGCTAATATGAATATT
ATTTAACTGTAATGTTTTAATATCGCTGGACATTACTAATAAACCCACTA
TAAACACATGTACATATGTATGTTTTGGCATACAATGAGTAGTTGGGGAA
AAAATGTGTAAAAGCACCGTGACCATCACAGCATAAAGATAACCAGCTGA
AGTATCGAATATGAGTAACCCCCAAATTGAATCACATGCCGCAACTGATA
GGACCCATGGAAGTACACTCTTCATGGCGATATACAAGACACACACAAGC
ACGAACACCCAGTTGCGGAGGAAATTCTCCGTAAATGAAAACCCAATCGG
CGAACAATTCATACCCATATATGGTAAAAGTTTTGAACGCGACTTGAGAG
CGGAGAGCATTGCGGCTGATAAGGTTTTAGCGCTAAGCGGGCTTTATAAA
ACGGGCTGCGGGACCAGTTTTCATATCACTACCGTTTGAGTTCTTGTGCT
GTGTGGATACTCCTCCCGACACAAAGCCGCTCCATCAGCCAGCAGTCGTC
TAATCCAGAGAC SEQ ID NO: 7:
pOPIE2
GTCATGATGATAAACAATGTATGGTGCTAATGTTGCTTCAACAACAATTC
TGTTGAACTGTGTTTTCATGTTTGCCAACAAGCACCTTTATACTCGGTGG
CCTCCCCACCACCAACTTTTTTGCACTGCAAAAAAACACGCTTTTGCACG
CGGGCCCATACATAGTACAAACTCTACGTTTCGTAGACTATTTTACATAA
ATAGTCTACACCGTTGTATACGCTCCAAATACACTACCACACATTGAACC
TTTTTGCAGTGCAAAAAGTACGTGTCGGCAGTCACGTAGGCCGGCCTTA
TCGGGTCGCGTCCTGTCACGTACGAATCACATTATCGGACCGGACGAGTG
TTGTCTTATCGTGACAGGACGCCAGCTTCCTGTGTTGCTAACCGCAGCCG
GACGCAACTCCTTATCGGAACAGGACGCGCCTCCATATCAGCCGCGCGTT
ATCTCATGCGCGTGACCGGACACGAGGCGCCCGTCCCGCTTATCGCGCCT
ATAAATACAGCCCGCAACGATCTGGTAAACACAGTTGAACAGTCATCTGTT
```

SEQ ID NO: 8:
Gypsy insulator from (Pubmed: gi|12237306:
1188-1574 Stinger GFP transformation vector)
TCACGTAATAAGTGTGCGTTGAATTTATTCGCAAAAACATTGCATATTTT

CGGCAAAGTAAAATTTTGTTGCATACCTTATCAAAAAATAAGTGCTGCAT

ACTTTTTAGAGAAACCAAATAATTTTTATTGCATACCCGTTTTTAATAA

AATACATTGCATACCCTCTTTTAATAAAAAATATTGCATACTTTGACGAA

ACAAATTTTCGTTGCATACCCAATAAAAGATTATTATATTGCATACCCGT

TTTTAATAAAATACATTGCATACCCTCTTTTAATAAAAAATATTGCATAC

GTTGACGAAACAAATTTTCGTTGCATACCCAATAAAAGATTATTATATTG

CATACCTTTTCTTGCCATACCATTTAGCCGATCAATT

Primer List

| Name | Oligo Sequence | SEQ ID NO: |
|---|---|---|
| 2007 | CGCTCAGTGGAACGAAAACTCACG | 9 |
| 4003 | AAGGGATTTTGGTCATGAACAATAAAACTGTCTGCTTACATAAACAGTAATACAAGGGGTGTTCATAGTATAATACGACTCACTATAGGAGGGCCACCATGGCCAAGTTGAC | 10 |
| 4004 | GCAGACAGTTTTATTGTTCATGACCAAAATCCCTTGCAGAGATCCGAATTAATTCG | 11 |
| 4009 | CACCCAGGCCAGGGTGTTGTCCGGC | 12 |
| 4032 | GTTTTATTGTTCATGACCAAAATCCC | 13 |
| 4035 | GCGCCTCGAATGTTCGCGAACTTAAGAGCGCCGGAGTATAAATAG | 14 |
| 4036 | CTATTTATACTCCGGCGCTCTTAAGTTCGCGAACATTCGAGGCGC | 15 |
| 4037 | GTAAAAGTTTTGAACGCGACTTAAGGAGAGCGGAGAGCATTGCGG | 16 |
| 4038 | CCGCAATGCTCTCCGCTCTCCTTAAGTCGCGTTCAAAACTTTTAC | 17 |
| 590 | TTCACTGCATTCTAGTTGTGG | 18 |
| 917 | CTAAGATTTAGTCAGATATCG | 19 |
| 975 | CATCAATGTATCTTATCATGTCTGCTAGCGGATCATGATGATAAACAATGT | 20 |
| 976 | ACATTGTTTATCATCATGATCCGCTAGCAGACATGATAAGATACATTGATG | 21 |
| 979 | TCTGCTAGCTAAAAAAAATCATGAATGGC | 22 |
| 980 | CCAAGCTTGTCTCTGGATTAGACGACTG | 23 |
| 981 | TGCTAGCCTCGAGAAATTTCTCTGGC | 24 |
| 982 | CCAAGCTTCTGCAGATTGTTTAGCTTG | 25 |
| 986 | AGAATTCAGCTGAGCTCGAGGGTACCAAGC | 26 |
| 987 | GGTTTGTCCAAACTCATCAATGTAT | 27 |
| 990 | TTATTGCCATGTGTGTGCAG | 28 |
| 992 | CGATGCAACGAAATGATCAA | 29 |
| 993 | GGCTGATAAGGTTTTAGCGCTA | 30 |
| 994 | CAAATTATTTGAAAGAGAATTAG | 31 |
| 995 | GTTTTAATATCGCTGGACATTAC | 32 |

SEQ ID NO: 33: pAC5.1 actin
promoter (2516 bp) sequence:
TAAAAAAAATCATGAATGGCATCAACTCTGAATCAAATCTTTGCAGATG
CACCTACTTCTCATTTCCACTGTCACATCATTTTTCCAGATCTCGCTGC
CTGTTATGTGGCCCACAAACCAAGACACGTTTTATGGCCATTAAAGCTG
GCTGATCGTCGCCAAACACCAAATACATATCAATATGTACATTCGAGAA
AGAAGCGATCAAAGAAGCGTCTTCGGGCGAGTAGGAGAATGCGGAGGAG
AAGGAGAACGAGCTGATCTAGTATCTCTCCACAATCCAATGCCAACTGA
CCAACTGGCCATATTCGGAGCAATTTGAAGCCAATTTCCATCGCCTGGC
GATCGCTCCATTCTTGGCTATATGTTTTTCACCGTTACCCGGGGCCATT
TTCAAAGACTCGTCGGCAAGATAAGATTGTGTCACTCGCTGTCTCTCTT
CATTTGTCGAAGAATGCTGAGGAATTTCGCGATGACGTCGGCGAGTATT
TTGAAGAATGAGAATAATTTGTATTTATACGAAAATCAGTTAGTGGAAT
TTTCTACAAAAACATGTTATCTATAGATAATTTTGTTGCAAAATATGTT
GACTATGACAAAGATTGTATGTATATACCTTTAATGTATTCTCATTTTC
TTATGTATTTATAATGGCAATGATGATACTGATGATATTTTAAGATGAT
GCCAGACCAAAAGGCTTGAATTTCTGCGTCTTTTGCCGAACGCAGTGCA
TGTGCAATTGTTGTTTTTTGGAATATTCAATTTTCGGACTGTCCGCTTT
GATTTCAGTTTCTTGGCTTATTCAAAAAGCAAAGTAAAGCCAAAAAAGC
GAGATGGCAATACCAAATGCGGCAAAACGGTAGTGGAAGGAAAGGGGTG
CGGGGCAGCGGAAGGAAGGGTGGGGCGGGGCGTGGCGGGGTCTGTGGCT
GGGCGCGACGTCACCGACGTTGGAGCCACTCCTTTGACCATGTGTGCGT
GTGTGTATTATTCGTGTCTCGCCACTCGCCGGTTGTTTTTTTCTTTTTA
TGCTGCGCTCTCTCTAGCGCCATCTCGCTTACGCATGCTCAACGCACCG
CATGTTGCCGTTTCCTTTTATGCGTCATTTTGGCTCGAAATAGGCAATT
ATTTAAACAAAGATTAGTCAACGAAAACGCTAAAATAAATAAGTCTACA
ATATGGTTACTTATTGCCATGTGTGTGCAGCCAACGATAGCAACAAAAG
CAACAACACAGGTGGCTTTCCCTCTTTCACTTTTTGTTTGCAAGCCGCG
TGCGAGCAAGACGGCACGACCGGCAAACGCAATTACGCTGACAAAGAGC
AGACGAAGTTTTGGCGAAAAACATCAAGGCGCCTGATACGAATGCATTT
GCAATAACAATTGCGATATTTAATATTGTTTATGAAGCTGTTTGACTTC
AAAACACACAAAAAAAAAATAAAACAATTATTTGAAAGAGAATTAGG
AATCGGACGCTTATCGTTAGGGTAACAACAAGAAATGCTTACTGAGTCA
CAGCCTCTGGAAAACTGCCGCAAGCCAGAGAGAGAGAAAAGAGGGA
GAGCAGCTTAGACCGCATGTGCTTGTGTGTGAGGCGTCTCTCTCTTCGT
CTCTGTTGCGCAAACGCATAGACTGCACTGAAAAAATCGATTACCTATT
TTTTATGAATGAATATTTGCACTATTACTATTCAAAACTATTAAGATAG
CAATCACATTCAATAGCCAAATACTATACCACCTGAGCGATGCAACGAA
ATGATCAATTTGAGCAAAAATGCTGCATATTTAGGACGGCATCATTATA
GAAATGCTTCTTGCTGTGTACTTTTCTCTCGTCTGGCAGCTGTTTCGCC
GTTATTGTTAAAACCGGCTTAAGTTAGGTGTGTTTTCTACGACTAGTGA
ATGCCCTACTAGAAGATGTGTGTTGCACAAAATGTCCCTGGAATAACCA
ATTTGAAGTGCAGATAGCAGTAAACGTAAGCTAATATGAATATTATTTA
ACTGTAATGTTTTAATATCGCTGGACATTACTAATAAACCCACTATAAA
CACATGTACATATGTATGTTTTGGCATACAATGAGTAGTTGGGGAAAAA
ATGTGTAAAAGCACCGTGACCATCACAGCATAAAGATAACCAGCTGAAG
TATCGAATATGAGTAACCCCCAAATTGAATCACATGCCGCAACTGATAG
GACCCATGGAAGTACACTCTTCATGGCGATATACAAGACACACACAAGC
ACGAACACCCAGTTGCGGAGGAAATTCTCCGTAAATGAAAACCCAATCG
GCGAACAATTCATACCCATATATGGTAAAAGTTTTGAACGCGACTTGAG
AGCGGAGAGCATTGCGGCTGATAAGGTTTTAGCGCTAAGCGGGCTTTAT
AAAACGGGCTGCGGGACCAGTTTTCATATCACTACCGTTTGAGTTCTTG
TGCTGTGTGGATACTCCTCCCGACACAAAGCCGCTCCATCAGCCAGCAG
TCGTCTAATCCAGAGAC SEQ ID NO: 34: pHP15c_su(hw) vector:
CATAGTATAATACGACTCACTATAGGAGGGCCACCATGGCCAAGTTGAC
CAGTGCCGTTCCGGTGCTCACCGCGCGCGACGTCGCCGGAGCGGTCGAG
TTCTGGACCGACCGGCTCGGGTTCTCCCGGGACTTCGTGGAGGACGACT
TCGCCGGTGTGGTCCGGGACGACGTGACCCTGTTCATCAGCGCGGTCCA
GGACCAGGTGGTGCCGGACAACACCCTGGCCTGGGTGTGGGTGCGCGGC
CTGGACGAGCTGTACGCCGAGTGGTCGGAGGTCGTGTCCACGAACTTCC
GGGACGCCTCCGGGCCGGCCATGACCGAGATCGGCGAGCAGCCGTGGGG
GCGGGAGTTCGCCCTGCGCGACCCGGCCGGCAACTGCGTGCACTTCGTG
GCCGAGGAGCAGGACTGACCGACGCCGACCAACACCGCCGGTCCGACGG
CGGCCCACGGGTCCCAGGGGGTCGACCTCGAAACTTGTTTATTGCAGC
TTATAATGGTTACAAATAAAGCAATAGCATCACAAATTTCACAAATAAA
GCATTTTTTTCACTGCATTCTAGTTGTGGTTTGTCCAAACTCATCAATG
TATCTTATCATGTCTGCTAGCTCACGTAATAAGTGTGCGTTGAATTTAT
TCGCAAAAACATTGCATATTTTCGGCAAAGTAAAATTTTGTTGCATACC
TTATCAAAAAATAAGTGCTGCATACTTTTTAGAGAAACCAAATAATTTT
TTATTGCATACCCGTTTTTAATAAAATACATTGCATACCCTTTTAATAA
AAAATATTGCATACTTTGACGAAACAAATTTTCGTTGCATACCCAATAA
AAGATTATTATATTGCATACCCGTTTTTAATAAAATACATTGCATACCC
TCTTTTAATAAAAATATTGCATACGTTGACGAAACAAATTTTCGTTGC
ATACCCAATAAAAGATTATTATATTGCATACCTTTTCTTGCCATACCAT
TTAGCCGATCAATTCTCGAGAAATTTCTGGCCGTTATTCGTTATTCT
CTCTTTTCTTTTTGGGTCTCTCCCTCTCTGCACTAATGCTCTCTCACTC
TGTCACACAGTAAACGGCATACTGCTCTCGTTGGTTCGAGAGAGCGCGC
CTCGAATGTTCGCGAAAAGAGCGCCGGAGTATAAATAGAGGCGCTTCGT
CTACGGAGCGACAATTCAATTCAAACAAGCAAAGTGAACACGTCGCTAA
GCGAAAGCTAAGCAAATAAACAAGCGCAGCTGAACAAGCTAAACAATCT
GCAGAAGCTTGGTACCCTCGAGCTCAGCTGAATTCTGGATCCTCTAGAC

```
CGGTCATATGCGGCCGCGGATCGATCGATATCTGACTAAATCTTAGTTT
GTATTGTCATGTTTTAATACAATATGTTATGTTTAAATATGTTTTTAAT
AAATTTTATAAAATAATTTCAACTTTTATTGTAACAACATTGTCCATTT
ACACACTCCTTTCAAGCGCGTGGGACTCGATGCTCTCACGTAATAAGTG
TGCGTTGAATTTATTCGCAAAAACATTGCATATTTTCGGCAAAGTAAAA
TTTTGTTGCATACCTTATCAAAAAATAAGTGCTGCATACTTTTTAGAGA
AACCAAATAATTTTTTATTGCATACCCGTTTTTAATAAAATACATTGCA
TACCCTCTTTTAATAAAAAATATTGCATACTTTGACGAAACAAATTTTC
GTTGCATACCCAATAAAGATTATTATATTGCATACCCGTTTTTAATAA
AATACATTGCATACCCTCTTTTAATAAAAAATATTGCATACGTTGACGA
AACAAATTTTCGTTGCATACCCAATAAAGATTATTATATTGCATACCT
TTTCTTGCCATACCATTTAGCCGATCAATTACTCAAAGGCGGTAATACG
GTTATCCACAGAATCAGGGGATAACGCAGGAAAGAACATGTGAGCAAAA
GGCCAGCAAAAGGCCAGGAACCGTAAAAAGGCCGCGTTGCTGGCGTTTT
TCCATAGGCTCCGCCCCCTGACGAGCATCACAAAAATCGACGCTCAAG
TCAGAGGTGGCGAAACCCGACAGGACTATAAAGATACCAGGCGTTTCCC
CCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCAATG
CTCACGCTGTAGGTATCTCAGTTCGGTGTAGGTCGTTCGCTCCAAGCTG
GGCTGTGTGCACGAACCCCCCGTTCAGCCCGACCGCTGCGCCTTATCCG
GTAACTATCGTCTTGAGTCCAACCCGGTAAGACACGACTTATCGCCACT
GGCAGCAGCCACTGGTAACAGGATTAGCAGAGCGAGGTATGTAGGCGGT
GCTACAGAGTTCTTGAAGTGGTGGCCTAACTACGGCTACACTAGAAGGA
CAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGT
TTTTTTGTTTGCAAGCAGCAGATTACGCGCAGAAAAAAAGGATCTCAAG
AAGATCCTTTGATCTTTTCTACGGGGTCTGACGCTCAGTGGAACGAAAA
CTCACGTTAAGGGATTTTGCATGCGCTAAGCGGGCTTTATAAAACGGGC
TGCGGGACCAGTTTTCATATCACTACCGTTTGAGTTCTTGTGCTGTGTG
GATACTCCTCCCGACACCGAATTAATTCGGATCTCTGCAAGGGATTTTG
GTCATGAACAATAAAACTGTCTGCTTACATAAACAGTAATACAAGGGGT
GTT

SEQ ID NO: 35: pHP15c vector:
CATAGTATAATACGACTCACTATAGGAGGGCCACCATGGCCAAGTTGAC
CAGTGCCGTTCCGGTGCTCACCGCGCGCGACGTCGCCGGAGCGGTCGAG
TTCTGGACCGACCGGCTCGGGTTCTCCCGGGACTTCGTGGAGGACGACT
TCGCCGGTGTGGTCCGGGACGACGTGACCCTGTTCATCAGCGCGGTCCA
GGACCAGGTGGTGCCGGACAACACCCTGGCCTGGGTGTGGGTGCGCGGC
CTGGACGAGCTGTACGCCGAGTGGTCGGAGGTCGTGTCCACGAACTTCC
GGGACGCCTCCGGGCCGGCCATGACCGAGATCGGCGAGCAGCCGTGGGG
GCGGGAGTTCGCCCTGCGCGACCCGGCCGGCAACTGCGTGCACTTCGTG
GCCGAGGAGCAGGACTGACCGACGCCGACCAACACCGCCGGTCCGACGG
CGGCCCACGGGTCCCAGGGGGGTCGACCTCGAAACTTGTTTATTGCAGC
TTATAATGGTTACAAATAAAGCAATAGCATCACAAATTTCACAAATAAA
GCATTTTTTCACTGCATTCTAGTTGTGGTTTGTCCAAACTCATCAATG
TATCTTATCATGTCTGCTAGCCTCGAGAAATTTCTCTGGCCGTTATTCG
TTATTCTCTCTTTTCTTTTTGGGTCTCTCCCTCTCTGCACTAATGCTCT
CTCACTCTGTCACACAGTAAACGGCATACTGCTCTCGTTGGTTCGAGAG
AGCGCGCCTCGAATGTTCGCGAAAAGAGCGCGGAGTATAAATAGAGGC
GCTTCGTCTACGGAGCGACAATTCAATTCAAACAAGCAAAGTGAACACG
TCGCTAAGCGAAAGCTAAGCAAATAAACAAGCGCAGCTGAACAAGCTAA
ACAATCTGCAGAAGCTTGGTACCCTCGAGCTCAGCTGAATTCTGGATCC
TCTAGACCGGTCATATGCGGCCGCGGATCGATCGATATCTGACTAAATC
TTAGTTTGTATTGTCATGTTTTAATACAATATGTTATGTTTAAATATGT
TTTTAATAAATTTTATAAAATAATTTCAACTTTTATTGTAACAACATTG
TCCATTTACACACTCCTTTCAAGCGCGTGGGACTCGATGCTCACTCAAA
GGCGGTAATACGGTTATCCACAGAATCAGGGGATAACGCAGGAAAGAAC
ATGTGAGCAAAAGGCCAGCAAAAGGCCAGGAACCGTAAAAAGGCCGCGT
TGCTGGCGTTTTTCCATAGGCTCCGCCCCCTGACGAGCATCACAAAAA
TCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGC
GCTTTCTCAATGCTCACGCTGTAGGTATCTCAGTTCGGTGTAGGTCGTT
CGCTCCAAGCTGGGCTGTGTGCACGAACCCCCCGTTCAGCCCGACCGCT
GCGCCTTATCCGGTAACTATCGTCTTGAGTCCAACCCGGTAAGACACGA
CTTATCGCCACTGGCAGCAGCCACTGGTAACAGGATTAGCAGAGCGAGG
TATGTAGGCGGTGCTACAGAGTTCTTGAAGTGGTGGCCTAACTACGGCT
ACACTAGAAGGACAGTATTTGGTATCTGCGCTCTGCTGAAGCCAGTTAC
CTTCGGAAAAAGAGTTGGTAGCTCTTGATCCGGCAAACAAACCACCGCT
GGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCA
GTGGAACGAAAACTCACGTTAAGGGATTTTGCATGCGCTAAGCGGGCTT
TATAAAACGGGCTGCGGGACCAGTTTTCATATCACTACCGTTTGAGTTC
TTGTGCTGTGTGGATACTCCTCCCGACACCGAATTAATTCGGATCTCTG
CAAGGGATTTTGGTCATGAACAATAAAACTGTCTGCTTACATAAACAGT
AATACAAGGGGTGTT SEQ ID NO: 36: ACTIN 5C CORE PROMOTER FROM PHP10
CORRESPONDING TO NT 478 TO NT 572 OF
SEQ ID NO: 6:
TAGCGCTAAGCGGGCTTTATAAAACGGGCTGCGGGACCAGTTTTCATAT
CACTACCGTTTGAGTTCTTGTGCTGTGTGGATACTCCTCCCGACAC SEQ ID NO: 37: HSP70 CORE PROMOTER
GAGCGCCGGAGTATAAATAGAGGCGCTTCGTCTACGGAGCGACAATTCA
```

-continued
ATTCAAACAAGCAAAGTGAACACGTCGCTAAGCGAAAGCTA

SEQ ID NO: 38: HIS-tag sequence according to the invention:
ATGAAACACCAACACCAACATCAACATCAACATCAACATCAA -continued
GGACTCCCAGCAATGTCAACGACCGACCTTGAGGCCTACTTCAAAGACT

GTGTGTTTAAGGACTGGGAGGAGCTGGGGGAGGAGATTAGGTTAAAGGT

CTTTGTATTAGGAGGCTGTATGCATAAATTGGTCTG GCGGCCGC TTTA

| Name | Oligo Sequence | SEQ ID NO: |
|---|---|---|
| 1892 | CCTGCGTTATCCCCTGATTCTGTG | 41 |
| 2232 | GCCACCACTTCAAGAACTCT | 42 |
| 2233 | CACGAGGGAGCTTCCAGGGG | 43 |
| 2234 | GGAAAGAACATGTGAGCAAA | 44 |
| 2235 | TTCGCTCCAAGCTGGGCTGT | 45 |
| 2236 | ACAAACCACCGCTGGTAGCG | 46 |
| 901 | GGCCTTTTGCTGGCCTTTTGCTC | 47 |
| 983 | CTGCTAGCCTAGAATCCCAAAACAAACT | 48 |
| 984 | CCAAGCTTTATTCAGAGTTCTCTTCTTGTATTC | 49 |
| 993 | GGCTGATAAGGTTTTAGCGCTA | 50 |
| 2509 | CCCGAGCGAGAGGCCAACAAAGGCCAC | 51 |
| 4000 | GCGAAAGCTAAGCAAATAAACAAGCG | 52 |
| 4001 | CCGGGGCATGCCTCGAGAAATTTCTCTGGCCG | 53 |
| 4002 | CCCGGGAATTAATTCGCTGCAGATTGTTTAGCTTGTTCAG | 54 |
| 4007 | CCGTTTGAGTTCTTGTGCTGTGTGGATACTCCTCCCGACACCGAATTAATTCGGATCTCTGCTTGACAATTAATCATCCGGCTCGTATAATGCATAGTATAATACGACTCACTATAGG | 55 |
| 4008 | CCACACAGCACAAGAACTCAAACGGTAGTGATATGAAAACTGGTCCCGCAGCCCGTTTTATAAAGCCCGCTTAGCGCATGCAAAATCCCTTAACGTGAGTTTTCGTTCC | 56 |
| 4009 | CACCCAGGCCAGGGTGTTGTCCGGC | 57 |

-continued
SEQ ID NO: 39: The 72 bp element sequence with Xba1 and Not1 restriction sites (boxed)
TGC TCTAGA ATGCTTTGCATACTTCTGCCTGCTGGGGAGCCTGGGGAC

TTTCCACACCCTAACTGACACACATTCCACAGCTGGTT GCGGCCGC TT

TA

SEQ ID NO: 40: PRE sequence of HBV with Xba1 and Not1 restriction sites (boxed) (SEQ ID 40):
TGC TCTAGA CGTGGAACCTTTGTGGCTCCTCTGCCGATCCATACTGCG

GAACTCCTAGCCGCTTGTTTTGCTCGCAGCCGGTCTGGAGCAAAGCTCA

TCGGAACTGACAATTCTGTCGTCCTCTCGCGGAAATATACATCGTTTCC

ATGGCTGCTAGGCTGTACTGCCAACTGGATCCTTCGCGGGACGTCCTTT

GTTTACGTCCCGTCGGCGCTGAATCCCGCGGACGACCCCTCGCGGGGCC

GCTTGGGACTCTCTCGTCCCCTTCTCCGTCTGCCGTTCCAGCCGACCAC

GGGGCGCACCTCTCTTTACGCGGTCTCCCCGTCTGTGCCTTCTCATCTG

CCGGTCCGTGTGCACTTCGCTTCACCTCTGCACGTTGCATGGAGACCAC

CGTGAACGCCCATCAGATCCTGCCCAAGGTCTTACATAAGAGGACTCTT

SEQ ID NO: 58:
VECTOR PHP34S (CREATED FROM SYNTHETIC DNA):
AAAGATAACCAGCTGAAGTATCGAATATGAGTAACCCCCAAATTGAATCA

CATGCCGCAACTGATAGGACCCATGGAAGTACACTCTTCATGGCGATATA

CAAGACACACACAAGCACGAACACCCAGTTGCGGAGGAAATTCTCCGTAA

ATGAAAACCCAATCGGCGAACAATTCATACCCATATATGGTAAAAGTTTT

GAACGCGACTTAAGGAGAGCGGAGAGCATTGCGGCTGATAAGGTTTTAGC

GCTAAGCGGGCTTTATAAAACGGGCTGCGGGACCAGTTTTCATATCACTA

CCGTTTGAGTTCTTGTGCTGTGTGGATACTCCTCCCGACACAAAGCCGCT

CCATCAGCCAGCAGTCGTCTAATCCAGAGACAAGCTTGGTACCCTCGAGC

TCAGCTGAATTCTGGATCCTCTAGACGGTCATATGCGGCCGCGGATCGA

TCGATATCTGACTAAATCTTAGTTTGTATTGTCATGTTTTAATACAATAT

GTTATGTTTAAATATGTTTTTAATAAATTTTATAAAATAATTTCAACTTT

TATTGTAACAACATTGTCCATTTACACACTCCTTTCAAGCGCGTGGGACT

CGATGCTCGGCGCCACTCAAAGGCGGTAATACGGTTATCCACAGAATCAG

GGGATAACGCAGGAAAGAACATGTGAGCAAAAGGCCAGCAAAAGGCCAGG

AACCGTAAAAAGGCCGCGTTGCTGGCGTTTTTCCATAGGCTCCGCCCCCC

TGACGAGCATCACAAAAATCGACGCTCAAGTCAGAGGTGGCGAAACCCGA

CAGGACTATAAAGATACCAGGCGTTTCCCCCTGGAAGCTCCCTCGTGCGC

TCTCCTGTTCCGACCCTGCCGCTTACCGGATACCTGTCCGCCTTTCTCCC

TTCGGGAAGCGTGGCGCTTTCTCAATGCTCACGCTGTAGGTATCTCAGTT

CGGTGTAGGTCGTTCGCTCCAAGCTGGGCTGTGTGCACGAACCCCCCGTT

CAGCCCGACCGCTGCGCCTTATCCGGTAACTATCGTCTTGAGTCCAACCC

GGTAAGACACGACTTATCGCCACTGGCAGCAGCCACTGGTAACAGGATTA

GCAGAGCGAGGTATGTAGGCGGTGCTACAGAGTTCTTGAAGTGGTGGCCT

AACTACGGCTACACTAGAAGGACAGTATTTGGTATCTGCGCTCTGCTGAA

GCCAGTTACCTTCGGAAAAAGAGTTGGTAGCTCTTGATCCGGCAAACAAA

CCACCGCTGGTAGCGGTGGTTTTTTTGTTTGCAAGCAGCAGATTACGCGC

AGAAAAAAAGGATCTCAAGAAGATCCTTTGATCTTTTCTACGGGGTCTGA

CGCTCAGTGGAACGAAAACTCACGTTAAGGGATTTTGCATGCGCTAAGCG

GGCTTTATAAAACGGGCTGCGGGACCAGTTTTCATATCACTACCGTTTGA

GTTCTTGTGCTGTGTGGATACTCCTCCCGACACCGAATTAATTCGGATCT

CTGCAAGGGATTTTGGTCATGAACAATAAAACTGTCTGCTTACATAAACA

GTAATACAAGGGGTGTTCATAGTATAATACGACTCACTATAGGAGGGCCA

CCATGGCCAAGTTGACCAGTGCCGTTCCGGTGCTCACCGCGCGCGACGTC

GCCGGAGCGGTCGAGTTCTGGACCGACCGGCTCGGGTTCAGCCGGGACTT

CGTGGAGGACGACTTCGCCGGTGTGGTCCGGGACGACGTGACCCTGTTCA

TCAGCGCGGTCCAGGACCAGGTGGTGCCGGACAACACCCTGGCCTGGGTG

TGGGTGCGCGGCCTGGACGAGCTGTACGCCGAGTGGTCGGAGGTCGTGTC

CACGAACTTCCGGGACGCCTCCGGGCCGGCCATGACCGAGATCGGCGAGC

AGCCGTGGGGGCGGAGTTCGCCCTGCGCGACCCGGCCGGCAACTGCGTG

CACTTCGTGGCCGAGGAGCAGGACTGACGACGCCGACCAACACCGCCGG

TCCGACGGCGGCCCACGGGTCCCAGGGGGTCGACCTCGAAACTTGTTTA

TTGCAGCTTATAATGGTTACAAATAAAGCAATAGCATCACAAATTTCACA

AATAAAGCATTTTTTTCACTGCATTCTAGTTGTGGTTTGTCCAAACTCAT

CAATGTATCTTATCATGTCTTCACGTAATAAGTGTGCGGCTAGCAGTCAA

CTACTAGTGAATGCCCTACTAGAAGATGTGTGTTGCACAAAATGTCCCTG

GAATAACCAATTTGAAGTGCAGATAGCAGTAAACGTAAGCTAATATGAAT

ATTATTTAACTGTAATGTTTTAATATCGCTGGACATTACTAATAAACCCA

CTATAAACACATGTACATATGTATGTTTGGCATACAATGAGTAGTTGGG

GAAAAAATGTGTAAAAGCACCGTGACCATCACAGCAT

SEQ ID NO: 59:
MATRIX ATTACHMENT REGION SEQUENCE (NAMED HSAR
IN VECTOR MAPS):
CTAGAATATTCGCTTTATTTTGGAAATTTCTTTATAAATACGGCTGCTTA

AGTTAATTATG1TAGAGATAATCGAAGGGTTTGTTACGCGGATGTTGTCC

GCCAGAAAGGCCTATGGAACTTTGACAAGATATTCTTAAAAATGTATTTA

CATACTAACTTAAAAAAGCTATTTATTTATTAGATTAATACAGACAATTG

CATGCAGATGATTGTTAGTGTTTTTTATTTAAAATTACGTAAAGGTTGTC

AAGACTGTTGTTGTCAACTGTTTACACTGTGAAATAAGTTGAATTTTTCG

CTTTAAAGGTAAATATGAAGGTTTCTTTGCTTAATTAAACGCAATTTTTT

TATTCAATATAAACAATATTTATTTTACTTATAAATCAAAAACAAATTAA

AAATATTAAATATACAAGAAAATAAACAACAAATTCCAAGTTTGCACACT

TTTGAGTCTATATATAAACGTTAGAAGATCACACAGATTTACATATGTAT

GTACATATGTACTTATGCATGCAAAAGCATATGCAAAAACCGTGTCTTTT

ATGAAAACTAAAGTTAAATAAAGTTAAATACTAAGATATATGTATTTTTG

AATCTTTTTATTGCAGGAAGGGATATTGAACTACATACATATACATACAT

ACATATGTATGTACTTGTACATTTGTAAGCGCGGTATTTACATTTAAACC

AATTAAAATTTTGTATAATCTGGGAGCTTTACAGATTTTTGGGATGGTTA

CAACTCAAAGGGGCGTGGCAATGTAAATAAAATCTGTTCTGGTTATAATG

TGTACATATTCTGTCTCAACTTTCTAAGGCATATGTATAAATACATACAT

AATATATGTATATGTATATATGTACATACATATGTACATATGTAAATATT

TAATTCAATGAATCTACGGCTATAAAAATAATAGGCTTGCCTCATTGACT

GGAGCTATCCGCATAAGCAACATATGTACATACATACATATGTAAA

AAAAAGTAGCAACTAAATTCTAATACATTTTCCG

SEQ ID NO: 60:
INTRON (NAMED INTRN IN VECTOR MAPS) WITH
SACI AND ECORI DIGESTION SITES (UNDERLINED)
ON EITHER END:
<u>GAGCTC</u>GTAAGTATCAAGGTTACAAGACAGGTTTAAGGAGACCAATAGAA

ACTGGGCTTGTCGAGACAGAGAAGACTCTTGCGTTTCTGATAGGCACCTA

TTGGTCTTACTGACATCCACTTTGCCTTTCTCTCCACAG<u>GAATTC</u>

SEQ ID NO: 61:
HA (MODIFIED H5N1 VIETNAM) SEQUENCE IN VECTORS
(INSERTED BETWEEN UNDERLINED ECORI AND NOTI
SITES):
<u>GAATTC</u>GCCACCATGAAGCTGTGCATCCTGCTGGCCGTGGTGGCCTTCGT

GGGCCTGAGCCTGGGCATGAAGCACCAACATCAGCACCAGCACCAACATC

AACACCAGGGTCCAGGTGCCAAGTTCGTGGCCGCTTGGACCCTGAAGGCC

GCCGCCGATCAGATCTGCATTGGATACCACGCCAACAACAGCACCGAGCA

GGTGGACACCATCATGGAGAAGAACGTGACCGTGACCCACGCCCAGGACA

TTCTGGAGAAGAAGCACAACGGCAAGCTGTGCGATCTGGATGGCGTGAAG

CCCCTGATCCTGCGCGATTGCAGCGTGGCCGGCTGGCTGCTGGGCAACCC

CATGTGCGATGAGTTCATCAACGTGCCCGAGTGGAGCTACATCGTGGAGA

AGGCCAACCCCGTGAACGATCTGTGCTACCCCGGCGATTTCAACGATTAC

GAGGAGCTGAAGCACCTGCTGTCCCGCATCAACCACTTCGAGAAGATCCA

GATCATCCCCAAGAGCAGCTGGTCCAGCCACGAGGCTAGCCTGGGCGTGA

GCAGCGCCTGCCCGTACCAGGGCAAGTCCAGCTTCTTCCGCAACGTGGTG

TGGCTGATCAAGAAGAACAGCACCTACCCCACCATCAAGCGCAGCTACAA

CAACACCAACCAGGAGGATCTGCTGGTGCTGTGGGGCATCCACCACCCCA

ACGATGCCGCCGAGCAGACCAAGCTGTACCAGAACCCCACCACCTACATC

-continued
AGCGTGGGCACCTCCACCCTGAACCAGCGCCTGGTGCCCCGCATTGCCAC

CCGCAGCAAGGTGAACGGCCAGTCGGGCCGCATGGAGTTCTTTTGGACCA

TCCTGAAGCCCAACGACGCCATCAACTTCGAGAGCAACGGCAACTTCATC

GCCCCCGAGTACGCCTACAAGATCGTGAAGAAGGGCGATAGCACCATCAT

GAAGAGCGAGCTGGAGTACGGCAACTGCAACACCAAGTGCCAGACCCCCA

TGGGCGCCATCAACAGCAGCATGCCCTTCCACAACATCCACCCCCTGACC

ATCGGCGAGTGCCCCAAGTACGTGAAGAGCAACCGCCTGGTGCTGGCCAC

CGGCCTGCGCAACAGCCCACAGCGCGAGCGCCGCCGCAAGAAGCGCGGCC

TGTTCGGCGCCATCGCCGGCTTCATCGAGGGCGGCTGGCAGGGCATGGTG

GATGGCTGGTACGGCTACCACCACTCGAACGAGCAGGGCAGCGGCTACGC

CGCCGATAAGGAGTCGACCCAGAAGGCCATCGATGGCGTGACCAACAAGG

TGAACAGCATCATCGACAAGATGAACACCCAGTTCGAGGCCGTGGGCCGC

GAGTTCAACAACCTGGAGCGCCGCATCGAGAACCTGAACAAGAAGATGGA

GGACGGCTTCCTGGATGTGTGGACCTACAACGCCGAGCTGCTGGTGCTGA

TGGAGAACGAGCGCACCCTGGATTTCCACGATAGCAACGTGAAGAACCTG

TACGATAAGGTGCGCCTGCAGCTGCGCGATAACGCCAAGGAGCTGGGCAA

CGGCTGCTTCGAGTTCTACCACAAGTGCGACAACGAGTGCATGGAGAGCG

TGCGCAACGGCACCTACGATTACCCCCAGTACAGCGAGGAGGCCCGCCTG

AAGCGCGAGGAGATCAGCTCCGGCCGCCTGGTGCCACGCGGCAGCCCAGG

CTCCGGCTACATCCCCGAGGCCCCACGCGATGGCCAGGCCTACGTGCGCA

AGGATGGCGAGTGGGTGCTGCTGTCCACCTTCCTGTAATAAGCGGCCGC

SEQ ID NO: 62:
KANAMYCIN/GENETICIN (G418) EXPRESSION CASSETTE
INSERTED BETWEEN UNDERLINED XMNI AND SALI
SITES:
GAATTAATTCGGATCTCTGCAAGGGATTTTGGTCATGAACAATAAAACTG

TCTGCTTACATAAACAGTAATACAAGGGGTGTTCATAGTATAATACGACT

CACTATAGGAGGGCCACCATGAGCCACATCCAGCGCGAAACCAGCTGCAG

CCGTCCGCGCCTGAACAGCAACATGGATGCCGATCTGTACGGCTACAAAT

GGGCCCGCGATAACGTGGGCCAGAGCGGCGCTACCATCTACCGCCTGTAC

GGCAAACCGGATGCCCCGGAACTGTTCCTGAAACACGGCAAAGGCAGCGT

GGCCAACGATGTGACCGATGAAATGGTGCGCCTGAACTGGCTGACCGAGT

TCATGCCGCTGCCGACCATCAAACACTTCATCCGCACCCCGGATGATGCC

TGGCTGCTGACCACCGCCATTCCGGGCAAAACCGCCTTCCAGGTGCTGGA

AGAATACCCGGATAGCGGCGAAAACATCGTGGATGCCCTGGCCGTGTTCC

TGCGCCGCCTGCACAGCATCCCGGTGTGCAACTGCCCGTTCAACAGCGAT

CGCGTGTTCCGCCTGGCTCAGGCCCAGAGCCGCATGAACAACGGCCTGGT

GGATGCCAGCGATTTCGATGATGAACGCAACGGCTGGCCGGTGGAACAGG

TGTGGAAAGAGATGCACAAACTGCTGCCGTTCAGCCCGGATTCCGTGGTG

ACCCACGGCGATTTCAGCCTGGATAACCTGATCTTCGATGAGGGCAAACT

GATCGGCTGCATCGATGTGGGCCGCGTGGGCATTGCCGATCGCTACCAGG

ATCTGGCCATCCTGTGGAACTGCCTGGGCGAGTTCAGCCCGAGCCTGCAG

AAACGCCTGTTCCAGAAGTACGGCATCGATAACCCGGATATGAACAAACT

-continued
GCAGTTCCACCTGATGCTGGATGAGTTCTTCTAATAAGTCGAC

SEQ ID NO: 63:
pKanR sequence used according to the present
examples:
AAGGGATTTTGGTCATGAACAATAAAACTGTCTGCTTACATAAACAGTAA

TACAAGGGGTGTTCATAGTATAATACGACTCACTATAGGAGGGCC

PCR Primers for pHP34s Constructs:

(SEQ ID NO: 64)
GCGAACTTAAGAGCGCCGGAGTATAAATAG (SEQ ID NO: 65)
CCAAGCTTCTGCAGATTGTTTAGCTTG (SEQ ID NO: 66)
GGTTTGTCCAAACTCATCAATGTAT (SEQ ID NO: 67)
TATACTCCGGCGCTCTTAAGTTCGCTCGCGTTCAAAACTTTTACC

SEQ ID NO: 68:
Hybrid promoter sequence (with SpeI (upstream)
and HindIII (downstream) restriction sites,
both underlined)
ACTAGTGAATGCCCTACTAGAAGATGTGTGTTGCACAAAATGTCCCTGGA

ATAACCAATTTGAAGTGCAGATAGCAGTAAACGTAAGCTAATATGAATAT

TATTTAACTGTAATGTTTTAATATCGCTGGACATTACTAATAAACCCACT

ATAAACACATGTACATATGTATGTTTTGGCATACAATGAGTAGTTGGGGA

AAAAATGTGTAAAAGCACCGTGACCATCACAGCATAAAGATAACCAGCTG

AAGTATCGAATATGAGTAACCCCCAAATTGAATCACATGCCGCAACTGAT

AGGACCCATGGAAGTACACTCTTCATGGCGATATACAAGACACACACAAG

CACGAACACCCAGTTGCGGAGGAAATTCTCCGTAAATGAAAACCCAATCG

GCGAACAATTCATACCCATATATGGTAAAAGTTTTGAACGCGAGCGAACT

TAAGAGCGCCGGAGTATAAATAGAGGCGCTTCGTCTACGGAGCGACAATT

CAATTCAAACAAGCAAAGTGAACACGTCGCTAAGCGAAAGCTAAGCAAAT

AAACAAGCGCAGCTGAACAAGCTAAACAATCTGCAGAAGCTT

SEQ ID NO: 69:
Sequence pLIC-Ex-His1 (LIC enabled pHP34s-Hybrid
for extracellular expression using BIP signal
sequence)
CCTGTTCACTGACTCCCGCGGATCAAAATGACGATTGACGGCATTACGT

CTAACGATATTTACATGCTTGGTTATGTTTCTAATTCTTTAACTGGCCCA

TACAAGCCGCTGAACAAAACTGGCCTTGTGTTAAAAATGGATCTTGATCC

TAACGATGTAACCTTTACTTACTCACACTTCGCTGTACCTCAAGCGAAAG

GAAACAATGTCGTGATTACAAGCTATATGACAAACAGAGGATTCTACGCA

GACAAACAATCAACGTTTGCGCCTAGCTTCCTGCTGAACATCAAAGGCAA

GAAAACATCTGTTGTCAAAGACAGCATCCTTGAACAAGGACAATTAACAG

TTAACAAATAAAAACGCAAAAGAAATGCCGATATCCTATTGGCATTGAC

GTCAGGTGGCACACCTGCAGAGAACCTCTACTTCCAATCGCACCATCATC

ACCACCATGATTACAAGGATGACGACGATAAGTGAGGATCCGAATTCGAG

CTCCGTCGACAAGCTTGCGGCCGCGGATCGATCGATATCTGACTAAATCT

TAGTTTGTATTGTCATGTTTTAATACAATATGTTATGTTTAAATATGTTT

```
TTAATAAATTTTATAAAATAATTTCAACTTTTATTGTAACAACATTGTCC
ATTTACACACTCCTTTCAAGCGCGTGGGACTCGATGCTCGGCGCCACTCA
AAGGCGGTAATACGGTTATCCACAGAATCAGGGGATAACGCAGGAAAGAA
CATGTGAGCAAAAGGCCAGCAAAAGGCCAGGAACCGTAAAAAGGCCGCGT
TGCTGGCGTTTTTCCATAGGCTCCGCCCCCCTGACGAGCATCACAAAAAT
CGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTT
TCTCAATGCTCACGCTGTAGGTATCTCAGTTCGGTGTAGGTCGTTCGCTC
CAAGCTGGGCTGTGTGCACGAACCCCCCGTTCAGCCCGACCGCTGCGCCT
TATCCGGTAACTATCGTCTTGAGTCCAACCCGGTAAGACACGACTTATCG
CCACTGGCAGCAGCCACTGGTAACAGGATTAGCAGAGCGAGGTATGTAGG
CGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAA
AGAGTTGGTAGCTCTTGATCCGGCAAACAAACCACCGCTGGTAGCGGTGG
TTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAAC
TCACGTTAAGGGATTTTGCATGCGCTAAGCGGGCTTTATAAAACGGGCTG
CGGGACCAGTTTTCATATCACTACCGTTTGAGTTCTTGTGCTGTGTGGAT
ACTCCTCCCGACACCGAATTAATTCGGATCTCTGCAAGGGATTTTGGTCA
TGAACAATAAAACTGTCTGCTTACATAAACAGTAATACAAGGGGTGTTCA
TAGTATAATACGACTCACTATAGGAGGGCCACCATGGCCAAGTTGACCAG
TGCCGTTCCGGTGCTCACCGCGCGCGACGTCGCCGGAGCGGTCGAGTTCT
GGACCGACCGGCTCGGGTTCAGCCGGGACTTCGTGGAGGACGACTTCGCC
GGTGTGGTCCGGGACGACGTGACCCTGTTCATCAGCGCGGTCCAGGACCA
GGTGGTGCCGGACAACACCCTGGCCTGGGTGTGGGTGCGCGGCCTGGACG
AGCTGTACGCCGAGTGGTCGGAGGTCGTGTCCACGAACTTCCGGGACGCC
TCCGGGCCGGCCATGACCGAGATCGGCGAGCAGCCGTGGGGGCGGGAGTT
CGCCCTGCGCGACCCGGCCGGCAACTGCGTGCACTTCGTGGCCGAGGAGC
AGGACTGACCGACGCCGACCAACACCGCCGGTCCGACGGCGGCCCACGGG
TCCCAGGGGGGTCGACCTCGAAACTTGTTTATTGCAGCTTATAATGGTTA
CAAATAAAGCAATAGCATCACAAATTTCACAAATAAAGCATTTTTTTCAC
TGCATTCTAGTTGTGGTTTGTCCAAACTCATCAATGTATCTTATCATGTC
TTCACGTAATAAGTGTGCGGCTAGCAGTCAACTACTAGCAGTCAACACTT
GGTCTGACAGTTACCAATGCTTAATCAGTGAGGCACCTATCTCAGCGATC
TGTCTATTTCGTTCATCCATAGTTGCCTGACTCCCCGTCGTGTAGATAAC
TACGATACGGGAGGGCTTACCATCTGGCCCCAGTGCTGCAATGATACCGC
GAGAACCACGCTCACCGGCTCCAGATTTATCAGCAATAAACCAGCCAGCC
GGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGT
TACATGATCCCCCATGTTGTGCAAAAAAGCGGTTAGCTCCTTCGGTCCTC
CGATCGTTGTCAGAAGTAAGTTGGCCGCAGTGTTATCACTCATGGTTATG
GCAGCACTGCATAATTCTCTTACTGTCATGCCATCCGTAAGATGCTTTTC
TGTGACTGGTGAGTACTCAACCAAGTCATTCTGAGAATAGTGTATGCGGC
GACCGAGTTGCTCTTGCCCGGCGTCAATACGGGATAATACCGCGCCACAT
AGCAGAACTTTAAAAGTGCTCATCATTGGAAAACGTTCTTCGGGGCGAAA
ACTCTCAAGGATCTTACCGCTGTTGAGATCCAGTTCGATGTAACCCACTC
GTGCACCCAACTGATCTTCAGCATCTTTTACTTTCACCAGCGTTTCTGGG
TGAGCAAAAACAGGAAGGCAAAATGCCGCAAAAAAGGGAATAAGGGCGAC
ACGGAAATGTTGAATACTCATACTCTTCCTTTTTCAATATTATTGAAGCA
TTTATCAGGGTTATTGTCTCATGAGCGGATACATATTTGAATGTATTTAG
AAAAATAAACAAATAGGGGTTCCGCGCACATTTCCCCGAAAAGTGCCACC
TACTAGTGAATGCCCTACTAGAAGATGTGTGTTGCACAAAATGTCCCTGG
AATAACCAATTTGAAGTGCAGATAGCAGTAAACGTAAGCTAATATGAATA
TTATTTAACTGTAATGTTTTAATATCGCTGGACATTACTAATAAACCCAC
TATAAACACATGTACATATGTATGTTTTGGCATACAATGAGTAGTTGGGG
AAAAAATGTGTAAAAGCACCGTGACCATCACAGCATAAAGATAACCAGCT
GAAGTATCGAATATGAGTAACCCCCAAATTGAATCACATGCCGCAACTGA
TAGGACCCATGGAAGTACACTCTTCATGGCGATATACAAGACACACACAA
GCACGAACACCCAGTTGCGGAGGAAATTCTCCGTAAATGAAAACCCAATC
GGCGAACAATTCATACCCATATATGGTAAAAGTTTTGAACGCGAGCGAAC
TTAAGAGCGCCGGAGTATAAATAGAGGCGCTTCGTCTACGGAGCGACAAT
TCAATTCAAACAAGCAAAGTGAACACGTCGCTAAGCGAAAGCTAAGCAAA
TAAACAAGCGCAGCTGAACAAGCTAAACAATCTGCAGAAGCTTGGTACCC
TCGAGCTCAGCTGAATTCTGGATCCTCTAGAAATAATTTTGTTTAACCTT
AAGAAGGAGATATACTCAAAATGAAGCTGTGCATACTGCTGGCCGTCGTG
GCCTTTGTTGGCCTCTCGCTCGGGGAAGAGAAAAAGCTAAGCAGGTCGTT
CACTATTATTTAGTGAAATGAGATATTATGATATTTTCTGAATTGTGATT
AAAAAGGCAACTTTATGCCCATGCAACAGAAACTATAAAAAATACAGAGA
ATGAAAAGAAACAGATAGATTTTTTAGTTCTTTAGGCCCGTAGTCTGCAA
ATCCTTTTATGATTTTCTATCAAACAAAAGAGGAAAATAGACCAGTTGCA
ATCCAAACGAGAGTCTAATAGAATGAGGTCGAAAAGTAAATCGCGCGGGT
TTGTTACTGATAAAGCAGGCAAGACCTAAAATGTGTAAAGGGCAAAGTGT
ATACTTTGGCGTCACCCCTTACATATTTTAGGTCTTTTTTTATTGTGCGT
AACTAACTTGCCATCTTCAAACAGGAGGGCTGGAAGAAGCAGACCGCTAA
CACAGTACATAAAAAGGAGACATGAACGATGAACATCAAAAAGTTTGCA
AAACAAGCAACAGTATTAACCTTTACTACCGCACTGCTGGCAGGAGGCGC
AACTCAAGCGTTTGCGAAAGAAACGAACCAAAAGCCATATAAGGAAACAT
ACGGCATTTCCCATATTACACGCCATGATATGCTGCAAATCCCTGAACAG
```

CAAAAAAATGAAAAATATAAAGTTCCTGAGTTCGATTCGTCCACAATTAA

AAATATCTCTTCTGCAAAAGGCCTGGACGTTTGGGACAGCTGGCCATTAC

AAAACACTGACGGCACTGTCGCAAACTATCACGGCTACCACATCGTCTTT

GCATTAGCCGGAGATCCTAAAAATGCGGATGACACATCGATTTACATGTT

CTATCAAAAAGTCGGCGAAACTTCTATTGACAGCTGGAAAAACGCTGGCC

GCGTCTTTAAAGACAGCGACAAATTCGATGCAAATGATTCTATCCTAAAA

GACCAAACACAAGAATGGTCAGGTTCAGCCACATTTACATCTGACGGAAA

AATCCGTTTATTCTACACTGATTTCTCCGGTAAACATTACGGCAAACAAA

CACTGACAACTGCACAAGTTAACGTATCAGCATCAGACAGCTCTTTGAAC

ATCAACGGTGTAGAGGATTATAAATCAATCTTTGACGGTGACGGAAAAAC

GTATCAAAATGTACAGCAGTTCATCGATGAAGGCAACTACAGCTCAGGCG

ACAACCATACGCTGAGAGATCCTCACTACGTAGAAGATAAAGGCCACAAA

TACTTAGTATTTGAAGCAAACACTGGAACTGAAGATGGCTACCAAGGCGA

AGAATCTTTATTTAACAAAGCATACTATGGCAAAAGCACATCATTCTTCC

GTCAAGAAAGTCAAAAACTTCTGCAAAGCGATAAAAAACGCACGGCTGAG

TTAGCAAACGGCGCTCTCGGTATGATTGAGCTAAACGATGATTACACACT

GAAAAAAGTGATGAAACCGCTGATTGCATCTAACACAGTAACAGATGAAA

TTGAACGCGCGAACGTCTTTAAAATGAACGGCAAATGGTA

SEQ ID NO: 70:
Sequence pLIC-His-Int (LIC enabled pHP34s-Hybrid
for intracellular expression):
CTAGCAGTCAACACTTGGTCTGACAGTTACCAATGCTTAATCAGTGAGGC

ACCTATCTCAGCGATCTGTCTATTTCGTTCATCCATAGTTGCCTGACTCC

CCGTCGTGTAGATAACTACGATACGGGAGGGCTTACCATCTGGCCCCAGT

GCTGCAATGATACCGCGAGAACCACGCTCACCGGCTCCAGATTTATCAGC

AATAAACCAGCCAGCCGGAAGGGCCGAGCGCAGAAGTGGTCCTGCAACTT

TATCCGCCTCCATCCAGTCTATTAATTGTTGCCGGGAAGCTAGAGTAAGT

AGTTCGCCAGTTAATAGTTTGCGCAACGTTGTTGCCATTGCTACAGGCAT

CGTGGTGTCACGCTCGTCGTTTGGTATGGCTTCATTCAGCTCCGGTTCCC

AACGATCAAGGCGAGTTACATGATCCCCCATGTTGTGCAAAAAAGCGGTT

AGCTCCTTCGGTCCTCCGATCGTTGTCAGAAGTAAGTTGGCCGCAGTGTT

ATCACTCATGGTTATGGCAGCACTGCATAATTCTCTTACTGTCATGCCAT

CCGTAAGATGCTTTTCTGTGACTGGTGAGTACTCAACCAAGTCATTCTGA

GAATAGTGTATGCGGCGACCGAGTTGCTCTTGCCCGGCGTCAATACGGGA

TAATACCGCGCCACATAGCAGAACTTTAAAAGTGCTCATCATTGGAAAAC

GTTCTTCGGGGCGAAAACTCTCAAGGATCTTACCGCTGTTGAGATCCAGT

TCGATGTAACCCACTCGTGCACCCAACTGATCTTCAGCATCTTTTACTTT

CACCAGCGTTTCTGGGTGAGCAAAACAGGAAGGCAAAATGCCGCAAAAA

AGGGAATAAGGGCGACACGGAAATGTTGAATACTCATACTCTTCCTTTTT

CAATATTATTGAAGCATTTATCAGGGTTATTGTCTCATGAGCGGATACAT

ATTTGAATGTATTTAGAAAAATAAACAAATAGGGGTTCCGCGCACATTTC

CCCGAAAAGTGCCACCTACTAGTGAATGCCCTACTAGAAGATGTGTGTTG

CACAAAATGTCCCTGGAATAACCAATTTGAAGTGCAGATAGCAGTAAACG

TAAGCTAATATGAATATTATTTAACTGTAATGTTTTAATATCGCTGGACA

TTACTAATAAACCCACTATAAACACATGTACATATGTATGTTTTGGCATA

CAATGAGTAGTTGGGGAAAAAATGTGTAAAAGCACCGTGACCATCACAGC

ATAAAGATAACCAGCTGAAGTATCGAATATGAGTAACCCCCAAATTGAAT

CACATGCCGCAACTGATAGGACCCATGGAAGTACACTCTTCATGGCGATA

TACAAGACACACAAGCACGAACACCCAGTTGCGGAGGAAATTCTCCGT

AAATGAAAACCCAATCGGCGAACAATTCATACCCATATATGGTAAAAGTT

TTGAACGCGAGCGAACTTAAGAGCGCCGGAGTATAAATAGAGGCGCTTCG

TCTACGGAGCGACAATTCAATTCAAACAAGCAAAGTGAACACGTCGCTAA

GCGAAAGCTAAGCAAATAAACAAGCGCAGCTGAACAAGCTAAACAATCTG

CAGAAGCTTGGTACCCTCGAGCTCAGCTGAATTCTGGATCCTCTAGAAAT

AATTTTGTTTAACTTTAAGAAGGAGATATCAAAATGCACCATCATCATCA

TCATTCTTCTGGTGTAGATCTGGGTACCGAGAACCTGTACTTCCAATCCA

TGGAGACCGACGTCCACATATACCTGCCGTTCACTATTATTTAGTGAAAT

GAGATATTATGATATTTTCTGAATTGTGATTAAAAAGGCAACTTTATGCC

CATGCAACAGAAACTATAAAAAATACAGAGAATGAAAAGAAACAGATAGA

TTTTTTAGTTCTTTAGGCCCGTAGTCTGCAAATCCTTTTATGATTTTCTA

TCAAACAAAAGAGGAAAATAGACCAGTTGCAATCCAAACGAGAGTCTAAT

AGAATGAGGTCGAAAAGTAAATCGCGCGGGTTTGTTACTGATAAAGCAGG

CAAGACCTAAAATGTGTAAAGGGCAAAGTGTATACTTTGGCGTCACCCCT

TACATATTTTAGGTCTTTTTTTATTGTGCGTAACTAACTTGCCATCTTCA

AACAGGAGGGCTGGAAGAAGCAGACCGCTAACACAGTACATAAAAAGGA

GACATGAACGATGAACATCAAAAAGTTTGCAAAACAAGCAACAGTATTAA

CCTTTACTACCGCACTGCTGGCAGGAGGCGCAACTCAAGCGTTTGCGAAA

GAAACGAACCAAAAGCCATATAAGGAAACATACGGCATTTCCCATATTAC

ACGCCATGATATGCTGCAAATCCCTGAACAGCAAAAAAATGAAAATATA

AAGTTCCTGAGTTCGATTCGTCCACAATTAAAAATATCTCTTCTGCAAAA

GGCCTGGACGTTTGGGACAGCTGGCCATTACAAAACACTGACGGCACTGT

CGCAAACTATCACGGCTACCACATCGTCTTTGCATTAGCCGGAGATCCTA

AAAATGCGGATGACACATCGATTTACATGTTCTATCAAAAGTCGGCGAA

ACTTCTATTGACAGCTGGAAAAACGCTGGCCGCGTCTTTAAAGACAGCGA

CAAATTCGATGCAAATGATTCTATCCTAAAAGACCAAACACAAGAATGGT

CAGGTTCAGCCACATTTACATCTGACGGAAAAATCCGTTTATTCTACACT

GATTTCTCCGGTAAACATTACGGCAAACAAACACTGACAACTGCACAAGT

TAACGTATCAGCATCAGACAGCTCTTTGAACATCAACGGTGTAGAGGATT

ATAAATCAATCTTTGACGGTGACGGAAAAACGTATCAAAATGTACAGCAG

TTCATCGATGAAGGCAACTACAGCTCAGGCGACAACCATACGCTGAGAGA

TCCTCACTACGTAGAAGATAAAGGCCACAAATACTTAGTATTTGAAGCAA

ACACTGGAACTGAAGATGGCTACCAAGGCGAAGAATCTTTATTTAACAAA

-continued

GCATACTATGGCAAAAGCACATCATTCTTCCGTCAAGAAAGTCAAAAACT
TCTGCAAAGCGATAAAAAACGCACGGCTGAGTTAGCAAACGGCGCTCTCG
GTATGATTGAGCTAAACGATGATTACACACTGAAAAAAGTGATGAAACCG
CTGATTGCATCTAACACAGTAACAGATGAAATTGAACGCGCGAACGTCTT
TAAAATGAACGGCAAATGGTACCTGTTCACTGACTCCCGCGGATCAAAAA
TGACGATTGACGGCATTACGTCTAACGATATTTACATGCTTGGTTATGTT
TCTAATTCTTTAACTGGCCCATACAAGCCGCTGAACAAAACTGGCCTTGT
GTTAAAAATGGATCTTGATCCTAACGATGTAACCTTTACTTACTCACACT
TCGCTGTACCTCAAGCGAAAGGAAACAATGTCGTGATTACAAGCTATATG
ACAAACAGAGGATTCTACGCAGACAAACAATCAACGTTTGCGCCTAGCTT
CCTGCTGAACATCAAAGGCAAGAAAACATCTGTTGTCAAAGACAGCATCC
TTGAACAAGGACAATTAACAGTTAACAAATAAAAACGCAAAAGAAAATGC
CGATATCCTATTGGCATTGACGGTCTCCAGTAAAGGTGGATACGGATCCG
AATTCGAGCTCCGTCGACAAGCTTGCGGCCGCGGATCGATCGATATCTGA
CTAAATCTTAGTTTGTATTGTCATGTTTTAATACAATATGTTATGTTTAA
ATATGTTTTTAATAAATTTTATAAAATAATTTCAACTTTTATTGTAACAA
CATTGTCCATTTACACACTCCTTTCAAGCGCGTGGGACTCGATGCTCGGC
GCCACTCAAAGGCGGTAATACGGTTATCCACAGAATCAGGGGATAACGCA
GGAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCC
GACCCTGCCGCTTACCGGATACCTGTCCGCCTTTCTCCCTTCGGGAAGCG
TGGCGCTTTCTCAATGCTCACGCTGTAGGTATCTCAGTTCGGTGTAGGTC
GTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACG
ACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTA
CACTAGAAGGACAGTATTTGGTATCTGCGCTCTGCTGAAGCCAGTTACCT
TCGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAGG
ATCTCAAGAAGATCCTTTGATCTTTTCTACGGGGTCTGACGCTCAGTGGA
ACGAAAACTCACGTTAAGGGATTTTGCATGCGCTAAGCGGGCTTATAAA
ACGGGCTGCGGGACCAGTTTTCATATCACTACCGTTTGAGTTCTTGTGCT
GTGTGGATACTCCTCCCGACACCGAATTAATTCGGATCTCTGCAAGGGAT
TTTGGTCATGAACAATAAAACTGTCTGCTTACATAAACAGTAATACAAGG
GGTGTTCATAGTATAATACGACTCACTATAGGAGGGCCACCATGGCCAAG
TTGACCAGTGCCGTTCCGGTGCTCACCGCGCGCGACGTCGCCGGAGCGGT
CGAGTTCTGGACCGACCGGCTCGGGTTCAGCCGGGACTTCGTGGAGGACG
ACTTCGCCGGTGTGGTCCGGGACGACGTGACCCTGTTCATCAGCGCGGTC
CAGGACCAGGTGGTGCCGGACAACACCCTGGCCTGGGTGTGGGTGCGCGG

-continued

CCTGGACGAGCTGTACGCCGAGTGGTCGGAGGTCGTGTCCACGAACTTCC
GGGACGCCTCCGGGCCGGCCATGACCGAGATCGGCGAGCAGCCGTGGGGG
CGGGAGTTCGCCCTGCGCGACCCGGCCGGCAACTGCGTGCACTTCGTGGC
CGAGGAGCAGGACTGACCGACGCCGACCAACACCGCCGGTCCGACGGCGG
CCCACGGGTCCCAGGGGGTCGACCTCGAAACTTGTTTATTGCAGCTTAT
AATGGTTACAAATAAAGCAATAGCATCACAAATTTCACAATAAAGCATT
TTTTTCACTGCATTCTAGTTGTGGTTTGTCCAAACTCATCAATGTATCTT
ATCATGTCTTCACGTAATAAGTGTGCGGCTAGCAGTCAA

SEQ ID NO: 71:
Sequence pLIC-His-Ex (LIC enabled pHP34s-Hybrid
for extracellular expression)
CTAGCAGTCAACACTTGGTCTGACAGTTACCAATGCTTAATCAGTGAGGC
ACCTATCTCAGCGATCTGTCTATTTCGTTCATCCATAGTTGCCTGACTCC
CCGTCGTGTAGATAACTACGATACGGGAGGGCTTACCATCTGGCCCCAGT
GCTGCAATGATACCGCGAGAACCACGCTCACCGGCTCCAGATTTATCAGC
AATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCAT
CGTGGTGTCACGCTCGTCGTTTGGTATGGCTTCATTCAGCTCCGGTTCCC
AACGATCAAGGCGAGTTACATGATCCCCCATGTTGTGCAAAAAAGCGGTT
AGCTCCTTCGGTCCTCCGATCGTTGTCAGAAGTAAGTTGGCCGCAGTGTT
ATCACTCATGGTTATGGCAGCACTGCATAATTCTCTTACTGTCATGCCAT
CCGTAAGATGCTTTTCTGTGACTGGTGAGTACTCAACCAAGTCATTCTGA
GAATAGTGTATGCGGCGACCGAGTTGCTCTTGCCCGGCGTCAATACGGGA
TAATACCGCGCCACATAGCAGAACTTTAAAAGTGCTCATCATTGGAAAAC
GTTCTTCGGGGCGAAAACTCTCAAGGATCTTACCGCTGTTGAGATCCAGT
TCGATGTAACCCACTCGTGCACCCAACTGATCTTCAGCATCTTTTACTTT
CACCAGCGTTTCTGGGTGAGCAAAAACAGGAAGGCAAAATGCCGCAAAAA
AGGGAATAAGGGCGACACGGAAATGTTGAATACTCATACTCTTCCTTTTT
CAATATTATTGAAGCATTTATCAGGGTTATTGTCTCATGAGCGGATACAT
ATTTGAATGTATTTAGAAAAATAAACAAATAGGGGTTCCGCGCACATTTC
CCCGAAAAGTGCCACCTACTAGTGAATGCCCTACTAGAAGATGTGTGTTG
CACAAAATGTCCCTGGAATAACCAATTTGAAGTGCAGATAGCAGTAAACG
TAAGCTAATATGAATATTATTTAACTGTAATGTTTTAATATCGCTGGACA
TTACTAATAAACCCACTATAAACACATGTACATATGTATGTTTTGGCATA
CAATGAGTAGTTGGGAAAAAATGTGTAAAAGCACCGTGACCATCACAGC
ATAAAGATAACCAGCTGAAGTATCGAATATGAGTAACCCCCAAATTGAAT
CACATGCCGCAACTGATAGGACCCATGGAAGTACACTCTTCATGGCGATA
TACAAGACACACAAGCACGAACACCCAGTTGCGGAGGAAATTCTCCGT
AAATGAAAACCCAATCGGCGAACAATTCATACCCATATATGGTAAAGTT
TTGAACGCGAGCGAACTTAAGAGCGCCGGAGTATAAATAGAGGCGCTTCG
TCTACGGAGCGACAATTCAATTCAAACAAGCAAAGTGAACACGTCGCTAA -continued

GCGAAAGCTAAGCAAATAAACAAGCGCAGCTGAACAAGCTAAACAATCTG

CAGAAGCTTGGTACCCTCGAGCTCAGCTGAATTCTGGATCCTCTAGAAAT

AATTTTGTTTAACTTTAAGAAGGAGATATCAAAATGAAGCTGTGCATACT

GCTGGCCGTCGTGGCCTTTGTTGGCCTCTCGCTCGGGCACCATCATCATC

ATCATTCTTCTGGTGTAGATCTGGGTACCGAGAACCTGTACTTCCAATCC

ATGGAGACCGACGTCCACATATACCTGCCGTTCACTATTATTTAGTGAAA

TGAGATATTATGATATTTTCTGAATTGTGATTAAAAAGGCAACTTTATGC

CCATGCAACAGAAACTATAAAAAATACAGAGAATGAAAAGAAACAGATAG

ATTTTTTAGTTCTTTAGGCCCGTAGTCTGCAAATCCTTTTATGATTTTCT

ATCAAACAAAGAGGAAAATAGACCAGTTGCAATCCAAACGAGAGTCTAA

TAGAATGAGGTCGAAAAGTAAATCGCGCGGGTTTGTTACTGATAAAGCAG

GCAAGACCTAAAATGTGTAAAGGGCAAAGTGTATACTTTGGCGTCACCCC

TTACATATTTTAGGTCTTTTTTTATTGTGCGTAACTAACTTGCCATCTTC

AAACAGGAGGGCTGGAAGAAGCAGACCGCTAACACAGTACATAAAAAAGG

AGACATGAACGATGAACATCAAAAAGTTTGCAAAACAAGCAACAGTATTA

ACCTTTACTACCGCACTGCTGGCAGGAGGCGCAACTCAAGCGTTTGCGAA

AGAAACGAACCAAAAGCCATATAAGGAAACATACGGCATTTCCCATATTA

CACGCCATGATATGCTGCAAATCCCTGAACAGCAAAAAAATGAAAAATAT

AAAGTTCCTGAGTTCGATTCGTCCACAATTAAAAATATCTCTTCTGCAAA

AGGCCTGGACGTTTGGGACAGCTGGCCATTACAAAACACTGACGGCACTG

TCGCAAACTATCACGGCTACCACATCGTCTTTGCATTAGCCGGAGATCCT

AAAAAATGCGGATGACACATCGATTTACATGTTCTATCAAAAGTCGGCGA

AACTTCTATTGACAGCTGGAAAAACGCTGGCCGCGTCTTTAAAGACAGCG

ACAAATTCGATGCAAATGATTCTATCCTAAAAGACCAAACACAAGAATGG

TCAGGTTCAGCCACATTTACATCTGACGGAAAAATCCGTTTATTCTACAC

TGATTTCTCCGGTAAACATTACGGCAAACAAACACTGACAACTGCACAAG

TTAACGTATCAGCATCAGACAGCTCTTTGAACATCAACGGTGTAGAGGAT

TATAAATCAATCTTTGACGGTGACGGAAAAACGTATCAAAATGTACAGCA

GTTCATCGATGAAGGCAACTACAGCTCAGGCGACAACCATACGCTGAGAG

ATCCTCACTACGTAGAAGATAAAGGCCACAAATACTTAGTATTTGAAGCA

AACACTGGAACTGAAGATGGCTACCAAGGCGAAGAATCTTTATTTAACAA

AGCATACTATGGCAAAAGCACATCATTCTTCCGTCAAGAAAGTCAAAAAC

TTCTGCAAAGCGATAAAAACGCACGGCTGAGTTAGCAAACGGCGCTCTC

GGTATGATTGAGCTAAACGATGATTACACACTGAAAAAAGTGATGAAACC

GCTGATTGCATCTAACACAGTAACAGATGAAATTGAACGCGCGAACGTCT

TTAAAATGAACGGCAAATGGTACCTGTTCACTGACTCCCGCGGATCAAAA

ATGACGATTGACGGCATTACGTCTAACGATATTTACATGCTTGGTTATGT

TTCTAATTCTTTAACTGGCCCATACAAGCCGCTGAACAAAACTGGCCTTG

TGTTAAAAATGGATCTTGATCCTAACGATGTAACCTTTACTTACTCACAC

TTCGCTGTACCTCAAGCGAAAGGAAACAATGTCGTGATTACAAGCTATAT

-continued

GACAAACAGAGGATTCTACGCAGACAAACAATCAACGTTTGCGCCTAGCT

TCCTGCTGAACATCAAAGGCAAGAAAACATCTGTTGTCAAAGACAGCATC

CTTGAACAAGGACAATTAACAGTTAACAAATAAAAACGCAAAAGAAAATG

CCGATATCCTATTGGCATTGACGGTCTCCAGTAAAGGTGGATACGGATCC

GAATTCGAGCTCCGTCGACAAGCTTGCGGCCGCGGATCGATCGATATCTG

ACTAAATCTTAGTTTGTATTGTCATGTTTTAATACAATATGTTATGTTTA

AATATGTTTTTAATAAATTTTATAAAATAATTTCAACTTTTATTGTAACA

ACATTGTCCATTTACACACTCCTTTCAAGCGCGTGGGACTCGATGCTCGG

CGCCACTCAAAGGCGGTAATACGGTTATCCACAGAATCAGGGGATAACGC

AGGAAAGAACATGTGAGCAAAAGGCCAGCAAAAGGCCAGGAACCGTAAAA

AGGCCGCGTTGCTGGCGTTTTTCCATAGGCTCCGCCCCCCTGACGAGCAT

CACAAAAATCGACGCTCAAGTCAGAGGTGGCGAAACCCGACAGGACTATA

AAGATACCAGGCGTTTCCCCCTGGAAGCTCCCTCGTGCGCTCTCCTGTTC

CGACCCTGCCGCTTACCGGATACCTGTCCGCCTTTCTCCCTTCGGGAAGC

GTGGCGCTTTCTCAATGCTCACGCTGTAGGTATCTCAGTTCGGTGTAGGT

CGTTCGCTCCAAGCTGGGCTGTGTGCACGAACCCCCCGTTCAGCCCGACC

GCTGCGCCTTATCCGGTAACTATCGTCTTGAGTCCAACCCGGTAAGACAC

GACTTATCGCCACTGGCAGCAGCCACTGGTAACAGGATTAGCAGAGCGAG

GTATGTAGGCGGTGCTACAGAGTTCTTGAAGTGGTGGCCTAACTACGGCT

ACACTAGAAGGACAGTATTTGGTATCTGCGCTCTGCTGAAGCCAGTTACC

TTCGGAAAAAGAGTTGGTAGCTCTTGATCCGGCAAACAAACCACCGCTGG

TAGCGGTGGTTTTTTTGTTTGCAAGCAGCAGATTACGCGCAGAAAAAAAG

GATCTCAAGAAGATCCTTTGATCTTTTCTACGGGGTCTGACGCTCAGTGG

AACGAAAACTCACGTTAAGGGATTTTGCATGCGCTAAGCGGGCTTTATAA

AACGGGCTGCGGGACCAGTTTTCATATCACTACCGTTTGAGTTCTTGTGC

TGTGTGGATACTCCTCCCGACACCGAATTAATTCGGATCTCTGCAAGGGA

TTTTGGTCATGAACAATAAAACTGTCTGCTTACATAAACAGTAATACAAG

GGGTGTTCATAGTATAATACGACTCACTATAGGAGGGCCACCATGGCCAA

GTTGACCAGTGCCGTTCCGGTGCTCACCGCGCGCGACGTCGCCGGAGCGG

TCGAGTTCTGGACCGACCGGCTCGGGTTCAGCCGGGACTTCGTGGAGGAC

GACTTCGCCGGTGTGGTCCGGGACGACGTGACCCTGTTCATCAGCGCGGT

CCAGGACCAGGTGGTGCCGGACAACACCCTGGCCTGGGTGTGGGTGCGCG

GCCTGGACGAGCTGTACGCCGAGTGGTCGGAGGTCGTGTCCACGAACTTC

CGGGACGCCTCCGGGCCGGCCATGACCGAGATCGGCGAGCAGCCGTGGGG

GCGGGAGTTCGCCCTGCGCGACCCGGCCGGCAACTGCGTGCACTTCGTGG

CCGAGGAGCAGGACTGACCGACGCCGACCAACACCGCCGGTCCGACGGCG

GCCCACGGGTCCCAGGGGGGTCGACCTCGAAACTTGTTTATTGCAGCTTA

TAATGGTTACAAATAAAGCAATAGCATCACAAATTTCACAAATAAAGCAT

TTTTTTCACTGCATTCTAGTTGTGGTTTGTCCAAACTCATCAATGTATCT

TATCATGTCTTCACGTAATAAGTGTGCGGCTAGCAGTCAA

SEQ ID NO: 72:
Sequence pLIC-Int-His1 (LIC enabled pHP34s-Hybrid
for intracellular expression):
CCTGTTCACTGACTCCCGCGGATCAAAAATGACGATTGACGGCATTACGT
CTAACGATATTTACATGCTTGGTTATGTTTCTAATTCTTTAACTGGCCCA
TACAAGCCGCTGAACAAAACTGGCCTTGTGTTAAAAATGGATCTTGATCC
TAACGATGTAACCTTTACTTACTCACACTTCGCTGTACCTCAAGCGAAAG
GAAACAATGTCGTGATTACAAGCTATATGACAAACAGAGGATTCTACGCA
GACAAACAATCAACGTTTGCGCCTAGCTTCCTGCTGAACATCAAAGGCAA
GAAAACATCTGTTGTCAAAGACAGCATCCTTGAACAAGGACAATTAACAG
TTAACAAATAAAAACGCAAAAGAAAATGCCGATATCCTATTGGCATTGAC
GTCAGGTGGCACACCTGCAGAGAACCTCTACTTCCAATCGCACCATCATC
ACCACCATGATTACAAGGATGACGACGATAAGTGAGGATCCGAATTCGAG
CTCCGTCGACAAGCTTGCGGCCGCGGATCGATCGATATCTGACTAAATCT
TAGTTTGTATTGTCATGTTTTAATACAATATGTTATGTTTAAATATGTTT
TTAATAAATTTTATAAAATAATTTCAACTTTTATTGTAACAACATTGTCC
ATTTACACACTCCTTTCAAGCGCGTGGGACTCGATGCTCGGCGCCACTCA
AAGGCGGTAATACGGTTATCCACAGAATCAGGGGATAACGCAGGAAAGAA
CATGTGAGCAAAAGGCCAGCAAAAGGCCAGGAACCGTAAAAAGGCCGCGT
TGCTGGCGTTTTTCCATAGGCTCCGCCCCCCTGACGAGCATCACAAAAAT
CGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTT
TCTCAATGCTCACGCTGTAGGTATCTCAGTTCGGTGTAGGTCGTTCGCTC
CAAGCTGGGCTGTGTGCACGAACCCCCCGTTCAGCCCGACCGCTGCGCCT
TATCCGGTAACTATCGTCTTGAGTCCAACCCGGTAAGACACGACTTATCG
CCACTGGCAGCAGCCACTGGTAACAGGATTAGCAGAGCGAGGTATGTAGG
CGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAA
AGAGTTGGTAGCTCTTGATCCGGCAAACAAACCACCGCTGGTAGCGGTGG
TTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAAC
TCACGTTAAGGGATTTTGCATGCGCTAAGCGGGCTTTATAAAACGGGCTG
CGGGACCAGTTTTCATATCACTACCGTTTGAGTTCTTGTGCTGTGTGGAT
ACTCCTCCCGACACCGAATTAATTCGGATCTCTGCAAGGGATTTTGGTCA
TGAACAATAAAACTGTCTGCTTACATAAACAGTAATACAAGGGGTGTTCA
TAGTATAATACGACTCACTATAGGAGGGCACCATGGCCAAGTTGACCAG
TGCCGTTCCGGTGCTCACCGCGCGCGACGTCGCCGGAGCGGTCGAGTTCT
GGACCGACCGGCTCGGGTTCAGCCGGGACTTCGTGGAGGACGACTTCGCC
GGTGTGGTCCGGGACGACGTGACCCTGTTCATCAGCGCGGTCCAGGACCA
GGTGGTGCCGGACAACACCCTGGCCTGGGTGTGGGTGCGCGGCCTGGACG
AGCTGTACGCCGAGTGGTCGGAGGTCGTGTCCACGAACTTCCGGGACGCC
TCCGGGCCGGCCATGACCGAGATCGGCGAGCAGCCGTGGGGGCGGGAGTT
CGCCCTGCGCGACCCGGCCGGCAACTGCGTGCACTTCGTGGCCGAGGAGC
AGGACTGACCGACGCCGACCAACACCGCCGGTCCGACGGCGGCCCACGGG
TCCCAGGGGGGTCGACCTCGAAACTTGTTTATTGCAGCTTATAATGGTTA
CAAATAAAGCAATAGCATCACAAATTTCACAAATAAAGCATTTTTTTCAC
TGCATTCTAGTTGTGGTTTGTCCAAACTCATCAATGTATCTTATCATGTC
TTCACGTAATAAGTGTGCGGCTAGCAGTCAACTACTAGCAGTCAACACTT
GGTCTGACAGTTACCAATGCTTAATCAGTGAGGCACCTATCTCAGCGATC
TGTCTATTTCGTTCATCCATAGTTGCCTGACTCCCCGTCGTGTAGATAAC
TACGATACGGGAGGGCTTACCATCTGGCCCCAGTGCTGCAATGATACCGC
GAGAACCACGCTCACCGGCTCCAGATTTATCAGCAATAAACCAGCCAGCC
GGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGT
TACATGATCCCCCATGTTGTGCAAAAAAGCGGTTAGCTCCTTCGGTCCTC
CGATCGTTGTCAGAAGTAAGTTGGCCGCAGTGTTATCACTCATGGTTATG
GCAGCACTGCATAATTCTCTTACTGTCATGCCATCCGTAAGATGCTTTTC
TGTGACTGGTGAGTACTCAACCAAGTCATTCTGAGAATAGTGTATGCGGC
GACCGAGTTGCTCTTGCCCGGCGTCAATACGGGATAATACCGCGCCACAT
AGCAGAACTTTAAAAGTGCTCATCATTGGAAAACGTTCTTCGGGGCGAAA
ACTCTCAAGGATCTTACCGCTGTTGAGATCCAGTTCGATGTAACCCACTC
GTGCACCCAACTGATCTTCAGCATCTTTTACTTTCACCAGCGTTTCTGGG
TGAGCAAAAACAGGAAGGCAAAATGCCGCAAAAAAGGGAATAAGGGCGAC
ACGGAAATGTTGAATACTCATACTCTTCCTTTTTCAATATTATTGAAGCA
TTTATCAGGGTTATTGTCTCATGAGCGGATACATATTTGAATGTATTTAG
AAAAATAAACAAATAGGGGTTCCGCGCACATTTCCCCGAAAAGTGCCACC
TACTAGTGAATGCCCTACTAGAAGATGTGTGTTGCACAAAATGTCCCTGG
AATAACCAATTTGAAGTGCAGATAGCAGTAAACGTAAGCTAATATGAATA
TTATTTAACTGTAATGTTTTAATATCGCTGGACATTACTAATAAACCCAC
TATAAACACATGTACATATGTATGTTTTGGCATACAATGAGTAGTTGGGG
AAAAAATGTGTAAAAGCACCGTGACCATCACAGCATAAAGATAACCAGCT
GAAGTATCGAATATGAGTAACCCCCAAATTGAATCACATGCCGCAACTGA
TAGGACCCATGGAAGTACACTCTTCATGGCGATATACAAGACACACACAA
GCACGAACACCCAGTTGCGGAGGAAATTCTCCGTAAATGAAAACCCAATC
GGCGAACAATTCATACCCATATATGGTAAAAGTTTTGAACGCGAGCGAAC
TTAAGAGCGCCGGAGTATAAATAGAGGCGCTTCGTCTACGGAGCGACAAT
TCAATTCAAACAAGCAAAGTGAACACGTCGCTAAGCGAAAGCTAAGCAAA
TAAACAAGCGCAGCTGAACAAGCTAAACAATCTGCAGAAGCTTGGTACCC
TCGAGCTCAGCTGAATTCTGGATCCTCTAGAAATAATTTTGTTTAACCTT

```
AAGAAGGAGATACAAAGCAGGTCGTTCACTATTATTTAGTGAAATGAGAT

ATTATGATATTTTCTGAATTGTGATTAAAAAGGCAACTTTATGCCCATGC

AACAGAAACTATAAAAAATACAGAGAATGAAAAGAAACAGATAGATTTTT

TAGTTCTTTAGGCCCGTAGTCTGCAAATCCTTTTATGATTTTCTATCAAA

CAAAAGAGGAAAATAGACCAGTTGCAATCCAAACGAGAGTCTAATAGAAT

GAGGTCGAAAAGTAAATCGCGCGGGTTTGTTACTGATAAAGCAGGCAAGA

CCTAAAATGTGTAAAGGGCAAAGTGTATACTTTGGCGTCACCCCTTACAT

ATTTTAGGTCTTTTTTTATTGTGCGTAACTAACTTGCCATCTTCAAACAG

GAGGGCTGGAAGAAGCAGACCGCTAACACAGTACATAAAAAAGGAGACAT

GAACGATGAACATCAAAAAGTTTGCAAAACAAGCAACAGTATTAACCTTT

ACTACCGCACTGCTGGCAGGAGGCGCAACTCAAGCGTTTGCGAAAGAAAC

GAACCAAAAGCCATATAAGGAAACATACGGCATTTCCCATATTACACGCC

ATGATATGCTGCAAATCCCTGAACAGCAAAAAAATGAAAAATATAAAGTT

CCTGAGTTCGATTCGTCCACAATTAAAAATATCTCTTCTGCAAAAGGCCT

GGACGTTTGGGACAGCTGGCCATTACAAAACACTGACGGCACTGTCGCAA

ACTATCACGGCTACCACATCGTCTTTGCATTAGCCGGAGATCCTAAAAAT

GCGGATGACACATCGATTTACATGTTCTATCAAAAAGTCGGCGAAACTTC

TATTGACAGCTGGAAAAACGCTGGCCGCGTCTTTAAAGACAGCGACAAAT

TCGATGCAAATGATTCTATCCTAAAAGACCAAACACAAGAATGGTCAGGT

TCAGCCACATTTACATCTGACGGAAAAATCCGTTTATTCTACACTGATTT

CTCCGGTAAACATTACGGCAAACAAACACTGACAACTGCACAAGTTAACG

TATCAGCATCAGACAGCTCTTTGAACATCAACGGTGTAGAGGATTATAAA

TCAATCTTTGACGGTGACGGAAAAACGTATCAAAATGTACAGCAGTTCAT

CGATGAAGGCAACTACAGCTCAGGCGACAACCATACGCTGAGAGATCCTC

ACTACGTAGAAGATAAAGGCCACAAATACTTAGTATTTGAAGCAAACACT

GGAACTGAAGATGGCTACCAAGGCGAAGAATCTTTATTTAACAAAGCATA

CTATGGCAAAAGCACATCATTCTTCCGTCAAGAAAGTCAAAAACTTCTGC

AAAGCGATAAAAAACGCACGGCTGAGTTAGCAAACGGCGCTCTCGGTATG

ATTGAGCTAAACGATGATTACACACTGAAAAAAGTGATGAAACCGCTGAT

TGCATCTAACACAGTAACAGATGAAATTGAACGCGCGAACGTCTTTAAAA

TGAACGGCAAATGGTA

SEQ ID NO: 73:
Sequence pLIC-TEV-Ex-His1 (LIC enabled
pHP34s-Hybrid for extracellular expression)
TTCTCAATGCTCACGCTGTAGGTATCTCAGTTCGGTGTAGGTCGTTCGCT

CCAAGCTGGGCTGTGTGCACGAACCCCCCGTTCAGCCCGACCGCTGCGCC

TTATCCGGTAACTATCGTCTTGAGTCCAACCCGGTAAGACACGACTTATC

GCCACTGGCAGCAGCCACTGGTAACAGGATTAGCAGAGCGAGGTATGTAG

GCGGTGCTACAGAGTTCTTGAAGTGGTGGCCTAACTACGGCTACACTAGA

AGGACAGTATTTGGTATCTGCGCTCTGCTGAAGCCAGTTACCTTCGGAAA

AAGAGTTGGTAGCTCTTGATCCGGCAAACAAACCACCGCTGGTAGCGGTG

GTTTTTTTGTTTGCAAGCAGCAGATTACGCGCAGAAAAAAGGATCTCAA

GAAGATCCTTTGATCTTTTCTACGGGGTCTGACGCTCAGTGGAACGAAAA

CTCACGTTAAGGGATTTTGCATGCGCTAAGCGGGCTTTATAAAACGGGCT

GCGGGACCAGTTTTCATATCACTACCGTTTGAGTTCTTGTGCTGTGTGGA

TACTCCTCCCGACACCGAATTAATTCGGATCTCTGCAAGGGATTTTGGTC

ATGAACAATAAAACTGTCTGCTTACATAAACAGTAATACAAGGGGTGTTC

ATAGTATAATACGACTCACTATAGGAGGGCCACCATGGCCAAGTTGACCA

GTGCCGTTCCGGTGCTCACCGCGCGCGACGTCGCCGGAGCGGTCGAGTTC

TGGACCGACCGGCTCGGGTTCAGCCGGGACTTCGTGGAGGACGACTTCGC

CGGTGTGGTCCGGGACGACGTGACCCTGTTCATCAGCGCGGTCCAGGACC

AGGTGGTGCCGGACAACACCCTGGCCTGGGTGTGGGTGCGCGGCCTGGAC

GAGCTGTACGCCGAGTGGTCGGAGGTCGTGTCCACGAACTTCCGGGACGC

CTCCGGGCCGGCCATGACCGAGATCGGCGAGCAGCCGTGGGGCGGGAGT

TCGCCCTGCGCGACCCGGCCGGCAACTGCGTGCACTTCGTGGCCGAGGAG

CAGGACTGACCGACGCCGACCAACACCGCCGGTCCGACGGCGGCCCACGG

GTCCCAGGGGGTCGACCTCGAAACTTGTTTATTGCAGCTTATAATGGTT

ACAAATAAAGCAATAGCATCACAAATTTCACAAATAAAGCATTTTTTTCA

CTGCATTCTAGTTGTGGTTTGTCCAAACTCATCAATGTATCTTATCATGT

CTTCACGTAATAAGTGTGCGGCTAGCAGTCAACTAGCAGTCAACACTTGG

TCTGACAGTTACCAATGCTTAATCAGTGAGGCACCTATCTCAGCGATCTG

TCTATTTCGTTCATCCATAGTTGCCTGACTCCCCGTCGTGTAGATAACTA

CGATACGGGAGGGCTTACCATCTGGCCCCAGTGCTGCAATGATACCGCGA

GAACCACGCTCACCGGCTCCAGATTTATCAGCAATAAACCAGCCAGCCGG

AAGGGCCGAGCGCAGAAGTGGTCCTGCAACTTTATCCGCCTCCATCCAGT

CTATTAATTGTTGCCGGGAAGCTAGAGTAAGTAGTTCGCCAGTTAATAGT

TTGCGCAACGTTGTTGCCATTGCTACAGGCATCGTGGTGTCACGCTCGTC

GTTTGGTATGGCTTCATTCAGCTCCGGTTCCCAACGATCAAGGCGAGTTA

CATGATCCCCCATGTTGTGCAAAAAAGCGGTTAGCTCCTTCGGTCCTCCG

ATCGTTGTCAGAAGTAAGTTGGCCGCAGTGTTATCACTCATGGTTATGGC

AGCACTGCATAATTCTCTTACTGTCATGCCATCCGTAAGATGCTTTTCTG

TGACTGGTGAGTACTCAACCAAGTCATTCTGAGAATAGTGTATGCGGCGA

CCGAGTTGCTCTTGCCCGGCGTCAATACGGGATAATACCGCGCCACATAG

CAGAACTTTAAAAGTGCTCATCATTGGAAAACGTTCTTCGGGGCGAAAAC

TCTCAAGGATCTTACCGCTGTTGAGATCCAGTTCGATGTAACCCACTCGT

GCACCCAACTGATCTTCAGCATCTTTTACTTTCACCAGCGTTTCTGGGTG

AGCAAAAACAGGAAGGCAAAATGCCGCAAAAAAGGGAATAAGGGCGACAC

GGAAATGTTGAATACTCATACTCTTCCTTTTTCAATATTATTGAAGCATT

TATCAGGGTTATTGTCTCATGAGCGGATACATATTTGAATGTATTTAGAA

AAATAAACAAATAGGGGTTCCGCGCACATTTCCCCGAAAAGTGCCACCTA

CTAGTGAATGCCTACTAGAAGATGTGTGTTGCACAAAATGTCCCTGGAA

TAACCAATTTGAAGTGCAGATAGCAGTAAACGTAAGCTAATATGAATATT

ATTTAACTGTAATGTTTTAATATCGCTGGACATTACTAATAAACCCACTA
```

TAAACACATGTACATATGTATGTTTTGGCATACAATGAGTAGTTGGGGAA

AAAATGTGTAAAAGCACCGTGACCATCACAGCATAAAGATAACCAGCTGA

AGTATCGAATATGAGTAACCCCCAAATTGAATCACATGCCGCAACTGATA

GGACCCATGGAAGTACACTCTTCATGGCGATATACAAGACACACACAAGC

ACGAACACCCAGTTGCGGAGGAAATTCTCCGTAAATGAAAACCCAATCGG

CGAACAATTCATACCCATATATGGTAAAAGTTTTGAACGCGAGCGAACTT

AAGAGCGCCGGAGTATAAATAGAGGCGCTTCGTCTACGGAGCGACAATTC

AATTCAAACAAGCAAAGTGAACACGTCGCTAAGCGAAAGCTAAGCAAATA

AACAAGCGCAGCTGAACAAGCTAAACAATCTGCAGAAGCTTGGTACCCTC

GAGCTCAGCTGAATTCTGGATCCTCTAGAAATAATTTTGTTTAACCTTAA

GAAGGAGATATACTCAAAATGAAGCTGTGCATACTGCTGGCCGTCGTGGC

CTTTGTTGGCCTCTCGCTCGGGGAAAATTTGTATTTTCAATGCAGGTCGT

TCACTATTATTTAGTGAAATGAGATATTATGATATTTTCTGAATTGTGAT

TAAAAAGGCAACTTTATGCCCATGCAACAGAAACTATAAAAAATACAGAG

AATGAAAAGAAACAGATAGATTTTTTAGTTCTTTAGGCCCGTAGTCTGCA

AATCCTTTTATGATTTTCTATCAAACAAAAGAGGAAAATAGACCAGTTGC

AATCCAAACGAGAGTCTAATAGAATGAGGTCGAAAAGTAAATCGCGCGGG

TTTGTTACTGATAAAGCAGGCAAGACCTAAAATGTGTAAAGGGCAAAGTG

TATACTTTGGCGTCACCCCTTACATATTTTAGGTCTTTTTTTATTGTGCG

TAACTAACTTGCCATCTTCAAACAGGAGGGCTGGAAGAAGCAGACCGCTA

ACACAGTACATAAAAAAGGAGACATGAACGATGAACATCAAAAGTTTGC

AAAACAAGCAACAGTATTAACCTTTACTACCGCACTGCTGGCAGGAGGCG

CAACTCAAGCGTTTGCGAAAGAAACGAACCAAAAGCCATATAAGGAAACA

TACGGCATTTCCCATATTACACGCCATGATATGCTGCAAATCCCTGAACA

GCAAAAAATGAAAAATATAAAGTTCCTGAGTTCGATTCGTCCACAATTA

AAAATATCTCTTCTGCAAAAGGCCTGGACGTTTGGGACAGCTGGCCATTA

CAAAACACTGACGGCACTGTCGCAAACTATCACGGCTACCACATCGTCTT

TGCATTAGCCGGAGATCCTAAAAATGCGGATGACACATCGATTTACATGT

TCTATCAAAAGTCGGCGAAACTTCTATTGACAGCTGGAAAAACGCTGGC

CGCGTCTTTAAAGACAGCGACAAATTCGATGCAAATGATTCTATCCTAAA

AGACCAAACACAAGAATGGTCAGGTTCAGCCACATTTACATCTGACGGAA

AAATCCGTTTATTCTACACTGATTTCTCCGGTAAACATTACGGCAAACAA

ACACTGACAACTGCACAAGTTAACGTATCAGCATCAGACAGCTCTTTGAA

CATCAACGGTGTAGAGGATTATAAATCAATCTTTGACGGTGACGGAAAAA

CGTATCAAAATGTACAGCAGTTCATCGATGAAGGCAACTACAGCTCAGGC

GACAACCATACGCTGAGAGATCCTCACTACGTAGAAGATAAAGGCCACAA

ATACTTAGTATTTGAAGCAAACACTGGAACTGAAGATGGCTACCAAGGCG

AAGAATCTTTATTTAACAAAGCATACTATGGCAAAAGCACATCATTCTTC

CGTCAAGAAAGTCAAAAACTTCTGCAAAGCGATAAAAAACGCACGGCTGA

GTTAGCAAACGGCGCTCTCGGTATGATTGAGCTAAACGATGATTACACAC

TGAAAAAGTGATGAAACCGCTGATTGCATCTAACACAGTAACAGATGAA

ATTGAACGCGCGAACGTCTTTAAAATGAACGGCAAATGGTACCTGTTCAC

TGACTCCCGCGGATCAAAAATGACGATTGACGGCATTACGTCTAACGATA

TTTACATGCTTGGTTATGTTTCTAATTCTTTAACTGGCCCATACAAGCCG

CTGAACAAAACTGGCCTTGTGTTAAAAATGGATCTTGATCCTAACGATGT

AACCTTTACTTACTCACACTTCGCTGTACCTCAAGCGAAAGGAAACAATG

TCGTGATTACAAGCTATATGACAAACAGAGGATTCTACGCAGACAAACAA

TCAACGTTTGCGCCTAGCTTCCTGCTGAACATCAAAGGCAAGAAAACATC

TGTTGTCAAAGACAGCATCCTTGAACAAGGACAATTAACAGTTAACAAAT

AAAAACGCAAAGAAAATGCCGATATCCTATTGGCATTGACGTCAGGTGG

CACACCTGCAGAGAACCTCTACTTCCAATCGCACCATCATCACCACCATG

ATTACAAGGATGACGACGATAAGTGAGGATCCGAATTCGAGCTCCGTCGA

CAAGCTTGCGGCCGCGGATCGATCGATATCTGACTAAATCTTAGTTTGTA

TTGTCATGTTTTAATACAATATGTTATGTTTAAATATGTTTTTAATAAAT

TTTATAAAATAATTTCAACTTTTATTGTAACAACATTGTCCATTTACACA

CTCCTTTCAAGCGCGTGGGACTCGATGCTCGGCGCCACTCAAAGGCGGTA

ATACGGTTATCCACAGAATCAGGGGATAACGCAGGAAAGAACATGTGAGC

AAAAGGCCAGCAAAAGGCCAGGAACCGTAAAAAGGCCGCGTTGCTGGCGT

TTTTCCATAGGCTCCGCCCCCCTGACGAGCATCACAAAAATCGACGCTCA

AGTCAGAGGTGGCGAAACCCGACAGGACTATAAAGATACCAGGCGTTTCC

CCCTGGAAGCTCCCTCGTGCGCTCTCCTGTTCCGACCCTGCCGCTTACCG

GATACCTGTCCGCCTTTCTCCCTTCGGGAAGCGTGGCGCT

---

The invention claimed is:

1. An isolated DNA polynucleotide suitable for heterologous expression of a polypeptide of interest in an insect cell, said DNA polynucleotide comprising a promoter DNA polynucleotide comprising a chimeric sequence comprising residues 7-586 of SEQ ID NO: 68, SEQ ID NO: 68, or the nucleotide sequence SEQ ID NO: 3, SEQ ID NO: 4, SEQ ID NO: 5, SEQ ID NO: 6, or SEQ ID NO: 33, wherein in each of SEQ ID NOs: 3-6 and 33, having SEQ ID NO: 36 found therein, has SEQ ID NO: 36 substituted by SEQ ID NO: 37.

2. The isolated DNA polynucleotide according to claim 1, wherein said promoter DNA polynucleotide exhibits an increased protein expression level as compared to the protein expression level of any one of the promoter DNA polynucleotides having the sequence of SEQ ID NO:1 or SEQ ID NO:4.

3. The isolated DNA polynucleotide according to claim 2, wherein the increase in protein expression level is from about 50 percent to about 300 percent relative to the protein expression level of any one of the promoter DNA polynucleotides having the sequence of SEQ ID NO:1 or SEQ ID NO:4.

4. The isolated DNA polynucleotide according to claim 2, wherein the increase in protein expression level is 2 fold to 10 fold relative to the protein expression level of any one of the promoter DNA polynucleotides having the sequence of SEQ ID NO:1 or SEQ ID NO:4, or to the pOPIE2 promoter.

5. The isolated DNA polynucleotide according to claim 1, which further comprises a selection marker.

6. The isolated DNA polynucleotide according to claim 5, which further comprises a bacterial promoter.

7. The isolated DNA polynucleotide according to claim 5, which further comprises a second promoter DNA polynucleotide suitable to drive the expression of the selection marker in an insect cell.

8. The isolated DNA polynucleotide according to claim 5, wherein the selection marker is selected from the group consisting of a Zeocin selection marker, a Neomycin selection marker, a Hygromycin selection marker, a Puromycin selection marker, and a Blasticidin selection marker.

9. The isolated DNA polynucleotide according to claim 6, wherein the bacterial promoter is a pKANR bacterial promoter.

10. The isolated DNA polynucleotide according to claim 7, wherein said second promoter is selected from the group consisting of a nucleotide sequence of SEQ ID NO:1, SEQ ID NO:2, SEQ ID NO:3, SEQ ID NO:4, SEQ ID NO:5, SEQ ID NO:6, SEQ ID NO:33, SEQ ID NO:36, SEQ ID NO:37, or a nucleotide sequence comprising residues 7-586 of SEQ ID NO: 68.

11. The isolated DNA polynucleotide according to claim 1, which further comprises at least one ubiquitous chromatin opening element upstream and/or downstream relative to a multiple cloning site.

12. The isolated DNA polynucleotide according to claim 1, which further comprises at least one Transcriptional insulator element.

13. The isolated DNA polynucleotide according to claim 12, wherein the transcriptional insulator element is a Gypsy (gsu(Hw)) insulator sequence.

14. The isolated DNA polynucleotide according to claim 1, which further comprises a dihydrofolate reductase (dhfr) coding sequence suitable for selection in insect cells.

15. The isolated DNA polynucleotide according to claim 1, which further comprises at least one polyadenylation signal sequence.

16. The isolated DNA polynucleotide according to claim 15, wherein the polyadenylation sequence is selected from a SV40 polyA signal, an OPIE2 polyA signal, and a combined SV40 polyA signal and OPIE2 polyA signal.

17. The isolated DNA polynucleotide according to claim 1, which further comprises an *E. coli* origin of replication.

18. The isolated DNA polynucleotide according to claim 1, which further comprises at least one protein export signal polynucleotide sequence.

19. The isolated DNA polynucleotide according to claim 18, wherein the protein export sequence is selected from BIP and CPY.

20. The isolated DNA polynucleotide according to claim 1, which is essentially free of viral DNA.

21. The isolated DNA polynucleotide according to claim 1, which further comprises at least one HIS-tag sequence.

22. The isolated DNA polynucleotide according to claim 1, which further comprises a multiple cloning site downstream of said promoter DNA polynucleotide for insertion of the gene encoding a polypeptide of interest into said isolated DNA polynucleotide.

23. The isolated DNA polynucleotide according to claim 22, comprising the intron shown in SEQ ID NO: 60 including or excluding the flanking restriction sites.

24. The isolated DNA polynucleotide according to claim 1, which further comprises at least one 72 bp element from SV40.

25. The isolated DNA polynucleotide according to claim 1, which further comprises at least one amplification control element.

26. The isolated DNA polynucleotide according to claim 1, which further comprises at least one Ori-beta element.

27. The isolated DNA polynucleotide according to claim 1, which further comprises at least one matrix attachment region (MAR) element.

28. The isolated DNA polynucleotide according to claim 1, which further comprises at least one PRE element from Hepatitis B virus.

29. The isolated DNA polynucleotide according to claim 28, comprising the a PRE element from Hepatitis B virus according to SEQ ID NO:40.

30. The isolated DNA polynucleotide according to claim 28, comprising nucleotides 10 to 574 of SEQ ID NO:40.

31. The isolated DNA polynucleotide according to claim 1, wherein the promoter DNA polynucleotide sequence controls the expression of a gene or other DNA sequence to which it is linked.

32. The isolated DNA polynucleotide according to claim 1, which further comprises at least one intron downstream of the promoter DNA polynucleotide sequence and upstream of a multiple cloning site.

33. The isolated DNA polynucleotide according to claim 1, which is adapted for ligation independent cloning (LIC).

34. The isolated DNA polynucleotide according to claim 1, which further comprises at least one polynucleotide sequence encoding a polypeptide heterologous to said promoter DNA polynucleotide sequence.

35. An isolated cell comprising the isolated DNA polynucleotide according to claim 1.

36. The isolated cell according to claim 35, which is an insect cell.

37. The isolated cell according to claim 35, which is stably transfected with said isolated DNA polynucleotide.

38. The isolated cell according to claim 37, which is a *Drosophila melanogaster* cell.

39. A method for the production of a polypeptide of interest encoded by a polynucleotide the method comprising the steps of
    (a) obtaining a polynucleotide sequence encoding the polypeptide of interest;
    (b) inserting said polynucleotide sequence encoding the polypeptide of interest into the isolated DNA polynucleotide according to claim 1;
    (c) transforming a host cell with the polynucleotide obtained under step (b);
    (d) allowing for the expression of said polynucleotide obtained under step (b) to produce the polypeptide; and
    (e) obtaining the polypeptide there from.

\* \* \* \* \*

SEQUENCE LISTING

<160> NUMBER OF SEQ ID NOS: 74

<210> SEQ ID NO 1
<211> LENGTH: 457
<212> TYPE: DNA
<213> ORGANISM: Drosophila melanogaster

<400> SEQUENCE: 1
ctagaatccc aaaacaaact ggttattgtg gtaggtcatt tgtttggcag aaagaaaact      60
cgagaaattt ctctggccgt tattcgttat tctctctttt cttttgggt ctctccctct      120

```
ctgcactaat gctctctcac tctgtcacac agtaaacggc atactgctct cgttggttcg      180
agagagcgcg cctcgaatgt tcgcgaaaag agcgccggag tataaataga ggcgcttcgt      240
ctacggagcg acaattcaat tcaaacaagc aaagtgaaca cgtcgctaag cgaaagctaa      300
gcaaataaac aagcgcagct gaacaagcta acaatctgc agtaaagtgc aagttaaagt       360
gaatcaatta aaagtaacca gcaaccaagt aaatcaactg caactactga atctgccaa       420 gaagtaatta ttgaatacaa gaagagaact ctgaata                               457

<210> SEQ ID NO 2
<211> LENGTH: 284
<212> TYPE: DNA
<213> ORGANISM: Drosophila melanogaster

<400> SEQUENCE: 2
ctcgagaaat ttctctggcc gttattcgtt attctctctt ttcttttttgg gtctctccct    60 ctctgcacta atgctctctc actctgtcac acagtaaacg gcatactgct ctcgttggtt    120
cgagagagcg cgcctcgaat gttcgcgaaa agagcgccgg agtataaata gaggcgcttc    180
gtctacggag cgacaattca attcaaacaa gcaaagtgaa cacgtcgcta agcgaaagct    240
aagcaaataa acaagcgcag ctgaacaagc taaacaatct gcag                     284

<210> SEQ ID NO 3
<211> LENGTH: 2532
<212> TYPE: DNA
<213> ORGANISM: Drosophila melanogaster

<400> SEQUENCE: 3
gctagctaaa aaaatcatg aatggcatca actctgaatc aaatctttgc agatgcacct     60
acttctcatt tccactgtca catcattttt ccagatctcg ctgcctgtta tgtggcccac    120
aaaccaagac acgttttatg gccattaaag ctggctgatc gtcgccaaac accaaataca    180
taatgaatat gtacacattc gagaaagaag cgatcaaaga agcgtcttcg ggcggagtag    240
gagaatgcgg aggagaagga gaacgagctg atctagtatc tctccacaat ccaatgccaa    300
ctgaccaact ggccatattc ggagcaattt gaagccaatt tccatcgcct ggcgatcgct    360
ccattcttgg ctatatgttt ttcaccgtta cccggggcca ttttcaaaga ctcgtcggca    420
agataagatt gtgtcactcg ctgtctctct tcatttgtcg aagaatgctg aggaatttcg    480
cgatgacgtc ggcgagtatt ttgaagaatg agaataattt gtatttatac gaaaatcagt    540
tagtggaatt ttctacaaaa acatgttatc tatagataat tttgttgcaa aatatgttga    600
ctatgacaaa gattgtatgt ataccctttt aatgtattct cattttctta tgtatttata    660
atggcaatga tgtactgat gatattttaa gatgatgcca gaccaaaagg cttgaatttc     720
tgcgtctttt gccgaacgca gtgcatgtgc aattgttgtt ttttggaata ttcaattttc    780
ggactgtccg ctttgatttc agtttcttgg cttattcaaa aagcaaagta aagccaaaaa    840
agcgagatgg caataccaaa tgcggcaaaa cggtagtgga aggaaagggg tgcggggcag    900
cggaaggaag ggtggggcgg ggcgtggcgg ggtctgtggc tgggcgcgac gtcaccgacg    960
ttggagccac tcctttgacc atgtgtgcgt gtgtgtatta ttcgtgtctc gccactcgcc   1020
ggttgttttt ttcttttat gctgcgctct ctctagcgcc atctcgctta cgcatgctca    1080
acgcaccgca tgttgccgtt tccttttatg cgtcattttg gctcgaaata ggcaattatt   1140
taaacaaaga ttagtcaacg aaaacgctaa aataaataag tctacaatat ggttacttat   1200
```

-continued

```
tgccatgtgt gtgcagccaa cgatagcaac aaaagcaaca acacaggtgg ctttccctct    1260
ttcactttt gtttgcaagc cgcgtgcgag caagacggca cgaccggcaa acgcaattac    1320
gctgacaaag agcagacgaa gttttggcga aaaacatcaa ggcgcctgat acgaatgcat    1380
ttgcaataac aattgcgata tttaatattg tttatgaagc tgtttgactt caaaacacac    1440
aaaaaaaaaa ataaaacaaa ttatttgaaa gagaattagg aatcggacgc ttatcgttag    1500
ggtaacaaca agaaatgctt actgagtcac agcctctgga aaactgccgc aagccagaga    1560
gagagagaaa aagagggaga gcagcttaga ccgcatgtgc ttgtgtgtga ggcgtctctc    1620
tcttcgtctc tgttgcgcaa acgcatagac tgcactgaaa aaatcgatta cctattttt    1680
atgaatgaat atttgcacta ttactattca aaactattaa gatagcaatc acattcaata    1740
gccaaatact ataccacctg agcgatgcaa cgaaatgatc aatttgagca aaaatgctgc    1800
atatttagga cggcatcatt atagaaatgc ttcttgctgt gtacttttct ctcgtctggc    1860
agctgtttcg ccgttattgt taaaaccggc ttaagttagg tgtgttttct acgactagtg    1920
aatgccctac tagaagatgt gtgttgcaca aaatgtccct ggaataacca atttgaagtg    1980
cagatagcag taaacgtaag ctaatatgaa tattattaa ctgtaatgtt ttaatatcgc    2040
tggacattac taataaaccc actataaaca catgtacata tgtatgtttt ggcatacaat    2100
gagtagttgg ggaaaaaatg tgtaaaagca ccgtgaccat cacagcataa agataaccag    2160
ctgaagtatc aatatgagt aaccccccaaa ttgaatcaca tgccgcaact gataggaccc    2220
atggaagtac actcttcatg gcgatataca agacacacac aagcacgaac acccagttgc    2280
ggaggaaatt ctccgtaaat gaaaacccaa tcggcgaaca attcatatccc atatatggta    2340
aaagttttga acgcgacttg agagcggaga gcattgcggc tgataaggtt ttagcgctaa    2400
gcgggcttta taaacgggc tgcgggacca gttttcatat cactaccgtt tgagttcttg    2460
tgctgtgtgg atactcctcc cgacacaaag ccgctccatc agccagcagt cgtctaatcc    2520
agagacaagc tt                                                        2532
```

<210> SEQ ID NO 4
<211> LENGTH: 2538
<212> TYPE: DNA
<213> ORGANISM: Drosophila melanogaster

<400> SEQUENCE: 4

```
gatacttcta aaaaaaatca tgaatggcat caactctgaa tcaaatcttt gcagatgcac      60
ctacttctca tttccactgt cacatcattt ttccagatct cgctgcctgt tatgtggccc     120
acaaaccaag acacgtttta tggccattaa agctggctga tcgtcgccaa acaccaaata     180
catatcaata tgtacattcg agaaagaagc gatcaaagaa gcgtcttcgg gcgagtagga     240
gaatgcggag gagaaggaga acgagctgat ctagtatctc tccacaatcc aatgccaact     300
gaccaactgg ccatattcgg agcaattga agccaatttc catcgcctgg cgatcgctcc     360
attcttggct atatgtttt caccgttccc ggggccattt tcaaagactc gtcggtaaga     420
taagattgtg tcactcgctg tctctcttca tttgtcgaag aatgctgagg aattcgcga     480
tgacgtcggc gagtatttg aagaatgaga ataatttgta tttatacgaa aatcagttag     540
tggaatttc tacaaaaaca tgttatctat agataatttt gttgcaaaat atgttgacta     600
tgacaaagat tgtatgtata taccctttaat gtattctcat tttcttatgt atttataatg     660
gcaatgatga tactgatgat attttaagat gatgccagac cacaggctga tttctgcgtc     720
ttttgccgaa cgcagtgcat gtgcggttgt tgttttttgg aatagtttca attttcggac     780
```

-continued

| | |
|---|---|
| tgtccgcttt gatttcagtt tcttggctta ttcaaaaagc aaagtaaagc caaaaaagcg | 840 |
| agatggcaat accaaatgcg gcaaaacggt agtggaagga aaggggtgcg gggcagcgga | 900 |
| aggaagggtg gggcggggcg tggcggggtc tgtggctggg cgcgacgtca ccgacgttgg | 960 |
| agccactcct ttgaccatgt gtgcgtgtgt gtattattcg tgtctcgcca ctcgccggtt | 1020 |
| gttttttttct ttttatctcg ctctctctag cgccatctcg tacgcatgct caacgcaccg | 1080 |
| catgttgccg tgtcctttat gcgtcatttt ggctcgaaat aggcaattat ttaaacaaag | 1140 |
| attagtcaac gaaaacgcta aataaataa gtctacaata tggttactta ttgccatgtg | 1200 |
| tgtgcagcca acgatagcaa caaaagcaac aacacagtgg cttccctct ttcactttt | 1260 |
| gtttgcaagc gcgtgcgagc aagacggcac gaccggcaaa cgcaattacg ctgacaaaga | 1320 |
| gcagacgaag ttttggccga aaacatcaa ggcgcctgat acgaatgcat ttgcaataac | 1380 |
| aattgcgata tttaatattg tttatgaagc tgtttgactt caaaacacac aaaaaaaaaa | 1440 |
| ataaaacaaa ttatttgaaa gagaattagg aatcggacag cttatcgtta cgggctaaca | 1500 |
| gcacaccgag acgaaatagc ttacctgacg tcacagcctc tggaagaact gccgccaagc | 1560 |
| agagagagag agaaaaagag ggagagcagc ttagaccgca tgtgcttgtg tgtgaggcgt | 1620 |
| ctctctcttc gtctcctgtt tgcgcaaacg catagactgc actgagaaaa tcgattacct | 1680 |
| atttttatg aatgaatatt tgcactatta ctattcaaaa ctattaagat agcaatcaca | 1740 |
| ttcaatagcc aaatactata ccacctgagc gatgcaacga aatgatcaat tgagcaaaa | 1800 |
| atgctgcata tttaggacgg catcattata gaaatgcttc ttgctgtgta cttttctctc | 1860 |
| gtctggcagc tgtttcgccg ttattgttaa accggctta agttaggtgt gttttctacg | 1920 |
| actagtgatg cccctactag aagatgtgtg ttgcacaaat gtccctgaat aaccaatttg | 1980 |
| aagtgcagat agcagtaaac gtaagctaat atgaatatta tttaactgta atgttttaat | 2040 |
| atcgctggac attactaata aacccactat aaacacatgt acatatgtat gttttggcat | 2100 |
| acaatgagta gttggggaaa aatgtgtaa aagcaccgtg accatcacag cataaagata | 2160 |
| accagctgaa gtatcgaata tgagtaaccc ccaaattgaa tcacatgccg caactgatag | 2220 |
| gacccatgga agtacactct tcatggcgat atacaagaca cacacaagca cgaacaccca | 2280 |
| gttgcggagg aaattctccg taaatgaaaa cccaatcggc gaacaattca tacccatata | 2340 |
| tggtaaaagt tttgaacgcg acttgagagc ggagagcatt gcggctgata aggttttagc | 2400 |
| gctaagcggg ctttataaaa cgggctgcgg gaccagtttt catatcacta ccgtttgagt | 2460 |
| tcttgtgctg tgtggatact cctcccgaca caaagccgct ccatcagcca gcagtcgtct | 2520 |
| aatccagaga ccccggat | 2538 |

<210> SEQ ID NO 5
<211> LENGTH: 1468
<212> TYPE: DNA
<213> ORGANISM: Drosophila melanogaster

<400> SEQUENCE: 5

| | |
|---|---|
| gcatgctcaa cgcaccgcat gttgccgtgt cctttatgcg tcattttggc tcgaaatagg | 60 |
| caattattta aacaaagatt agtcaacgaa aacgctaaaa taataagtc tacaatatgg | 120 |
| ttacttattg ccatgtgtgt gcagccaacg atagcaacaa aagcaacaac acagtggctt | 180 |
| tccctctttc acttttttgtt tgcaagcgcg tgcgagcaag acggcacgac cggcaaacgc | 240 |
| aattacgctg acaaagagca gacgaagttt tggccgaaaa catcaaggc gcctgatacg | 300 |

```
aatgcatttg caataacaat tgcgatattt aatattgttt atgaagctgt ttgacttcaa    360
aacacacaaa aaaaaaaata aaacaaatta tttgaaagag aattaggaat cggacagctt    420
atcgttacgg gctaacagca caccgagacg aaatagctta cctgacgtca cagcctctgg    480
aagaactgcc gccaagcaga gagagagaga aaagaggga gagcagctta gaccgcatgt    540
gcttgtgtgt gaggcgtctc tctcttcgtc tcctgtttgc gcaaacgcat agactgcact    600
gagaaaatcg attacctatt ttttatgaat gaatatttgc actattacta ttcaaaacta    660
ttaagatagc aatcacattc aatagccaaa tactatacca cctgagcgat gcaacgaaat    720
gatcaatttg agcaaaaatg ctgcatattt aggacggcat cattatagaa atgcttcttg    780
ctgtgtactt ttctctcgtc tggcagctgt ttcgccgtta ttgttaaaac cggcttaagt    840
taggtgtgtt ttctacgact agtgatgccc ctactagaag atgtgtgttg cacaaatgtc    900
cctgaataac caatttgaag tgcagatagc agtaaacgta agctaatatg aatattattt    960
aactgtaatg ttttaatatc gctggacatt actaataaac ccactataaa cacatgtaca   1020
tatgtatgtt ttggcataca atgagtagtt ggggaaaaaa tgtgtaaaag caccgtgacc   1080
atcacagcat aaagataacc agctgaagta tcgaatatga gtaaccccca aattgaatca   1140
catgccgcaa ctgataggac ccatggaagt acactcttca tggcgatata caagacacac   1200
acaagcacga acaccccagtt gcggaggaaa ttctccgtaa atgaaaaccc aatcggcgaa   1260
caattcatac ccatatatgg taaaagtttt gaacgcgact tgagagcgga gagcattgcg   1320
gctgataagg ttttagcgct aagcgggctt tataaaacgg gctgcgggac cagttttcat   1380
atcactaccg tttgagttct tgtgctgtgt ggatactcct cccgacacaa agccgctcca   1440
tcagccagca gtcgtctaat ccagagac                                      1468

<210> SEQ ID NO 6
<211> LENGTH: 612
<212> TYPE: DNA
<213> ORGANISM: Drosophila melanogaster

<400> SEQUENCE: 6
ctagtgaatg ccctactaga agatgtgtgt tgcacaaaat gtccctggaa taaccaattt     60
gaagtgcaga tagcagtaaa cgtaagctaa tatgaatatt atttaactgt aatgttttaa    120
tatcgctgga cattactaat aaacccacta taaacacatg tacatatgta tgttttggca    180
tacaatgagt agttggggaa aaaatgtgta aaagcaccgt gaccatcaca gcataaagat    240
aaccagctga gtatcgaat atgagtaacc cccaaattga atcacatgcc gcaactgata    300
ggacccatgg aagtacactc ttcatggcga tatacaagac acacacaagc acgaacaccc    360
agttgcggag gaaattctcc gtaaatgaaa acccaatcgg cgaacaattc atacccatat    420
atggtaaaag ttttgaacgc gacttgagag cggagagcat tgcggctgat aaggttttag    480
cgctaagcgg gctttataaa acgggctgcg gaccagtttt tcatatcact accgtttgag    540
ttcttgtgct gtgtggatac tcctcccgac acaaagccgc tccatcagcc agcagtcgtc    600
taatccagag ac                                                       612

<210> SEQ ID NO 7
<211> LENGTH: 550
<212> TYPE: DNA
<213> ORGANISM: Orgyia pseudotsugata multicapsid nucleopolyhedrosis
      virus

<400> SEQUENCE: 7
```

-continued

```
gtcatgatga taaacaatgt atggtgctaa tgttgcttca acaacaattc tgttgaactg    60
tgttttcatg tttgccaaca agcaccttta tactcgtgg cctccccacc accaacttt    120 ttgcactgca aaaaacacg cttttgcacg cgggcccata catagtacaa actctacgtt    180
tcgtagacta ttttacataa atagtctaca ccgttgtata cgctccaaat acactaccac    240
acattgaacc tttttgcagt gcaaaaaagt acgtgtcggc agtcacgtag gccggcctta    300
tcgggtcgcg tcctgtcacg tacgaatcac attatcggac cggacgagtg ttgtcttatc    360
gtgacaggac gccagcttcc tgtgttgcta accgcagccg acgcaactc cttatcggaa    420 caggacgcgc ctccatatca gccgcgcgtt atctcatgcg cgtgaccgga cacgaggcgc    480
ccgtcccgct tatcgcgcct ataaatacag cccgcaacga tctggtaaac acagttgaac    540
agcatctgtt                                                            550

<210> SEQ ID NO 8
<211> LENGTH: 387
<212> TYPE: DNA
<213> ORGANISM: Drosophila melanogaster

<400> SEQUENCE: 8
tcacgtaata agtgtgcgtt gaatttattc gcaaaaacat tgcatatttt cggcaaagta    60 aaatttgtt gcataccta tcaaaaaata agtgctgcat acttttaga gaaaccaaat     120 aatttttat tgcatacccg ttttaataa atacattgc ataccctctt ttaataaaaa     180
atattgcata ctttgacgaa acaaattttc gttgcatacc caataaaaga ttattatatt    240 gcataccgt ttttaataaa atacattgca taccctcttt taataaaaaa tattgcatac    300
gttgacgaaa caaattttcg ttgcataccc aataaaagat tattatattg cataccttt    360 cttgccatac catttagccg atcaatt                                         387

<210> SEQ ID NO 9
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 9
cgctcagtgg aacgaaaact cacg                                            24

<210> SEQ ID NO 10
<211> LENGTH: 112
<212> TYPE: DNA
<213> ORGANISM: Artificial sequence
<220> FEATURE:
<223> OTHER INFORMATION: Synthetic DNA primer

<400> SEQUENCE: 10
aagggatttt ggtcatgaac aataaaactg tctgcttaca taaacagtaa tacaaggggt    60
gttcatagta taatacgact cactatagga gggccaccat ggccaagttg ac           112

<210> SEQ ID NO 11
<211> LENGTH: 56
<212> TYPE: DNA
<213> ORGANISM: Artificial sequence
<220> FEATURE:
<223> OTHER INFORMATION: Synthetic DNA primer

<400> SEQUENCE: 11
gcagacagtt ttattgttca tgaccaaaat cccttgcaga gatccgaatt aattcg         56
```

-continued

<210> SEQ ID NO 12
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 12
cacccaggcc agggtgttgt ccggc                                         25

<210> SEQ ID NO 13
<211> LENGTH: 26
<212> TYPE: DNA
<213> ORGANISM: Artificial sequence
<220> FEATURE:
<223> OTHER INFORMATION: Synthetic DNA primer

<400> SEQUENCE: 13
gttttattgt tcatgaccaa aatccc                                        26

<210> SEQ ID NO 14
<211> LENGTH: 45
<212> TYPE: DNA
<213> ORGANISM: Artificial sequence
<220> FEATURE:
<223> OTHER INFORMATION: Synthetic DNA primer

<400> SEQUENCE: 14
gcgcctcgaa tgttcgcgaa cttaagagcg ccggagtata aatag                   45

<210> SEQ ID NO 15
<211> LENGTH: 45
<212> TYPE: DNA
<213> ORGANISM: Artificial sequence
<220> FEATURE:
<223> OTHER INFORMATION: Synthetic DNA primer

<400> SEQUENCE: 15
ctatttatac tccggcgctc ttaagttcgc gaacattcga ggcgc                   45

<210> SEQ ID NO 16
<211> LENGTH: 45
<212> TYPE: DNA
<213> ORGANISM: Artificial sequence
<220> FEATURE:
<223> OTHER INFORMATION: Synthetic DNA primer

<400> SEQUENCE: 16
gtaaaagttt tgaacgcgac ttaaggagag cggagagcat tgcgg                   45

<210> SEQ ID NO 17
<211> LENGTH: 45
<212> TYPE: DNA
<213> ORGANISM: Artificial sequence
<220> FEATURE:
<223> OTHER INFORMATION: Synthetic DNA primer

<400> SEQUENCE: 17
ccgcaatgct ctccgctctc cttaagtcgc gttcaaaact tttac                   45

<210> SEQ ID NO 18
<211> LENGTH: 21
<212> TYPE: DNA
<213> ORGANISM: Artificial sequence
<220> FEATURE:

<223> OTHER INFORMATION: Synthetic DNA primer

<400> SEQUENCE: 18
ttcactgcat tctagttgtg g                                             21

<210> SEQ ID NO 19
<211> LENGTH: 21
<212> TYPE: DNA
<213> ORGANISM: Artificial sequence
<220> FEATURE:
<223> OTHER INFORMATION: Synthetic DNA primer

<400> SEQUENCE: 19
ctaagattta gtcagatatc g                                             21

<210> SEQ ID NO 20
<211> LENGTH: 51
<212> TYPE: DNA
<213> ORGANISM: Artificial sequence
<220> FEATURE:
<223> OTHER INFORMATION: Synthetic DNA primer

<400> SEQUENCE: 20
catcaatgta tcttatcatg tctgctagcg gatcatgatg ataaacaatg t            51

<210> SEQ ID NO 21
<211> LENGTH: 51
<212> TYPE: DNA
<213> ORGANISM: Artificial sequence
<220> FEATURE:
<223> OTHER INFORMATION: Synthetic DNA primer

<400> SEQUENCE: 21
acattgttta tcatcatgat ccgctagcag acatgataag atacattgat g            51

<210> SEQ ID NO 22
<211> LENGTH: 29
<212> TYPE: DNA
<213> ORGANISM: Artificial sequence
<220> FEATURE:
<223> OTHER INFORMATION: Synthetic DNA primer

<400> SEQUENCE: 22
tctgctagct aaaaaaaatc atgaatggc                                     29

<210> SEQ ID NO 23
<211> LENGTH: 28
<212> TYPE: DNA
<213> ORGANISM: Artificial sequence
<220> FEATURE:
<223> OTHER INFORMATION: Synthetic DNA primer

<400> SEQUENCE: 23
ccaagcttgt ctctggatta gacgactg                                      28

<210> SEQ ID NO 24
<211> LENGTH: 26
<212> TYPE: DNA
<213> ORGANISM: Artificial sequence
<220> FEATURE:
<223> OTHER INFORMATION: Synthetic DNA primer

<400> SEQUENCE: 24
tgctagcctc gagaaatttc tctggc                                        26

```
<210> SEQ ID NO 25
<211> LENGTH: 27
<212> TYPE: DNA
<213> ORGANISM: Artificial sequence
<220> FEATURE:
<223> OTHER INFORMATION: Synthetic DNA primer

<400> SEQUENCE: 25
ccaagcttct gcagattgtt tagcttg                                       27

<210> SEQ ID NO 26
<211> LENGTH: 30
<212> TYPE: DNA
<213> ORGANISM: Artificial sequence
<220> FEATURE:
<223> OTHER INFORMATION: Synthetic DNA primer

<400> SEQUENCE: 26
agaattcagc tgagctcgag ggtaccaagc                                    30

<210> SEQ ID NO 27
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 27
ggtttgtcca aactcatcaa tgtat                                         25

<210> SEQ ID NO 28
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 28
ttattgccat gtgtgtgcag                                               20

<210> SEQ ID NO 29
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 29
cgatgcaacg aaatgatcaa                                               20

<210> SEQ ID NO 30
<211> LENGTH: 22
<212> TYPE: DNA
<213> ORGANISM: Artificial sequence
<220> FEATURE:
<223> OTHER INFORMATION: Synthetic DNA primer

<400> SEQUENCE: 30
ggctgataag gttttagcgc ta                                            22

<210> SEQ ID NO 31
<211> LENGTH: 23
<212> TYPE: DNA
<213> ORGANISM: Artificial sequence
<220> FEATURE:
<223> OTHER INFORMATION: Synthetic DNA primer
```

```
<400> SEQUENCE: 31
caaattattt gaaagagaat tag                                              23

<210> SEQ ID NO 32
<211> LENGTH: 23
<212> TYPE: DNA
<213> ORGANISM: Artificial sequence
<220> FEATURE:
<223> OTHER INFORMATION: Synthetic DNA primer

<400> SEQUENCE: 32
gttttaatat cgctggacat tac                                              23

<210> SEQ ID NO 33
<211> LENGTH: 2516
<212> TYPE: DNA
<213> ORGANISM: Artificial sequence
<220> FEATURE:
<223> OTHER INFORMATION: Recombinant plasmid DNA

<400> SEQUENCE: 33
taaaaaaaat catgaatggc atcaactctg aatcaaatct ttgcagatgc acctacttct        60
catttccact gtcacatcat ttttccagat ctcgctgcct gttatgtggc ccacaaacca       120
agacacgttt tatggccatt aaagctggct gatcgtcgcc aaacaccaaa tacatatcaa       180
tatgtacatt cgagaaagaa gcgatcaaag aagcgtcttc gggcgagtag gagaatgcgg       240
aggagaagga gaacgagctg atctagtatc tctccacaat ccaatgccaa ctgaccaact       300
ggccatattc ggagcaattt gaagccaatt ccatcgcct ggcgatcgct ccattcttgg        360
ctatatgttt ttcaccgtta cccggggcca ttttcaaaga ctcgtcggca agataagatt       420
gtgtcactcg ctgtctctct tcatttgtcg aagaatgctg aggaatttcg cgatgacgtc       480
ggcgagtatt ttgaagaatg agaataattt gtatttatac gaaatcagt tagtggaatt        540 ttctacaaaa acatgttatc tatagataat tttgttgcaa aatatgttga ctatgacaaa       600
gattgtatgt atataccttt aatgtattct cattttctta tgtatttata atggcaatga       660
tgatactgat gatattttaa gatgatgcca gaccaaaagg cttgaatttc tgcgtctttt       720
gccgaacgca gtgcatgtgc aattgttgtt ttttggaata ttcaattttc ggactgtccg       780
ctttgatttc agtttcttgg cttattcaaa aagcaaagta aagccaaaaa agcgagatgg       840
caataccaaa tgcggcaaaa cggtagtgga aggaaagggg tgcggggcag cggaaggaag       900
ggtggggcgg ggcgtggcgg ggtctgtggc tgggcgcgac gtcaccgacg ttggagccac       960
tcctttgacc atgtgtgcgt gtgtgtatta ttcgtgtctc gccactcgcc ggttgttttt      1020 ttcttttttat gctgcgctct ctctagcgcc atctcgctta cgcatgctca acgcaccgca      1080
tgttgccgtt tccttttatg cgtcattttg gctcgaaata ggcaattatt taaacaaaga      1140
ttagtcaacg aaaacgctaa aataaataag tctacaatat ggttacttat tgccatgtgt      1200
gtgcagccaa cgatagcaac aaaagcaaca acacaggtgg cttccctct ttcactttt        1260 gtttgcaagc cgcgtgcgag caagacggca cgaccggcaa acgcaattac gctgacaaag      1320
agcagacgaa gttttggcga aaaacatcaa ggcgcctgat acgaatgcat ttgcaataac      1380
aattgcgata tttaatattg tttatgaagc tgtttgactt caaaacacac aaaaaaaaaa      1440
ataaaacaaa ttatttgaaa gagaattagg aatcggacgc ttatcgttag ggtaacaaca      1500
agaaatgctt actgagtcac agcctctgga aaactgccgc aagccagaga gagagagaaa      1560
aagagggaga gcagcttaga ccgcatgtgc ttgtgtgtga ggcgtctctc tcttcgtctc      1620
```

```
tgttgcgcaa acgcatagac tgcactgaaa aaatcgatta cctatttttt atgaatgaat    1680
atttgcacta ttactattca aaactattaa gatagcaatc acattcaata gccaaatact    1740
ataccacctg agcgatgcaa cgaaatgatc aatttgagca aaaatgctgc atatttagga    1800
cggcatcatt atagaaatgc ttcttgctgt gtacttttct ctcgtctggc agctgtttcg    1860
ccgttattgt taaaaccggc ttaagttagg tgtgttttct acgactagtg aatgccctac    1920
tagaagatgt gtgttgcaca aaatgtccct ggaataacca atttgaagtg cagatagcag    1980
taaacgtaag ctaatatgaa tattatttaa ctgtaatgtt ttaatatcgc tggacattac    2040
taataaaccc actataaaca catgtacata tgtatgtttt ggcatacaat gagtagttgg    2100
ggaaaaaatg tgtaaaagca ccgtgaccat cacagcataa agataaccag ctgaagtatc    2160
gaatatgagt aacccccaaa ttgaatcaca tgccgcaact gataggaccc atggaagtac    2220
actcttcatg gcgatataca agacacacac aagcacgaac acccagttgc ggaggaaatt    2280
ctccgtaaat gaaaacccaa tcggcgaaca attcataccc atatatggta aaagttttga    2340
acgcgacttg agagcggaga gcattgcggc tgataaggtt ttagcgctaa gcgggcttta    2400
taaaacgggc tgcgggacca gttttcatat cactaccgtt tgagttcttg tgctgtgtgg    2460
atactcctcc cgacacaaag ccgctccatc agccagcagt cgtctaatcc agagac        2516

<210> SEQ ID NO 34
<211> LENGTH: 2847
<212> TYPE: DNA
<213> ORGANISM: Artificial sequence
<220> FEATURE:
<223> OTHER INFORMATION: Recombinant plasmid DNA

<400> SEQUENCE: 34
catagtataa tacgactcac tataggaggg ccaccatggc caagttgacc agtgccgttc      60
cggtgctcac cgcgcgcgac gtcgccgagc ggtcgagtt ctggaccgac cggctcgggt     120
tctcccggga cttcgtggag gacgacttcg ccggtgtggg ccgggacgac gtgaccctgt     180
tcatcagcgc ggtccaggac caggtggtgc cggacaacac cctggcctgg gtgtgggtgc     240
gcggcctgga cgagctgtac gccgagtggt cggaggtcgt gtccacgaac ttccgggacg     300
cctccgggcc ggccatgacc gagatcggcg agcagccgtg ggggcgggag ttcgccctgc     360
gcgacccggc cggcaactgc gtgcacttcg tggccgagga gcaggactga ccgacgccga     420
ccaacaccgc cggtccgacg gcggcccacg ggtcccaggg gggtcgacct cgaaacttgt     480
ttattgcagc ttataatggt tacaaataaa gcaatagcat cacaaatttc acaaataaag     540
catttttttc actgcattct agttgtggtt tgtccaaact catcaatgta tcttatcatg     600
tctgctagct cacgtaataa gtgtgcgttg aattattcg caaaaacatt gcatattttc     660
ggcaaagtaa aattttgttg catacccttat caaaaaataa gtgctgcata ctttttagag     720
aaaccaaata attttttatt gcatacccgt ttttaataaa atacattgca taccctcttt     780
taataaaaaa tattgcatac tttgacgaaa caaattttcg ttgcataccc aataaaagat     840
tattatattg catacccgtt tttaataaaa tacattgcat accctctttt aataaaaaat     900
attgcatacg ttgacgaaac aaattttcgt tgcatacccca ataaaagatt attatattgc     960 atacctttc ttgccatacc atttagccga tcaattctcg agaaatttct ctggccgtta    1020
ttcgttattc tctcttttct ttttgggtct ctccctctct gcactaatgc tctctcactc    1080
tgtcacacag taaacggcat actgctctcg ttggttcgag agagcgcgcc tcgaatgttc    1140
```

| | | | | |
|---|---|---|---|---|
| gcgaaaagag | cgccggagta | taaatagagg | cgcttcgtct | acggagcgac aattcaattc | 1200 |
| aaacaagcaa | agtgaacacg | tcgctaagcg | aaagctaagc | aaataaacaa gcgcagctga | 1260 |
| acaagctaaa | caatctgcag | aagcttggta | ccctcgagct | cagctgaatt ctggatcctc | 1320 |
| tagaccggtc | atatgcggcc | gcggatcgat | cgatatctga | ctaaatctta gtttgtattg | 1380 |
| tcatgtttta | atacaatatg | ttatgtttaa | atatgttttt | aataaatttt ataaaataat | 1440 |
| ttcaacttt | attgtaacaa | cattgtccat | ttacacactc | ctttcaagcg cgtgggactc | 1500 |
| gatgctctca | cgtaataagt | gtgcgttgaa | tttattcgca | aaaacattgc atattttcgg | 1560 |
| caaagtaaaa | ttttgttgca | taccttatca | aaaataagt | gctgcatact ttttagagaa | 1620 |
| accaaataat | tttttattgc | atacccgttt | ttaataaaat | acattgcata ccctcttta | 1680 |
| ataaaaaata | ttgcatactt | tgacgaaaca | aattttcgtt | gcatacccaa taaaagatta | 1740 |
| ttatattgca | taccgttttt | taataaaata | cattgcatac | cctctttaa taaaaaatat | 1800 |
| tgcatacgtt | gacgaaacaa | attttcgttg | catacccaat | aaaagattat tatattgcat | 1860 |
| acctttctt | gccataccat | ttagccgatc | aattactcaa | aggcggtaat acggttatcc | 1920 |
| acagaatcag | gggataacgc | aggaaagaac | atgtgagcaa | aaggccagca aaaggccagg | 1980 |
| aaccgtaaaa | aggccgcgtt | gctggcgttt | ttccataggc | tccgccccc tgacgagcat | 2040 |
| cacaaaaatc | gacgctcaag | tcagaggtgg | cgaaacccga | caggactata aagataccag | 2100 |
| gcgtttcccc | ctggaagctc | cctcgtgcgc | tctcctgttc | cgaccctgcc gcttaccgga | 2160 |
| tacctgtccg | cctttctccc | ttcgggaagc | gtggcgcttt | ctcaatgctc acgctgtagg | 2220 |
| tatctcagtt | cggtgtaggt | cgttcgctcc | aagctgggct | gtgtgcacga accccccgtt | 2280 |
| cagcccgacc | gctgcgcctt | atccggtaac | tatcgtcttg | agtccaaccc ggtaagacac | 2340 |
| gacttatcgc | cactggcagc | agccactggt | aacaggatta | gcagagcgag gtatgtaggc | 2400 |
| ggtgctacag | agttcttgaa | gtggtggcct | aactacggct | acactagaag gacagtattt | 2460 |
| ggtatctgcg | ctctgctgaa | gccagttacc | ttcggaaaaa | gagttggtag ctcttgatcc | 2520 |
| ggcaaacaaa | ccaccgctgg | tagcggtggt | ttttttgttt | gcaagcagca gattacgcgc | 2580 |
| agaaaaaaag | gatctcaaga | agatcctttg | atcttttcta | cggggtctga cgctcagtgg | 2640 |
| aacgaaaact | cacgttaagg | gattttgcat | gcgctaagcg | ggctttataa aacgggctgc | 2700 |
| gggaccagtt | ttcatatcac | taccgtttga | gttcttgtgc | tgtgtggata ctcctcccga | 2760 |
| caccgaatta | attcggatct | ctgcaaggga | ttttggtcat | gaacaataaa actgtctgct | 2820 |
| tacataaaca | gtaatacaag | gggtgtt | | | 2847 |

<210> SEQ ID NO 35
<211> LENGTH: 2073
<212> TYPE: DNA
<213> ORGANISM: Artificial sequence
<220> FEATURE:
<223> OTHER INFORMATION: Recombinant plasmid DNA

<400> SEQUENCE: 35

| | | | | |
|---|---|---|---|---|
| catagtataa | tacgactcac | tataggaggg | ccaccatggc | caagttgacc agtgccgttc | 60 |
| cggtgctcac | cgcgcgcgac | gtcgccgag | cggtcgagtt | ctggaccgac cggctcgggt | 120 |
| tctcccggga | cttcgtggag | gacgacttcg | ccggtgtggt | ccgggacgac gtgaccctgt | 180 |
| tcatcagcgc | ggtccaggac | caggtggtgc | cggacaacac | cctggcctgg gtgtgggtgc | 240 |
| gcggcctgga | cgagctgtac | gccgagtggt | cggaggtcgt | gtccacgaac ttccgggacg | 300 |
| cctccgggcc | ggccatgacc | gagatcggcg | agcagccgtg | ggggcgggag ttcgccctgc | 360 |

```
gcgacccggc cggcaactgc gtgcacttcg tggccgagga gcaggactga ccgacgccga    420
ccaacaccgc cggtccgacg gcggcccacg ggtcccaggg gggtcgacct cgaaacttgt    480
ttattgcagc ttataatggt tacaaataaa gcaatagcat cacaaatttc acaaataaag    540
catttttttc actgcattct agttgtggtt tgtccaaact catcaatgta tcttatcatg    600
tctgctagcc tcgagaaatt tctctggccg ttattcgtta ttctctcttt tcttttgggg    660
tctctccctc tctgcactaa tgctctctca ctctgtcaca cagtaaacgg catactgctc    720
tcgttggttc gagagagcgc gcctcgaatg ttcgcgaaaa gagcgccgga gtataaatag    780
aggcgcttcg tctacggagc gacaattcaa ttcaaacaag caaagtgaac acgtcgctaa    840
gcgaaagcta agcaaataaa caagcgcagc tgaacaagct aaacaatctg cagaagcttg    900
gtaccctcga gctcagctga attctggatc ctctagaccg gtcatatgcg gccgcggatc    960
gatcgatatc tgactaaatc ttagtttgta ttgtcatgtt ttaatacaat atgttatgtt   1020
taaatatgtt tttaataaat tttataaaat aatttcaact tttattgtaa caacattgtc   1080
catttacaca ctcctttcaa gcgcgtggga ctcgatgctc actcaaaggc ggtaatacgg   1140
ttatccacag aatcagggga taacgcagga agaacatgt gagcaaaagg ccagcaaaag   1200
gccaggaacc gtaaaaaggc cgcgttgctg gcgttttttcc ataggctccg ccccctgac   1260 gagcatcaca aaaatcgacg ctcaagtcag aggtggcgaa acccgacagg actataaaga   1320
taccaggcgt ttccccctgg aagctccctc gtgcgctctc ctgttccgac cctgccgctt   1380
accggatacc tgtccgcctt tctcccttcg ggaagcgtgg cgctttctca atgctcacgc   1440
tgtaggtatc tcagttcggt gtaggtcgtt cgctccaagc tgggctgtgt gcacgaaccc   1500
cccgttcagc ccgaccgctg cgccttatcc ggtaactatc gtcttgagtc aacccggta   1560 agacacgact tatcgccact ggcagcagcc actggtaaca ggattagcag agcgaggtat   1620
gtaggcggtg ctacagagtt cttgaagtgg tggcctaact acggctacac tagaaggaca   1680
gtatttggta tctgcgctct gctgaagcca gttaccttcg gaaaaagagt tggtagctct   1740
tgatccggca acaaaccac cgctggtagc ggtggttttt tgtttgcaa gcagcagatt   1800 acgcgcagaa aaaaggatc tcaagaagat cctttgatct tttctacggg gtctgacgct   1860
cagtggaacg aaaactcacg ttaagggatt ttgcatgcgc taagcgggct ttataaaacg   1920
ggctgcggga ccagttttca tatcactacc gtttgagttc ttgtgctgtg tggatactcc   1980
tcccgacacc gaattaattc ggatctctgc aagggatttt ggtcatgaac aataaaactg   2040
tctgcttaca taaacagtaa tacaagggg gtt                                 2073
```

<210> SEQ ID NO 36
<211> LENGTH: 95
<212> TYPE: DNA
<213> ORGANISM: Drosophila melanogaster

<400> SEQUENCE: 36

```
tagcgctaag cgggctttat aaaacgggct gcgggaccag ttttcatatc actaccgttt    60
gagttcttgt gctgtgtgga tactcctccc gacac                               95
```

<210> SEQ ID NO 37
<211> LENGTH: 90
<212> TYPE: DNA
<213> ORGANISM: Drosophila melanogaster

<400> SEQUENCE: 37
gagcgccgga gtataaatag aggcgcttcg tctacggagc gacaattcaa ttcaaacaag    60
caaagtgaac acgtcgctaa gcgaaagcta                                     90

<210> SEQ ID NO 38
<211> LENGTH: 42
<212> TYPE: DNA
<213> ORGANISM: Artificial sequence
<220> FEATURE:
<223> OTHER INFORMATION: Synthetic DNA primer

<400> SEQUENCE: 38
atgaaacacc aacaccaaca tcaacatcaa catcaacatc aa                        42

<210> SEQ ID NO 39
<211> LENGTH: 98
<212> TYPE: DNA
<213> ORGANISM: Artificial sequence
<220> FEATURE:
<223> OTHER INFORMATION: Synthetic DNA primer

<400> SEQUENCE: 39
tgctctagaa tgctttgcat acttctgcct gctggggagc ctggggactt tccacaccct    60
aactgacaca cattccacag ctggttgcgg ccgcttta                             98

<210> SEQ ID NO 40
<211> LENGTH: 586
<212> TYPE: DNA
<213> ORGANISM: Artificial sequence
<220> FEATURE:
<223> OTHER INFORMATION: PRE sequence of HBV with Xba1 and Not1
      restriction sites

<400> SEQUENCE: 40
tgctctagac gtggaacctt tgtggctcct ctgccgatcc atactgcgga actcctagcc    60
gcttgttttg ctcgcagccg gtctggagca aagctcatcg gaactgacaa ttctgtcgtc   120
ctctcgcgga aatatacatc gtttccatgg ctgctaggct gtactgccaa ctggatcctg   180
cgcgggacgt cctttgttta cgtcccgtcg gcgctgaatc ccgcggacga ccccctcgcgg   240 ggccgcttgg gactctctcg tccccttctc cgtctgccgt tccagccgac cacggggcgc   300
acctctcttt acgcggtctc cccgtctgtg ccttctcatc tgccggtccg tgtgcacttc   360
gcttcacctc tgcacgttgc atggagacca ccgtgaacgc ccatcagatc ctgcccaagg   420
tcttacataa gaggactctt ggactcccag caatgtcaac gaccgacctt gaggcctact   480
tcaaagactg tgtgtttaag gactgggagg agctggggga ggagattagg ttaaaggtct   540
ttgtattagg aggctgtatg cataaattgg tctggcggcc gcttta                  586

<210> SEQ ID NO 41
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 41
cctgcgttat cccctgattc tgtg                                           24

<210> SEQ ID NO 42
<211> LENGTH: 20
<212> TYPE: DNA
<213> ORGANISM: Artificial sequence
<220> FEATURE:

```
<223> OTHER INFORMATION: Synthetic DNA primer

<400> SEQUENCE: 42
gccaccactt caagaactct                                              20

<210> SEQ ID NO 43
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 43
cacgagggag cttccagggg                                              20

<210> SEQ ID NO 44
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 44
ggaaagaaca tgtgagcaaa                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 45
ttcgctccaa gctgggctgt                                              20

<210> SEQ ID NO 46
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 46
acaaaccacc gctggtagcg                                              20

<210> SEQ ID NO 47
<211> LENGTH: 23
<212> TYPE: DNA
<213> ORGANISM: Artificial sequence
<220> FEATURE:
<223> OTHER INFORMATION: Synthetic DNA primer

<400> SEQUENCE: 47
ggccttttgc tggccttttg ctc                                          23

<210> SEQ ID NO 48
<211> LENGTH: 28
<212> TYPE: DNA
<213> ORGANISM: Artificial sequence
<220> FEATURE:
<223> OTHER INFORMATION: Synthetic DNA primer

<400> SEQUENCE: 48
ctgctagcct agaatcccaa aacaaact                                     28
```

```
<210> SEQ ID NO 49
<211> LENGTH: 33
<212> TYPE: DNA
<213> ORGANISM: Artificial sequence
<220> FEATURE:
<223> OTHER INFORMATION: Synthetic DNA primer

<400> SEQUENCE: 49 ccaagctttta ttcagagttc tcttcttgta ttc                                33

<210> SEQ ID NO 50
<211> LENGTH: 22
<212> TYPE: DNA
<213> ORGANISM: Artificial sequence
<220> FEATURE:
<223> OTHER INFORMATION: Synthetic DNA primer

<400> SEQUENCE: 50
ggctgataag gttttagcgc ta                                             22

<210> SEQ ID NO 51
<211> LENGTH: 27
<212> TYPE: DNA
<213> ORGANISM: Artificial sequence
<220> FEATURE:
<223> OTHER INFORMATION: Synthetic DNA primer

<400> SEQUENCE: 51
cccgagcgag aggccaacaa aggccac                                        27

<210> SEQ ID NO 52
<211> LENGTH: 26
<212> TYPE: DNA
<213> ORGANISM: Artificial sequence
<220> FEATURE:
<223> OTHER INFORMATION: Synthetic DNA primer

<400> SEQUENCE: 52
gcgaaagcta agcaaataaa caagcg                                         26

<210> SEQ ID NO 53
<211> LENGTH: 32
<212> TYPE: DNA
<213> ORGANISM: Artificial sequence
<220> FEATURE:
<223> OTHER INFORMATION: Synthetic DNA primer

<400> SEQUENCE: 53
ccggggcatg cctcgagaaa tttctctggc cg                                  32

<210> SEQ ID NO 54
<211> LENGTH: 40
<212> TYPE: DNA
<213> ORGANISM: Artificial sequence
<220> FEATURE:
<223> OTHER INFORMATION: Synthetic DNA primer

<400> SEQUENCE: 54
cccgggaatt aattcgctgc agattgttta gcttgttcag                          40

<210> SEQ ID NO 55
<211> LENGTH: 118
<212> TYPE: DNA
<213> ORGANISM: Artificial sequence
<220> FEATURE:
<223> OTHER INFORMATION: Synthetic DNA primer
```

<400> SEQUENCE: 55

```
ccgtttgagt tcttgtgctg tgtggatact cctcccgaca ccgaattaat tcggatctct    60
gcttgacaat taatcatccg gctcgtataa tgcatagtat aatacgactc actatagg    118
```

<210> SEQ ID NO 56
<211> LENGTH: 109
<212> TYPE: DNA
<213> ORGANISM: Artificial sequence
<220> FEATURE:
<223> OTHER INFORMATION: Synthetic DNA primer

<400> SEQUENCE: 56

```
ccacacagca caagaactca aacggtagtg atatgaaaac tggtcccgca gcccgtttta    60
taaagcccgc ttagcgcatg caaaatccct taacgtgagt tttcgttcc    109
```

<210> SEQ ID NO 57
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 57

```
cacccaggcc agggtgttgt ccggc    25
```

<210> SEQ ID NO 58
<211> LENGTH: 2437
<212> TYPE: DNA
<213> ORGANISM: Artificial sequence
<220> FEATURE:
<223> OTHER INFORMATION: Synthetic plasmid DNA

<400> SEQUENCE: 58

```
aaagataacc agctgaagta tcgaatatga gtaaccccca aattgaatca catgccgcaa    60
ctgataggac ccatggaagt acactcttca tggcgatata caagacacac acaagcacga    120
acacccagtt gcggaggaaa ttctccgtaa atgaaaaccc aatcggcgaa caattcatac    180
ccatatatgg taaaagtttt gaacgcgact taaggagagc ggagagcatt gcggctgata    240
aggttttagc gctaagcggg ctttataaaa cgggctgcgg gaccagtttt catatcacta    300
ccgtttgagt tcttgtgctg tgtggatact cctcccgaca caaagccgct ccatcagcca    360
gcagtcgtct aatccagaga caagcttggt accctcgagc tcagctgaat tctggatcct    420
ctagaccggt catatgcggc cgcggatcga tcgatatctg actaaatctt agtttgtatt    480
gtcatgtttt aatacaatat gttatgttta aatatgtttt taataaattt tataaaataa    540
tttcaacttt tattgtaaca acattgtcca tttacacact cctttcaagc gcgtgggact    600
cgatgctcgg cgccactcaa aggcggtaat acggttatcc acagaatcag gggataacgc    660
aggaaagaac atgtgagcaa aaggccagca aaaggccagg aaccgtaaaa aggccgcgtt    720
gctggcgttt ttccataggc tccgcccccc tgacgagcat cacaaaaatc gacgctcaag    780
tcagaggtgg cgaaacccga caggactata agataccagg cgtttccccc tggaagctc    840
cctcgtgcgc tctcctgttc cgaccctgcc gcttaccgga tacctgtccg cctttctccc    900
ttcgggaagc gtggcgcttt ctcaatgctc acgctgtagg tatctcagtt cggtgtaggt    960
cgttcgctcc aagctgggct gtgtgcacga accccccgtt cagcccgacc gctgcgcctt    1020
atccggtaac tatcgtcttg agtccaaccc ggtaagacac gacttatcgc cactggcagc    1080
agccactggt aacaggatta gcagagcgag gtatgtaggc ggtgctacag agttcttgaa    1140
```

```
gtggtggcct aactacggct acactagaag gacagtattt ggtatctgcg ctctgctgaa    1200
gccagttacc ttcggaaaaa gagttggtag ctccttgatcc ggcaaacaaa ccaccgctgg   1260
tagcggtggt ttttttgttt gcaagcagca gattacgcgc agaaaaaaag gatctcaaga   1320
agatcctttg atctttttcta cggggtctga cgctcagtgg aacgaaaact cacgttaagg   1380
gattttgcat gcgctaagcg ggctttataa aacgggctgc gggaccagtt ttcatatcac   1440
taccgtttga gttcttgtgc tgtgtggata ctcctcccga caccgaatta attcggatct   1500
ctgcaaggga ttttggtcat gaacaataaa actgtctgct tacataaaca gtaatacaag   1560
gggtgttcat agtataatac gactcactat aggagggcca ccatggccaa gttgaccagt   1620
gccgttccgg tgctcaccgc gcgcgacgtc gccggagcgg tcgagttctg gaccgaccgg   1680
ctcgggttca gccgggactt cgtggaggac gacttcgccg tgtggtccg ggacgacgtg    1740 accctgttca tcagcgcggt ccaggaccag gtggtgccgg acaacaccct ggcctgggtg   1800
tgggtgcgcg gcctggacga gctgtacgcc gagtggtcgg aggtcgtgtc cacgaacttc   1860
cgggacgcct ccgggccggc catgaccgag atcggcgagc agccgtgggg gcgggagttc   1920
gccctgcgcg accggccgg caactgcgtg cacttcgtgg ccgaggagca ggactgaccg    1980
acgccgacca acaccgccgg tccgacggcg gcccacgggt cccaggggg tcgacctcga    2040 aacttgttta ttgcagctta taatggttac aaataaagca atagcatcac aaatttcaca   2100
aataaagcat ttttttcact gcattctagt tgtggtttgt ccaaactcat caatgtatct   2160
tatcatgtct tcacgtaata agtgtgcggc tagcagtcaa ctactagtga atgccctact   2220
agaagatgtg tgttgcacaa aatgtccctg gaataaccaa tttgaagtgc agatagcagt   2280
aaacgtaagc taatatgaat attatttaac tgtaatgttt taatatcgct ggacattact   2340
aataaaccca ctataaacac atgtacatat gtatgttttg gcatacaatg agtagttggg   2400
gaaaaaatgt gtaaaagcac cgtgaccatc acagcat                            2437
```

<210> SEQ ID NO 59
<211> LENGTH: 1034
<212> TYPE: DNA
<213> ORGANISM: Drosophila melanogaster

<400> SEQUENCE: 59

```
ctagaatatt cgctttattt tggaaatttc tttataaata cggctgctta agttaattat    60
gttagagata atcgaagggt tgttacgcg gatgttgtcc gccagaaagg cctatggaac    120
tttgacaaga tattcttaaa aatgtattta catactaact taaaaaagct atttatttat   180
tagattaata cagacaattg catgcagatg attgttagtg ttttttattt aaaattacgt   240
aaaggttgtc aagactgttg ttgtcaactg tttacactgt gaaataagtt gaattttcg    300 ctttaaggt aaatatgaag gtttctttgc ttaattaaac gcattttttt tattcaatat   360
aaacaatatt tattttactt ataaatcaaa aacaaattaa aatattaaa tatacaagaa    420 aataaacaac aaattccaag tttgcacact tttgagtcta tatataaacg ttagaagatc    480
acacagattt acatatgtat gtacatatgt acttatgcat gcaaaagcat atgcaaaaac   540
cgtgtctttt atgaaaacta agttaaaata agttaaata ctaagatata tgtattttg     600 aatcttttta ttgcaggaag ggatattgaa ctacatacat atacatacat acatatgtat   660
gtacttgtac atttgtaagc gcggtattta catttaaacc aattaaaatt ttgtataatc   720
tgggagcttt acagattttt gggatggtta caactcaaag gggcgtggca atgtaaataa    780
```

-continued

| | |
|---|---|
| aatctgttct ggttataatg tgtacatatt ctgtctcaac tttctaaggc atatgtataa | 840 |
| atacatacat aatatatgta tatgtatata tgtacataca tatgtacata tgtaaatatt | 900 |
| taattcaatg aatctacggc tataaaaata ataggcttgc ctcattgact ggagctatcc | 960 |
| gcataagcaa catatgtaca tacatacata catatgtaaa aaaaagtagc aactaaattc | 1020 |
| taatacattt tccg | 1034 |

<210> SEQ ID NO 60
<211> LENGTH: 145
<212> TYPE: DNA
<213> ORGANISM: Artificial sequence
<220> FEATURE:
<223> OTHER INFORMATION: Intron with SacI and EcoRI digestion sites

<400> SEQUENCE: 60

| | |
|---|---|
| gagctcgtaa gtatcaaggt tacaagacag gtttaaggag accaatagaa actgggcttg | 60 |
| tcgagacaga gaagactctt gcgtttctga taggcaccta ttggtcttac tgacatccac | 120 |
| tttgcctttc tctccacagg aattc | 145 |

<210> SEQ ID NO 61
<211> LENGTH: 1799
<212> TYPE: DNA
<213> ORGANISM: Artificial sequence
<220> FEATURE:
<223> OTHER INFORMATION: Modified H5N1 Vietnam sequence with SacI and
        EcoRI sites

<400> SEQUENCE: 61

| | |
|---|---|
| gaattcgcca ccatgaagct gtgcatcctg ctggccgtgg tggccttcgt gggcctgagc | 60 |
| ctgggcatga agcaccaaca tcagcaccag caccaacatc aacaccaggg tccaggtgcc | 120 |
| aagttcgtgg ccgcttggac cctgaaggcc gccgccgatc agatctgcat tggataccac | 180 |
| gccaacaaca gcaccgagca ggtggacacc atcatggaga gaacgtgac cgtgacccac | 240 |
| gcccaggaca ttctggagaa gaagcacaac ggcaagctgt gcgatctgga tggcgtgaag | 300 |
| cccctgatcc tgcgcgattg cagcgtggcc ggctggctgc tgggcaaccc catgtgcgat | 360 |
| gagttcatca acgtgcccga gtggagctac atcgtggaga aggccaaccc cgtgaacgat | 420 |
| ctgtgctacc ccggcgattt caacgattac gaggagctga agcacctgct gtcccgcatc | 480 |
| aaccacttcg agaagatcca gatcatcccc aagagcagct ggtccagcca cgaggctagc | 540 |
| ctgggcgtga gcagcgcctg cccgtaccag ggcaagtcca gcttcttccg caacgtggtg | 600 |
| tggctgatca agaagaacag cacctacccc accatcaagc gcagctacaa caacaccaac | 660 |
| caggaggatc tgctggtgct gtggggcatc caccacccca cgatgccgc cgagcagacc | 720 |
| aagctgtacc agaaccccac cacctacatc agcgtgggca cctccaccct gaaccagcgc | 780 |
| ctggtgcccc gcattgccac ccgcagcaag gtgaacggcc agtcgggccg catggagttc | 840 |
| ttttggacca tcctgaagcc caacgacgcc atcaacttcg agagcaacgg caacttcatc | 900 |
| gcccccgagt acgcctacaa gatcgtgaag aagggcgata gcaccatcat gaagagcgag | 960 |
| ctggagtacg gcaactgcaa caccaagtgc cagacccca tgggcgccat caacagcagc | 1020 |
| atgcccttcc acaacatcca cccctgacc atcggcgagt gccccaagta cgtgaagagc | 1080 |
| aaccgcctgg tgctggccac cggcctgcgc aacagcccac agcgcgagcg ccgccgcaag | 1140 |
| aagcgcggcc tgttcggcgc catcgccggc ttcatcgagg gcggctggca gggcatggtg | 1200 |
| gatggctggt acggctacca ccactcgaac gagcagggca cgggctacgc cgccgataag | 1260 |

```
gagtcgaccc agaaggccat cgatggcgtg accaacaagg tgaacagcat catcgacaag    1320
atgaacaccc agttcgaggc cgtgggccgc gagttcaaca acctggagcg ccgcatcgag    1380
aacctgaaca agaagatgga ggacggcttc ctggatgtgt ggacctacaa cgccgagctg    1440
ctggtgctga tggagaacga gcgcaccctg gatttccacg atagcaacgt gaagaacctg    1500
tacgataagg tgcgcctgca gctgcgcgat aacgccaagg agctgggcaa cggctgcttc    1560
gagttctacc acaagtgcga caacgagtgc atggagagcg tgcgcaacgg cacctacgat    1620 taccccagt acagcgagga ggcccgcctg aagcgcgagg agatcagctc cggccgcctg    1680
gtgccacgcg gcagcccagg ctccggctac atccccgagg ccccacgcga tggccaggcc    1740
tacgtgcgca aggatggcga gtgggtgctg ctgtccacct tcctgtaata agcggccgc    1799

<210> SEQ ID NO 62
<211> LENGTH: 943
<212> TYPE: DNA
<213> ORGANISM: Artificial sequence
<220> FEATURE:
<223> OTHER INFORMATION: Kanamycin/Geniticin expression cassette

<400> SEQUENCE: 62
gaattaattc ggatctctgc aagggatttt ggtcatgaac aataaaactg tctgcttaca      60
taaacagtaa tacaaggggt gttcatagta taatacgact cactatagga gggccaccat     120
gagccacatc cagcgcgaaa ccagctgcag ccgtccgcgc ctgaacagca acatggatgc     180
cgatctgtac ggctacaaat gggcccgcga taacgtgggc cagagcggcg ctaccatcta     240
ccgcctgtac ggcaaaccgg atgccccgga actgttcctg aaaacgcca aaggcagcgt     300 ggccaacgat gtgaccgatg aaatggtgcg cctgaactgg ctgaccgagt tcatgccgct     360
gccgaccatc aaaacacttca tccgcacccc ggatgatgcc tggctgctga ccaccgccat     420
tccgggcaaa accgccttcc aggtgctgga agaatacccg atagcggcg aaaacatcgt     480 ggatgccctg gccgtgttcc tgcgccgcct gcacagcatc ccggtgtgca actgcccgtt     540
caacagcgat cgcgtgttcc gcctggctca ggcccagagc cgcatgaaca acggcctggt     600
ggatgccagc gatttcgatg atgaacgcaa cggctggccg gtggaacagg tgtggaaaga     660
gatgcacaaa ctgctgccgt tcagcccgga ttccgtggtg acccacggcg atttcagcct     720
ggataacctg atcttcgatg agggcaaact gatcggctgc atcgatgtgg gccgcgtggg     780
cattgccgat cgctaccagg atctggccat cctgtggaac tgcctgggcg agttcagccc     840
gagcctgcag aaacgcctgt tccagaagta cggcatcgat aacccggata tgaacaaact     900
gcagttccac ctgatgctgg atgagttctt ctaataagtc gac                      943

<210> SEQ ID NO 63
<211> LENGTH: 95
<212> TYPE: DNA
<213> ORGANISM: Artificial sequence
<220> FEATURE:
<223> OTHER INFORMATION: pKanR sequence

<400> SEQUENCE: 63
aagggatttt ggtcatgaac aataaaactg tctgcttaca taaacagtaa tacaagggt      60 gttcatagta taatacgact cactatagga gggcc                                95

<210> SEQ ID NO 64
<211> LENGTH: 30
<212> TYPE: DNA
<213> ORGANISM: Artificial sequence
```

<220> FEATURE:
<223> OTHER INFORMATION: Synthetic DNA primer

<400> SEQUENCE: 64
gcgaacttaa gagcgccgga gtataaatag                                    30

<210> SEQ ID NO 65
<211> LENGTH: 27
<212> TYPE: DNA
<213> ORGANISM: Artificial sequence
<220> FEATURE:
<223> OTHER INFORMATION: Synthetic DNA primer

<400> SEQUENCE: 65
ccaagcttct gcagattgtt tagcttg                                       27

<210> SEQ ID NO 66
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 66
ggtttgtcca aactcatcaa tgtat                                         25

<210> SEQ ID NO 67
<211> LENGTH: 45
<212> TYPE: DNA
<213> ORGANISM: Artificial sequence
<220> FEATURE:
<223> OTHER INFORMATION: Synthetic DNA primer

<400> SEQUENCE: 67
tatactccgg cgctcttaag ttcgctcgcg ttcaaaactt ttacc                   45

<210> SEQ ID NO 68
<211> LENGTH: 592
<212> TYPE: DNA
<213> ORGANISM: Artificial sequence
<220> FEATURE:
<223> OTHER INFORMATION: Hybrid promoter sequence

<400> SEQUENCE: 68
actagtgaat gccctactag aagatgtgtg ttgcacaaaa tgtccctgga ataaccaatt    60
tgaagtgcag atagcagtaa acgtaagcta atatgaatat tatttaactg taatgtttta   120
atatcgctgg acattactaa taaacccact ataaacacat gtacatatgt atgttttggc   180
atacaatgag tagttgggga aaaaatgtgt aaaagcaccg tgaccatcac agcataaaga   240
taaccagctg aagtatcgaa tatgagtaac ccccaaattg aatcacatgc cgcaactgat   300
aggacccatg gaagtacact cttcatggcg atatacaaga cacacacaag cacgaacacc   360
cagttgcgga ggaaattctc cgtaaatgaa aacccaatcg gcgaacaatt catacccata   420
tatggtaaaa gttttgaacg cgagcgaact taagagcgcc ggagtataaa tagaggcgct   480
tcgtctacgg agcgacaatt caattcaaac aagcaaagtg aacacgtcgc taagcgaaag   540
ctaagcaaat aaacaagcgc agctgaacaa gctaaacaat ctgcagaagc tt           592

<210> SEQ ID NO 69
<211> LENGTH: 5540
<212> TYPE: DNA
<213> ORGANISM: Artificial sequence
<220> FEATURE:

<223> OTHER INFORMATION: Ligation independent cloning enabled pHP34s hybrid

<400> SEQUENCE: 69

| | | | | | |
|---|---|---|---|---|---|
| cctgttcact | gactcccgcg | gatcaaaaat | gacgattgac | ggcattacgt | ctaacgatat | 60 |
| ttacatgctt | ggttatgttt | ctaattcttt | aactggccca | tacaagccgc | tgaacaaaac | 120 |
| tggccttgtg | ttaaaaatgg | atcttgatcc | taacgatgta | acctttactt | actcacactt | 180 |
| cgctgtacct | caagcgaaag | gaaacaatgt | cgtgattaca | agctatatga | caaacagagg | 240 |
| attctacgca | gacaaacaat | caacgtttgc | gcctagcttc | ctgctgaaca | tcaaaggcaa | 300 |
| gaaaacatct | gttgtcaaag | acagcatcct | gaacaagga | caattaacag | ttaacaaata | 360 |
| aaaacgcaaa | agaaaatgcc | gatatcctat | tggcattgac | gtcaggtggc | acacctgcag | 420 |
| agaacctcta | cttccaatcg | caccatcatc | accaccatga | ttacaaggat | gacgacgata | 480 |
| agtgaggatc | cgaattcgag | ctccgtcgac | aagcttgcgg | ccgcggatcg | atcgatatct | 540 |
| gactaaatct | tagtttgtat | tgtcatgttt | taatacaata | tgttatgttt | aaatatgttt | 600 |
| ttaataaatt | ttataaaata | atttcaactt | ttattgtaac | aacattgtcc | atttacacac | 660 |
| tcctttcaag | cgcgtgggac | tcgatgctcg | gcgccactca | aaggcggtaa | tacggttatc | 720 |
| cacagaatca | ggggataacg | caggaaagaa | catgtgagca | aaaggccagc | aaaaggccag | 780 |
| gaaccgtaaa | aaggccgcgt | tgctggcgtt | tttccatagg | ctccgccccc | ctgacgagca | 840 |
| tcacaaaaat | cgacgctcaa | gtcagaggtg | gcgaaacccg | acaggactat | aaagatacca | 900 |
| ggcgtttccc | cctggaagct | ccctcgtgcg | ctctcctgtt | ccgaccctgc | cgcttaccgg | 960 |
| atacctgtcc | gcctttctcc | cttcgggaag | cgtggcgctt | tctcaatgct | cacgctgtag | 1020 |
| gtatctcagt | tcggtgtagg | tcgttcgctc | caagctgggc | tgtgtgcacg | aaccccccgt | 1080 |
| tcagcccgac | cgctgcgcct | tatccggtaa | ctatcgtctt | gagtccaacc | cggtaagaca | 1140 |
| cgacttatcg | ccactggcag | cagccactgg | taacaggatt | agcagagcga | ggtatgtagg | 1200 |
| cggtgctaca | gagttcttga | agtggtggcc | taactacggc | tacactagaa | ggacagtatt | 1260 |
| tggtatctgc | gctctgctga | agccagttac | cttcggaaaa | agagttggta | gctcttgatc | 1320 |
| cggcaaacaa | accaccgctg | gtagcggtgg | tttttttgtt | tgcaagcagc | agattacgcg | 1380 |
| cagaaaaaaa | ggatctcaag | aagatccttt | gatcttttct | acggggtctg | acgctcagtg | 1440 |
| gaacgaaaac | tcacgttaag | ggattttgca | tgcgctaagc | gggctttata | aaacgggctg | 1500 |
| cgggaccagt | tttcatatca | ctaccgtttg | agttcttgtg | ctgtgtggat | actcctcccg | 1560 |
| acaccgaatt | aattcggatc | tctgcaaggg | attttggtca | tgaacaataa | aactgtctgc | 1620 |
| ttacataaac | agtaatacaa | ggggtgttca | tagtataata | cgactcacta | taggagggcc | 1680 |
| accatggcca | agttgaccag | tgccgttccg | gtgctcaccg | cgcgcgacgt | cgccggagcg | 1740 |
| gtcgagttct | ggaccgaccg | gctcgggttc | agccgggact | tcgtggagga | cgacttcgcc | 1800 |
| ggtgtggtcc | gggacgacgt | gaccctgttc | atcagcgcgg | tccaggacca | ggtggtgccg | 1860 |
| gacaacaccc | tggcctgggt | gtgggtgcgc | ggcctggacg | agctgtacgc | cgagtggtcg | 1920 |
| gaggtcgtgt | ccacgaactt | ccgggacgcc | tccgggccgg | ccatgaccga | gatcggcgag | 1980 |
| cagccgtggg | ggcgggagtt | cgccctgcgc | gacccggccg | gcaactgcgt | gcacttcgtg | 2040 |
| gccgaggagc | aggactgacc | gacgccgacc | aacaccgccg | gtccgacggc | ggcccacggg | 2100 |
| tcccaggggg | gtcgacctcg | aaacttgttt | attgcagctt | ataatggtta | caaataaagc | 2160 |
| aatagcatca | caaatttcac | aaataaagca | ttttttcac | tgcattctag | ttgtggtttg | 2220 |

```
tccaaactca tcaatgtatc ttatcatgtc ttcacgtaat aagtgtgcgg ctagcagtca    2280
actactagca gtcaacactt ggtctgacag ttaccaatgc ttaatcagtg aggcacctat    2340
ctcagcgatc tgtctatttc gttcatccat agttgcctga ctccccgtcg tgtagataac    2400
tacgatacgg gagggcttac catctggccc cagtgctgca atgataccgc gagaaccacg    2460
ctcaccggct ccagatttat cagcaataaa ccagccagcc ggaagggccg agcgcagaag    2520
tggtcctgca actttatccg cctccatcca gtctattaat tgttgccggg aagctagagt    2580
aagtagttcg ccagttaata gtttgcgcaa cgttgttgcc attgctacag gcatcgtggt    2640
gtcacgctcg tcgtttggta tggcttcatt cagctccggt tcccaacgat caaggcgagt    2700
tacatgatcc cccatgttgt gcaaaaaagc ggttagctcc ttcggtcctc cgatcgttgt    2760
cagaagtaag ttggccgcag tgttatcact catggttatg gcagcactgc ataattctct    2820
tactgtcatg ccatccgtaa gatgcttttc tgtgactggt gagtactcaa ccaagtcatt    2880
ctgagaatag tgtatgcggc gaccgagttg ctcttgcccg gcgtcaatac gggataatac    2940
cgcgccacat agcagaactt taaaagtgct catcattgga aaacgttctt cggggcgaaa    3000
actctcaagg atcttaccgc tgttgagatc cagttcgatg taacccactc gtgcacccaa    3060
ctgatcttca gcatctttta ctttcaccag cgtttctggg tgagcaaaaa caggaaggca    3120
aaatgccgca aaaagggaa taagggcgac acggaaatgt tgaatactca tactcttcct    3180
ttttcaatat tattgaagca tttatcaggg ttattgtctc atgagcggat acatatttga    3240
atgtatttag aaaaataaac aaatagggt tccgcgcaca tttccccgaa aagtgccacc    3300
tactagtgaa tgcccctacta gaagatgtgt gttgcacaaa atgtccctgg aataaccaat    3360
ttgaagtgca gatagcagta aacgtaagct aatatgaata ttatttaact gtaatgtttt    3420
aatatcgctg gacattacta ataaacccac tataaacaca tgtacatatg tatgttttgg    3480
catacaatga gtagttgggg aaaaaatgtg taaaagcacc gtgaccatca cagcataaag    3540
ataaccagct gaagtatcga atatgagtaa cccccaaatt gaatcacatg ccgcaactga    3600
taggacccat ggaagtacac tcttcatggc gatatacaag acacacacaa gcacgaacac    3660
ccagttgcgg aggaaattct ccgtaaatga aaacccaatc ggcgaacaat tcatacccat    3720
atatggtaaa agttttgaac gcgagcgaac ttaagagcgc cggagtataa atagaggcgc    3780
ttcgtctacg gagcgacaat tcaattcaaa caagcaaagt gaacacgtcg ctaagcgaaa    3840
gctaagcaaa taaacaagcg cagctgaaca agctaaacaa tctgcagaag cttggtaccc    3900
tcgagctcag ctgaattctg gatcctctag aaataatttt gtttaacctt aagaaggaga    3960
tatactcaaa atgaagctgt gcatactgct ggccgtcgtg gcctttgttg gcctctcgct    4020
cggggaagag aaaagctaa gcaggtcgtt cactattatt tagtgaaatg agatattatg    4080 atatttctg aattgtgatt aaaaaggcaa ctttatgccc atgcaacaga actataaaa    4140 aatacagaga atgaaagaa acagatagat tttttagttc tttaggcccg tagtctgcaa    4200
atccttttat gattttctat caaacaaaag aggaaaatag accagttgca atccaaacga    4260
gagtctaata gaatgaggtc gaaaagtaaa tcgcgcgggt ttgttactga taaagcaggc    4320
aagacctaaa atgtgtaaag ggcaaagtgt atactttggc gtcacccctt acatatttta    4380 ggtcttttt tattgtgcgt aactaacttg ccatcttcaa acaggagggc tggaagaagc    4440
agaccgctaa cacagtacat aaaaaaggag acatgaacga tgaacatcaa aaagtttgca    4500
aaacaagcaa cagtattaac ctttactacc gcactgctgg caggaggcgc aactcaagcg    4560
tttgcgaaag aaacgaacca aaagccatat aaggaaacat acggcatttc ccatattaca    4620
```

```
cgccatgata tgctgcaaat ccctgaacag caaaaaaatg aaaaatataa agttcctgag   4680
ttcgattcgt ccacaattaa aaatatctct tctgcaaaag gcctggacgt ttgggacagc   4740
tggccattac aaaacactga cggcactgtc gcaaactatc acggctacca catcgtcttt   4800
gcattagccg gagatcctaa aaatgcggat gacacatcga tttacatgtt ctatcaaaaa   4860
gtcggcgaaa cttctattga cagctggaaa aacgctggcc gcgtctttaa agacagcgac   4920
aaattcgatg caaatgattc tatcctaaaa gaccaaacac aagaatggtc aggttcagcc   4980
acatttacat ctgacggaaa aatccgttta ttctacactg atttctccgg taaacattac   5040
ggcaaacaaa cactgacaac tgcacaagtt aacgtatcag catcagacag ctctttgaac   5100
atcaacggtg tagaggatta taaatcaatc tttgacggtg acggaaaaac gtatcaaaat   5160
gtacagcagt tcatcgatga aggcaactac agctcaggcg acaaccatac gctgagagat   5220
cctcactacg tagaagataa aggccacaaa tacttagtat ttgaagcaaa cactggaact   5280
gaagatggct accaaggcga agaatcttta tttaacaaag catactatgg caaaagcaca   5340
tcattcttcc gtcaagaaag tcaaaaactt ctgcaaagcg ataaaaaacg cacggctgag   5400
ttagcaaacg gcgctctcgg tatgattgag ctaaacgatg attacacact gaaaaaagtg   5460
atgaaaccgc tgattgcatc taacacagta acagatgaaa ttgaacgcgc gaacgtcttt   5520
aaaatgaacg gcaaatggta                                               5540

<210> SEQ ID NO 70
<211> LENGTH: 5489
<212> TYPE: DNA
<213> ORGANISM: Artificial sequence
<220> FEATURE:
<223> OTHER INFORMATION: Ligation independent cloning enabled hybrid

<400> SEQUENCE: 70
ctagcagtca acacttggtc tgacagttac caatgcttaa tcagtgaggc acctatctca     60
gcgatctgtc tatttcgttc atccatagtt gcctgactcc ccgtcgtgta gataactacg    120
atacgggagg gcttaccatc tggccccagt gctgcaatga taccgcgaga accacgctca    180
ccggctccag atttatcagc aataaaccag ccagccggaa gggccgagcg cagaagtggt    240
cctgcaactt tatccgcctc catccagtct attaattgtt gccgggaagc tagagtaagt    300
agttcgccag ttaatagttt gcgcaacgtt gttgccattg ctacaggcat cgtggtgtca    360
cgctcgtcgt ttggtatggc ttcattcagc tccggttccc aacgatcaag gcgagttaca    420
tgatccccca tgttgtgcaa aaaagcggtt agctccttcg gtcctccgat cgttgtcaga    480
agtaagttgg ccgcagtgtt atcactcatg gttatggcag cactgcataa ttctcttact    540
gtcatgccat ccgtaagatg cttttctgtg actggtgagt actcaaccaa gtcattctga    600
gaatagtgta tgcggcgacc gagttgctct tgcccggcgt caatacggga taataccgcg    660
ccacatagca gaactttaaa agtgctcatc attggaaaac gttcttcggg gcgaaaactc    720
tcaaggatct taccgctgtt gagatccagt tcgatgtaac ccactcgtgc acccaactga    780
tcttcagcat cttttacttt caccagcgtt tctgggtgag caaaaacagg aaggcaaaat    840
gccgcaaaaa agggaataag ggcgacacgg aaatgttgaa tactcatact cttccttttt    900
caatattatt gaagcattta tcagggttat tgtctcatga gcggatacat atttgaatgt    960
atttagaaaa ataaacaaat aggggttccg cgcacatttc cccgaaaagt gccacctact   1020
agtgaatgcc ctactagaag atgtgtgttg cacaaaatgt ccctggaata accaatttga   1080
```

-continued

```
agtgcagata gcagtaaacg taagctaata tgaatattat ttaactgtaa tgttttaata    1140
tcgctggaca ttactaataa acccactata aacacatgta catatgtatg ttttggcata    1200
caatgagtag ttggggaaaa aatgtgtaaa agcaccgtga ccatcacagc ataaagataa    1260
ccagctgaag tatcgaatat gagtaacccc caaattgaat cacatgccgc aactgatagg    1320
acccatggaa gtacactctt catggcgata tacaagacac acacaagcac gaacacccag    1380
ttgcggagga aattctccgt aaatgaaaac ccaatcggcg aacaattcat acccatatat    1440
ggtaaaagtt ttgaacgcga gcgaacttaa gagcgccgga gtataaatag aggcgcttcg    1500
tctacggagc gacaattcaa ttcaaacaag caaagtgaac acgtcgctaa gcgaaagcta    1560
agcaaataaa caagcgcagc tgaacaagct aaacaatctg cagaagcttg gtaccctcga    1620
gctcagctga attctggatc ctctagaaat aattttgttt aactttaaga aggagatatc    1680
aaaatgcacc atcatcatca tcattcttct ggtgtagatc tgggtaccga gaacctgtac    1740
ttccaatcca tggagaccga cgtccacata tacctgccgt tcactattat ttagtgaaat    1800
gagatattat gatattttct gaattgtgat taaaaaggca actttatgcc catgcaacag    1860
aaactataaa aaatacagag aatgaaaaga acagataga ttttttagtt ctttaggccc     1920
gtagtctgca aatcctttta tgattttcta tcaaacaaaa gaggaaaata gaccagttgc    1980
aatccaaacg agagtctaat agaatgaggt cgaaaagtaa atcgcgcggg tttgttactg    2040
ataaagcagg caagacctaa aatgtgtaaa gggcaaagtg tatactttgg cgtcacccct    2100
tacatatttt aggtcttttt ttattgtgcg taactaactt gccatcttca aacaggaggg    2160
ctggaagaag cagaccgcta acacagtaca taaaaaagga gacatgaacg atgaacatca    2220
aaaagtttgc aaaacaagca acagtattaa cctttactac cgcactgctg gcaggaggcg    2280
caactcaagc gtttgcgaaa gaaacgaacc aaaagccata taaggaaaca tacggcattt    2340
cccatattac acgccatgat atgctgcaaa tccctgaaca gcaaaaaaat gaaaatata    2400
aagttcctga gttcgattcg tccacaatta aaaatatctc ttctgcaaaa ggcctggacg    2460
tttgggacag ctggccatta caaaacactg acggcactgt cgcaaactat cacggctacc    2520
acatcgtctt tgcattagcc ggagatccta aaaatgcgga tgacacatcg atttacatgt    2580
tctatcaaaa agtcggcgaa acttctattg acagctggaa aaacgctggc cgcgtcttta    2640
aagacagcga caaattcgat gcaaatgatt ctatcctaaa agaccaaaca caagaatggt    2700
caggttcagc cacatttaca tctgacggaa aaatccgttt attctacact gatttctccg    2760
gtaaacatta cggcaaacaa acactgacaa ctgcacaagt taacgtatca gcatcagaca    2820
gctcttttgaa catcaacggt gtagaggatt ataaatcaat ctttgacggt gacggaaaaa    2880
cgtatcaaaa tgtacagcag ttcatcgatg aaggcaacta cagctcaggc gacaaccata    2940
cgctgagaga tcctcactac gtagaagata aaggccacaa atacttagta tttgaagcaa    3000
acactggaac tgaagatggc taccaaggcg aagaatcttt atttaacaaa gcatactatg    3060
gcaaaagcac atcattcttc cgtcaagaaa gtcaaaaact tctgcaaagc gataaaaaac    3120
gcacggctga gttagcaaac ggcgctctcg gtatgattga gctaaacgat gattacacac    3180
tgaaaaaagt gatgaaaccg ctgattgcat ctaacacagt aacagatgaa attgaacgcg    3240
cgaacgtctt taaatgaac ggcaaatggt acctgttcac tgactccgc ggatcaaaaa      3300
tgacgattga cggcattacg tctaacgata tttacatgct tggttatgtt tctaattctt    3360
taactggccc atacaagccg ctgaacaaaa ctggccttgt gttaaaaatg gatcttgatc    3420
ctaacgatgt aaccttactt tactcacact tcgctgtacc tcaagcgaaa ggaaacaatg    3480
```

```
tcgtgattac aagctatatg acaaacagag gattctacgc agacaaacaa tcaacgtttg   3540
cgcctagctt cctgctgaac atcaaaggca agaaaacatc tgttgtcaaa gacagcatcc   3600
ttgaacaagg acaattaaca gttaacaaat aaaaacgcaa agaaaatgc cgatatccta    3660 ttggcattga cggtctccag taaaggtgga tacggatccg aattcgagct ccgtcgacaa   3720
gcttgcggcc gcggatcgat cgatatctga ctaaatctta gtttgtattg tcatgtttta   3780
atacaatatg ttatgtttaa atatgttttt aataaatttt ataaaataat ttcaactttt   3840
attgtaacaa cattgtccat ttacacactc ctttcaagcg cgtgggactc gatgctcggc   3900
gccactcaaa ggcggtaata cggttatcca cagaatcagg ggataacgca ggaaagaaca   3960
tgtgagcaaa aggccagcaa aaggccagga accgtaaaaa ggccgcgttg ctggcgtttt   4020
tccataggct ccgcccccct gacgagcatc acaaaaatcg acgctcaagt cagaggtggc   4080
gaaacccgac aggactataa agataccagg cgtttccccc tggaagctcc ctcgtgcgct   4140
ctcctgttcc gaccctgccg cttaccggat acctgtccgc ctttctccct cgggaagcg   4200 tggcgctttc tcaatgctca cgctgtaggt atctcagttc ggtgtaggtc gttcgctcca   4260
agctgggctg tgtgcacgaa ccccccgttc agcccgaccg ctgcgcctta tccggtaact   4320
atcgtcttga gtccaacccg gtaagacacg acttatcgcc actggcagca gccactggta   4380
acaggattag cagagcgagg tatgtaggcg gtgctacaga gttcttgaag tggtggccta   4440
actacggcta cactagaagg acagtatttg gtatctgcgc tctgctgaag ccagttacct   4500
tcggaaaaag agttggtagc tcttgatccg gcaaacaaac caccgctggt agcggtggtt   4560
tttttgtttg caagcagcag attacgcgca gaaaaaaagg atctcaagaa gatcctttga   4620
tcttttctac ggggtctgac gctcagtgga acgaaaactc acgttaaggg attttgcatg   4680
cgctaagcgg gctttataaa acgggctgcg ggaccagttt tcatatcact accgtttgag   4740
ttcttgtgct gtgtggatac tcctcccgac accgaattaa ttcggatctc tgcaagggat   4800
tttggtcatg aacaataaaa ctgtctgctt acataaacag taatacaagg ggtgttcata   4860
gtataatacg actcactata ggagggccac catggccaag ttgaccagtg ccgttccggt   4920
gctcaccgcg cgcgacgtcg ccggagcggt cgagttctgg accgaccggc tcgggttcag   4980
ccgggacttc gtggaggacg acttcgccgg tgtggtccgg gacgacgtga ccctgttcat   5040
cagcgcggtc caggaccagg tggtgccgga caacaccctg gctgggtgt gggtgcgcgg   5100 cctggacgag ctgtacgccg agtggtcgga ggtcgtgtcc acgaacttcc gggacgcctc   5160
cgggccggcc atgaccgaga tcggcagca gccgtgggg cggagttcg ccctgcgcga   5220 cccggccggc aactgcgtgc acttcgtggc cgaggagcag gactgaccga cgccgaccaa   5280
caccgccggt ccgacggcgg cccacgggtc ccagggggt cgacctcgaa acttgtttat   5340
tgcagcttat aatggttaca aataaagcaa tagcatcaca aatttcacaa ataaagcatt   5400 ttttcactg cattctagtt gtggtttgtc caaactcatc aatgtatctt atcatgtctt   5460
cacgtaataa gtgtgcggct agcagtcaa                                    5489
```

<210> SEQ ID NO 71
<211> LENGTH: 5540
<212> TYPE: DNA
<213> ORGANISM: Artificial sequence
<220> FEATURE:
<223> OTHER INFORMATION: Ligation independent cloning enabled hybrid

<400> SEQUENCE: 71

```
ctagcagtca acacttggtc tgacagttac caatgcttaa tcagtgaggc acctatctca      60
gcgatctgtc tatttcgttc atccatagtt gcctgactcc ccgtcgtgta gataactacg     120
atacgggagg gcttaccatc tggcccagt gctgcaatga taccgcgaga accacgctca      180
ccggctccag atttatcagc aataaaccag ccagccggaa gggccgagcg cagaagtggt     240
cctgcaactt tatccgcctc catccagtct attaattgtt gccgggaagc tagagtaagt     300
agttcgccag ttaatagttt gcgcaacgtt gttgccattg ctacaggcat cgtggtgtca     360
cgctcgtcgt ttggtatggc ttcattcagc tccggttccc aacgatcaag gcgagttaca     420
tgatccccca tgttgtgcaa aaaagcggtt agctccttcg gtcctccgat cgttgtcaga     480
agtaagttgg ccgcagtgtt atcactcatg gttatggcag cactgcataa ttctcttact     540
gtcatgccat ccgtaagatg cttttctgtg actggtgagt actcaaccaa gtcattctga     600
gaatagtgta tgcggcgacc gagttgctct tgcccggcgt caatacggga taataccgcg     660
ccacatagca gaactttaaa agtgctcatc attggaaaac gttcttcggg gcgaaaactc     720
tcaaggatct taccgctgtt gagatccagt tcgatgtaac ccactcgtgc acccaactga     780
tcttcagcat cttttacttt caccagcgtt tctgggtgag caaaaacagg aaggcaaaat     840
gccgcaaaaa agggaataag ggcgacacgg aaatgttgaa tactcatact cttccttttt     900
caatattatt gaagcattta tcagggttat tgtctcatga gcggatacat atttgaatgt     960
atttagaaaa ataaacaaat aggggttccg cgcacatttc cccgaaaagt gccacctact    1020
agtgaatgcc ctactagaag atgtgtgttg cacaaaatgt ccctggaata accaatttga    1080
agtgcagata gcagtaaacg taagctaata tgaatattat ttaactgtaa tgttttaata    1140
tcgctggaca ttactaataa acccactata acacatgta catatgtatg ttttggcata    1200
caatgagtag ttggggaaaa aatgtgtaaa agcaccgtga ccatcacagc ataaagataa    1260
ccagctgaag tatcgaatat gagtaacccc caaattgaat cacatgccgc aactgatagg    1320
acccatggaa gtacactctt catggcgata tacaagacac acacaagcac gaacacccag    1380
ttgcggagga aattctccgt aaatgaaaac ccaatcggcg aacaattcat acccatatat    1440
ggtaaaagtt ttgaacgcga gcgaacttaa gagcgccgga gtataaatag aggcgcttcg    1500
tctacggagc gacaattcaa ttcaaacaag caaagtgaac acgtcgctaa gcgaaagcta    1560
agcaaataaa caagcgcagc tgaacaagct aaacaatctg cagaagcttg gtaccctcga    1620
gctcagctga attctggatc ctctagaaat aattttgttt aactttaaga aggagatatc    1680
aaaatgaagc tgtgcatact gctggccgtc gtggccttg ttggcctctc gctcgggcac    1740
catcatcatc atcattcttc tggtgtagat ctgggtaccg agaacctgta cttccaatcc    1800
atggagaccg acgtccacat atacctgccg ttcactatta tttagtgaaa tgagatatta    1860 tgatatttc tgaattgtga ttaaaaaggc aactttatgc ccatgcaaca gaaactataa    1920
aaaatacaga gaatgaaaag aaacagatag atttttttagt tctttaggcc cgtagtctgc    1980
aaatcctttt atgattttct atcaaacaaa agaggaaaat agaccagttg caatccaaac    2040
gagagtctaa tagaatgagg tcgaaaagta atcgcgcgg gtttgttact gataaagcag    2100
gcaagaccta aatgtgtaa agggcaaagt gtatactttg gcgtcacccc ttacatattt    2160
taggtctttt tttattgtgc gtaactaact tgccatcttc aaacaggagg gctggaagaa    2220
gcagaccgct aacacagtac ataaaaaagg agacatgaac gatgaacatc aaaaagtttg    2280
caaaacaagc aacagtatta acctttacta ccgcactgct ggcaggaggc gcaactcaag    2340
cgtttgcgaa agaaacgaac caaaagccat ataaggaaac atacggcatt tcccatatta    2400
```

```
cacgccatga tatgctgcaa atccctgaac agcaaaaaaa tgaaaaatat aaagttcctg    2460
agttcgattc gtccacaatt aaaaatatct cttctgcaaa aggcctggac gtttgggaca    2520
gctggccatt acaaaacact gacggcactg tcgcaaacta tcacggctac cacatcgtct    2580
ttgcattagc cggagatcct aaaaatgcgg atgacacatc gatttacatg ttctatcaaa    2640
aagtcggcga aacttctatt gacagctgga aaaacgctgg ccgcgtcttt aaagacagcg    2700
acaaattcga tgcaaatgat tctatcctaa agaccaaac acaagaatgg tcaggttcag     2760
ccacatttac atctgacgga aaaatccgtt tattctacac tgatttctcc ggtaaacatt    2820
acggcaaaca aacactgaca actgcacaag ttaacgtatc agcatcagac agctctttga    2880
acatcaacgg tgtagaggat tataaatcaa tctttgacgg tgacggaaaa acgtatcaaa    2940
atgtacagca gttcatcgat gaaggcaact acagctcagg cgacaaccat acgctgagag    3000
atcctcacta cgtagaagat aaaggccaca atacttagt atttgaagca aacactggaa     3060
ctgaagatgg ctaccaaggc gaagaatctt tatttaacaa agcatactat ggcaaaagca    3120
catcattctt ccgtcaagaa agtcaaaaac ttctgcaaag cgataaaaaa cgcacggctg    3180
agttagcaaa cggcgctctc ggtatgattg agctaaacga tgattacaca ctgaaaaaag    3240
tgatgaaacc gctgattgca tctaacacag taacagatga aattgaacgc gcgaacgtct    3300
ttaaaatgaa cggcaaatgg tacctgttca ctgactcccg cggatcaaaa atgacgattg    3360
acggcattac gtctaacgat atttacatgc ttggttatgt ttctaattct taactggcc     3420 catacaagcc gctgaacaaa actggccttg tgttaaaaat ggatcttgat cctaacgatg    3480
taacctttac ttactcacac ttcgctgtac ctcaagcgaa aggaaacaat gtcgtgatta    3540
caagctatat gacaaacaga ggattctacg cagacaaaca atcaacgttt gcgcctagct    3600
tcctgctgaa catcaaaggc aagaaaacat ctgttgtcaa agacagcatc cttgaacaag    3660
gacaattaac agttaacaaa taaaaacgca aagaaaatg ccgatatcct attggcattg     3720
acggtctcca gtaaaggtgg atacggatcc gaattcgagc tccgtcgaca agcttgcggc    3780
cgcggatcga tcgatatctg actaaatctt agtttgtatt gtcatgtttt aatacaatat    3840
gttatgttta aatatgtttt taataaattt tataaaataa tttcaacttt tattgtaaca    3900
acattgtcca tttacacact cctttcaagc gcgtgggact cgatgctcgg cgccactcaa    3960
aggcggtaat acggttatcc acagaatcag gggataacgc aggaaagaac atgtgagcaa    4020
aaggccagca aaaggccagg aaccgtaaaa aggccgcgtt gctggcgttt ttccataggc    4080
tccgcccccc tgacgagcat cacaaaaatc gacgctcaag tcagaggtgg cgaaacccga    4140
caggactata agataccag gcgtttcccc ctggaagctc cctcgtgcgc tctcctgttc      4200
cgaccctgcc gcttaccgga tacctgtccg ccttctctcc ttcgggaagc gtggcgcttt    4260
ctcaatgctc acgctgtagg tatctcagtt cggtgtaggt cgttcgctcc aagctgggct    4320
gtgtgcacga accccccgtt cagcccgacc gctgcgcctt atccggtaac tatcgtcttg    4380
agtccaaccc ggtaagacac gacttatcgc cactggcagc agccactggt aacaggatta    4440
gcagagcgag gtatgtaggc ggtgctacag agttcttgaa gtggtggcct aactacggct    4500
acactagaag gacagtattt ggtatctgcg ctctgctgaa gccagttacc ttcggaaaaa    4560
gagttggtag ctcttgatcc ggcaaacaaa ccaccgctgg tagcggtggt ttttttgttt    4620
gcaagcagca gattacgcgc agaaaaaaag gatctcaaga agatcctttg atcttttcta    4680
cggggtctga cgctcagtgg aacgaaaact cacgttaagg gattttgcat gcgctaagcg    4740
```

```
ggctttataa aacgggctgc gggaccagtt ttcatatcac taccgtttga gttcttgtgc      4800
tgtgtggata ctcctcccga caccgaatta attcggatct ctgcaaggga ttttggtcat      4860
gaacaataaa actgtctgct tacataaaca gtaatacaag gggtgttcat agtataatac      4920
gactcactat aggagggcca ccatggccaa gttgaccagt gccgttccgg tgctcaccgc      4980
gcgcgacgtc gccggagcgg tcgagttctg gaccgaccgg ctcgggttca gccgggactt      5040
cgtggaggac gacttcgccg gtgtggtccg ggacgacgtg accctgttca tcagcgcggt      5100
ccaggaccag gtggtgccgg acaacaccct ggcctgggtg tgggtgcgcg gcctggacga      5160
gctgtacgcc gagtggtcgg aggtcgtgtc cacgaacttc cgggacgcct ccgggccggc      5220
catgaccgag atcggcgagc agccgtgggg gcgggagttc gccctgcgcg acccggccgg      5280
caactgcgtg cacttcgtgg ccgaggagca ggactgaccg acgccgacca acaccgccgg      5340
tccgacggcg gcccacgggt cccagggggg tcgacctcga aacttgttta ttgcagctta      5400
taatggttac aaataaagca atagcatcac aaatttcaca ataaagcat ttttttcact       5460 gcattctagt tgtggtttgt ccaaactcat caatgtatct tatcatgtct tcacgtaata      5520
agtgtgcggc tagcagtcaa                                                  5540

<210> SEQ ID NO 72
<211> LENGTH: 5466
<212> TYPE: DNA
<213> ORGANISM: Artificial sequence
<220> FEATURE:
<223> OTHER INFORMATION: Ligation independent cloning enabled hybrid

<400> SEQUENCE: 72
cctgttcact gactcccgcg gatcaaaaat gacgattgac ggcattacgt ctaacgatat        60
ttacatgctt ggttatgttt ctaattcttt aactggccca tacaagccgc tgaacaaaac       120
tggccttgtg ttaaaaatgg atcttgatcc taacgatgta accttctactt actcacactt      180 cgctgtacct caagcgaaag gaaacaatgt cgtgattaca agctatatga caaacagagg       240
attctacgca gacaaacaat caacgtttgc gcctagcttc ctgctgaaca tcaaaggcaa       300
gaaaacatct gttgtcaaag acagcatcct gaacaagga caattaacag ttaacaaata       360
aaaacgcaaa agaaaatgcc gatatcctat tggcattgac gtcaggtggc acacctgcag       420
agaacctcta cttccaatcg caccatcatc accaccatga ttacaaggat gacgacgata       480
agtgaggatc cgaattcgag ctccgtcgac aagcttgcgg ccgcggatcg atcgatatct       540
gactaaatct tagtttgtat tgtcatgttt taatacaata tgttatgttt aaatatgttt       600
ttaataaatt ttataaaata atttcaactt ttattgtaac aacattgtcc atttacacac       660 tccttttcaag cgcgtgggac tcgatgctcg gcgccactca aaggcggtaa tacggttatc      720
cacagaatca ggggataacg caggaaagaa catgtgagca aaaggccagc aaaaggccag       780
gaaccgtaaa aaggccgcgt tgctggcgtt tttccatagg ctccgccccc ctgacgagca       840
tcacaaaaat cgacgctcaa gtcagaggtg gcgaaaccccg acaggactat aaagatacca       900
ggcgtttccc cctggaagct ccctcgtgcg ctctcctgtt ccgaccctgc cgcttaccgg       960
atacctgtcc gcctttctcc cttcgggaag cgtggcgctt tctcaatgct cacgctgtag      1020
gtatctcagt tcggtgtagg tcgttcgctc caagctgggc tgtgtgcacg aaccccccgt      1080
tcagcccgac cgctgcgcct tatccggtaa ctatcgtctt gagtccaacc cggtaagaca      1140
cgacttatcg ccactggcag cagccactgg taacaggatt agcagagcga ggtatgtagg      1200
cggtgctaca gagttcttga agtggtggcc taactacggc tacactagaa ggacagtatt      1260
```

```
tggtatctgc gctctgctga agccagttac cttcggaaaa agagttggta gctcttgatc   1320
cggcaaacaa accaccgctg gtagcggtgg ttttttttgtt tgcaagcagc agattacgcg   1380
cagaaaaaaa ggatctcaag aagatccttt gatcttttct acggggtctg acgctcagtg   1440
gaacgaaaac tcacgttaag ggattttgca tgcgctaagc gggctttata aaacgggctg   1500
cgggaccagt tttcatatca ctaccgtttg agttcttgtg ctgtgtggat actcctcccg   1560
acaccgaatt aattcggatc tctgcaaggg attttggtca tgaacaataa aactgtctgc   1620
ttacataaac agtaatacaa ggggtgttca tagtataata cgactcacta taggagggcc   1680
accatggcca agttgaccag tgccgttccg gtgctcaccg cgcgcgacgt cgccggagcg   1740
gtcgagttct ggaccgaccg gctcgggttc agccgggact tcgtggagga cgacttcgcc   1800
ggtgtggtcc gggacgacgt gaccctgttc atcagcgcgg tccaggacca ggtggtgccg   1860
gacaacaccc tggcctgggt gtgggtgcgc ggcctggacg agctgtacgc cgagtggtcg   1920
gaggtcgtgt ccacgaactt ccgggacgcc tccgggccgg ccatgaccga gatcggcgag   1980
cagccgtggg ggcgggagtt cgccctgcgc gacccggccg gcaactgcgt gcacttcgtg   2040
gccgaggagc aggactgacc gacgccgacc aacaccgccg gtccgacggc ggcccacggg   2100
tcccaggggg gtcgacctcg aaacttgttt attgcagctt ataatggtta caaataaagc   2160
aatagcatca caaatttcac aaataaagca ttttttttcac tgcattctag ttgtggtttg   2220
tccaaactca tcaatgtatc ttatcatgtc ttcacgtaat aagtgtgcgg ctagcagtca   2280
actactagca gtcaacactt ggtctgacag ttaccaatgc ttaatcagtg aggcacctat   2340
ctcagcgatc tgtctatttc gttcatccat agttgcctga ctccccgtcg tgtagataac   2400
tacgatacgg gagggcttac catctggccc cagtgctgca atgataccgc gagaaccacg   2460
ctcaccggct ccagatttat cagcaataaa ccagccagcc ggaagggccg agcgcagaag   2520
tggtcctgca actttatccg cctccatcca gtctattaat tgttgccggg aagctagagt   2580
aagtagttcg ccagttaata gtttgcgcaa cgttgttgcc attgctacag gcatcgtggt   2640
gtcacgctcg tcgtttggta tggcttcatt cagctccggt tcccaacgat caaggcgagt   2700
tacatgatcc cccatgttgt gcaaaaaagc ggttagctcc ttcggtcctc cgatcgttgt   2760
cagaagtaag ttggccgcag tgttatcact catggttatg gcagcactgc ataattctct   2820
tactgtcatg ccatccgtaa gatgcttttc tgtgactggt gagtactcaa ccaagtcatt   2880
ctgagaatag tgtatgcggc gaccgagttg ctcttgcccg gcgtcaatac gggataatac   2940
cgcgccacat agcagaactt taaaagtgct catcattgga aaacgttctt cggggcgaaa   3000
actctcaagg atcttaccgc tgttgagatc cagttcgatg taacccactc gtgcacccaa   3060
ctgatcttca gcatctttta ctttcaccag cgtttctggg tgagcaaaaa caggaaggca   3120
aaatgccgca aaaaagggaa taagggcgac acggaaatgt tgaatactca tactcttcct   3180
ttttcaatat tattgaagca tttatcaggg ttattgtctc atgagcggat acatatttga   3240
atgtatttag aaaaataaac aaataggggt tccgcgcaca tttccccgaa aagtgccacc   3300
tactagtgaa tgccctacta gaagatgtgt gttgcacaaa atgtccctgg ataaccaat   3360 ttgaagtgca gatagcagta aacgtaagct aatatgaata ttatttaact gtaatgtttt   3420
aatatcgctg gacattacta ataaacccac tataaacaca tgtacatatg tatgttttgg   3480
catacaatga gtagttgggg aaaaaatgtg taaaagcacc gtgaccatca cagcataaag   3540
ataaccagct gaagtatcga atatgagtaa cccccaaatt gaatcacatg ccgcaactga   3600
```

```
taggacccat ggaagtacac tcttcatggc gatatacaag acacacacaa gcacgaacac    3660
ccagttgcgg aggaaattct ccgtaaatga aacccaatc ggcgaacaat tcatacccat     3720
atatggtaaa agttttgaac gcgagcgaac ttaagagcgc cggagtataa atagaggcgc    3780
ttcgtctacg gagcgacaat tcaattcaaa caagcaaagt gaacacgtcg ctaagcgaaa    3840
gctaagcaaa taaacaagcg cagctgaaca agctaaacaa tctgcagaag cttggtaccc    3900
tcgagctcag ctgaattctg gatcctctag aataatttt gtttaacctt aagaaggaga    3960
tacaaagcag gtcgttcact attatttagt gaaatgagat attatgatat tttctgaatt    4020
gtgattaaaa aggcaacttt atgcccatgc aacagaaact ataaaaaata cagagaatga    4080
aaagaaacag atagattttt tagttcttta ggcccgtagt ctgcaaatcc ttttatgatt    4140
ttctatcaaa caaagagga aaatagacca gttgcaatcc aaacgagagt ctaatagaat    4200
gaggtcgaaa agtaaatcgc gcgggtttgt tactgataaa gcaggcaaga cctaaaatgt    4260
gtaaagggca aagtgtatac tttggcgtca ccccttacat attttaggtc ttttttttatt    4320 gtgcgtaact aacttgccat cttcaaacag gagggctgga agaagcagac cgctaacaca    4380
gtacataaaa aaggagacat gaacgatgaa catcaaaaag tttgcaaaac aagcaacagt    4440
attaaccttt actaccgcac tgctggcagg aggcgcaact caagcgtttg cgaaagaaac    4500
gaaccaaaag ccatataagg aaacatacgg catttcccat attacacgcc atgatatgct    4560
gcaaatccct gaacagcaaa aaatgaaaa atataaagtt cctgagttcg attcgtccac    4620
aattaaaaat atctcttctg caaaaggcct ggacgtttgg gacagctggc cattacaaaa    4680
cactgacggc actgtcgcaa actatcacgg ctaccacatc gtctttgcat tagccggaga    4740
tcctaaaaat gcggatgaca catcgattta catgttctat caaaagtcg gcgaaacttc    4800 tattgacagc tggaaaaacg ctggccgcgt ctttaagac agcgacaaat tcgatgcaaa    4860
tgattctatc ctaaaagacc aaacacaaga atggtcaggt tcagccacat ttacatctga    4920
cggaaaaatc cgtttattct acactgattt ctccggtaaa cattacggca aacaaacact    4980
gacaactgca caagttaacg tatcagcatc agacagctct ttgaacatca acggtgtaga    5040
ggattataaa tcaatctttg acggtgacgg aaaaacgtat caaatgtac agcagttcat    5100 cgatgaaggc aactacagct caggcgacaa ccatacgctg agagatcctc actacgtaga    5160
agataaaggc cacaaatact tagtatttga agcaaacact ggaactgaag atggctacca    5220
aggcgaagaa tctttattta acaaagcata ctatggcaaa agcacatcat tcttccgtca    5280
agaaagtcaa aaacttctgc aaagcgataa aaaacgcacg gctgagttag caaacggcgc    5340
tctcggtatg attgagctaa acgatgatta cactgaaa aaagtgatga aaccgctgat    5400
tgcatctaac acagtaacag atgaaattga acgcgcgaac gtctttaaaa tgaacggcaa    5460
atggta                                                             5466
```

<210> SEQ ID NO 73
<211> LENGTH: 5540
<212> TYPE: DNA
<213> ORGANISM: Artificial sequence
<220> FEATURE:
<223> OTHER INFORMATION: Ligation independent cloning enabled hybrid

<400> SEQUENCE: 73

```
ttctcaatgc tcacgctgta ggtatctcag ttcggtgtag gtcgttcgct ccaagctggg      60
ctgtgtgcac gaacccccg ttcagcccga ccgctgcgcc ttatccggta actatcgtct      120
tgagtccaac ccgtaagac acgacttatc gccactggca gcagccactg gtaacaggat      180
```

```
tagcagagcg aggtatgtag gcggtgctac agagttcttg aagtggtggc ctaactacgg      240
ctacactaga aggacagtat ttggtatctg cgctctgctg aagccagtta ccttcggaaa      300
aagagttggt agctcttgat ccggcaaaca aaccaccgct ggtagcggtg gttttttgt       360 ttgcaagcag cagattacgc gcagaaaaaa aggatctcaa gaagatcctt tgatcttttc      420
tacggggtct gacgctcagt ggaacgaaaa ctcacgttaa gggattttgc atgcgctaag      480
cgggctttat aaaacgggct gcgggaccag ttttcatatc actaccgttt gagttcttgt      540
gctgtgtgga tactcctccc gacaccgaat taattcggat ctctgcaagg gattttggtc      600
atgaacaata aaactgtctg cttacataaa cagtaataca aggggtgttc atagtataat      660
acgactcact ataggagggc caccatggcc aagttgacca gtgccgttcc ggtgctcacc      720
gcgcgcgacg tcgccggagc ggtcgagttc tggaccgacc ggctcgggtt cagccgggac      780
ttcgtggagg acgacttcgc cggtgtggtc cgggacgacg tgaccctgtt catcagcgcg      840
gtccaggacc aggtggtgcc ggacaacacc ctggcctggg tgtgggtgcg cggcctggac      900
gagctgtacg ccgagtggtc ggaggtcgtg tccacgaact ccgggacgc ctccgggccg       960 gccatgaccg agatcggcga gcagccgtgg gggcgggagt tcgccctgcg cgacccggcc     1020
ggcaactgcg tgcacttcgt ggccgaggag caggactgac cgacgccgac caacaccgcc     1080
ggtccgacgg cggcccacgg gtcccagggg ggtcgacctc gaaacttgtt tattgcagct     1140
tataatggtt acaaataaag caatagcatc acaaatttca caaataaagc atttttttca     1200
ctgcattcta gttgtggttt gtccaaactc atcaatgtat cttatcatgt cttcacgtaa     1260
taagtgtgcg gctagcagtc aactagcagt caacacttgg tctgacagtt accaatgctt     1320
aatcagtgag gcacctatct cagcgatctg tctatttcgt tcatccatag ttgcctgact     1380
ccccgtcgtg tagataacta cgatacggga gggcttacca tctggcccca gtgctgcaat     1440
gataccgcga gaaccacgct caccggctcc agatttatca gcaataaacc agccagccgg     1500
aagggccgag cgcagaagtg gtcctgcaac tttatccgcc tccatccagt ctattaattg     1560
ttgccgggaa gctagagtaa gtagttcgcc agttaatagt ttgcgcaacg ttgttgccat     1620
tgctacaggc atcgtggtgt cacgctcgtc gtttggtatg gcttcattca gctccggttc     1680
ccaacgatca aggcgagtta catgatcccc catgttgtgc aaaaaagcgg ttagctcctt     1740
cggtcctccg atcgttgtca gaagtaagtt ggccgcagtg ttatcactca tggttatggc     1800
agcactgcat aattctctta ctgtcatgcc atccgtaaga tgcttttctg tgactggtga     1860
gtactcaacc aagtcattct gagaatagtg tatgcggcga ccgagttgct cttgcccggc     1920
gtcaatacgg gataataccg cgccacatag cagaacttta aaagtgctca tcattggaaa     1980
acgttcttcg gggcgaaaac tctcaaggat cttaccgctg ttgagatcca gttcgatgta     2040
acccactcgt gcacccaact gatcttcagc atcttttact ttcaccagcg tttctgggtg     2100
agcaaaaaca ggaaggcaaa atgccgcaaa aaagggaata agggcgacac ggaaatgttg     2160
aatactcata ctcttccttt ttcaatatta ttgaagcatt tatcagggtt attgtctcat     2220
gagcggatac atatttgaat gtatttagaa aaataaacaa ataggggttc cgcgcacatt     2280
tccccgaaaa gtgccaccta ctagtgaatg ccctactaga agatgtgtgt tgcacaaaat     2340
gtccctggaa taaccaattt gaagtgcaga tagcagtaaa cgtaagctaa tatgaatatt     2400
atttaactgt aatgttttaa tatcgctgga cattactaat aaacccacta taaacacatg     2460
tacatatgta tgttttggca tacaatgagt agttggggaa aaaatgtgta aaagcaccgt     2520
```

```
gaccatcaca gcataaagat aaccagctga agtatcgaat atgagtaacc cccaaattga    2580
atcacatgcc gcaactgata ggacccatgg aagtacactc ttcatggcga tatacaagac    2640
acacacaagc acgaacaccc agttgcggag gaaattctcc gtaaatgaaa acccaatcgg    2700
cgaacaattc atacccatat atggtaaaag ttttgaacgc gagcgaactt aagagcgccg    2760
gagtataaat agaggcgctt cgtctacgga gcgacaattc aattcaaaca agcaaagtga    2820
acacgtcgct aagcgaaagc taagcaaata aacaagcgca gctgaacaag ctaaacaatc    2880
tgcagaagct tggtaccctc gagctcagct gaattctgga tcctctagaa ataattttgt    2940
ttaaccttaa gaaggagata tactcaaaat gaagctgtgc atactgctgg ccgtcgtggc    3000
ctttgttggc ctctcgctcg gggaaaattt gtattttcaa tgcaggtcgt tcactattat    3060
ttagtgaaat gagatattat gatattttct gaattgtgat taaaaaggca actttatgcc    3120
catgcaacag aaactataaa aaatacagag aatgaaaaga aacagataga ttttttagtt    3180
ctttaggccc gtagtctgca aatccttttta tgattttcta tcaaacaaaa gaggaaaata    3240
gaccagttgc aatccaaacg agagtctaat agaatgaggc gaaaagtaa atcgcgcggg    3300 tttgttactg ataaagcagg caagacctaa aatgtgtaaa gggcaaagtg tatactttgg    3360
cgtcacccct tacatatttt aggtcttttt ttattgtgcg taactaactt gccatcttca    3420
aacaggaggg ctggaagaag cagaccgcta acacagtaca taaaaaagga gacatgaacg    3480
atgaacatca aaaagtttgc aaaacaagca acagtattaa cctttactac cgcactgctg    3540
gcaggaggcg caactcaagc gtttgcgaaa gaaacgaacc aaaagccata taggaaaca    3600 tacggcattt cccatattac acgccatgat atgctgcaaa tccctgaaca gcaaaaaat    3660 gaaaaatata agttcctga gttcgattcg tccacaatta aaaatatctc ttctgcaaaa    3720
ggcctggacg tttgggacag ctggccatta caaaacactg acggcactgt cgcaaactat    3780
cacggctacc acatcgtctt tgcattagcc ggagatccta aaaatgcgga tgacacatcg    3840
atttacatgt tctatcaaaa agtcggcgaa acttctattg acagctggaa aaacgctggc    3900
cgcgtcttta aagacagcga caaattcgat gcaaatgatt ctatcctaaa agaccaaaca    3960
caagaatggt caggttcagc cacatttaca tctgacggaa aaatccgttt attctacact    4020
gatttctccg gtaaacatta cggcaaacaa acactgacaa ctgcacaagt taacgtatca    4080
gcatcagaca gctcttttgaa catcaacggt gtagaggatt ataaatcaat ctttgacggt    4140
gacggaaaaa cgtatcaaaa tgtacagcag ttcatcgatg aaggcaacta cagctcaggc    4200
gacaaccata cgctgagaga tcctcactac gtagaagata aaggccacaa atacttagta    4260
tttgaagcaa acactggaac tgaagatggc taccaaggcg aagaatcttt atttaacaaa    4320
gcatactatg gcaaaagcac atcattcttc cgtcaagaaa gtcaaaaact tctgcaaagc    4380
gataaaaaac gcacggctga gttagcaaac ggcgctctcg gtatgattga gctaaacgat    4440
gattacacac tgaaaaaagt gatgaaaccg ctgattgcat ctaacacagt aacagatgaa    4500
attgaacgcg cgaacgtctt taaaatgaac ggcaaatggt acctgttcac tgactcccgc    4560
ggatcaaaaa tgacgattga cggcattacg tctaacgata tttacatgct tggttatgtt    4620
tctaattctt taactggccc atacaagccg ctgaacaaaa ctggccttgt gttaaaaatg    4680
gatcttgatc ctaacgatgt aaccttact tactcacact tcgctgtacc tcaagcgaaa    4740
ggaaacaatg tcgtgattac aagctatatg acaaacagag gattctacgc agacaaacaa    4800
tcaacgtttg cgcctagctt cctgctgaac atcaaaggca gaaaacatc tgttgtcaaa    4860 gacagcatcc ttgaacaagg acaattaaca gttaacaaat aaaaacgcaa aagaaaatgc    4920
```

```
cgatatccta ttggcattga cgtcaggtgg cacacctgca gagaacctct acttccaatc    4980
gcaccatcat caccaccatg attacaagga tgacgacgat aagtgaggat ccgaattcga    5040
gctccgtcga caagcttgcg gccgcggatc gatcgatatc tgactaaatc ttagtttgta    5100
ttgtcatgtt ttaatacaat atgttatgtt taaatatgtt tttaataaat tttataaaat    5160
aatttcaact tttattgtaa caacattgtc catttacaca ctcctttcaa gcgcgtggga    5220
ctcgatgctc ggcgccactc aaaggcggta atacggttat ccacagaatc aggggataac    5280
gcaggaaaga acatgtgagc aaaaggccag caaaaggcca ggaaccgtaa aaaggccgcg    5340
ttgctggcgt ttttccatag gctccgcccc cctgacgagc atcacaaaaa tcgacgctca    5400
agtcagaggt ggcgaaaccc gacaggacta taaagatacc aggcgtttcc ccctggaagc    5460
tccctcgtgc gctctcctgt tccgaccctg ccgcttaccg gatacctgtc cgcctttctc    5520
ccttcgggaa gcgtggcgct                                                5540

<210> SEQ ID NO 74
<211> LENGTH: 77
<212> TYPE: DNA
<213> ORGANISM: Simian vacuolating virus 40

<400> SEQUENCE: 74
atgctttgca tacttctgcc tgctggggag cctggggact ttccacaccc taactgacac    60
acattccaca gctggtt                                                   77
```